US00RE39762E

(19) United States
(12) Reissued Patent
Reeves et al.

(10) Patent Number: US RE39,762 E
(45) Date of Reissued Patent: Aug. 7, 2007

(54) POLYKETIDE SYNTHASE ENZYMES AND RECOMBINANT DNA CONSTRUCTS THEREFOR

(75) Inventors: Christopher Reeves, Orinda, CA (US); Daniel Chu, Santa Clara, CA (US); Chaitan Khosla, Palo Alto, CA (US); Daniel Santi, San Francisco, CA (US); Kai Wu, Foster City, CA (US)

(73) Assignee: Kosan Biosciences, Inc., Hayward, CA (US)

(21) Appl. No.: 11/299,244

(22) Filed: Dec. 9, 2005

Related U.S. Patent Documents

Reissue of:
(64) Patent No.: 6,660,862
Issued: Dec. 9, 2003
Appl. No.: 09/825,621
Filed: Apr. 3, 2001

U.S. Applications:
(62) Division of application No. 09/410,551, filed on Oct. 1, 1999, now Pat. No. 6,503,737
(60) Provisional application No. 60/102,748, filed on Oct. 2, 1998, provisional application No. 60/123,810, filed on Mar. 11, 1999, and provisional application No. 60/139,650, filed on Jun. 17, 1999.

(51) Int. Cl.
*C07D 515/00* (2006.01)
*C07D 498/00* (2006.01)

(52) U.S. Cl. ..... 546/92; 546/90
(58) Field of Classification Search ..... 546/90, 546/92
See application file for complete search history.

(56) References Cited

U.S. PATENT DOCUMENTS

| | | | | | |
|---|---|---|---|---|---|
| 4,874,748 | A | * | 10/1989 | Katz et al. | 514/29 |
| 5,063,155 | A | * | 11/1991 | Cox et al. | 435/76 |
| 5,098,837 | A | * | 3/1992 | Beckmann et al. | 435/6 |
| 5,149,639 | A | * | 9/1992 | Katz et al. | 435/76 |
| 5,189,042 | A | * | 2/1993 | Goulet et al. | 514/291 |
| 5,672,491 | A | * | 9/1997 | Khosla et al. | 435/148 |
| 5,712,146 | A | * | 1/1998 | Khosla et al. | 435/252.35 |
| 5,824,513 | A | * | 10/1998 | Katz et al. | 435/76 |
| 5,830,750 | A | * | 11/1998 | Khosla et al. | 435/252.35 |
| 5,843,718 | A | * | 12/1998 | Khosla et al. | 435/69.1 |
| 5,962,290 | A | * | 10/1999 | Khosla et al. | 435/183 |
| 5,968,921 | A | | 10/1999 | Gold | |
| 6,022,731 | A | * | 2/2000 | Khosla et al. | 435/252.35 |
| 6,077,696 | A | * | 6/2000 | Khosla et al. | 435/135 |
| 6,150,513 | A | * | 11/2000 | Wu | 536/23.2 |
| 6,210,974 | B1 | | 4/2001 | Gold | |

FOREIGN PATENT DOCUMENTS

| | | | |
|---|---|---|---|
| EP | 0 184 162 | | 6/1986 |
| EP | 0323042 | A * | 7/1989 |
| EP | 0356399 | A * | 2/1990 |
| EP | 0463690 | A * | 1/1992 |
| WO | WO 93/13663 | * | 7/1993 |
| WO | WO 95/08548 | * | 3/1995 |
| WO | WO 96/40968 | * | 12/1996 |
| WO | WO 97/02358 | * | 1/1997 |
| WO | WO 98/27203 | * | 6/1998 |
| WO | WO 98/49315 | * | 11/1998 |
| WO | WO 00/2000 | * | 4/2000 |
| WO | WO 00/20601 | * | 4/2000 |

OTHER PUBLICATIONS

Chen, TS et al (1992) 'Microbial Transformation of Immunosuppressive Compounds. II. Specific desmethyltion of 13–methoxy group of FK 506 and FR 9500520 by *Actinomycete* sp. ATCC 53828,' J. Antibiot 45(4):577–580.*
Dumont, FJ et al (1992). 'The Immunosuppressive and Toxic Effects of FK–506 Are Mechanically–Related: Pharamacology of a Novel Antagonist of FK–506 and Rapamycin,' J of Exp Medicine 179(3):751–760.*
Fu et al, 1994, Biochemistry 33:9321–9326.*
Iwasaki et al, (1993) Drug Metabolism and Disposition 21:971–977.*
Iwasaki et al, (1995) Drug Metabolism and Disposition 23:28–34.*
Kawai et al, (1993) FEBS Letters 316(2):107–113.*
Kholsa C. (1997). 'Harnessing the Biosynthetic Potential of Modular Polyketide Synthases,' Chemical Reviews 97(7):2577–2590.*
Motamedi et al, (1996) J. Bacteriol. 178:5243–5248.*
Motamedi et al, (1997) Eur J Biochem 244:78–80.*
Motamedi and Shafiee, (1998) Eur J Biochem 256:528.*
Reynolds KA et al (1997) 'Rapaycin, FK506 and Ascomycin–related Compounds,' Drugs Pharm Sci 82:497–520.*
Shafiee, A et al (1993) 'Enzymatic Synthes and Immunosuppressive Activity of Novel Desmethylated Immonomycins (Ascomycins),' J Antibiot 46(9):1397–1405.*
Stassi, DL et al (1998). 'Ethyl–substituted Erythromycin Derivatives Produced by Directed Metabolic Engineering,' Proc Natl Acad Sci USA 95 (13):7305–7309.*

(Continued)

*Primary Examiner*—Amelia A. Owens
(74) *Attorney, Agent, or Firm*—Morrison & Foerster LLP

(57) ABSTRACT

Polyketide compounds of the formula but not including FK-506, FK-520, 18-hydroxy-FK520 and 18-hydroxy-FK-506.

46 Claims, 9 Drawing Sheets

OTHER PUBLICATIONS

Wu et al, (200) Gene 251:81–90.*
Iwasaki et al, (1995), Further metabolism of FK506 (tacrolimus); Identification and biological activities of the metabolites oxidized at multiple sites of FK506, Drug Metabolism & Disposition 23:28–34.*
Iwasaki et al, (1993), Isolation, identification and biological activities of oxidative metabolites of FK506, a potent immunosuppressive macrolide lactone, Drug Metabolism & Disposition 21:971–977.*
Kawai et al, Jan. 1993, Structure–activity profiles of macrolactam immunosuppressant FK–506 analogues, FEBS Letters 316(2):107–113.*
Motamedi et al , 1998, The biosynthetic gene cluster for the macrolactone ring of the immunosuppressnt FK506, Eur J Biochem 256:528–534.*
Motamedi et al, 1997, Structural organization of a multifunctional polyketide synthase involved in the biosynthesis of the macrolide immunosuppressant FK506, Eur J Biochem 244:74–80.*
Motamedi et al, 1996, Characterization of methyltransferase and hydroxylase genes involved in the biosynthesis of the immunosuppressants FK506 and FK520, J Bacteriol 178:5243–5248.*
Caffrey et al, FEBS Letters (1992) 34:205.*
Fu et al, Biochemistry (1994) 33:9321–9326.*
McDaniel et al, Science (1993) 263:1546–1550.*
Rohr, Angew Chem Int Ed Engl. (1995) 34(8):881–888.*
Gold et al., Journal of Neuroscience (1995) 15:7509–7516.
Gold et al., J. Pharm. Exp. Ther. (1999) 289(3):1202–1210.
Harrison's Principles of Internal Medicine, 14th edition, McGraw Hill (1998) Ch. 14, 20, 21 and 64–67.
Lyons et al., Proc. Natl. Acad. Sci. USA (1994) 91:3191–3195.
Shiraga et al., Biochem. Pharmacol. (1994) 47:727–735.
Steiner et al., Proc. Natl. Acad. Sci. USA (1997) 94:2019–2024.
Vincent et al., Arch. Biochem. Biophys. (1992) 294:454–460.
Wu et al., Gene (2000) 251:81–90.

* cited by examiner

Part A

Part B

POLYKETIDE SYNTHASE ENZYMES AND RECOMBINANT DNA CONSTRUCTS THEREFOR

Matter enclosed in heavy brackets [ ] appears in the original patent but forms no part of this reissue specification; matter printed in italics indicates the additions made by reissue.

CROSS-REFERENCE TO RELATED APPLICATIONS

The present application is a divisional application which claims priority to related U.S. patent application Ser. No. 60/102,748, filed Oct. 2, 1998; No. 60/139,650, filed Jun. 17, 1999; No. 60/123,810, filed Mar. 11, 1999, and Ser. No. 09/410,551, filed Oct. 10, 1999, now U.S. Pat. No. 6,503,737 and PCT/US99/22886, filed Oct. 10, 1999, each of which is incorporated herein by reference.

The present application claims priority to related U.S. patent application Ser. No. 60/102,748, filed Oct. 2, 1998; Ser. No. 60/139,650, filed Jun. 17, 1999; and Ser. No. 60/123,810, filed Mar. 11, 1999, each of which is incorporated herein by reference.

FIELD OF THE INVENTION

The present invention relates to polyketides and the polyketide synthase (PKS) enzymes that produce them. The invention also relates generally to genes encoding PKS enzymes and to recombinant host cells containing such genes and in which expression of such genes leads to the production of polyketides. The present invention also relates to compounds useful as medicaments having immunosuppressive and/or neurotrophic activity. Thus, the invention relates to the fields of chemistry, molecular biology, and agricultural, medical, and veterinary technology.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothiline, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672,491; 5,712,146; 5,830,750; and 5,843,718; and Fu et al., 1994, Biochemistry 33: 9321–9326; McDaniel et al., 1993, Science 262: 1546–1550; and Rohr, 1995, Angew. Chem. Int. Ed. Engl. 34(8): 881–888, each of which is incorporated herein by reference.

Polyketides are synthesized in nature by PKS enzymes. These enzymes, which are complexes of multiple large proteins, are similar to the synthases that catalyze condensation of 2-carbon units in the biosynthesis of fatty acids. PKSs catalyze the biosynthesis of polyketides through repeated, decarboxylative Claisen condensations between acylthioester building blocks. The building blocks used to form complex polyketides are typically acylthioesters, such as acetyl, butyryl, propionyl, malonyl, hydroxymalonyl, methylmalonyl, and ethylmalonyl CoA. Other building blocks include amino acid like acylthioesters. PKS enzymes that incorporate such building blocks include an activity that functions as an amino acid ligase (an AMP ligase) or as a non-ribosomal peptide synthetase (NRPS). Two major types of PKS enzymes are known; these differ in their composition and mode of synthesis of the polyketide synthesized. These two major types of PKS enzymes are commonly referred to as Type I or "modular" and Type II "iterative" PKS enzymes.

In the Type I or modular PKS enzyme group, a set of separate catalytic active sites (each active site is termed a "domain", and a set thereof is termed a "module") exists for each cycle of carbon chain elongation and modification in the polyketide synthesis pathway. The typical modular PKS is composed of several large polypeptides, which can be segregated from amino to carboxy termini into a loading module, multiple extender modules, and a releasing (or thioesterase) domain. The PKS enzyme known as 6-deoxyerythronolide B synthase (DEBS) is a Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See Caffrey et al., 1992, FEBS Letters 304: 205, and U.S. Pat. No. 5,824,513, each of which is incorporated herein by reference.

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated ketosynthase (KS) domain and AT and ACP domains. This inactivated KS is in some instances called $KS^{Q}$, where the superscript letter is the abbreviation for the amino acid, glutamine, that is present instead of the active site cysteine required for ketosynthase activity. In other PKS enzymes, including the FK-506 PKS, the loading module incorporates an unusual starter unit and is composed of a CoA ligase like activity domain. In any event, the loading module recognizes a particular acyl-CoA (usually acetyl or propionyl but sometimes butyryl or other acyl-CoA) and transfers it as a thiol ester to the ACP of the loading module.

The AT on each of the extender modules recognizes a particular extender-CoA (malonyl or alpha-substituted malonyl, i.e., methylmalonyl, ethylmalonyl, and 2-hydroxymalonyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module.

Each extender module of a modular PKS contains a KS, AT, ACP, and zero, one, two, or three domains that modify the beta-carbon of the growing polyketide chain. A typical (non-loading) minimal Type I PKS extender module is exemplified by extender module three of DEBS, which contains a KS domain, an AT domain, and an ACP domain. These three domains are sufficient to activate a 2-carbon extender unit and attach it to the growing polyketide molecule. The next extender module, in turn, is responsible for attaching the next building block and transferring the growing compound to the next extender module until synthesis is complete.

Once the PKS is primed with acyl- and malonyl-ACPs, the acyl group of the loading module is transferred to form a thiol ester (trans-esterification) at the KS of the first extender module; at this stage, extender module one possesses an acyl-KS and a malonyl (or substituted malonyl) ACP. The acyl group derived from the loading module is then covalently attached to the alpha-carbon of the malonyl group to form a carbon—carbon bond, driven by concomitant decarboxylation, and generating a new acyl-ACP that has a backbone two carbons longer than the loading building block (elongation or extension).

The polyketide chain, growing by two carbons each extender module, is sequentially passed as covalently bound thiol esters from extender module to extender module, in an assembly line-like process. The carbon chain produced by this process alone would possess a ketone at every other carbon atom, producing a polyketone, from which the name polyketide arises. Most commonly, however, additional enzymatic activities modify the beta keto group of each two carbon unit just after it has been added to the growing polyketide chain but before it is transferred to the next module.

Thus, in addition to the minimal module containing KS, AT, and ACP domains necessary to form the carbon—carbon bond, and as noted above, other domains that modify the beta-carbonyl moiety can be present. Thus, modules may contain a ketoreductase (KR) domain that reduces the keto group to an alcohol. Modules may also contain a KR domain plus a dehydratase (DH) domain that dehydrates the alcohol to a double bond. Modules may also contain a KR domain, a DH domain, and an enoylreductase (ER) domain that converts the double bond product to a saturated single bond using the beta carbon as a methylene function. An extender module can also contain other enzymatic activities, such as, for example, a methylase or dimethylase activity.

After traversing the final extender module, the polyketide encounters a releasing domain that cleaves the polyketide from the PKS and typically cyclizes the polyketide. For example, final synthesis of 6-dEB is regulated by a TE domain located at the end of extender module six. In the synthesis of 6-dEB, the TE domain catalyzes cyclization of the macrolide ring by formation of an ester linkage. In FK-506, FK-520, rapamycin, and similar polyketides, the TE activity is replaced by a RapP (for rapamycin) or RapP like activity that makes a linkage incorporating a pipecolate acid residue. The enzymatic activity that catalyzes this incorporation for the rapamycin enzyme is known as RapP, encoded by the RapP gene. The polyketide can be modified further by tailoring enzymes; these enzymes add carbohydrate groups or methyl groups, or make other modifications, i.e., oxidation or reduction, on the polyketide core molecule. For example, 6-dEB is hydroxylated at C-6 and C-12 and glycosylated at C-3 and C-5 in the synthesis of erythromycin A.

In Type I PKS polypeptides, the order of catalytic domains is conserved. When all beta-keto processing domains are present in a module, the order of domains in that module from N-to-C-terminus is always KS, AT, DH, ER, KR, and ACP. Some or all of the beta-keto processing domains may be missing in particular modules, but the order of the domains present in a module remains the same. The order of domains within modules is believed to be important for proper folding of the PKS polypeptides into an active complex. Importantly, there is considerable flexibility in PKS enzymes, which allows for the genetic engineering of novel catalyst complexes. The engineering of these enzymes is achieved by modifying, adding, or deleting domains, or replacing them with those taken from other Type I PKS enzymes. It is also achieved by deleting, replacing, or adding entire modules with those taken from other sources. A genetically engineered PKS complex should of course have the ability to catalyze the synthesis of the product predicted from the genetic alterations made.

Alignments of the many available amino acid sequences for Type I PKS enzymes has approximately defined the boundaries of the various catalytic domains. Sequence alignments also have revealed linker regions between the catalytic domains and at the N- and C-termini of individual polypeptides. The sequences of these linker regions are less well conserved than are those for the catalytic domains, which is in part how linker regions are identified. Linker regions can be important for proper association between domains and between the individual polypeptides that comprise the PKS complex. One can thus view the linkers and domains together as creating a scaffold on which the domains and modules are positioned in the correct orientation to be active. This organization and positioning, if retained, permits PKS domains of different or identical substrate specificities to be substituted (usually at the DNA level) between PKS enzymes by various available methodologies. In selecting the boundaries of, for example, an AT replacement, one can thus make the replacement so as to retain the linkers of the recipient PKS or to replace them with the linkers of the donor PKS AT domain, or, preferably, make both constructs to ensure that the correct linker regions between the KS and AT domains have been included in at least one of the engineered enzymes. Thus, there is considerable flexibility in the design of new PKS enzymes with the result that known polyketides can be produced more effectively, and novel polyketides useful as pharmaceuticals or for other purposes can be made.

By appropriate application of recombinant DNA technology, a wide variety of polyketides can be prepared in a variety of different host cells provided one has access to nucleic acid compounds that encode PKS proteins and polyketide modification enzymes. The present invention helps meet the need for such nucleic acid compounds by providing recombinant vectors that encode the FK-520 PKS enzyme and various FK-520 modification enzymes. Moreover, while the FK-506 and FK-520 polyketides have many useful activities, there remains a need for compounds with similar useful activities but with better pharmacokinetic profile and metabolism and fewer side-effects. The present invention helps meet the need for such compounds as well.

SUMMARY OF THE INVENTION

In one embodiment, the present invention provides recombinant DNA vectors that encode all or part of the FK-520 PKS enzyme. Illustrative vectors of the invention include cosmid pKOS034-120, pKOS034-124, pKOS065-C31, pKOS065-C3, pKOS065-M27, and pKOS065-M21. The invention also provides nucleic acid compounds that encode the various domains of the FK-520 PKS, i.e., the KS, AT, ACP, KR, DH, and ER domains. These compounds can be readily used, alone or in combination with nucleic acids encoding other FK-520 or non-FK-520 PKS domains, as intermediates in the construction of recombinant vectors that encode all or part of PKS enzymes that make novel polyketides.

The invention also provides isolated nucleic acids that encode all or part of one or more modules of the FK-520 PKS, each module comprising a ketosynthase activity, an acyl transferase activity, and an acyl carrier protein activity. The invention provides an isolated nucleic acid that encodes one or more open reading frames of FK-520 PKS genes, said open reading frames comprising coding sequences for a CoA ligase activity, an NRPS activity, or two or more extender modules. The invention also provides recombinant expression vectors containing these nucleic acids.

In another embodiment, the invention provides isolated nucleic acids that encode all or a part of a PKS that contains at least one module in which at least one of the domains in the module is a domain from a non-FK-520 PKS and at least one domain is from the FK-520 PKS. The non-FK-520 PKS domain or module originates from the rapamycin PKS, the FK-506 PKS, DEBS, or another PKS. The invention also provides recombinant expression vectors containing these nucleic acids.

In another embodiment, the invention provides a method of preparing a polyketide, said method comprising transforming a host cell with a recombinant DNA vector that encodes at least one module of a PKS, said module comprising at least one FK-520 PKS domain, and culturing said host cell under conditions such that said PKS is produced and catalyzes synthesis of said polyketide. In one aspect, the method is practiced with a Streptomyces host cell. In another aspect, the polyketide produced is FK-520. In another aspect, the polyketide produced is a polyketide related in structure to FK-520. In another aspect, the polyketide produced is a polyketide related in structure to FK-506 or rapamycin.

In another embodiment, the invention provides a set of genes in recombinant form sufficient for the synthesis of ethylmalonyl CoA in a heterologous host cell. These genes and the methods of the invention enable one to create recombinant host cells with the ability to produce polyketides or other compounds that require ethylmalonyl CoA for biosynthesis. The invention also provides recombinant nucleic acids that encode AT domains specific for ethylmalonyl CoA. Thus, the compounds of the invention can be used to produce polyketides requiring ethylmalonyl CoA in host cells that otherwise are unable to produce such polyketides.

In another embodiment, the invention provides a set of genes in recombinant form sufficient for the synthesis of 2-hydroxymalonyl CoA and 2-methoxymalonyl CoA in a heterologous host cell. These genes and the methods of the invention enable one to create recombinant host cells with the ability to produce polyketides or other compounds that require 2-hydroxymalonyl CoA for biosynthesis. The invention also provides recombinant nucleic acids that encode AT domains specific for 2-hydroxymalonyl CoA and 2-methoxymalonyl CoA. Thus, the compounds of the invention can be used to produce polyketides requiring 2-hydroxymalonyl CoA or 2-methoxymalonyl CoA in host cells that are otherwise unable to produce such polyketides.

In another embodiment, the invention provides a compound related in structure to FK-520 or FK-506 that is useful in the treatment of a medical condition. These compounds include compounds in which the C-13 methoxy group is replaced by a moiety selected from the group consisting of hydrogen, methyl, and ethyl moieties. Such compounds are less susceptible to the main in vivo pathway of degradation for FK-520 and FK-506 and related compounds and thus exhibit an improved pharmacokinetic profile. The compounds of the invention also include compounds in which the C-15 methoxy group is replaced by a moiety selected from the group consisting of hydrogen, methyl, and ethyl moieties. The compounds of the invention also include the above compounds further modified by chemical methodology to produce derivatives such as, but not limited to, the C-18 hydroxyl derivatives, which have potent neurotrophin but not immunosuppresion activities.

Thus, the invention provides polyketides having the structure:

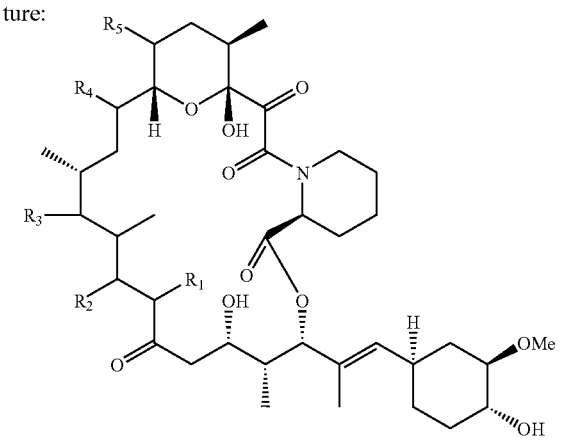

wherein, $R_1$ is hydrogen, methyl, ethyl, or allyl; $R_2$ is hydrogen or hydroxyl, provided that when $R_2$ is hydrogen, there is a double bond between C-20 and C-19; $R_3$ is hydrogen or hydroxyl; $R_4$ is methoxyl, hydrogen, methyl, or ethyl; and $R_5$ is methoxyl, hydrogen, methyl, or ethyl; but not including FK-506, FK-520, 18-hydroxy-FK-520, and 18-hydroxy-FK-506. The invention provides these compounds in purified form and in pharmaceutical compositions.

In another embodiment, the invention provides a method for treating a medical condition by administering a pharmaceutically efficacious dose of a compound of the invention. The compounds of the invention may be administered to achieve immunosuppression or to stimulate nerve growth and regeneration.

These and other embodiments and aspects of the invention will be more fully understood after consideration of the attached Drawings and their brief description below, together with the detailed description, examples, and claims that follow.

The second line shows a restriction map with selected restriction enzyme recognition sequences indicated. K is KpnI; X is XhoI, S is SacI; P is PstI; and E is EcoRI. The third line indicates the position of FK-520 PKS and related genes. Genes are abbreviated with a one letter designation, i.e., C is fkbC. Immediately under the third line are numbered segments showing where the loading module (L) and ten different extender modules (numbered 1–10) are encoded on the various genes shown. At the bottom of the Figure, the DNA inserts of various cosmids of the invention (i.e., 34–124 is cosmid pKOS034-124) are shown in alignment with the FK-520 biosynthetic gene cluster.

Figure 2:
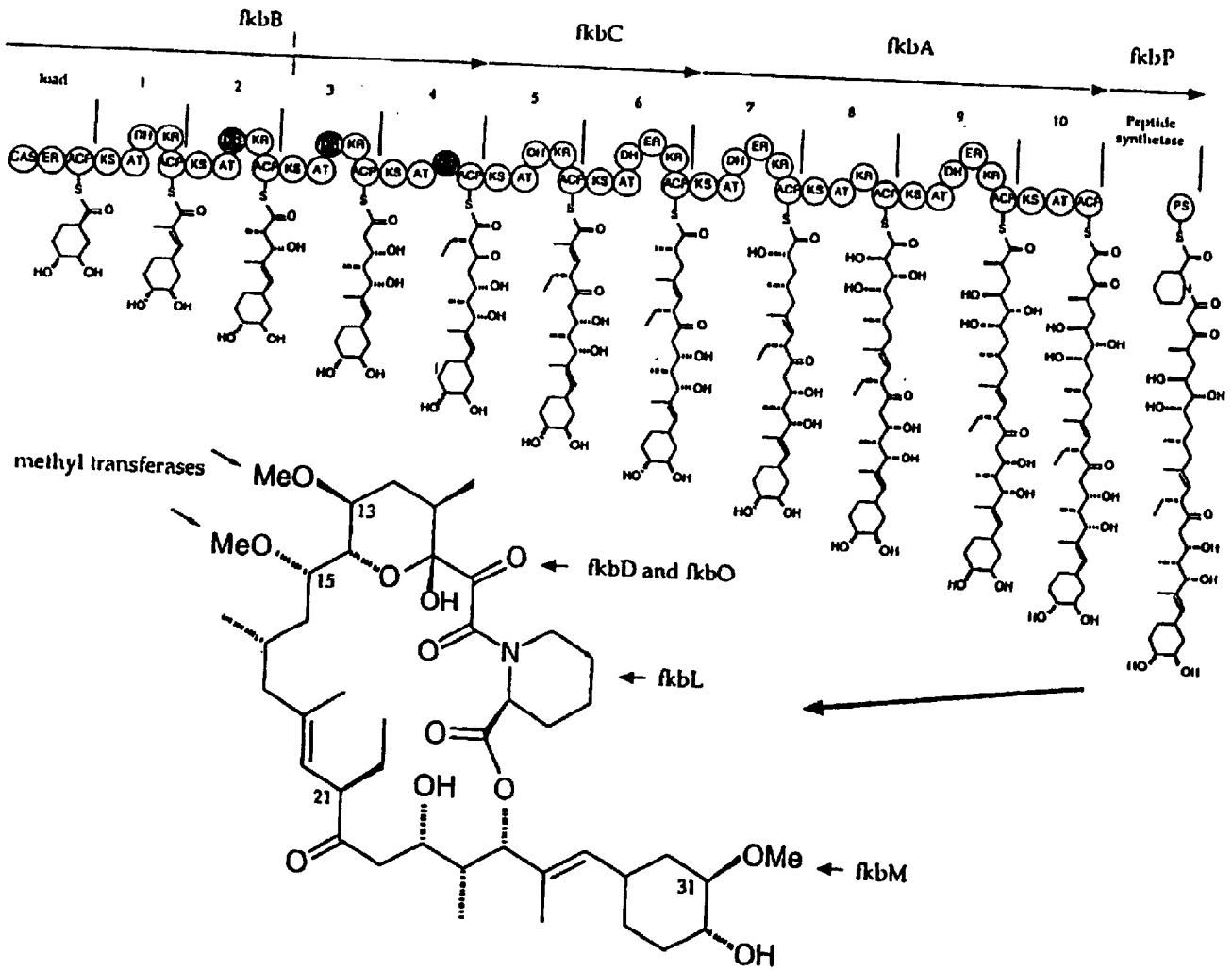

FIG. 2 shows the loading module (load), the ten extender modules, and the peptide synthetase domain of the FK-520 PKS, together with, on the top line, the genes that encode the various domains and modules. Also shown are the various intermediates in FK-520 biosynthesis, as well as the structure of FK-520, with carbons 13, 15, 21, and 31 numbered. The various domains of each module and subdomains of the loading module are also shown. The darkened circles showing the DH domains in modules 2, 3, and 4 indicate that the dehydratase domain is not functional as a dehydratase; this domain may affect the stereochemistry at the corresponding position in the polyketide. The substituents on the FK-520 structure that result from the action of non-PKS enzymes are also indicated by arrows, together with the types of enzymes or the genes that code for the enzymes that mediate the action. Although the methyltransferase is shown acting at the C-13 and C-15 hydroxyl groups after release of the polyketide from the PKS, the methyltransferase may act on the 2-hydroxymalonyl substrate prior to or contemporaneously with its incorporation during polyketide synthesis.

Figure 3:
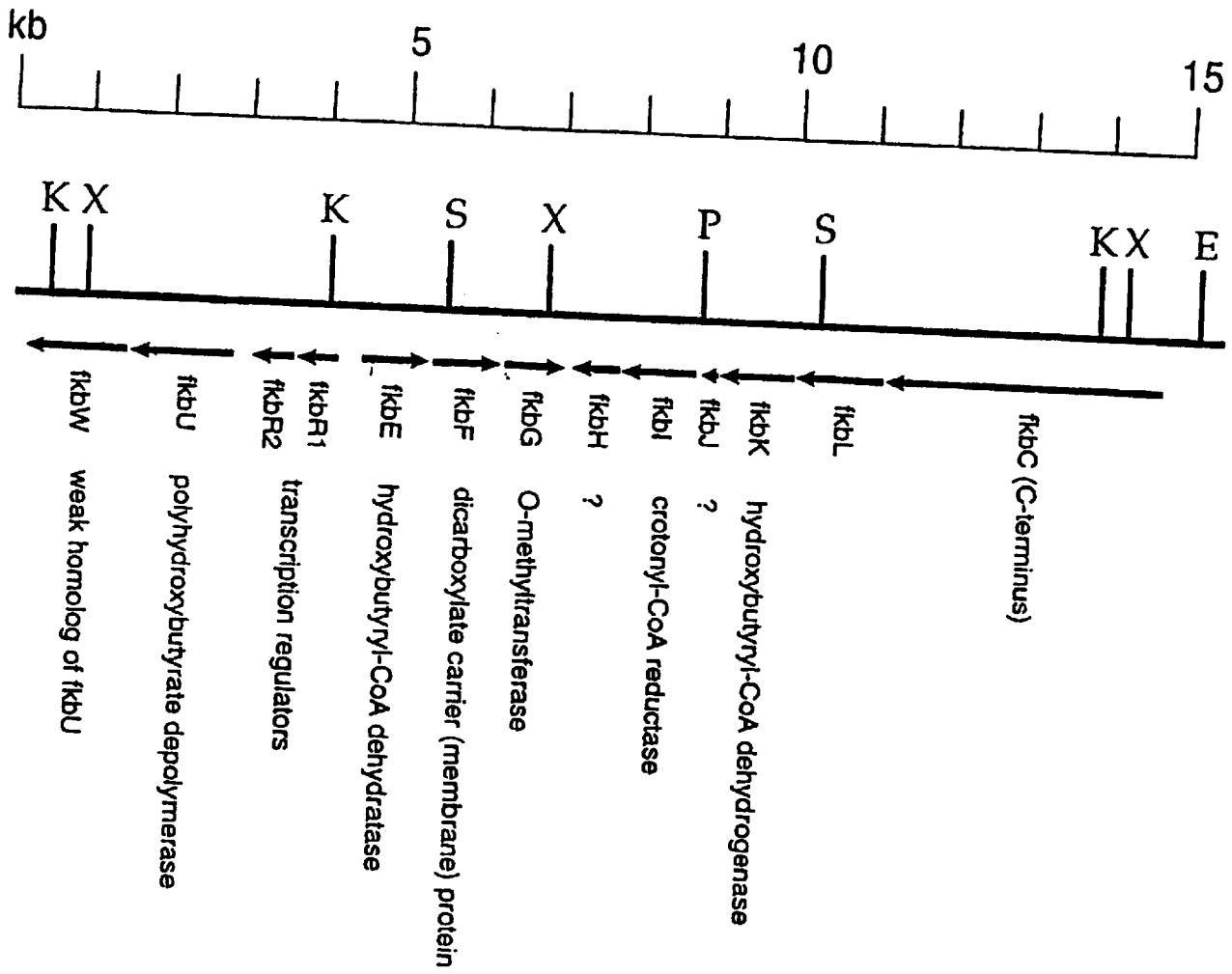

FIG. 3 shows a close-up view of the left end of the FK-520 gene cluster, which contains at least ten additional genes. The ethyl side chain on carbon 21 of FK-520 (FIG. 2) is derived from an ethylmalonyl CoA extender unit that is incorporated by an ethylmalonyl specific AT domain in extender module 4 of the PKS. At least four of the genes in this region code for enzymes involved in ethylmalonyl biosynthesis. The polyhydroxybutyrate depolymerase is involved in maintaining hydroxybutyryl-CoA pools during FK-520 production. Polyhydroxybutyrate accumulates during vegetative growth and disappears during stationary phase in other Streptomyces (Ranade and Vining, 1993, Can. J Microbiol. 39:377). Open reading frames with unknown function are indicated with a question mark.

Figure 4:
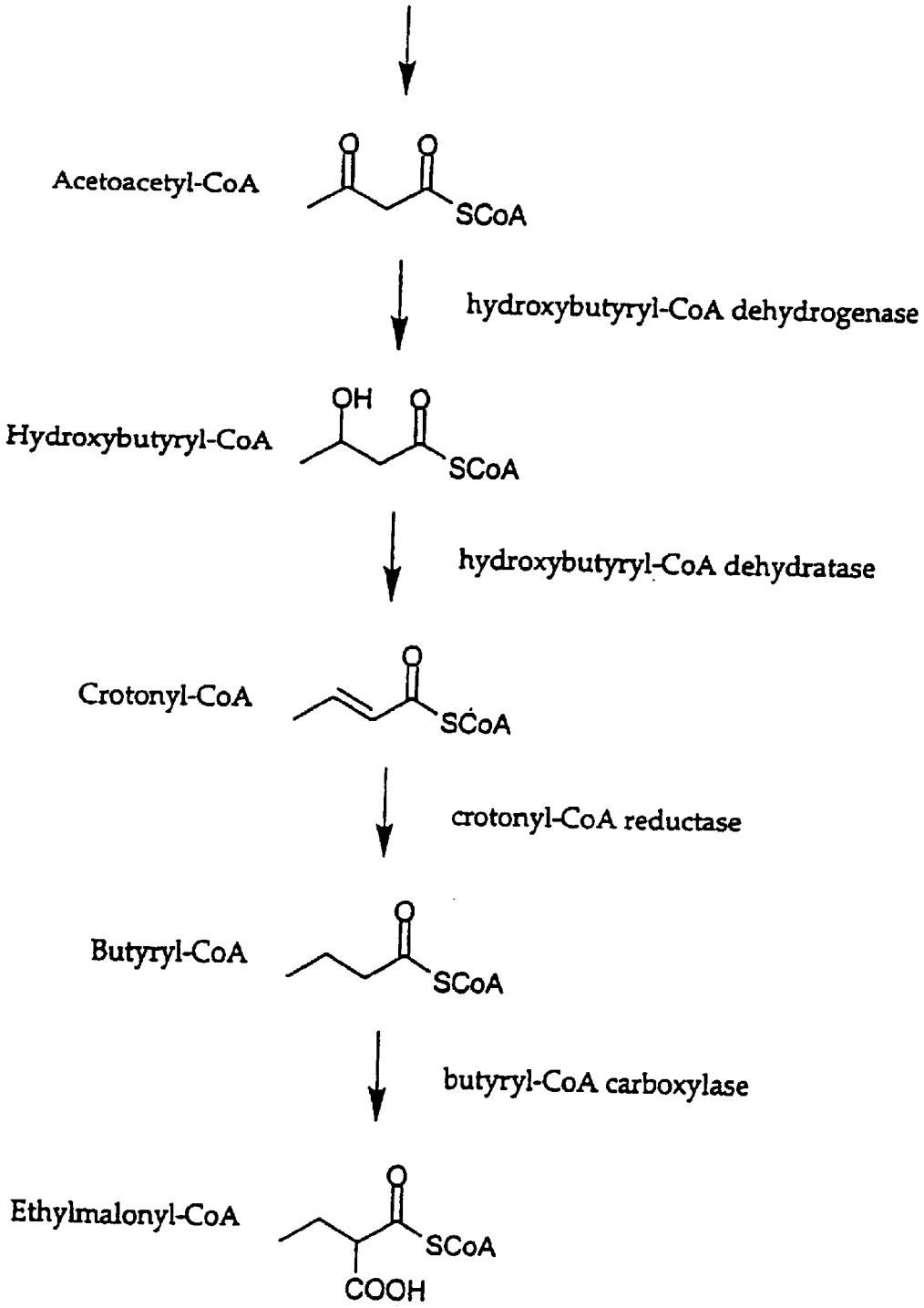

FIG. 4 shows a biosynthetic pathway for the biosynthesis of ethylmalonyl CoA from acetoacetyl CoA consistent with the function assigned to four of the genes in the FK-520 gene cluster shown in FIG. 3.

Figure 5:
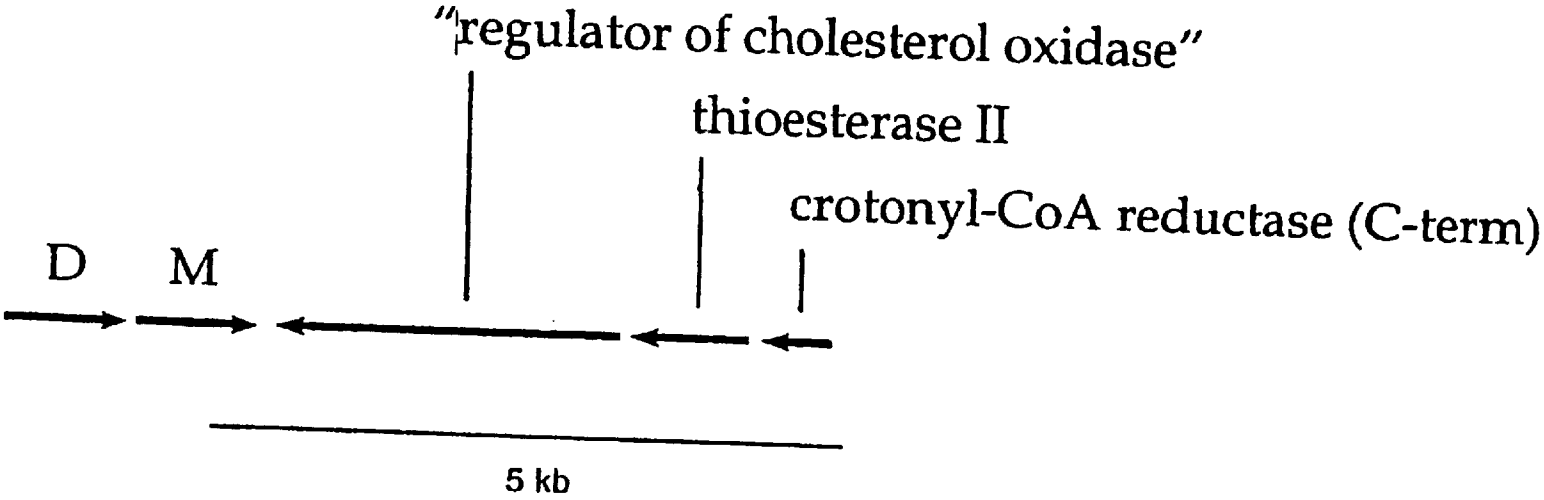

FIG. 5 shows a close-up view of the right-end of the FK-520 PKS gene cluster (and of the sequences on cosmid pKOS065-C31). The genes shown include fkbD, fkbM (a methyl transferase that methylates the hydroxyl group on C-31 of FK-520), fkbN (a homolog of a gene described as a regulator of cholesterol oxidase and that is believed to be a transcriptional activator), fkbQ (a type II thioesterase, which can increase polyketide production levels), and fkbS (a crotonyl-CoA reductase involved in the biosynthesis of ethylmalonyl CoA).

Figure 6:
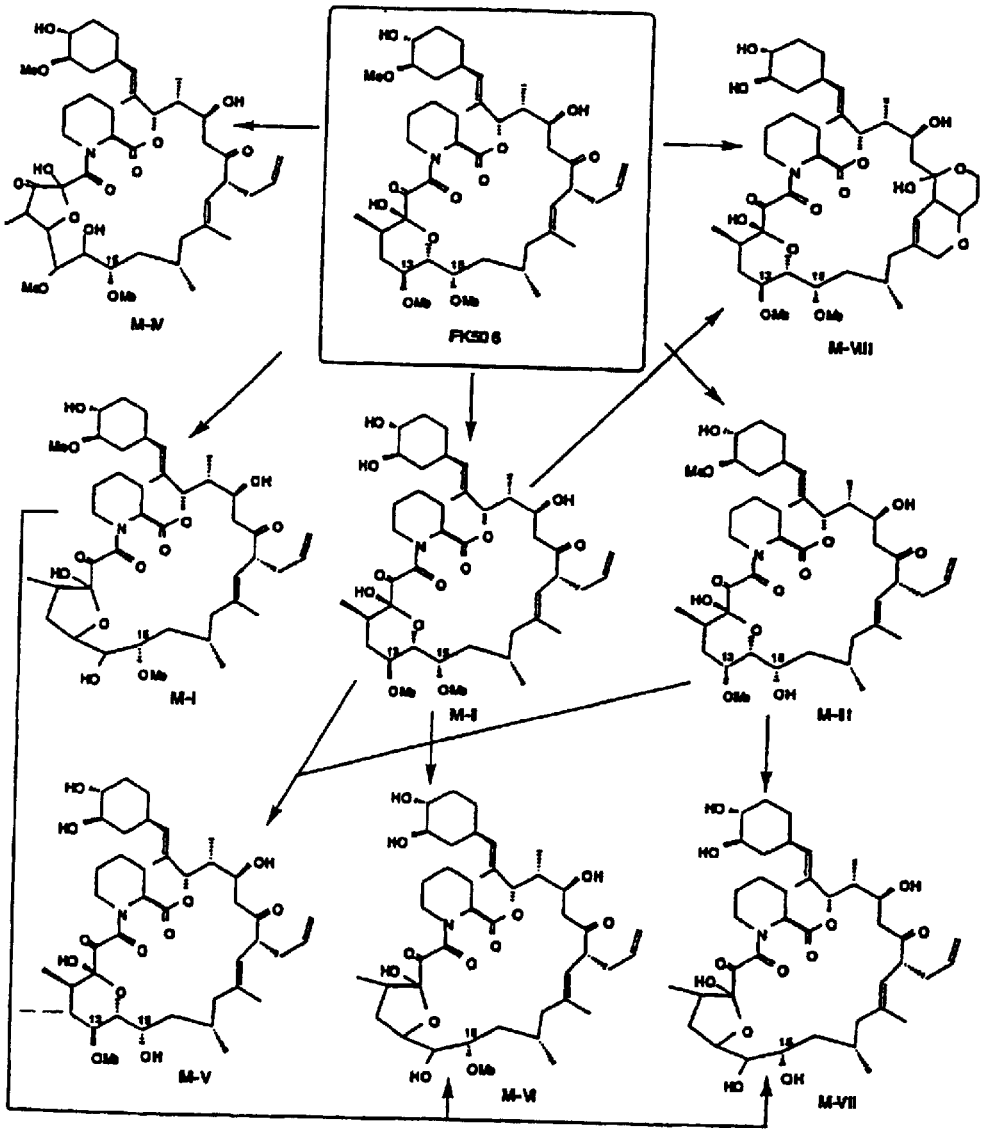

FIG. 6 shows the proposed degradative pathway for tacrolimus (FK-506) metabolism.

Figure 7:
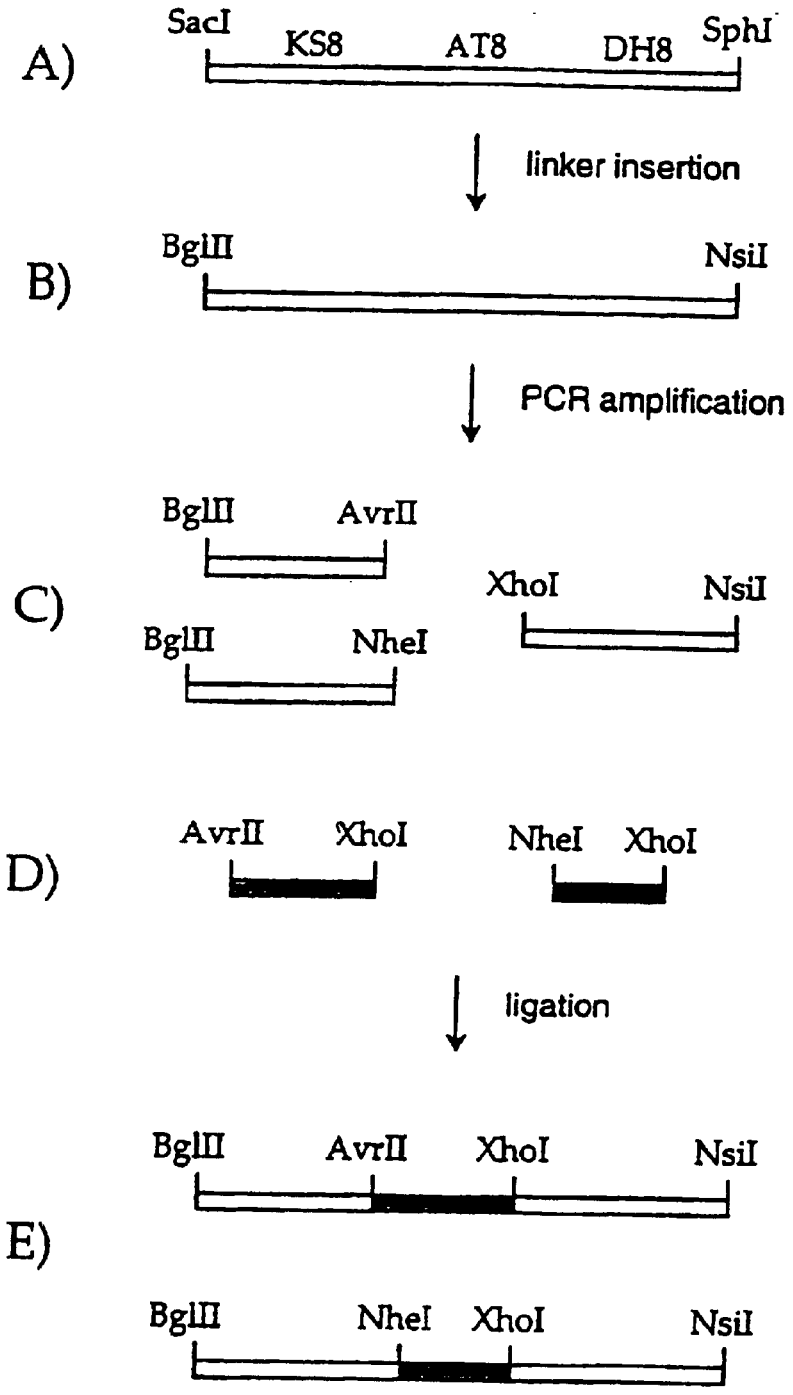

FIG. 7 shows a schematic process for the construction of recombinant PKS genes of the invention that encode PKS enzymes that produce 13-desmethoxy FK-506 and FK-520 polyketides of the invention, as described in Example 4, below.

Figure 8:
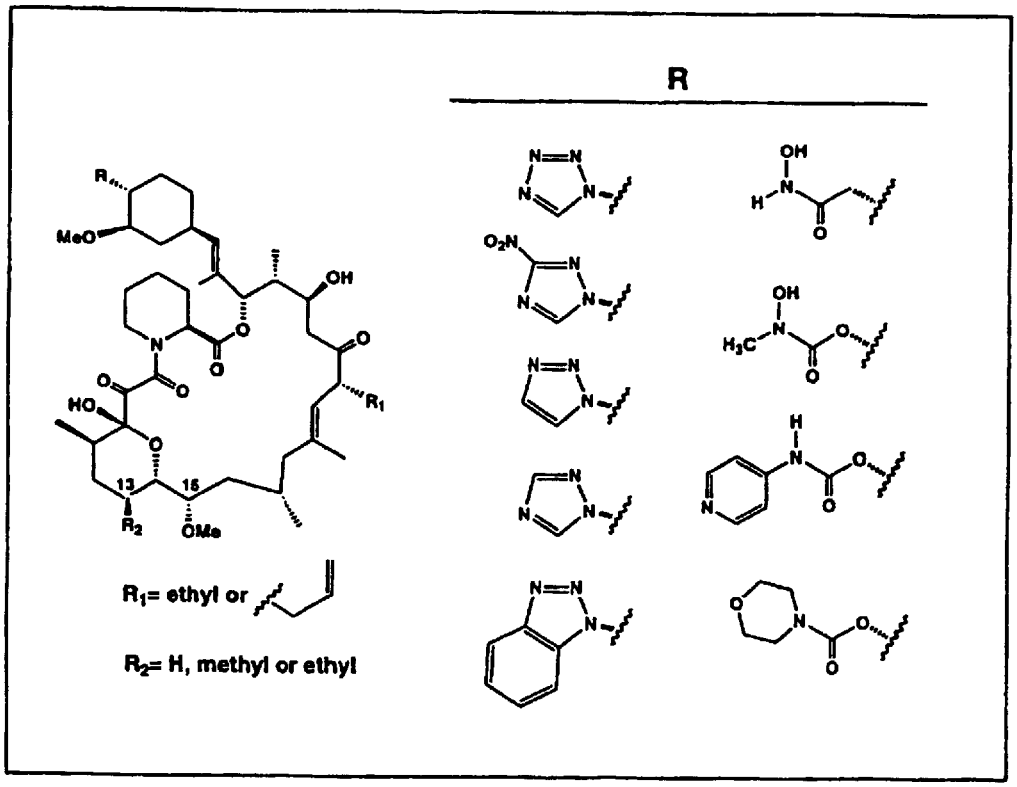
Figure 8:
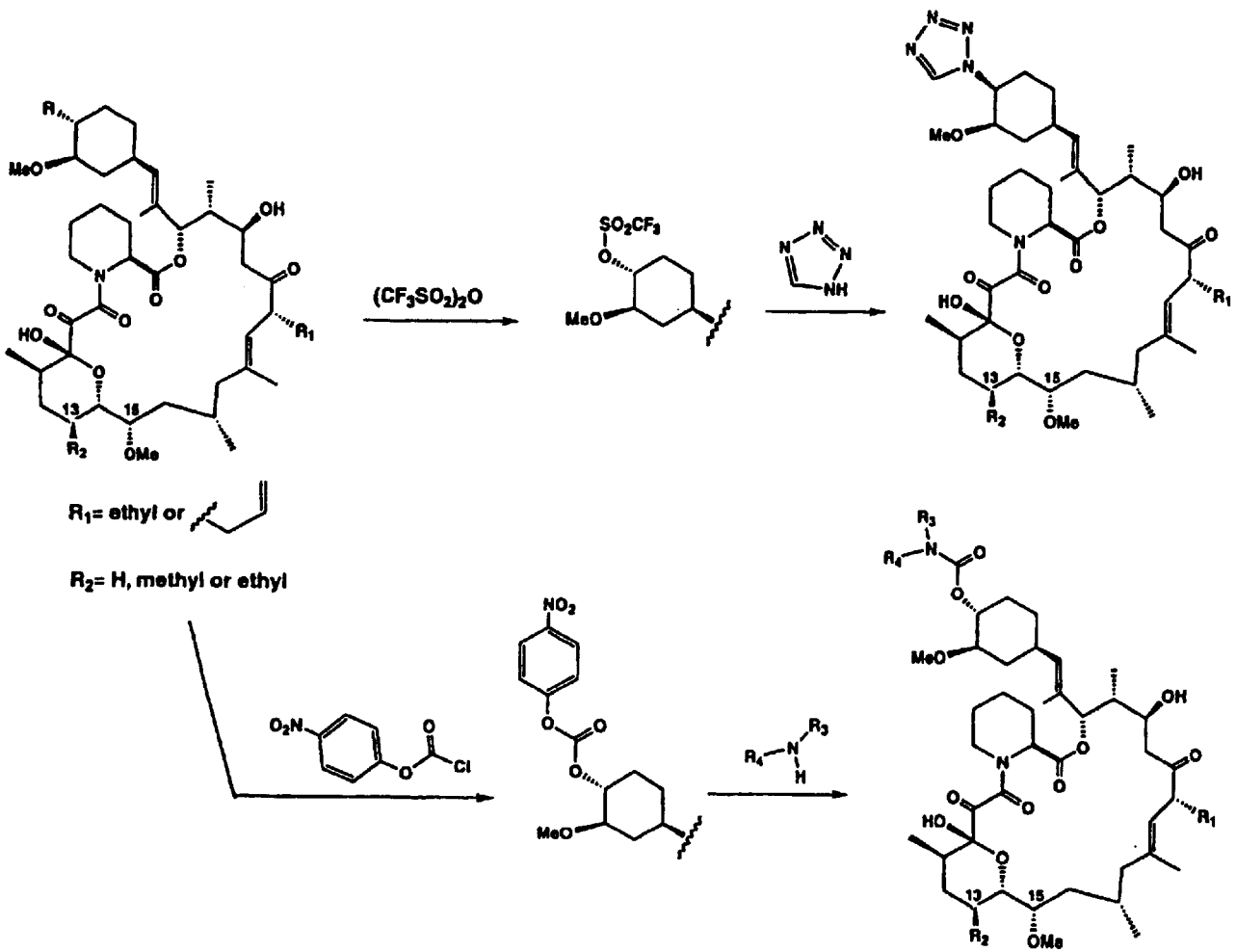

FIG. 8, in Parts A and B, shows certain compounds of the invention preferred for dermal application in Part A and a synthetic route for making those compounds in Part B.

DETAILED DESCRIPTION OF THE INVENTION

Given the valuable pharmaceutical properties of polyketides, there is a need for methods and reagents for producing large quantities of polyketides, as well as for producing related compounds not found in nature. The present invention provides such methods and reagents, with particular application to methods and reagents for producing the polyketides known as FK-520, also known as ascomycin or L-683,590 (see Holt et al., 1993, JACS 115:9925), and FK-506, also known as tacrolimus. Tacrolimus is a macrolide immunosuppressant used to prevent or treat rejection of transplanted heart, kidney, liver, lung, pancreas, and small bowel allografts. The drug is also useful for the prevention and treatment of graft-versus-host disease in patients receiving bone marrow transplants, and for the treatment of severe, refractory uveitis. There have been additional reports of the unapproved use of tacrolimus for other conditions, including alopecia universalis, autoimmune chronic active hepatitis, inflammatory bowel disease, multiple sclerosis, primary biliary cirrhosis, and scleroderma. The invention provides methods and reagents for making novel polyketides related in structure to FK-520 and FK-506. and structurally related polyketides such as rapamycin.

The FK-506 and rapamycin polyketides are potent immunosuppressants, with chemical structures shown below.

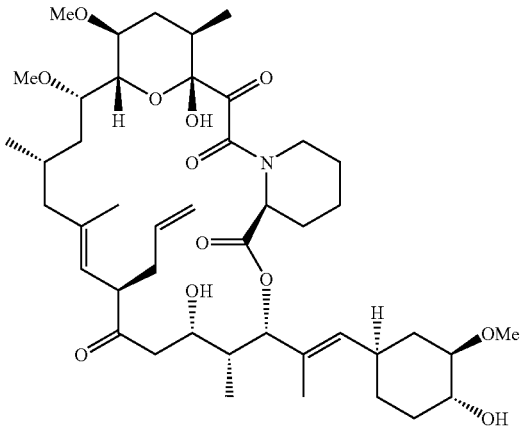

FK-506

-continued

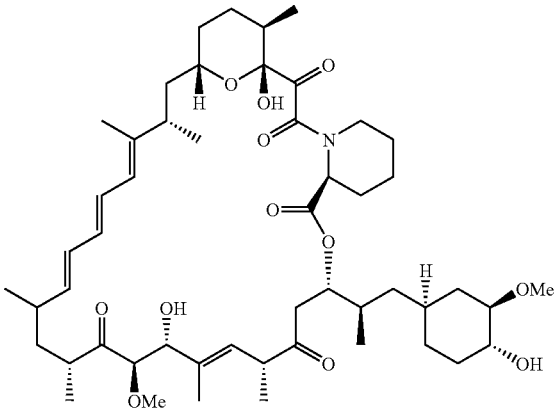

Rapamycin

FK-520 differs from FK-506 in that it lacks the allyl group at C-21 of FK-506, having instead an ethyl group at that position, and has similar activity to FK-506, albeit reduced immunosuppressive activity.

These compounds act through initial formation of an intermediate complex with protein "immunophilins" known as FKBPs (FK-506 binding proteins), including FKBP-12. Immunophilins are a class of cytosolic proteins that form complexes with molecules such as FK-506, FK-520, and rapamycin that in turn serve as ligands for other cellular targets involved in signal transduction. Binding of FK-506, FK-520, and rapamycin to FKBP occurs through the structurally similar segments of the polyketide molecules, known as the "FKBP-binding domain" (as generally but not precisely indicated by the stippled regions in the structures above). The FK-506-FKBP complex then binds calcineurin, while the rapamycin-FKBP complex binds to a protein known as RAFT-1. Binding of the FKBP-polyketide complex to these second proteins occurs through the dissimilar regions of the drugs known as the "effector" domains.

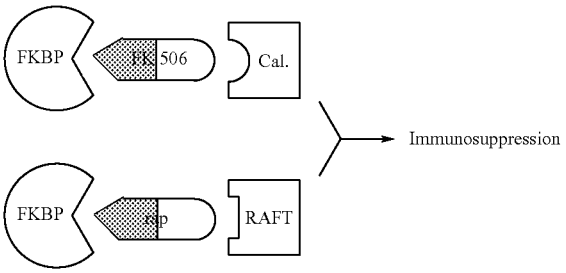

The three component FKBP-polyketide-effector complex is required for signal transduction and subsequent immunosuppressive activity of FK-506, FK-520, and rapamycin. Modifications in the effector domains of FK-506, FK-520, and rapamycin that destroy binding to the effector proteins (calcineurin or RAFT) lead to loss of immunosupressive activity, even through FKBP binding is unaffected. Further, such analogs antagonize the immunosuppressive effects of the parent polyketides, because they compete for FKBP. Such non-immunosuppressive analogs also show reduced toxicity (see Dumont et al., 1992, Journal of Experimental Medicine 176, 751–760), indicating that much of the toxicity of these drugs is not linked to FKBP binding.

In addition to immunosuppressive activity, FK-520, FK-506, and rapamycin have neurotrophic activity. In the central nervous system and in peripheral nerves, immunophilins are referred to as "neuroimmunophilins". The neuroimmunophilin FKBP is markedly enriched in the central nervous system and in peripheral nerves. Molecules that bind to the neuroimmunophilin FKBP, such as FK-506 and FK-520, have the remarkable effect of stimulating nerve growth. In vitro, they act as neurotrophins, i.e., they promote neurite outgrowth in NGF-treated PC12 cells and in sensory neuronal cultures, and in intact animals, they promote regrowth of damaged facial and sciatic nerves, and repair lesioned serotonin and dopamine neurons in the brain. See Gold et al. June 1999, J. Pharm. Exp. Ther. 289(3): 1202–1210; Lyons et al., 1994, Proc. National Academy of Science 91: 3191–3195; Gold et al., 1995, Journal of Neuroscience 15: 7509–7516; and Steiner et al., 1997, Proc. National Academy of Science 94: 2019–2024. Further, the restored central and peripheral neurons appear to be functional.

Compared to protein neurotrophic molecules (BNDF, NGF, etc.), the small-molecule neurotrophins such as FK-506, FK-520, and rapamycin have different, and often advantageous, properties. First, whereas protein neurotrophins are difficult to deliver to their intended site of action and may require intra-cranial injection, the small-molecule neurotrophins display excellent bioavailability; they are active when administered subcutaneously and orally. Second, whereas protein neurotrophins show quite specific effects, the small-molecule neurotrophins show rather broad effects. Finally, whereas protein neurotrophins often show effects on normal sensory nerves, the small-molecule neurotrophins do not induce aberrant sprouting of normal neuronal processes and seem to affect damaged nerves specifically. Neuroimmunophilin ligands have potential therapeutic utility in a variety of disorders involving nerve degeneration (e.g. multiple sclerosis, Parkinson's disease, Alzheimer's disease, stroke, traumatic spinal cord and brain injury, peripheral neuropathies).

Recent studies have shown that the immunosuppressive and neurite outgrowth activity of FK-506, FK-520, and rapamycin can be separated; the neuroregenerative activity in the absence of immunosuppressive activity is retained by agents which bind to FKBP but not to the effector proteins calcineurin or RAFT. See Steiner et al., 1997, Nature Medicine 3: 421–428.

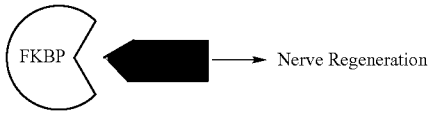

Available structure-activity data show that the important features for neurotrophic activity of rapamycin, FK-520, and FK-506 lie within the common, contiguous segments of the macrolide ring that bind to FKBP. This portion of the molecule is termed the "FKBP binding domain" (see VanDuyne et al., 1993, Journal of Molecular Biology 229: 105–124.). Nevertheless, the effector domains of the parent macrolides contribute to conformational rigidity of the binding domain and thus indirectly contribute to FKBP binding.

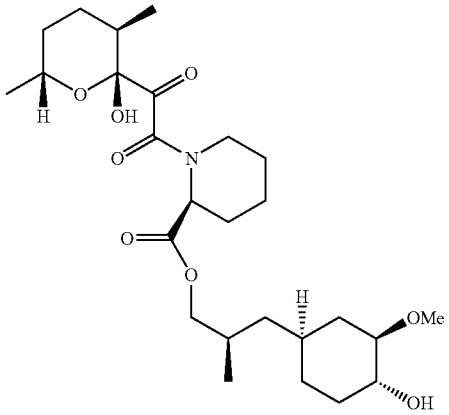

"FKBP binding domain"

There are a number of other reported analogs of FK-506, FK-520, and rapamycin that bind to FKBP but not the effector protein calcineurin or RAFT. These analogs show effects on nerve regeneration without immunosuppressive effects.

Naturally occur-ring FK-520 and FK-506 analogs include the antascomycins, which are FK-506-like macrolides that lack the functional groups of FK-506 that bind to calcineurin (see Fehr et al., 1996, The Journal of Antibiotics 49: 230–233). These molecules bind FKBP as effectively as does FK-506; they antagonize the effects of both FK-506 and rapamycin, yet lack immunosuppressive activity.

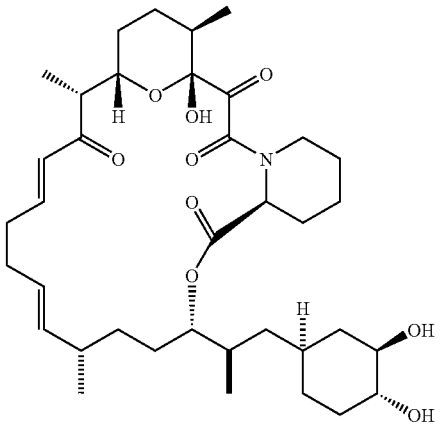

Antascomycin A

Other analogs can be produced by chemically modifying FK-506, FK-520, or rapamycin. One approach to obtaining neuroimmunophilin ligands is to destroy the effector binding region of FK-506, FK-520, or rapamycin by chemical modification. While the chemical modifications permitted on the parent compounds are quite limited, some useful chemically modified analogs exist. The FK-520 analog L-685,818 ($ED_{50}$=0.7 nM for FKBP binding; see Dumont et al., 1992), and the rapamycin analog WAY-124,466 ($IC_{50}$=12.5 nM; see Ocain et al., 1993, Biochemistry Biophysical Research Communications 192: 1340–134693) are about as effective as FK-506, FK-520, and rapamycin at promoting neurite outgrowth in sensory neurons (see Steiner et al., 1997).

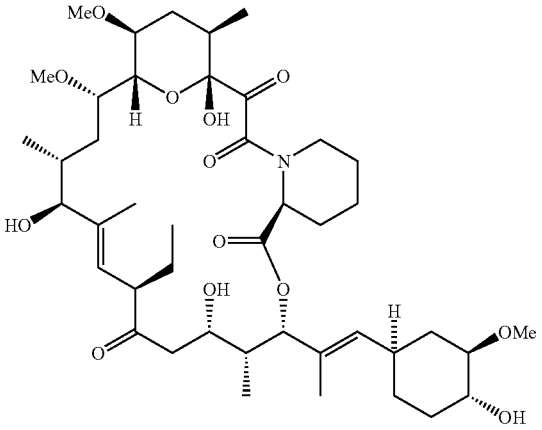

L-685.818

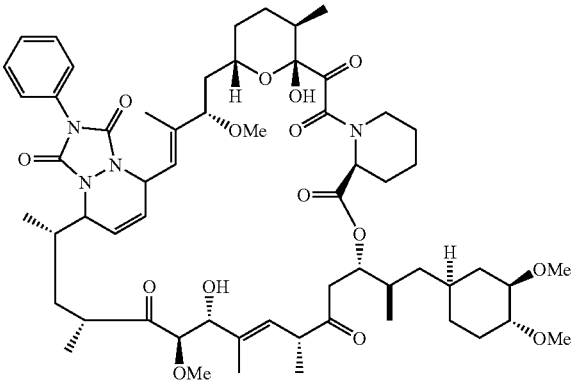

WAY-124,466

One of the few positions of rapamycin that is readily amenable to chemical modification is the allylic 16-methoxy group; this reactive group is readily exchanged by acid-catalyzed nucleophilic substitution. Replacement of the 16-methoxy group of rapamycin with a variety of bulky groups has produced analogs showing selective loss of immunosuppressive activity while retaining FKBP-binding (see Luengo et al., 1995, Chemistry & Biology 2: 471–481). One of the best compounds, 1, below, shows complete loss of activity in the splenocyte proliferation assay with only a 10-fold reduction in binding to FKBP.

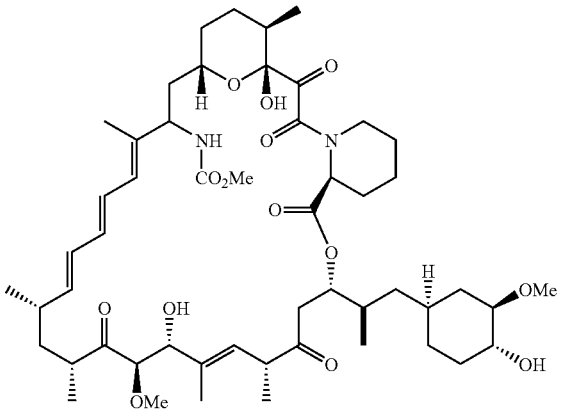

There are also synthetic analogs of FKBP binding domains. These compounds reflect an approach to obtaining neuroimmunophilin ligands based on "rationally designed" molecules that retain the FKBP-binding region in an appropriate conformation for binding to FKBP, but do not possess the effector binding regions. In one example, the ends of the FKBP binding domain were tethered by hydrocarbon chains (see Holt et al., 1993, Journal of the American Chemical Society 115: 9925–9938); the best analog, 2, below, binds to FKBP about as well as FK-506. In a similar approach, the ends of the FKBP binding domain were tethered by a tripeptide to give analog 3, below, which binds to FKBP about 20-fold poorer then FK-506. These compounds are anticipated to have neuroinimunophilin binding activity.

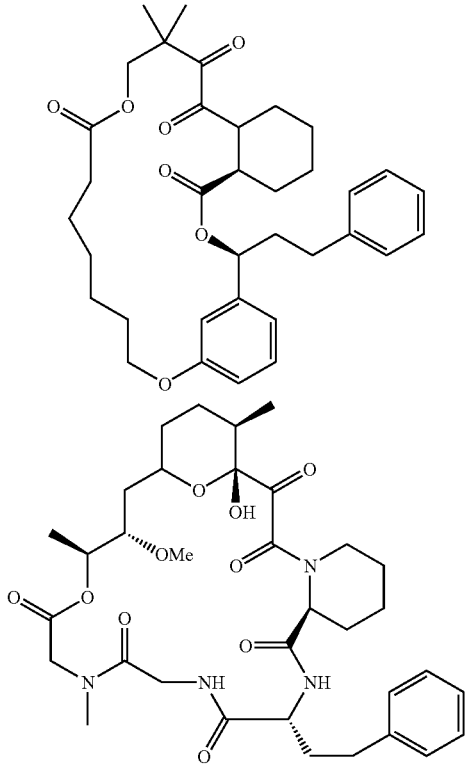

In a primate MPTP model of Parkinson's disease, administration of FKBP ligand GP1-1046 caused brain cells to regenerate and behavioral measures to improve. MPTP is a neurotoxin, which, when administered to animals, selectively damages nigral-striatal dopamine neurons in the brain, mimicking the damage caused by Parkinson's disease. Whereas, before treatment, animals were unable to use affected limbs, the FKBP ligand restored the ability of animals to feed themselves and gave improvements in measures of locomotor activity, neurological outcome, and fine motor control. There were also corresponding increases in regrowth of damaged nerve terminals. These results demonstrate the utility of FKBP ligands for treatment of diseases of the CNS.

From the above description, two general approaches towards the design of non-immunosuppressant, neuroimmunophilin ligands can be seen. The first involves the construction of constrained cyclic analogs of FK-506 in which the FKBP binding domain is fixed in a conformation optimal for binding to FKBP. The advantages of this approach are that the conformation of the analogs can be accurately modeled and predicted by computational methods, and the analogs closely resemble parent molecules that have proven pharmacological properties. A disadvantage is that the difficult chemistry limits the numbers and types of compounds that can be prepared. The second approach involves the trial and error construction of acyclic analogs of the FKBP binding domain by conventional medicinal chemistry. The advantages to this approach are that the chemistry is suitable for production of the numerous compounds needed for such interactive chemistry-bioassay approaches. The disadvantages are that the molecular types of compounds that have emerged have no known history of appropriate pharmacological properties, have rather labile ester functional groups, and are too conformationally mobile to allow accurate prediction of conformational properties.

The present invention provides useful methods and reagents related to the first approach, but with significant advantages. The invention provides recombinant PKS genes that produce a wide variety of polyketides that cannot otherwise be readily synthesized by chemical methodology alone. Moreover, the present invention provides polyketides that have either or both of the desired immunosuppressive and neurotrophic activities, some of which are produced only by fermentation and others of which are produced by fermentation and chemical modification. Thus, in one aspect, the invention provides compounds that optimally bind to FKBP but do not bind to the effector proteins. The methods and reagents of the invention can be used to prepare numerous constrained cyclic analogs of FK-520 in which the FKBP binding domain is fixed in a conformation optimal for binding to FKBP. Such compounds will show neuroimmunophilin binding (neurotrophic) but not immunosuppressive effects. The invention also shows direct manipulation of FK-520 and related chemical structures via genetic engineering of the enzymes involved in the biosynthesis of FK-520 (as well as related compounds, such as FK-506 and rapamycin); similar chemical modifications are simply not possible because of the complexity of the structures. The invention can also be used to introduce "chemical handles" into normally inert positions that permit subsequent chemical modifications.

Several general approaches to achieve the development of novel neuroimmunophilin ligands are facilitated by the methods and reagents of the present invention. One approach is to make "point mutations" of the functional groups of the parent FK-520 structure that bind to the effector molecules to eliminate their binding potential. These types of structural modifications are difficult to perform by chemical modifications, but can be readily accomplished with the methods and reagents of the invention.

A second, more extensive approach facilitated by the present invention is to utilize molecular modeling to predict optimal structures ab initio that bind to FKBP but not effector molecules. Using the available X-ray crystal structure of FK-520 (or FK-506) bound to FKBP, molecular modeling can be used to predict polyketides that should optimally bind to FKBP but not calcineurin. Various macrolide structures can be generated by linking the ends of the FKBP-binding domain with "all possible" polyketide chains of variable length and substitution patterns that can be prepared by genetic manipulation of the FK-520 or FK-506 PKS gene cluster in accordance with the methods of the invention. The ground state conformations of the virtual library can be determined, and compounds that possess binding domains most likely to bind well to FKBP can be prepared and tested.

Once a compound is identified in accordance with the above approaches, the invention can be used to generate a focused library of analogs around the lead candidate, to "fine tune" the compound for optimal properties. Finally, the genetic engineering methods of the invention can be directed towards producing "chemical handles" that enable medicinal chemists to modify positions of the molecule previously inert to chemical modification. This opens the path to previously prohibited chemical optimization of lead compounds by time-proven approaches.

Moreover, the present invention provides polyketide compounds and the recombinant genes for the PKS enzymes that produce the compounds that have significant advantages over FK-506 and FK-520 and their analogs. The metabolism and pharmacokinetics of tacrolimus has been extensively studied, and FK-520 is believed to be similar in these respects. Absorption of tacrolimus is rapid, variable, and incomplete from the gastrointestinal tract (Harrison's Principles of Internal Medicine, 14th edition, 1998, McGraw Hill, 14, 20, 21, 64–67). The mean bioavailability of the oral dosage form is 27%, (range 5 to 65%). The volume of distribution (VolD) based on plasma is 5 to 65 L per kg of body weight (L/kg), and is much higher than the VolD based on whole blood concentrations, the difference reflecting the binding of tacrolimus to red blood cells. Whole blood concentrations may be 12 to 67 times the plasma concentrations. Protein binding is high (75 to 99%), primarily to albumin and alphal-acid glycoprotein. The half-life for distribution is 0.9 hour; elimination is biphasic and variable: terminal-l 1.3 hr (range, 3.5 to 40.5 hours). The time to peak concentration is 0.5 to 4 hours after oral administration.

Tacrolimus is metabolized primarily by cytochrome P450 3A enzymes in the liver and small intestine. The drug is extensively metabolized with less than 1% excreted unchanged in urine. Because hepatic dysfunction decreases clearance of tacrolimus, doses have to be reduced substantially in primary graft non-function, especially in children. In addition, drugs that induce the cytochrome P450 3A enzymes reduce tracrolimus levels, while drugs that inhibit these P450s increase tacrolimus levels. Tacrolimus bioavailability doubles with co-administration of ketoconazole, a drug that inhibits P450 3A. See, Vincent et al., 1992, In vitro metabolism of FK-506 in rat, rabbit, and human liver microsomes: Identification of a major metabolite and of cytochrome P450 3A as the major enzymes responsible for its metabolism, Arch. Biochem. Biophys. 294: 454–460; Iwasaki et al., 1993, Isolation, identification, and biological activities of oxidative metabolites of FK-506, a potent immunosuppressive macrolide lactone, Drug Metabolism & Disposition 21: 971–977; Shiraga et al., 1994, Metabolism of FK-506, a potent immunosuppressive agent, by cytochrome P450 3A enzymes in rat, dog, and human liver microsomes, Biochem. Pharmacol. 47: 727–735; and Iwasaki et al., 1995, Further metabolism of FK-506 (Tacrolimus); Identification and biological activities of the metabolites oxidized at multiple sites of FK-506, Drug Metabolism & Disposition 23: 28–34. The cytochrome P450 3A subfamily of isozymes has been implicated as important in this degradative process.

Structures of the eight isolated metabolites formed by liver microsomes are shown in FIG. 6. Four metabolites of FK-506 involve demethylation of the oxygens on carbons 13, 15, and 31, and hydroxylation of carbon 12. The 13-demethylated (hydroxy) compounds undergo cyclizations of the 13-hydroxy at C-10 to give MI, MVI and MVII, and the 12-hydroxy metabolite at C-10 to give 1. Another four metabolites formed by oxidation of the four metabolites mentioned above were isolated by liver microsomes from dexamethasone treated rats. Three of these are metabolites double demethylated at the methoxy groups on carbons 15 and 31 (M-V), 13 and 31 (M-VI), and 13 and 15 (M-VII). The fourth, M-VIII, was the metabolite produced after demethylation of the 31-methoxy group, followed by formation of a fused ring system by further oxidation. Among the eight metabolites, M-II has immunosuppressive activity comparable to that of FK-506, whereas the other metabolites exhibit weak or negligible activities. Importantly, the major metabolite of human, dog, and rat liver microsomes is the 13-demethylated and cyclized FK-506 (M-I).

Thus, the major metabolism of FK-506 proceeds via 13-demethylation followed by cyclization to the inactive M-I, this representing about 90% of the metabolic products after a 10 minute incubation with liver microsomes. Analogs of tacrolimus that do not possess a C-13 methoxy group would not be susceptible to the first and most important biotransformation in the destructive metabolism of tacrolimus (i.e. cyclization of 13-hydroxy to C-10). Thus, a 13-desmethoxy analog of FK-506 should have a longer half-life in the body than does FK-506. The C-13 methoxy group is believed not to be required for binding to FKBP or calcineurin. The C-13 methoxy is not present on the identical position of rapamycin, which binds to FKBP with equipotent affinity as tacrolimus. Also, analysis of the 3-dimensional structure of the FKBP-tacrolimus-calcineurin complex shows that the C-13 methoxy has no interaction with FKBP and only a minor interaction with calcineurin. The present invention provides C-13-desmethoxy analogs of FK-506 and FK-520, as well as the recombinant genes that encode the PKS enzymes that catalyze their synthesis and host cells that produce the compounds.

These compounds exhibit, relative to their naturally occurring counterparts, prolonged immunosuppressive action in vivo, thereby allowing a lower dosage and/or reduced frequency of administration. Dosing is more predictable, because the variability in FK-506 dosage is largely due to variation of metabolism rate. FK-506 levels in blood can vary widely depending on interactions with drugs that induce or inhibit cytochrome P450 3A (summarized in USP Drug Information for the Health Care Professional). Of particular importance are the numerous drugs that inhibit or compete for CYP 3A, because they increase FK-506 blood levels and lead to toxicity (Prograf package insert, Fujisawa□US, Rev 4/97, Rec 6/97). Also important are the drugs that induce P450 3A (e.g. Dexamethasone), because they decrease FK-506 blood levels and reduce efficacy. Because the major site of CYP 3A action on FK-506 is removed in the analogs provided by the present invention, those analogs are not as susceptible to drug interactions as the naturally occurring compounds.

Hyperglycemia, nephrotoxicity, and neurotoxicity are the most significant adverse effects resulting from the use of FK-506 and are believed to be similar for FK-520. Because these effects appear to occur primarily by the same mechanism as the immunosuppressive action (i.e. FKBP-calcineurin interaction), the intrinsic toxicity of the desmethoxy analogs may be similar to FK-506. However, toxicity of FK-506 is dose related and correlates with high blood levels of the drug (Prograf package insert, Fujisawa□US, Rev 4/97, Rec 6/97). Because the levels of the compounds provided by the present invention should be more controllable, the incidence of toxicity should be significantly decreased with the 13-desmethoxy analogs. Some reports show that certain FK-506 metabolites are more toxic than FK-506 itself, and this provides an additional reason to expect that a CYP 3A resistant analog can have lower toxicity and a higher therapeutic index.

Thus, the present invention provides novel compounds related in structure to FK-506 and FK-520 but with improved properties. The invention also provides methods for making these compounds by fermentation of recombinant host cells, as well as the recombinant host cells, the recombinant vectors in those host cells, and the recombinant proteins encoded by those vectors. The present invention also provides other valuable materials useful in the construction of these recombinant vectors that have many other important applications as well. In particular, the present invention provides the FK-520 PKS genes, as well as certain genes involved in the biosynthesis of FK-520 in recombinant form.

FK-520 is produced at relatively low levels in the naturally occurring cells, Streptomyces hygroscopicus var. ascomyceticus, in which it was first identified. Thus, another benefit provided by the recombinant FK-520 PKS and related genes of the present invention is the ability to produce FK-520 in greater quantities in the recombinant host cells provided by the invention. The invention also provides methods for making novel FK-520 analogs, in addition to the desmethoxy analogs described above, and derivatives in recombinant host cells of any origin.

The biosynthesis of FK-520 involves the action of several enzymes. The FK-520 PKS enzyme, which is composed of the fkbA, fkbB, fkbC, and fkbP gene products, synthesizes the core structure of the molecule. There is also a hydroxylation at C-9 mediated by the P450 hydroxylase that is the fkbD gene product and that is oxidized by the fkbO gene product to result in the formation of a keto group at C-9. There is also a methylation at C-31 that is mediated by an O-methyltransferase that is the fkbM gene product. There are also methylations at the C-13 and C-15 positions by a methyltransferase believed to be encoded by the fkbG gene; this methyltransferase may act on the hydroxymalonyl CoA substrates prior to binding of the substrate to the AT domains of the PKS during polyketide synthesis. The present invention provides the genes encoding these enzymes in recombinant form. The invention also provides the genes encoding the enzymes involved in ethylmalonyl CoA and 2-hydroxymalonyl CoA biosynthesis in recombinant form. Moreover, the invention provides Streptomyces hygroscopicus var. ascomyceticus recombinant host cells lacking one or more of these genes that are useful in the production of useful compounds.

The cells are useful in production in a variety of ways. First, certain cells make a useful FK-520-related compound merely as a result of inactivation of one or more of the FK-520 biosynthesis genes. Thus, by inactivating the C-31 O-methyltransferase gene in Streptomyces hygroscopicus var. ascomyceticus, one creates a host cell that makes a desmethyl (at C-31) derivative of FK-520. Second, other cells of the invention are unable to make FK-520 or FK-520 related compounds due to an inactivation of one or more of the PKS genes. These cells are useful in the production of other polyketides produced by PKS enzymes that are encoded on recombinant expression vectors and introduced into the host cell.

Moreover, if only one PKS gene is inactivated, the ability to produce FK-520 or an FK-520 derivative compound is restored by introduction of a recombinant expression vector that contains the functional gene in a modified or unmodified form. The introduced gene produces a gene product that, together with the other endogenous and functional gene products, produces the desired compound. This methodology enables one to produce FK-520 derivative compounds without requiring that all of the genes for the PKS enzyme be present on one or more expression vectors. Additional applications and benefits of such cells and methodology will be readily apparent to those of skill in the art after consideration of how the recombinant genes were isolated and employed in the construction of the compounds of the invention.

The FK-520 biosynthetic genes were isolated by the following procedure. Genomic DNA was isolated from Streptomyces hygroscopicus var. ascomyceticus (ATCC 14891) using the lysozyme/proteinase K protocol described in Genetic Manipulation of Streptomyces—A Laboratory Manual (Hopwood et al., 1986). The average size of the DNA was estimated to be between 80–120 kb by electrophoresis on 0.3% agarose gels. A library was constructed in the SuperCos™ vector according to the manufacturer's instructions and with the reagents provided in the commercially available kit (Stratagene). Briefly, 100 μg of genomic DNA was partially digested with 4 units of Sau3A I for 20 min. in a reaction volume of 1 mL, and the fragments were dephosphorylated and ligated to SuperCos vector arms. The ligated DNA was packaged and used to infect log-stage XL1-BlueMR cells. A library of about 10,000 independent cosmid clones was obtained.

Based on recently published sequence from the FK-506 cluster (Motamedi and Shafree, 1998, Eur. J Biochem. 256: 528), a probe for the fkbO gene was isolated from ATCC 14891 using PCR with degenerate primers. With this probe, a cosmid designated pKOS034-124 was isolated from the library. With probes made from the ends of cosmid pKOS034-124, an additional cosmid designated pKOS034-120 was isolated. These cosmids (pKOS034-124 and pKOS034-120) were shown to contain DNA inserts that overlap with one another. Initial sequence data from these two cosmids generated sequences similar to sequences from the FK-506 and rapamycin clusters, indicating that the inserts were from the FK-520 PKS gene cluster. Two EcoRI fragments were subcloned from cosmids pKOS034-124 and pKOS034-120. These subclones were used to prepare shotgun libraries by partial digestion with Sau3AI, gel purification of fragments between 1.5 kb and 3 kb in size, and ligation into the pLitmus28 vector (New England Biolabs). These libraries were sequenced using dye terminators on a Beckmann CEQ2000 capillary electrophoresis sequencer, according to the manufacturer's protocols.

Figure 1:
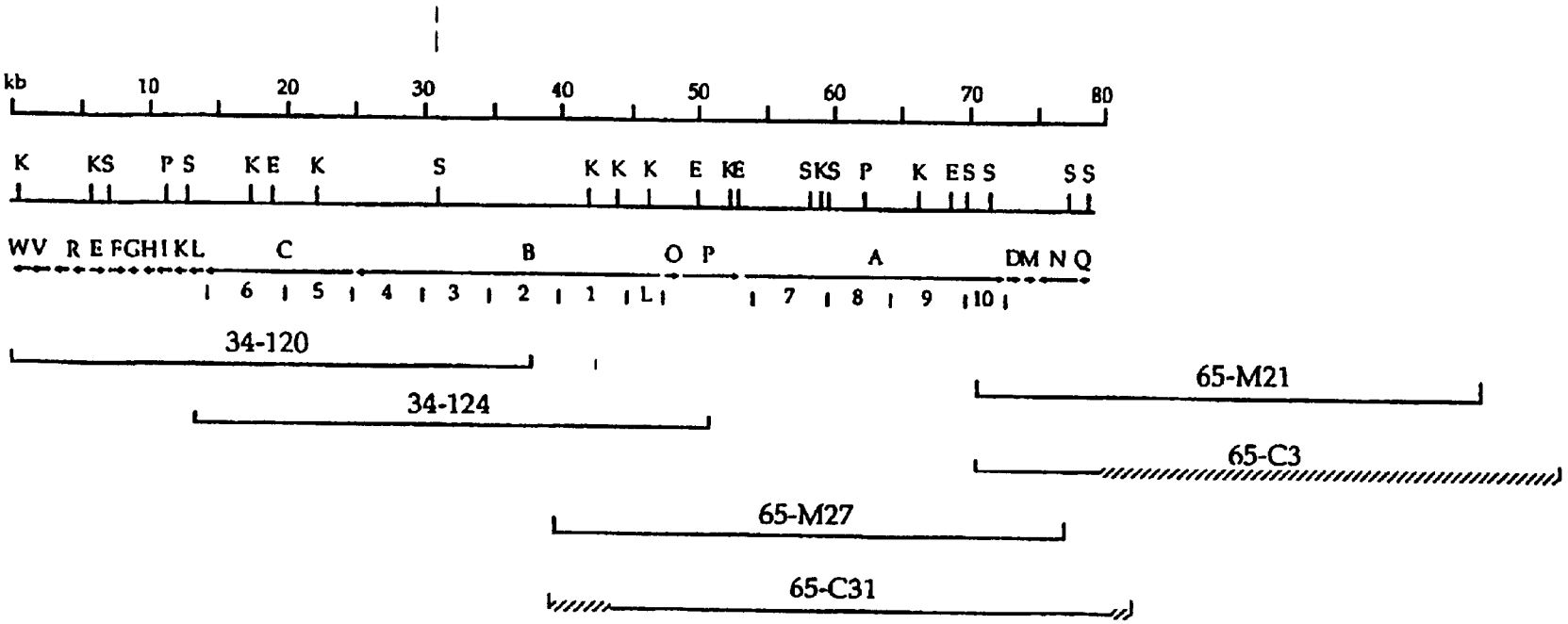
FIG. 1 shows a diagram of the FK-520 biosynthetic gene cluster. The top line provides a scale in kilobase pairs (kb).

To obtain cosmids containing sequence on the left and right sides of the sequenced region described above, a new cosmid library of ATCC 14891 DNA was prepared essentially as described above. This new library was screened with a new fkbM probe isolated using DNA from ATCC 14891. A probe representing the fkbP gene at the end of cosmid pKOS034-124 was also used. Several additional cosmids to the right of the previously sequenced region were identified. Cosmids pKOS065-C31 and pKOS065-C3 were identified and then mapped with restriction enzymes. Initial sequences from these cosmids were consistent with the expected organization of the cluster in this region. More extensive sequencing showed that both cosmids contained in addition to the desired sequences, other sequences not contiguous to the desired sequences on the host cell chromosomal DNA. Probing of additional cosmid libraries identified two additional cosmids, pKOS065-M27 and pKOS065-M21, that contained the desired sequences in a contiguous segment of chromosomal DNA. Cosmids pKOS034-124, pKOS034-120, pKOS065-M27, and pKOS065-M21 have been deposited with the American Type Culture Collection, Manassas, Va., USA. The complete nucleotide sequence of the coding sequences of the genes that encode the proteins of the FK-520 PKS are shown below but can also be determined from the cosmids of the invention deposited with the ATCC using standard methodology:

Referring to FIGS. 1 and 3, the FK-520 PKS gene cluster is composed of four open reading frames designated fkbB, fkbC, fkbA, and fkbP. The fkbB open reading frame encodes the loading module and the first four extender modules of the PKS. The fkbC open reading frame encodes extender modules five and six of the PKS. The fkbA open reading frame encodes extender modules seven, eight, nine, and ten of the PKS. The fkbP open reading frame encodes the NRPS of the PKS. Each of these genes can be isolated from the cosmids of the invention described above. The DNA sequences of these genes are provided below preceded by the following table identifying the start and stop codons of the open reading frames of each gene and the modules and domains contained therein.

| Nucleotides | Gene or Domain |
|---|---|
| complement (412–1836) | fkbW |
| complement (2020–3579) | fkbV |
| complement (3969–4496) | fkbR2 |
| complement (4595–5488) | fkbR1 |
| 5601–6818 | fkbE |
| 6808–8052 | fkbF |
| 8156–8824 | fkbG |
| complement (9122–9883) | fkbH |
| complement (9894–10994) | ftbI |
| complement (10987–11247) | fkbJ |
| complement (11244–12092) | fkbK |
| complement (12113–13150) | fkbL |
| complement (13212–23988) | fkbC |
| complement (23992–46573) | fkbB |

-continued

| Nucleotides | Gene or Domain |
|---|---|
| 46754–47788 | fkbO |
| 47785–52272 | fkbP |
| 52275–71465 | fkbA |
| 71462–72628 | fkbD |
| 72625–73407 | fkbM |
| complement (73460–76202) | fkbN |
| complement (76336–77080) | fkbQ |
| complement (77076–77535) | fkbS |
| complement (44974–46573) | CoA ligase of loading domain |
| complement (43777–44629) | ER of loading domain |
| complement (43144–43660) | ACP of loading domain |
| complement (41842–43093) | KS of extender module 1 (KS1) |
| complement (40609–41842) | AT1 |
| complement (39442–40609) | DH1 |
| complement (38677–39307) | KR1 |
| complement (38371–38581) | ACP1 |
| complement (37145–38296) | KS2 |
| complement (35749–37144) | AT2 |
| complement (34606–35749) | DH2 (inactive) |
| complement (33823–34480) | KR2 |
| complement (33505–33715) | ACP2 |
| complement (32185–33439) | KS3 |
| complement (31018–32185) | AT3 |
| complement (29869–31018) | DH3 (inactive) |
| complement (29092–29740) | KR3 |
| complement (28750–28960) | ACP3 |
| complement (27430–28684) | KS4 |
| complement (26146–27430) | AT4 |
| complement (24997–26146) | DH4 (inactive) |
| complement (24163–24373) | ACP4 |
| complement (22653–23892) | KS5 |
| complement (21420–22653) | AT5 |
| complement (20241–21420) | DH5 |
| complement (19464–20097) | KR5 |
| complement (19116–19326) | ACP5 |
| complement (17820–19053) | KS6 |
| complement (16587–17820) | AT6 |
| complement (15438–16587) | DH6 |
| complement (14517–15294) | ER6 |
| complement (13761–14394) | KR6 |
| complement (13452–13662) | ACP6 |
| 52362–53576 | KS7 |
| 53577–54716 | AT7 |
| 54717–55871 | DH7 |
| 56019–56819 | ER7 |
| 56943–57575 | KR7 |
| 57710–57920 | ACP7 |
| 57990–59243 | KS8 |
| 59244–60398 | AT8 |
| 60399–61412 | DH8 (inactive) |
| 61548–62180 | KR8 |
| 62328–62537 | ACP8 |
| 62598–63854 | KS9 |
| 63855–65084 | AT9 |
| 65085–66254 | DH9 |
| 66399–67175 | ER9 |
| 67299–67931 | KR9 |
| 68094–68303 | ACP9 |
| 68397–69653 | KS10 |
| 69654–70985 | AT10 |
| 71064–71273 | ACP10 |

```
   1 GATCTCAGGC ATGAAGTCCT CCAGGCGAGG CGCCGAGGTG GTGAACACCT CGCCGCTGCT
  61 TGTACGGACC ACTTCAGTCA GCGGCGATTG CGGAACCAAG TCATCCGGAA TAAAGGGCGG
 121 TTACAAGATC CTCACATTGC GCGACCGCCA GCATACGCTG AGTTGCCTCA GAGGCAAACC
 181 GAAAGGGCGC GGGCGGTCCG CACCAGGGCG GAGTACGCGA CGAGAGTGGC GCACCCGCGC
 241 ACCGTCACCT CTCTCCCCCG CCGGCGGGAT GCCCGGCGTG ACACGGTTGG GCTCTCCTCG
 301 ACGCTGAACA CCCGCGCGGT GTGGCGTCGG GGACACCGCC TGGCATCGGC CGGGTGACGG
 361 TACGGGGAGG GCGTACGGCG GCCGTGGCTC GTGCTCACGG CCGCCGGGCG GTCATCCGTC
 421 GAGACGGCAC TCGGCGAGCA GGGACGCCTG GTCGGCACCT GCGGGCCGGA CGACCGTGTG
 481 GTTCGCGGGC GGGCGGTGGC CGGTGGTGAG CCAGCTCTCC AGGGCGGTGA AGGCTGAGCG
 541 GTGACACGGC AGCAAAGGCC GGAGTCGGTC GGGGAAGGTG TCGACGAGGG CGTCGGTGTG
 601 CGTGCCGTCC TCGATGCGGT AGTAGCGGTA CCGGCCGCCA GGCCGCTGCC GGACATACGC
 661 GCGTACACGT CGGAGCCCGG GCGGCAGGCA GCAGCACGTC GAGAGTGCCT GGATGGTGAT
 721 CAGCGGCTTG CCGATACGAC CGGTCAACGC GATGCGTTCC ACGGCCGCGT GGACGCCGGA
 781 GGAGCGGGTG GCGTAGTCGT AGTCGGCATC GCAGCCCGGG ACCGTCCCCG GGGCGCAATA
 841 CGGTGTGCCG GCTTCCTTCT CCCCATCGAA GCCGGGGTCG AACTCCTCGC GGTAGACGCG
 901 CTGCGTCAGA TCCCAGTAGA CCTCGTGGTG GTACGGCCAC AAGAACTCGG AGTCGGCCGG
 961 GAACCCGGCG CGGAGCAGCG CCTCGCGCGC CTGGCCGGCT GCGGGGCCGC CTGCCGCGTA
1021 GGTGGGGTAG TCGCGCAGGG CGGCCGGCAG GAAGGTGAAG AGGTTGGGAC CCTCCGCGCG
1081 CCACAGGGTG CCTTCCCAGT CGACTCCTCC GTCGTACAGC TCGGGATGGT TCTCCAGCTG
1141 CCAGCGCACG AGGTAGCCGC CGTTGGACAT CCCGGTGACC AGGGTGCGCT CGAGCGGCCG
1201 GTGGTAGCGC TGGGCGACCG ACGCGCGGGC GGCCCGGGTC AGCTGGGTGA GGCGGGTGTT
1261 CCACTCGGCG ACGGCGTCGC CCGGCCGGGA GCCATCACGG TAGAACGCGG GGCCGGTGTT
1321 GCCCTTGTCG GTGGCGGCGT AGGCGTAACC GCGGGCGAGC ACCCAGTCGG CGATGGCCCG
1381 GTCGTTGGCG TACTGCTCGC CGTTACCGGG GGTGCCGGCC ACGACCAGGC CACCGTTCCA
1441 GCGGTCGGGC AGCCGGATGA CGAACTGGGC GTCGTGGTTC CACCCGTGGT TGGTGTTGGT
1501 GGTGGAGGTG TCGGGGAAGT AGCCGTCGAT CTGGATCCCG GGCACTCCGG TGGGAGTGGC
1561 CAGGTTCTTG GGCGTCAGCC CTGCCCAGTC CGCCGGGTCG GTGTGGCCGG TGGCCGCCGT
1621 TCCCGCCGTG GTCAGCTCGT CCAGGCAGTC GGCCTGCTGA CGTGCGGCCG CCGGGACACG
1681 CAGCTGGGAC AGACGGGCGC AGTGACCGTC CGGGGCATCG GGAGCAGGCC GGGCCGTGGC
1741 CGGTGAGGGG AGCAGGACGG CGACTGCGGC CAGGGTGAGA GCGCCGAGGC CGGTGCGTCT
1801 TCTCGGGGCC CGTCCGACAC CGAGGGGCAG AACCATGGAG AGCCTCCAGA CGTGCGGATG
1861 GATGACGGAC TGGAGGCTAG GTCGCGCACG GTGGAGACGA ACATGGGTGC GCCCGCCATG
1921 ACTGAGGCCC CTCAGAGGTG GGCCGCCGCC ATGACGGGCG CGGGACCGCG GGCGCTCCGG
1981 GGCGGTGCCC GCGGCCGCCA CCGGTTCCGG GTCCCCGGGT CAGGGACAGG TGTCGTTCGC
2041 GACGGTGAAG TAGCCGGTCG GCGACTCTTT CAAGGTGGTC GTGACGAAGG TGTTGTACAG
2101 GCCCATGTTC TGGCCGGAGC CCTTGGCGTA GGTGTAACCG GCGCTCGTCG TGGCGCGGCC
2161 CGCCTGGACG TGAGCGTAGT TGCCGGCGGT CCAGCAGACG GCCGTGGCAC CGGTCGTCTG
2221 CCCGGTGACC GCGCCCGAGA GCGGTCCGGC CTTGCCGTCC GCGTCCCGGG CGGCGACCGC
2281 TGAGGTGTGC GATGTGCCCG CCCTCAGGCC GGTGTCCGTG TACGACGTCG TGGCGGACGT
2341 GGTGATCTGG GCACCGTCGC GGTGGACGGC GTAGTCGGTG GCGCCGTCGA CGGGTTTCCA
```

-continued

2401 GGTCAGGCTG ATGGTGGTGT CGGTGGCGCC GGTGGCGGCC AGGCCGGACG GAGCGGGCAG

2461 CGAACCGGGG TCGGAGGCGG ATCCGCTCAG GCCGAAGAAC TGCGTGATCC AGTAGCTGGA

2521 ACAGATCGAG TCCAGGAAGT AGGCGGCGCC GGTGCTGCCG CACTGCTGTG CTCCGGTGCC

2581 GGGATCGACC GGGGTGCCGT GCCCGATGCC CGGCACCCGG TTCACCTCCA CGGCCACCGA

2641 TCCGTCCGCG GCCAGGTACT CCTCGTGCCG GGTGGAGTTC GGGCCGATCA CCGAGGTACG

2701 GTCCGGCGTC TGGGACACGC CGTGCACAGC GGTCCACTGG TCGCGCAACT CGTCGGCGTT

2761 GCGCGCCGCG ACGGTGGTGT CCTTGTCGCC GTGCCAGATG GCCACGCGCG GCCACGGGCC

2821 CGACCACGAG GGGTAGCCGT CACGGACCCG CCGCGCCCAC TGGTCCGCGG TCAGGTCGGT

2881 CCCGGGGTTC ATGCACAGGT ACGCGCTGCT GACGTCGGTG GCACAGCCGA AGGGCAGGCC

2941 GGCGACGACC GCGCCGGCCT GGAAGACGTC CGGATAGGTG GCGAGCATCA CCGACGTCAT

3001 GGCACCGCCG GCGGACAGCC CGGTGATGTA GGTGCGCTGG GGGTCCGCGC CGTAGGCGGA

3061 GGCACCGCCG GCGGACAGCC CGGTGATGTA GGTGCGCTGG GGGTCCGCGC CGTAGGCGGA

3121 GCTGCTCTGG AACCAGTTGA AGCACCTGTT CGCGTTGTTC GACGACGTGG TCTCGGCGAA

3181 CACGAGCAGG AAGCCATAGC GGTCCGCGAA TGAGAGCAGG CCGGAGTTGT CGGCGTAGCC

3241 CTGGGCGTCC TGGGTGCAAC CGTGCAGGGC GAACACCACC GCCGGCTCCG CGGGCAGGGA

3301 CGCGGGCCGG TAGACGTACA TGTTCAGCCG GCCCGGGTTC GTGCCGAACT CCGCGACCTC

3361 GGTCAGGTCC GCCTTGGTCA GACCGGGCTT GGCCAGGCCC GCCGCGGCGT GGGCCGTCGG

3421 CGCCGGGCCG AGCAGGGCCG CTCCGAGTAC GAGGGCCACG ACGGCCACGA GACGGGTGAG

3481 CACCCCCCGC CGTCCCGGAC GCGACAACGA CCCGACCGGC GGCGAGGAGG AGAGGGGGAA

3541 CAGCGGGGTG AGGATTCCCC GGAACGGCGG CGGCTGCATG GCGGCTCCCT CGATGTCGTG

3601 GGGGGGACAC GGAGGGCTCC CTGACGTCGA TCAGTGGGAG CGCCCCGGTG CCCGGCACCG

3661 TAGGGGTGGT TCAACCCGCA ACGGTATGGC CCGGAGCACC ACACCCCGCA CCGCGCGATG

3721 TGCGCCCGGA CGGATTGTGT CGCCTTGCGG AATCTGATAC CCGGACGCGA CGAACGCCCC

3781 ACCCGACACG GGTAGGGCCT CATCGTGTCC GACTCGCCCC GTCGGCCTTG CCTGCCCTGG

3841 ACGGACCGGG CGTCGGCGGA CCGCGCGTCG GCGGGCTGGG CGGTATGGCG GCCGAGGACG

3901 CCAGCCGCGT GGGGCGGCCG CGCCCAAGTG CAGTACGCCG ACCGTGGCCG GCGGGAGGGC

3961 CGGACCGGTC AGTGCAGTCC CGCGGCCCTG CGGGACCGCT CGTCCCAGAC GGGTTCCACC

4021 GCGGCGAACC GGGGTCCGTG TCCGCGGCGG TAGACCATCA GTGTCCGCTC GAAGGTGATG

4081 ACGATGACAC CGTCCTGGTT GTAGCCGATG GTGCGCACGC TGATGATGCC TACGTCAGGT

4141 CGGCTGGCGG ACTCCCGGGT GTTCAGGACC TCGGACTGCG AGTAGATGGT GTCGCCCTCG

4201 AAGACCGGGT TCGGCAGCCT GACCCGGTCC CAGCCGAGGT TGGCCATCAC ATGCTGGGAG

4261 ATGTCGGTGA CGCTCTGCCC GGTGACCAGG GCGAGGGTGA AGGTGGAGTC CACCAGCGGC

4321 TTGCCCCAGG TGGTGCCCGC CGAGTAGTGG CGGTCGAAGT GCAGCGGCGC GGTGTTCTGC

4381 GTCAGGAGCG TGAGCCAGGA GTTGTCGGTC TCCAGGACCG TGCGGCCCAG GGGGTGGCGG

4441 TACACGTCGC CGGTGCTGAA GTCCTGGAAG TAGCGGCCCT GCCAGCCCTC GACCACAGCG

4501 GTGCGGGTGG CGTCCTGGTC CGGGTTCTCA GTCGTCATGG CGCTCATTCT GGGAAGTCCC

4561 CGGTCCGCTG TGAAATGCCG AACCTTCACC GGGCTCATAC GTGCGGCGCA TGAGCCCTGG

4621 ACCGTACGTA GTCGTAGAAC CTCGCCACCA CTGGCGCGCG TGGTCCTCCG GCGAGTGTGA

4681 CCACGCCGAC CGTGCGCCGC GCCTGCGGGT CGTCGAGCGG CACGGCGACG GCGTGGTCAC

4741 CGGGCCCGGA CGCGCTCCCG GTGAGGGGGG CGACGGCCAC ACCGAGGCCG GCGGCGACCA

-continued

4801 GGGCCCGCAG CGTGCTCAGC TCGGTGCTCT CCAGGACGAC CCGCGGCACG AATCCGGCCG

4861 CGGCGCACAG CCGGTCGGTG ATCTGGCGCA GTCCGAAGAC CGGCTCCAGT GCCACGAACG

4921 CCTCATCGGC CAGCTCCGCG GTCCGCACCC GGCGGCGTCT GGCCAGAAGG TGTCCGGGTG

4981 CGACGAGCAG GCACAGTGCC TCGTCCCGCA GTGGTGTCCA CTCCACATCG TCCCCGGCGG

5041 GTCGTGGGCT GGTCAGCCCC AGGTCCAGCC TGCTGTTGCG GACGTCGTCG ACCACGGCGT

5101 CGGCGGCGTC GCCGCGCAGT TCGAAGGTGG TGCCGGGAGC CAGCCGGCGG TACCCGGCGA

5161 CGAGGTCGGG CACCAGCCAG GTGCCGTAGG AGTGCAGGAA ACCCAGTGCC ACGGTGCCGG

5221 TGTCGGGGTC GATCAGGGCG GTGATGCGCT GCTCGGCGCC GGAGACCTCA CTGATCGCGC

5281 GCAGGGCGTG GGCGCGGAAG ACCTCGCCGT ACTTGTTGAG CCGGAGCCGG TTCTGGTGCC

5341 GGTCGAACAG CGGCACGCCC ACTCGTCGCT CCAGCCGCCG GATGGCCCTG GACAGGGTCG

5401 GCTGGGAGAT GTTGAGCCGT TCCGCGGTGA TCGTCACGTG CTCGTGCTCG GCCAAGGCCG

5461 TGAACCACTG CAACTCCCGT ATCTCCATGC AGGGACTATA CGTACCGGGC ATGGTCCTGG

5521 CGAGGTTTCG TCATTTCACA GCGGCCGGGC GGCGGCCCAC AGTGAGTCCT CACCAACCAG

5581 GACCCCATCG GAGGGACCCC ATGTCCGAGC CGCATCCTCG CCCTGAACAG GAACGCCCCG

5641 CCGGGCCCCT GTCCGGTCTG CTCGTGGTTT CTTTGGAGCA GGCCGTCGCC GCTCCGTTCG

5701 CCACCCGCCA CCTGGCGGAC CTGGGCGCCC GTGTCATCAA GATCGAACGC CCCGGCAGCG

5761 GCGACCTCGC CCGCGGCTAC GACCGCACGG TGCGTGGCAT GTCCAGCCAC TTCGTCTGGC

5821 TGAACCGGGG GAAGGAGAGC GTCCAGCTCG ATGTGCGCTC GCCGGAGGGC AACCGGCACC

5881 TGCACGCCTT GGTGGACCGG GCCGATGTCC TGGTGCAGAA TCTGGCACCC GGCGCCGCGG

5941 GCCGCCTGGC ATCGGCCACC AGGTCCTCGC GCGGAGCCAC CGAGGCTGAT CACCTGCGGA

6001 CATATCCGGC TACGGCAGTA CCGGCTGCTA CCGCGGACCG CAAGGCGTAC GACCTCCTGG

6061 TCCAGTGCGA AGCGGGGCTG GTCTCCATCA CCGGCACCCC CGAGACCCCG TCCAAGGTGG

6121 GCCTGTCCAT CGCGGACATC TGTGCGGGGA TGTACGCGTA CTCCGGCATC CTCACGGCCC

6181 TGCTGAAGCG GGCCCGCACC GGCCGGGGCT CGCAGTTGGA GGTCTCGATG CTCGAAGCCC

6241 TCGGTGAATG GATGGGATAC GCCGAGTACT ACACGCGCTA CGGCGGCACC GCTCCGGCCC

6301 GCGCCGGCGC CAGCCACGCG ACGATCGCCC CCTACGGCCC GTTCACCACG CGCGACGGGC

6361 AGACGATCAA TCTCGGGCTC CAGAACGAGC GGGAGTGGGC TTCCTTCTGC GGTGTCGTGC

6421 TACAACGCCC CGGTCTCTGC GACGACCCGC GCTTTTCCGG CAACGCCGAC CGGGTGGCGC

6481 ACCGCACCGA GCTCGACGCC CTGGTGAGCG AGGTGACGGG CACGCTCACC GGCGAGGAAC

6541 TGGTGGCGCG GCTGGAGGAG GCGTCGATCG CCTACGCACG CCAGCGCACC GTGCGGGAGT

6601 TCAGCGAACA CCCCCAACTG CGTGACCGTG GACGCTGGGC TCCGTTCGAC AGCCCGGTCG

6661 GTGCGCTGGA GGGCCTGATC CCCCCGGTCA CCTTCCACGG CGAGCACCCG CGGCGGCTGG

6721 GCCGGGTCCC GGAGCTGGGC GAGCATACCG AGTCCGTCCT GGCGTGGCTG GCCGCGCCCC

6781 ACAGCGCCGA CCGCGAAGAG CCCGGCCATG CCGAATGAAC TCACCGGAGT CCTGATCCTG

6841 GCCGCCGTGT TCCTGCTCGC CGGCGTACGG GGGCTGAACA TGGGCCTGCT CGCGCTGGTC

6901 GCCACCTTTC TGCTCGGGGT GGTCGCACTC GACCGAACGC CGGACGAGGT GCTGGCGGGT

6961 TTCCCCGCGA GCATGTTCCT GGTGCTGGTC GCCGTCACGT TCCTCTTCGG GATCGCCCGC

7021 GTCAACGGCA CGGTGGACTG GCTGGTACGT GTCGCGGTGC GGGCGGTGGG GGCCCGGGTG

7081 GGAGCCGTCC CCTGGGTGCT CTTCGGCCTG GCGGCACTGC TCTGCGCGAC AGGCGCGGCC

7141 TCGCCCGCGG CGGTGGCGAT CGTGGCGCCG ATCAGCGTCG CGTTCGCCGT CAGGCACCGC

-continued

7201 ATCGATCCGC TCTACGCCGG ACTCATGGCG GTGAACGGGG CCGCAGCCGG CAGTTTCGCC

7261 CCCTCCGGGA TCCTGGGCGG CATCGTCCAC TCGGCGCTGG AGAAGAACCA TCTGCCCGTC

7321 AGCGGCGGGC TGCTCTTCGC AGGCACCTTC GCCTTCAACC TCGCGGTCGC CGCGGTGTCA

7381 TGGCTCCTCC TCGGGCGCAG GCGCCTCGAA CCACATGACC TGGACGAGGA CACCGATCCC

7441 ACGGAAGGGG ACCCGGCTTC CCGCCCCGGC GCGGAACACG TGATGACGCT GACCGCGATG

7501 GCCGCGCTGG TGCTGGGAAC CACGGTCCTC TCCCTGGACA CCGGCTTCCT GGCCCTCACC

7561 TTGGCGGCGT TGCTGGCGCT GCTCTTCCCG CGCACCTCCC AGCAGGCCAC CAAGGAGATC

7621 GCCTGGCCCG TGGTGCTGCT GGTATGCGGG ATCGTGACCT ACGTCGCCCT GCTCCAGGAG

7681 CTGGGCATCG TGGACTCCCT GGGGAAGATG ATCGCGGCGA TCGGCACCCC GCTGCTGGCC

7741 GCCCTGGTGA TCTGCTACGT GGGCGGTGTC GTCTCGGCCT TCGCCTCGAC CACCGGGATC

7801 CTCGGTGCCC TGATGCCGCT GTCCGAGCCG TTCCTGAAGT CCGGTGCCAT CGGGACGACC

7861 GGCATGGTGA TGGCCCTGGC GGCCGCGGCG ACCGTGGTGG ACGCGAGTCC CTTCTCCACC

7921 AATGGTGCTC TGGTGGTGGC CAACGCTCCC GAGCGGCTGC GGCCCGGCGT GTACCAGGGG

7981 TTGCTGTGGT GGGGCGCCGG GGTGTGCGCA CTGGCTCCCG CGGCCGCCTG GGCGGCCTTC

8041 GTGGTGGCGT GAGCGCAGCG GAGCGGGAAT CCCCTGGAGC CCGTTTCCCG TGCTGTGTCG

8101 CTGACGTAGC GTCAAGTCCA CGTGCCGGGC GGGCAGTACG CCTAGCATGT CGGGCATGGC

8161 TAATCAGATA ACCCTGTCCG ACACGCTGCT CGCTTACGTA CGGAAGGTGT CCCTGCGCGA

8221 TGACGAGGTC CTGAGCCGGC TGCGCGCGCA GACGGCCGAG CTGCCGGGCG GTGGCGTACT

8281 GCCGGTGCAG GCCGAGGAGG GACAGTTCCT CGAGTTCCTG GTGCGGTTGA CCGGCGCGCG

8341 TCAGGTGCTG GAGATCGGGA CGTACACCGG CTACAGCACG CTCTGCCTGG CCCGCGGATT

8401 GGCGCCCGGG GGCCGTGTGG TGACGTGCGA TGTCATGCCG AAGTGGCCCG AGGTGGGCGA

8461 GCGGTACTGG GAGGAGGCCG GGGTTGCCGA CCGGATCGAC GTCCGGATCG GCGACGCCCG

8521 GACCGTCCTC ACCGGGCTGC TCGACGAGGC GGGCGCGGGG CCGGAGTCGT TCGACATGGT

8581 GTTCATCGAC GCCGACAAGG CCGGCTACCC CGCCTACTAC GAGGCGGCGC TGCCGCTGGT

8641 ACGCCGCGGC GGGCTGATCG TCGTCGACAA CACGCTGTTC TTCGGCCGGG TGGCCGACGA

8701 AGCGGTGCAG GACCCGGACA CGGTCGCGGT ACGCGAACTC AACGCGGCAC TGCGCGACGA

8761 CGACCGGGTG GACCTGGCGA TGCTGACGAC GGCCGACGGC GTCACCCTGC TCCGGAAACG

8821 GTGACCGGGG CGATGTCGGC GGCGGTCAGC GTCAGCGTCG TCGGCGCGCG CCTCGCGGAG

8881 GGCTCCAGAT GCAGGCGTTC GACGCCGGCG GCGGAAGCGC CCGCCACCTC GGACACGCAG

8941 GGGCAGTCGG AGTCCGCGAA GCCCGCGAAC CGGTACGCGA TCTCCATCAT GCGGTTGCGG

9001 TCCGTACGCC GGAAGTCCGC CACCAGGTGC GCCCCCGCGC GGGCGCCCTG GTCCGTGAGC

9061 CAGTTCAGGA TCGTCGCACC GGCACCGAAC GACACGACCC GGCAGGACGT GGCGAGCAGT

9121 TTCAGGTGCC ACGTCGACGG CTTCTTCTCC AGCAGGATGA TGCCGACGGC GCCGTGCGGG

9181 CCGAAGCGGT CGCCCATGGT GACGACGAGG ACCTCATGGG CGGGATCGGT GAGCACGCGC

9241 GCAGGTCGGC GTCGGAGTAG TGCACGCCGG TCGCGTTCAT CTGGCTGGTC CGCAGCGTCA

9301 GTTCCTCGAC GCGGCTGAGT TCCTCCTCCC CCGCGGGTGC GATCGTCATG GAGAGGTCGA

9361 GCGAGCGCAG GAAGTCCTCG TCGGGACCGG AGTACGCCTC CCGGGCCTGG TCGCGCGCGA

9421 AACCCGCCTG GTACATCAGG CGGCGCCGAC GCGAGTCGAC CGTGGACACC GGCGGGCTGA

9481 ACTCCGGCAG CGACAGGAGC GTGGCCGCCT GCTCGGCCGG GTAGCACCGC ACCTCGGGCA

9541 GGTGGAACGC CACCTCGGCA CGCTCGGCGG GCTGGTCGTC GATGAACGCG ATCGTGGTCG

-continued

9601 GTGCGAAGTT CAGCTCCGTG GCGATCTCGC GGACGGACTG CGACTTCGGC CCCCATCCGA
9661 TGCGGGCCAG CACGAAGTAC TCCGCCACAC CGAGGCGTTC CAGACGCTCC CACGCGAGGT
9721 CGTGGTCGTT CTTGCTCGCC ACCGCCTGGA GGATGCCGCG GTCGTCGAGC GTGGTGATCA
9781 CCTCGCGGAT CTCGTCGGTG AGGACCACCT CGTCGTCCTC CAGCACGGTG CCCCGCCACA
9841 AGGTGTTGTC CAGGTCCCAG ACCAGACACT TGACAATGGT CATGGCTGTC CTCTCAAGCC
9901 GGGAGCGCCA GCGCGTGCTG GGCCAGCATC ACCCGGCACA TCTCGCTGCT GCCCTCGATG
9961 ATCTCCATGA GCTTGGCGTC GCGGTACGCC CGTTCGACGA CGTGTCCCTC TCTCGCGCCT
10021 GCCGACGCGA GCACCTGTGC GGCGGTCGCG GCCCCGGCGG CGGCTCGTTC GGCGGCGACG
10081 TGCTTGGCCA GGATCCTCGC GGGCACCATC TCGGCCGAGC CCTCGTCCCA CTGGTCGCTG
10141 GCGTACTCGC ACACGCGGGC CCCGATCTGC TCCGCGGTCC ACAGGTCGGC GATGTGCCCG
10201 GCGACGAGTT GGTGGTCGCC GAGCGGCCGG CCGAACTGCT CCCGGGTCCG GGCGTGGGCC
10261 ACCGCGGCGG TGCGGCAGGC CCGCAGGATC CCGACGCAGC CCCAGGCCAC CGACTTGCGC
10321 CCGTAGGCGA GTGACGCCGC GACCAGCATC GGCAGTGACG CGCCGGAGCC GGCCAGGACC
10381 GCGCCGGCCG GCACACGCAC CTGGTCCAGG TGCAGATCGG CGTGGCCGGC GGCGCGGCAG
10441 CCGGACGGCT TCGGGACGCG CTCGACGCGT ACGCCGGGGG TGTCGGCGGG CACGACCACC
10501 ACCGCACCGG AACCATCCTC CTGGAGACCG AAGACGACCA GGTGGTCCGC GTAGGCGGCG
10561 GCAGTCGTCC AGACCTTGTG GCCGTCGACG ACAGCGGTGT CCCCGTCCAG CCGAACCCGC
10621 GTCCGCATCG CCGACAGATC GCTGCCCGCC TGCCGCTCAC TGAAGCCGAC GGCCGCGAGT
10681 TTCCCGCTGG TCAGCTCCTT CAGGAAGGTC GCCCGCTGAC CGGCGTCGCC GAGCCGCTGC
10741 ACGGTCCACG CGGCCATGCC CTGCGACGTC ATGACACTGC GCAGCGAACT GCAGAGGCTG
10801 CCGACGTGTG CGGTGAACTC GCCGTTCTCC CGGCTGCCGA GTCCCAGACC GCCGTGCTCG
10861 GCCGCCACTT CCGCGCAGAG CAGGCCGTCG GCGCCGAGCC GGACGAGCAG GTCGCGCGGC
10921 AGTTCGCCGG ACGTGTCCCA CTCGGCCGCC CGGTCACCGA CAAGGTCGGT CAGCAGCGCG
10981 TCACGCTCAG GCATCGACGG CCCGCAGCCG GTGGACGAGT GCGACCATGG ACTCGACGGT
11041 ACGGAAGTTC GCGAGCTGGA GGTCCGGGCC GGCGATCGTG ACGTCGAACG TCTTCTCCAG
11101 GTACACGACC AGTTCCATCG CGAACAGCGA CGTGAGGCCG CCCTCCGCGA ACAGGTCGCG
11161 GTCCACGGGC CAGTCCGACC TGGTCTTCGT CTTGAGGAAC GCGACCAACG CGTGCGCGAC
11221 GGGGTCCTCC TTGACGGGTG CGGTCATGAG AACACCTTCT CGTATTCGTA GAAGCCCCGG
11281 CCGGTCTTCC GGCCGTGGTG TCCCTCGCGG ACCTTGCCCA GCAGCAGGTC ACAGGGGCGG
11341 CTGCGCTCGT CGCCGGTGCG TTTGTGCAGC ACCCACAGCG CGTCGACGAG GTTGTCGATG
11401 CCGATCAGGT CCGCGGTGCG CAGCGGCCCG GTCGGATGGC CGAGGCACCC CGTCATGAGC
11461 GCGTCGACGT CCTCGACGGA CGCGGTGCCC TCCTGCACGA TCCGCGCCGC GTCGTTGATC
11521 ATCGGGTGGA GCAGCCGGCT CGTGACGAAG CCGGGCGCGT CCCGGACGAC GATCGGCTTG
11581 CGCCGCAGCG CCGCGAGCAG GTCCCCGGCG GCGGCCATGG CCTTCTCACC GGTCCGGGGT
11641 CCTCGGATCA CCTCGACCGT CGGGATCAGG TACGACGGGT TCATGAAGTG CGTGCCGAGC
11701 AGGTCCTCGG GCCGGGCCAC GGAGTCGGCC AGTTCGTCAA CCGGGATCGA CGACGTGTTC
11761 GTGATGACCG GGATACCGGG CGCCGCTGCC GAGACCGTGG CGAGTACCTC CGCCTTGACC
11821 TCGGCGTCCT CGACGACGGC CTCGATCACC GCGGTGGCCG TACCGATCGC GGGCAGCGCG
11881 GACGTGGCCG TCCGCAGCAC ACCGGGGTCG GCCTCGGCGG GCCCGGCCAC GAGTTGTGCC
11941 GTCCGCAGTT CGGTGGCGAT CCGCGCCCGC GCCGCCGTAA GGATCTCCTC GGACGTGTCG

-continued

12001 ACGAGTGTCA CCGGGACGCC GTGGCGCAGC GCGAGCGTGG TGATGCCGGT GCCCATCACT

12061 CCCGCGCCGA GCACGATCAG CTGGTGGTCC ACGCTGTTTC CTCCCTCCGG GGTCACCATG

12121 GCAGCGAGTA CGGGTCGAGG ACGTCTTCCG GGGTCGACCC GATCGCGTCC TTGCGGCCGA

12181 GGCCGAGTTC GTCGGCGAAG CCGAGCAGCA CGTCGAACGC GATGTGGTCG GCGAACGCGC

12241 TGCCCGTCGA GTCGAGGACG CTCAGGCTGT CCCGGTGGTC CGCCGCGGTG TCCGGTGCCG

12301 CGCACAGGGC CGCCAGCGAC GGGCCGAGCT CGCGGTCCGG CAGTTGCTGG TACTCGCCCT

12361 CGGCGCGGGC CTGCCCCGGA TGGTCGACGC AGATGAACGC GTCGTCGAGC AGGGTCTTCG

12421 GCAGTTCGGT CTTGCCCGGC TCGTCGGCGC CGATGGCGTT CACATGCAGG TGCGGCAGCC

12481 GCGGCTCGGC GGGCAGCACC GGCCCTTTGC CCGAGGGCAC CGAGGTGACG GTGGACAGGA

12541 CATCCGCGGC GGCGGCGGCC TCCGCCGGAT CGGTCACCTT GACCGGCAGT CCGAGGAACG

12601 CGATGCGGTC CGCGAACGAC GCCGCGTGGC CGGGGTCGGT GTCGCTGACC AGGATCCGCT

12661 CGATGGGCAG GACCCTGCTG AGCGCGTGCG CCTGGGTCAC CGCCTGTGCG CCCGCGCCGA

12721 TCAGCGTGAG CGTGGCGCTG TCGGACCGGG CCAGCAGCCG GCTCGCGACG GCGGCGACCG

12781 CGCCGGTCCG CATCGCGGTG ATCACGCCTG CGTCGGCGAG GGCGGTCAGA CTGCCGCTGT

12841 CGTCGTCGAG GCGCGACATC GTGCCGACGA TCGTCGGCAC CCGGAAGCGC GGATAGTTGT

12901 GCGGACTGTA CGAAACCGTC TTCATGGTCA CGCCGACACC GGGGACCCGG TACGGCATGA

12961 ACTCGATGAC GCCGGGAATG TCGCCGCCGC GGACGAATCC GGTACGCGGC GGCGCCTCGG

13021 CGAACTCGCC GCGGCCGAGC GCGGCGAACC CGTCGTGCAG CTCGCTGATC AGCCGGTCCA

13081 TCATCACGTC GCGGCCGATC ACGGAGAGAA TCCGCTTGAT GTCACGTTGG CGCAGGACCC

13141 TGGTCTGCAT GTGTCACCTC CCTTTCGTGG CCGGAGCTGT CTTGGTGGTG CCGCTCGGGG

13201 CGGCTTCCGT TCTCATCGCA GCTCCCTGTC GATGAGGTCG AAAATCTCGT CCGCGGTCGC

13261 GTCCGCGGAC AGCACGCCGG CCGGCGTGGT CGGGCGGGTC TCCCGCCGCC AGCGGTTGAG

13321 CAGGGCGTCC AGCCGGGTTC CGATCGCGTC CGCCTGGCGG GCGCCCGGGT CGACACCGGC

13381 AACGAGTGCT TCCAGCCGGT CGAGCTGCGC GAGCACCACG GTCACCGGGT CGTCCGGGGA

13441 CAGCAGTTCA CCGATGCGCT CGGCGACTGC GCGCGGCGAC GGGTAGTCGA AGACGAGCGT

13501 GGCGGACAGT CGCAGACCGG TCGCCTCGTT GAGGCCGTTG CGCAGCTGCA CCGCGATGAG

13561 CGAGTCCACA CCGAGTTCCC GGAACGCCGC GTCCTCCGGG ATGTCCTCCG GGTCGGCGTG

13621 GCCCAGGACG GCCGCTGCCT TCTGCCGGAC GAGGGCGAGC AGGTCGGTGG GGCGTTCCTG

13681 CTCGTTGCGG GCGCTCCGGC GGGCCGACGG CTTGGGCCGG CCACGCAGCA GCGGGAGGTC

13741 CGGCGGCAGG TCGCCCGCCA CGGCGACGAC ACTGCCCGTT CCGGTGTGGA CGGCGGCGTC

13801 GTACATGCGC ATGCCCTGTT CGGCGGTGAG CGCGCTCGCC CCACCCTTGC GCATACGGCG

13861 CCGGTCGGCG TCGGTCAGGT CCGCGGTCAG GCCACTCGCC TGGTCCCACA GCCCCCACGC

13921 GATCGACAGC CCTGGCAGCC CTTGTGCACG CCGGTGTTCG GCGAGCGCGT CGAGGAACGC

13981 GTTCGCCGCC GCGTAGTTGC CCTGACCGGG GGTGCCCAGC ACACCGGCCG CCGACGAGTA

14041 GACGACGAAT GCGGCGAGGT CGTTGTCGCG GGTGAGCCGG TGCAGGTGCC AGGCGGCGTC

14101 GGCCTTGGGT TTGAGGACGG TGTCGATGCG GTCGGGGGTG AGGTTGTCGA GCAGGGCGTC

14161 GTCGAGGGTT CCGGCGGTGT GGAAGACGGC GGTGAGGGGT TGAGGGATGT GGGCGAGGGT

14221 GGTGGCGAGT TGGTGGGGGT CGCCGACGTC GCAGGGGAGG TGGGTGCCGG GGGTGGTGTC

14281 GGGGGGTGGG GTGCGGGAGA GGAGGTAGGT GTGGGGGTGG TTCAGGTGGC GGGCGAGGAT

14341 GCCGGCGAGG GTGCCGGAGC CGCCGGTGAT GACGACGGCC CCCTCGGGGT CCAGCGGCCG

-continued

14401 CGGGACCGTG AGGACGATCT TGCCGGTGTG CTCGCCGCGG CTCATGGTCG CCAGCGCCTC

14461 GCGGACCTGC CGCATGTCGT GCACCGTCAC CGGCAGCGGG TGCAGCACAC CGCGCGCGAA

14521 CAGGCCGAGC AGCTCCGCGA TGATCTCCTT GAGCCGGTCG GGCCCCGCGT CCATCAGGTC

14581 GAACGGTCGC TGGACGGCGT GCCGGATGTC CGTCTTCCCC ATCTCGATGA ACCGGCCACC

14641 CGGCGCGAGC AGGCCGACGG ACGCGTCGAG GAGTTCACCG GTGAGCGAGT TGAGCACGAC

14701 GTCGACCGGC GGGAACGCGT CGGCGAACGC GGTGCTGCGG GAATCGGCCA GATGCGCTCC

14761 GTCCAGGTCC ACCAGATGGC GCTTCGCGGC GCTGGTGGTC GCGTACACCT CCGCGCCCAG

14821 GTGCCGCGCG ATCTGCCGGG CGGCGGAACC GACACCGCCG GTGGCCGCGT GGATCAGGAC

14881 CTTCTCGCCG GGGCGCAGCC CGGCGAGGTC GACCAGGCCG TACCACGCGG TCGCGAACGC

14941 GGTCATCACG GACGCCGCCT GCGGGAACGT CCAGCCGTCC GGCATCCGGC CGAGCATCCG

15001 GTGGTCGGCG ATGACCGTGG GGCCGAAGCC GGTGCCGACG AGGCCGAAGA CGCGGTCGCC

15061 CGGTGCCAGA CCGGAGACGT CGGCGCCGGT CTCCAGGACG ATGCCCGCGG CCTCGCCGCC

15121 GAGCACGCCC TGACCGGGGT AGGTGCCGAG CGCGATCAGC ACATCGCGGA AGTTCAGGCC

15181 CGCCGCACGC ACACCGATCC GGACCTCGGC CGGGGCGAGG GGGCGCCGGG GCTCCGCCGA

15241 GTCGGCCGCG GTGAGGCCGT CGAGGGTGCC CGTCCGCGCC GGCCGGATCA GCCACGTGTC

15301 GCTGTCCGGC ACGGTGAGCG GCTCCGGCAC CCGGGTGAGG CGGGCCGCCT CGAACCGGCC

15361 GCCGCGCAGC CGCAGACGCG GCTCGCCGAG TGCGACGGCG ATGCGCTGCT GCTCGGGGGC

15421 GAGCGTGACG CCGGACTCGG TCTCGACGTG GACGAACCGG CCGGGCTGCT CGGCCTGGGC

15481 GGCGCGCAGC AGTCCGGCCG CCGCGCCGCT GGCGAGGCCC GCGGTGGTGT GCACGAGCAG

15541 ATCCCCGCCG GAGCCGGTCA GGGCGGTCAG CAGCCGGGTG GTGAGCGCAC GCGTCTCGGC

15601 CACCGGGTCG TCGCCATCAG CGGCAGGCAA CGTGATGACG TCCACGTCGG TCGCGGGGAC

15661 ATCCGTGGGT GCGGCGACCT CGATCCAGGT GAGACGCATC AGGCCGGTGC CGACGGGTGG

15721 GGACAGCGGG CGGGTGCGGA CCGTCCGGAT CTCGGCGACG AGTTGGCCGG CGGAGTCGGC

15781 GACGCGCAGA CTCAGCTCGT CGCCGTCACG AGTGATCACG GCTCGGAGCA TGGCCGAGCC

15841 CGTGGCGACG AACCGGGCCC CCTTCCAGCC GAACGGCAGA CCCGCAGCGC TGTCGTCCGG

15901 CGTGGTGAGG GCGACGGCGT GCAGGGCCGC GTCGAGCAGC GCCGGATGCA CACCGAAACC

15961 GTCCGCCTCG GCGGCCTGCT CGTCGGGCAG CGCCACCTCG GCATACACGG TGTCACCATC

16021 ACGCCAGGCA GCCCGCAACC CCTGGAACGC CGACCCGTAC TCATAACCGG CATCCCGCAG

16081 TTCGTCATAG AACCCCGAGA CGTCGACGGC CACGGCCGTG ACCGGCGGCC ACTGCGAGAA

16141 CGGCTCCACA CCGACAACAC CGGGGGTGTC GGGGGTGTCG GGGGTCAGGG TGCCGCTGGC

16201 GTGCCGGGTC CAGCTGCCCG TGCCCTCGGT ACGCGCGTGG ACGGTCACCG GCCGCCGTCC

16261 GGCCTCATCA GCCCCTTCCA CGGTCACCGA CACATCCACC GCTGCGGTCA CCGGCACCAC

16321 AAGGGGGGAT TCGATGACCA GCTCGTCCAC TATCCCGCAA CCGGTCTCGT CACCGGCCCG

16381 GATGACCAGC TCCACAAACG CCGTACCCGG CAGCAGGACC GTGCCCCGCA CCGCGTGATC

16441 AGCCAGCCAG GGGTGAGTGC GCAATGAGAT CCGGCCAGTG AGAACAACAC CACCATCGTC

16501 GGCGGGCAGC GCTGTGACAG CGGCCAGCAT CGGATGCGCC GCACCCGTCA ACCCCGCCGC

16561 CGACAGATCG GTGGCACCGG CCGCCTCCAG CCAGTACCGC CTGTGCTCGA ACGCGTACGT

16621 GGGCAGATCC AGCAGCCGTC CCGGCACCGG TTCGACCACC GTGTCCCAGT CCACTGCCGT

16681 GCCCAGGGTC CACGCCTGCG CCAACGCCGT CAGCCACCGC TCCCAGCCGC CGTCACCGGT

16741 CCGCAACGAC GCCACCGTGT GAGCCTGCTC CATCGCCGGC AGCAGCACCG GATGGGCACT

-continued

16801 GCACTCCACG AACACCGACC CATCCAGCTC CGCCACCGCC GCGTCCAACG CCACCGGACG

16861 ACGCAGATTC CGGTACCAGT ACCCCTCATC CACCGGCTCC GTCACCCAGG CGCTGTCCAC

16921 GGTCGACCAC CACGCCACCG ACGCGGCCTT CCCTGCCACC CCCTCCAGTA CCTTGGCCAC

16981 TTCATCCTCG ATGGCTTCCA CGTCGGGCGT GTGGGAGGCG TAGTCGACCG CGATACGACG

17041 CACCCGCACG CCTTCGGCCT CATACCGCGC CACCACCTCC TCCACCGCCG ACGGGTCCCC

17101 CGCCACCACC GTCGAAGCCG GGCCGTTACG CGCCGCGATC CACACACCCT CGACCAGACC

17161 GACCTCACCG GCCGCCAACG CCACCGAAGC CATCGCTCCC CGCCCGGCCA GTCGCGCCGC

17221 GATGACCTGA CTGCGCAATG CCACCACGCG GGCGGCGTCC TCGAGGCTGA GGGCTCCGGC

17281 CACGCACGCC GCCGCGATCT CGCCCTGGGA GTGTCCGATC ACCGCGTCCG GCACGACCCC

17341 ATGCGCCTGC CACAGCGCGG CCAGGCTCAC CGCGACCGCC CAGCTGGCCG GCTGGACCAC

17401 CTCCACCCGC TCCGCCACAT CCGGCCGCGC CAACATCTCC CGCACATCCC AGCCCGTGTG

17461 CGGCAGCAAC GCCTGAGCGC ACTCCTCCAT ACGCGCGGCG AACACCGCGG AGTGGGCCAT

17521 GAGTTCCACG CCCATGCCGA CCCACTGGGC GCCCTGGCCG GGGAAGACGA ACACCGTACG

17581 CGGCTGGTCC ACCGCCACAC CCGTCACCCG GGCATCGCCC AGCAGCACCG CACGGTGACC

17641 GAAGACAGCA CGCTCCCGCA CCAACCCCTG CGCGACCGCG GCCACATCCA CACCACCCCC

17701 GCGCAGATAC CCCTCCAGCC GCTCCACCTG CCCCCGCAGA CTCACCTCAC CACGAGCCGA

17761 CACCGGCAAC GGCACCAACC CGTCAACAAC CGACTCCCCA CGCGACGGCC CAGGAACACC

17821 CTCAAGGATC ACGTGCGCGT TCGTACCGCT CACCCCGAAC GACGACACAC CCGCATGCGG

17881 TGCCCGATCC GACTCGGGCC ACGGCCTCGC CTCGGTGAGC AGCTCCACCG CACCGGCCGA

17941 CCAGTCCACA TGCGACGACG GCTCGTCCAC ATGCAGCGTC TTCGGCGCGA TCCCGTACCG

18001 CATCGCCATG ACCATCTTGA TCACACCGGC GACACCCGCC GCCGCCTGCG CATGACCGAT

18061 GTTCGACTTC AACGAACCCA GCAGCAGCGG AACCTCACGC TCCTGCCCGT ACGTCGCCAG

18121 AATGGCCTGC GCCTCGATGG GATCGCCCAG CGTCGTCCCC GTCCCGTGCG CCTCCACCAC

18181 GTCCACATCG GCGGCGCGCA GTCCGGCGTT CACCAACGCC TGCTGGATGA CACGCTGCTG

18241 GGACGGGCCG TTGGGGGCGG ACAGCCCGTT GGAGGCACCG TCCTGGTTCA CCGCCGACCC

18301 GCGGACGACC GCGAGAACGG TGTGTCCCTT GCGCTCGGCG TCGGAGAGCC GCTCCAGCAC

18361 AAGAACGCCG GCGCCCTCCG CCCAGCCGGT GCCGTTGGCG GCGTCCGCGA ACGCGCGGCA

18421 GCGGCCGTCG GGGGAGAGTC CGCCCTGCTG CTGGAATTCC ACGAACCCGG TCGGGGTCGC

18481 CATGACGGTG ACACCGCCGA CCAGCGCCAG CGAGCACTCC CCGTGGCGCA GTGCGTGCCC

18541 GGCCTGGTGC AGCGCGACCA GCGACGACGA GCACGCCGTG TCCACCGTGA ACGCCGGTCC

18601 CTGGAGCCCA TAGAAGTACG AGATCCGGCC GGTGAGCACG CTGGGCTGCA TGCCGATCGA

18661 GCCGAACCCG TCCAGGTCCG CGCCGACGCC GTACCCGTAC GAGAAGGCGC CCATGAACAC

18721 GCCGGTGTCG CTGCCGCGCA GTGTGCCCGG CACGATGCCC GCGCTCTCGA ACGCCTCCCA

18781 TGTCGTTTCC AGCAGGATCC GCTGCTGGGG GTCCATGGCC CGTGCCTCAC GGGGGCTGAT

18841 GCCGAAGAAC GCGGCATCGA AGCCGGCGGC GTCGGAGAGG AAGCCGCCGC GGTCCGTGTC

18901 CGATCCGCCG GTGAGGCCGG ACGGGTCCCA GCCACGGTCG GCCGGGAAGC CGGTGACCGC

18961 GTCGCCGCCA CTGTCCACCA TGCGCCACAG GTCGTCGGGC GAGGTGACGC CGCCCGGCAG

19021 TCGGCAGGCC ATGCCCACGA TGGCCAGCGG TTCGTCACGG GTCGCGGCGG CTGTGGGAAC

19081 AGCGACCGCT GCGGCACCAC CGACCAGAGC CTCGTCCAAC CGCGACGCGA TGGCCCGCGG

19141 CGTCGGGTAG TCGAAGACAA GCGTGGCGGG CAGTCGGACA CCGGTCGCCG CGGCGAGTCG

-continued

19201 GTTCCGCAGT TCGACGGCGG TCAGCGAGTC GATACCCAGT TCCTTGAAGG CCGCGTCCGC

19261 GGACACGTCC GCGGCGTCCG CGTGGCCGAG CACCGCCGCC GCGTTGTCGC GGACCAGTGC

19321 CAGCAGCGCG GTGTCCCGCT CAGCGCCGGA CATGGTGCCG AGCCGGTCGG CGAGCGGAAC

19381 GGCGGTGGCC GCCGCCGGGC GCGATACGGC GCGGCGCAGA TCGGCGAAAA GCGGCGATGT

19441 GTGCGCGGTG AGGTCCATCG TGGCCGCCAC GGCGAACGCG GTGCCGGTTC CGGCCGCGGC

19501 TTCCAGCAGG CGCATGCCCA CACCGGCCGA CATGGGGCGG AAACCGCCGC GGCGGACACG

19561 GGTGCGGTTG GTGCCGCTCA TGCTGCCGGT GAGTCCGCTG TCATCGGCCC AGAGGCCCCA

19621 GGCCAGCGAC AGCGCGGGCA GTCCTTCGGC ATGGCGCAGC GTCGCGAGTC CGTCGAGGAA

19681 CCCGTTCGCC GCCGAGTAGT TGCCCTGGCC GCGGCCGCCC ATGATGCCCG CGACGGACGA

19741 GTAGAGGACG AACGAGCGCA GGTCCGCGTC CCGGGTCAGC TCGTGCAGGT GCCAGGCGCC

19801 GTCGGCTTTG GGGCGCAGTG TGGTGGCGAG CCGCTCCGGG GTGAGTGCCG TGGTCACGCC

19861 GTCGTCGAGC ACGGCTGCCG TGTGGAAGAC CGCCGTGAGC GGCCTGCCGG CGGCGGCGAG

19921 CGCGGCGGCG AGCTGGTCCC GGTCGGCGAC GTCACAGCGG ATGTGGACAC CGGGAGTGTC

19981 CGCCGGCGGT TCGCTGCGCG ACAGCAACAG GAGGTGGCGG GCGCCATGCT CGGCGACGAG

20041 ATGCCGGGCG AGGAGACCTG CCAGCACACC CGAGCCGCCG GTGATGACCA CCGTGCCGTC

20101 CGGGTCGAGC AGCGGTTCGG GCGTTTCCGC GGCGGCCGTG CGGGTGAACC GCGGCGCTTC

20161 GTACCGGCCG TCGGTGACGC GGACGTACGG CTCGGCCAGT GTCGTGGCGG CGGCCAGCGC

20221 CTCGATGGGG GTGTCGGTGC CGGTCTCCAC CAGCACGAAC CGGCCCGGGT GCTCGGCCTG

20281 GGCGGACCGG ACGAGGCCGG CGACCGCTCC TCCGACCGGT CCCGCGTCGA TCCGGACGAC

20341 GAGGGTGGTC TCCGCAGGGC CGTCCTCGGC GATCACCCGG TGCAGCTCGC CGAGCACGAA

20401 CTCGGTGAGC CGGTACGTCT CGTCGAGGAC ATCCGCGCCC GGTTCCGGGA GCGCGGAGAC

20461 GATGTGGACC GCGTCCGCAG GACCGGGCCC GGGAGTGGGC AGCTCGGTCC AGGAGAGGCC

20521 GTACAAGGAG TTCCGTACGA CGGCGGCGTC GCCGTCGACG TTCACCGGTC GCGCGGTCAG

20581 CGCGGCGACG GTCACCACCG GTTGGCCGAC CGGGTCCGTC GCATGCACGG CAGCGCCGTC

20641 CGGGCCCTGA GTGATCGTGA CGCGCAGCGT GGTGGCCCCG GTCGTGTGGA ACCGCACGCC

20701 GCTCCACGAG AACGGCAGCC GCACCTCCGC TTCCTGTTCC GCGAGCAGCG GCAGGCAGGT

20761 GACGTGCAAG GCCGCGTCGA ACAGCGCCGG GTGGACGCCA TAGTGCGGCG TGTCGTCCGC

20821 CTGTTCCCCG GCGATCTCCA CCTCGGCGTA CAGGGTTTCG CCGTCGCGCC AGGCGGTGCG

20881 CAGTCCCTGG AACGCTGGGC CGTAGCTGTA GCCGGTCTCG GCCAGCCGCT CGTAGAACGC

20941 GCTCACGTCG ACGCGTCGCG CGCCCGGCGG CGGCCACGCG GGCGGCGGGA CCGCCGCGAC

21001 GCTTCCGGCC CGGCCGAGGG TGCCGCTGGC GTGCCGGGTC CAGCTGTCCG TGCCCTCGGT

21061 ACGCGCGTGG ACGGTCACTC GCCGCCGTCC GGCCTCATCG GCCCCTTCGA CGGTCACCGA

21121 CACATCCACC GCGCCGGTCA CCGGCACCAC GAGCGGGGTC TCGATGACCA GTTCATCCAC

21181 CACCCCGCAA CCGGTCTCGT CACCGGCCCG GATGACCAGC TCCACAAACG CCGTACCCGG

21241 CAGCAGAACC GTGCCCCGCA CCGCGTGATC AGCCAGCCAG GGATGCGTAC GCAACGAGAT

21301 CCGGCCACTG AGAACAACAC CACCACCGTC GTCGGCGGGC AGTGCTGTGA CGGCGGCCAG

21361 CATCGGATGC GCCGCCCCGG TCAGCCCGGC CGCGGACAGA TCGGTGGCAC CGGCCGCCTC

21421 CAGCCAGTAC CGCCTGTGCT CGAACGCGTA GGTGGGCAGA TCGAGCAGCC GTCCCGGCAC

21481 CGGTTCGACC ACCGTGTCCC AGTCCACTGC CGTGCCCAGG GTCCACGCCT GCGCCAACGC

21541 CGTCAGCCAC CGCTCCCAGC CGCCGTCACC GGTCCGCAAC GACGCCACCG TGTGAGCCTG

-continued

21601 TTCCATCGCC GGCAGCAGCA CCGGATGGGC GCTGCACTCC ACGAACACGG ACCCGTCCAG

21661 CTCCGCCACC GCCGCGTCCA GCGCGACGGG GCGACGCAGG TTCCGGTACC AGTAGCCCTC

21721 ATCCACCGGC TCGGTCACCC AGGCGCTGTC CACCGTGGAC CACCAGGCCA CCGACCCGGT

21781 CCCGCCGGAA ATCCCCTCCA GTACCTCGGC CAACTCGTCC TCGATGGCTT CCACGTGGGG

21841 CGTGTGGGAG GCGTAGTCGA CCGCGATACG GCGCACTCGC ACGCCTTCGG CCTCGTACCG

21901 CGTCACCACT TCTTCCACCG CGGACGGGTC CCCCGCCACC ACAGTCGAAG ACGGGCCGTT

21961 ACGCGCCGCG ATCCACACGC CCTCGACCAG GTCCACCTCA CCGGCCGGCA ACGCCACCGA

22021 AGCCATCGCC CCCCGCCCGG CCAGCCGCCC GGCGATCACC TGGCTGCGCA AGGCCACCAC

22081 GCGGGCGGCG TCCTCAAGGC TGAGGGCTCC GGCCACACAC GCCGCCGCGA TCTCGCCCTG

22141 GGAGTGTCCG ACCACCGCGT CCGGCACGAC CCCATGCGCC TGCCACAGCG CGGCCAGGCT

22201 CACCGCGACC GCCCAGCTGG CCGGCTGGAC CACCTCCACC CGCTCCGCCA CATCCGGCCG

22261 CGCCAACATC TCCCGCACAT CCCAGCCCGT GTGCGGCAAC AACGCCCGCG CACACTCCTC

22321 CATACGAGCC GCGAACACCG CAGAACACGC CATCAACTCC ACACCCATGC CCACCCACTG

22381 AGCACCCTGC CCGGGAAAGA CGAACACCGT ACGCGGCTGA TCCACCGCCA CACCCATCAC

22441 CCGGGCATCG CCCAACAACA CCGCACGGTG ACCGAAGACA GCACGCTCAC GCACCAACCC

22501 CTGCGCGACC GCGGCCACAT CCACACCACC CCCGCGCAGA TACCCCTCCA GCCGCTCCAC

22561 CTGCCCCCGC AGACTCACCT CACTCCGAGC CGACACCGGC AACGGCACCA ACCCATCGAC

22621 AGCCGACTCC CCACGCGACG GCCCGGGAAC ACCCTCAAGG ATCACGTGCG CGTTCGTACC

22681 GCTCACCCCG AAAGCGGAGA CACCGGCCCG GCGCGGACGT CCCGCGTCGG GCCACGCCCG

22741 CGCCTCGGTG AGCAGTTCCA CCGCGCCCTC GGTCCAGTCC ACATGCGACG ACGGCTCGTC

22801 CACATGCAGC GTCTTCGGCG CGATGCCATA CCGCATCGCC ATGACCATCT TGATGACACC

22861 GGCGACACCC GCAGCCCCCT GCGCATGACC GATGTTCGAC TTCAACGAAC CCAGCAGCAG

22921 CGGAACCTCA CGCTCCTGCC CGTACGTCGC CAGAATCGCG TGCGCCTCGA TGGGATCGCC

22981 CAGCGTCGTC CCCGTCCCGT GCGCCTCCAC CACGTCCACG TCGGCGGGGG CGAGCCCCGC

23041 CTTGTGGAGG GCCTGGCGGA TGACGCGCTG CTGGGAGGGG CCGTTGGGTG CGGAGATGCC

23101 GTTGGAGGCG CCGTCCTGGT TGACGGCGGA GGAGCGGACG ACCGCGAGGA CGGTGTGTCC

23161 GTTGCGCTCG GCGTCGGAGA GCTTTTCGAC GACGAGGACG CCGGCCCCCT CGGCGAAACC

23221 GGTGCCGTCC GCCGCGTCAG CGAACGCCTT GCACCGTCCG TCCGGCGCGA CGCCGCCCTG

23281 CCGGGAGAAC TCCACGAAGG TCTGTGGTGA TGCCATCACT GTGACACCAC CGACCAGCGC

23341 CAGCGAGCAC TCCCCGGTCC GCAGCGCCTG CCCGGCCTGG TGCAGCGCGA CCAGCGACGA

23401 CGAACACGCC GTGTCGACCG TGACCGCCGG ACCCTCCATG CCGAAGAAGT ACGACAGCCG

23461 TCCGGCGAGC ACCGCGGGCT GTGTGCTGTA GGCGCCGAAT CCGCCCAGGT CCGCGCCCGT

23521 GCCGTAGCCG TAGTAGAAGC CGCCGACGAA GACGCCGGTG TCGCTGCCGC GCAGGGTGTC

23581 CGGCACGATG CCGGCGTGTT CGAGCGCCTC CCAGGCGATT TCGAGGAGGA TCCGCTGCTG

23641 CGGGTCGAGT GCGGTGGCCT CGCGCGGACT GATGCCGAAG AACGCGGCAT CGAAGTCGGC

23701 GGCGCCCGCG AGTGCGCCGG CCCGCCCGGT GGCGGACTCG GCGGCGGCGT GCAGCGCGGC

23761 CACGTCCCAG CCGCGGTCGG TGGGGAAGTC GCCGATCGCG TCGCGGCCGT CCGCGACGAG

23821 CTGCCACAGC TCTTCCGGTG AGGTGACGCC GCCCGGCAGT CGGCAGGCCA TGCCGACGAC

23881 GGCGAGCGGC TCGTTCGCCG CGGCGCGCAG CGCGGTGTTC TCCCGGCGGA GCTGCGCGTT

23941 GTCCTTGACC GACGTCCGCA GCGCCTCGAT CAGGTCGTTC TCGGCCATCG CCTCATCCCT

-continued

24001 TCAGCACGTG CGCGATGAGC GCGTCTGCGT CCATGTCGTC GAACAGTTCG TCGTCCGGCT

24061 CCGCGGTCGT GGTGCTCGCG GGTGCCTGTG CCGGTGGTTC ACCGCCGTCC GGGGTCCCGT

24121 TGTCGTCCGG GGTCCCGTTG ACGTCCGGGG CCAGGAGGGT CAGCAGATGA CGGGTGAGCG

24181 CGCCGGCGGC GGGATAGTCG AAGACGAGCG TGGCCGGCAG CGGAATGCCG AGGGCCTCGG

24241 AGAGCCGGTT GCGCAGGCCG AGCGCGGTGA GCGAGTCGAC CCCGAGGTCC TTGAACGCCG

24301 TGGTGGCCGT GACCGCCGCC GCGTCGGTGT GGCCCAGCAG GGTGGCGGCG GTGTCGCGGA

24361 CGACGCCGAG CAGCACCTGT TCCCGTTCCT TGTGGGGCAG GTCCGGCAGG CGTTCCAGCA

24421 GGGAGCCGCC GTCGGTCGCG GAGCGCCGGG TCGGGCGCTC GATCGGTCGC CACAGCGGTG

24481 ACGGGTCGCC GGGCCCGGGT GGGGCGGTCG CCACGACCAC CGCTTCCCCG GTGGCGCACG

24541 CGGCGTCGAG GAGGTCGGTC AGCCGGTCCG CCGCGGCGGT GAACGCCACG GCCGGCAGGC

24601 CTTGTGCCCG GCGCAGGTCG GCCAGGGCCT GGAGCGGTCC GGCCGCCTCG CCGGACGGAA

24661 CCGCGAGAAC GAACGCGGTC AGGTCGAGGT CGCGGGTCAG GCGGTGCAGT TCCCAGGCCG

24721 ACTCGGCGGT GCCGTCCGCG TGGACGACCG CGGTCACCGG GGTTTCCGCC ACTGTGCCCG

24781 GCTCGTACCG GATCACTTCG GCGCCGTGTC CGCCGAGGTG TCCGGCGAGT TCCTCCGAAC

24841 CGCCCGCGAG GAGGACGGTG TCGCCGTACG AGGCCGCGGC CGTGGTGGGC GCGGCGGGGA

24901 CGAGGCGGGG CGCTTCGAGG CGCCCGTCGG CCAGGCGCAC GTCCGGTTCG TCGAGGCGGG

24961 AGAGGGCGGC GGCGCGGCGG GGGGTGACCG TCTCGGTGGT CTCCACGAGC ACGAGCCGGC

25021 CCGGTTCCGC GGTGTCGAGC AGTGCGGCCA CGGCACCGGC GACGGGCCCC GCCTCGGCGG

25081 ACACCACCAG CGTGGCGCCG GCGGTCCTCG GGTCGTCCAG TGCGGTACGG ACCTCGTCGG

25141 GACCGGATAC CGGGACGACG ATGACGTCGG GCGTGGCGTC GTCGCCGAGG TCGGTGTACC

25201 GGCGGGCCGT GGTGCCGGGT GCCGCCGGGG CCCGGACGCC GGTCCAGGTG CGCCGGAACA

25261 GCCGCACGTC CCCGTCCGGG CCCGTCGTGG CGGGGGGCCG GGTGATGAGC GAGCCGATCT

25321 GAGCCACCGG CCGTCCCAGT TCGTCGGCGA GGTGCACGCG GGCGCCGCCC TCGCCCTCGC

25381 CGTGGACGAA GGTGACGCGC AGTTTCGTGG CGCCGCTGGT GTGGACACGG ACGCCGGTGA

25441 ACGCGAACGG CAACCGTACC CCCGCGTTCT CGGCGGCCGC GCCGATGCTG CCCGCTTGCA

25501 GCGCGGTGAC GAGCAGCGCC GGGTGCAGTG TGTAGCGGGC GGCGTCCCTG GCGAGGGCGC

25561 CGTCGAGGGC GACTTCGGCG CAGACGGTGT CTCCGTGGCT CCACGCGGCG GACATGCCGC

25621 GGAACTCGGG GCCGAACTCG TATCCCGCGT CGTCGAGTCG CTGGTAGAAG GCCGCGACGT

25681 CGACCGGTTC CGCGTGCTCG GGCGGCCAGG GCCCCGGCGT GGTGGCCGGT TCGGTGGTGG

25741 CGATGCCGGC GAAGCCGGAG GCGTGGCGGG TCCATGTCCG GTCGCCGTCC GTCCGGGCGT

25801 GGACGCGCAC GGCACGGCGT CCGGTGTCGT CGGGCGCGGC GACGGTCACG CGCACCTGGA

25861 CGGCGCCGGT GGCGGGCAGG ACCAGCGGTG TCTCGACGAC CAGTTCGTCG AGCAGGTCGC

25921 AGCCTGCCTC GTCGGCGCCG CGTCCGGCCA ATTCCAGGAA GGCGGGTCCG GGCAGCAGTA

25981 CGGCGCCGTC GACGGAGTGA CCGGCCAGCC ATGGGTGGGT GGCCAGCGAG AACCGGCCGG

26041 TGAGCAGCAC CTCGTCGGAG TCGGGGAGCG CCACCGACGC GGCGAGCAGC GGGTGGTCGA

26101 CGGCGTCGAG TCCGAGGCCG GAAGCGTCCG TGCCGGCCGC GGTCTCGATC CAGTAGCGCT

26161 CATGGTGGAA GGCGTATGTG GGCAGGTCGT GTGCCGTCGC CGTCGCGGGG ACGACCGCCG

26221 CCCAGTCGAC GGGCACGCCG GTTGTGTGCG CCTCGGCCAG CGCGGTGAGC AGCCGGTGGA

26281 CTCCCCCGCC GCGGCGGAGC GTGGCGACGG TCGCGCCGTC GATCGCGGGC AGCAGCACGG

26341 GGTGCGCGCT GACCTCGACG AACACGGTGT CACCCGGCTC GCGGGCAGCG GTCACGGCCG

-continued

26401 TGGCGAAGCC TACGGGGTGG CGCATGTTGC GGAACCAGTA CTCGTCGTCG AGCGGCGCGT

26461 CGATCCAGCG TTCGTCGGCG GTGGAGAACC ACGGGATCTC GGGCGTGCGC GAGGTGGTGT

26521 CCGCGACGAT CCGCTGGAGT TCGTCGTACA GCGGGTCGAC GAACGGGGTG TGGGTCGGGC

26581 AGTCGACGGC GATGCGGCGC ACCCAGACGC CGCGGGGCTC GTAGTCGGCG ATCAGCGTTT

26641 CGACGGCGTC CGGGCGCCCG GCGACGGTCG TGGTGGTGGC GCCGTTGCGG CCCGCGACCC

26701 AGACGCCGTC GATCCGGGCG GCATCCGCCT CGACGTCGGC GGCCGGGAGC GCGACCGAGC

26761 CCATCGCGCC GCGTCCGGCG AGTTCGCGCA GGAGCAGGAG AACGCTGCGC AGCGCGACGA

26821 GGCGGGCACC GTCCTCCAGG GTGAGCGCTC CGGCGACACA GGCCGCGGCG ATCTCGCCCT

26881 GGGAGTGTCC GATGACGGCG TCCGGGCGTA CGCCCGCGGC CTCCCACACG GCGGCCAGCG

26941 ACACCATGAC GGCCCAGCAG ACGGGGTGCA CGACGTCGAC GCGGCGGGTC ACCTCCGGGT

27001 CGTCGAGCAT GGCGATGGGG TCCCAGCCCG TGTGCGGGAT CAGCGCGTCG GCGCATTGGC

27061 GCATCCTGGC GGCGAACACC GGGGAGGCCG CCATCAGTTC GACGCCCATG CCGCGCCACT

27121 GCGGTCCTTG TCCGGGGAAG ACGAAGACGG TGCGCGGCTC GGTGAGCGCC GTGCCGGTGA

27181 CGACGTCGTC GTCGAGCAGC ACGGCGCGGT GCGGGAACGT CGTACGCCTG GCGAGCAGGC

27241 CCGCGGCGAT GGCGCGCGGG TCGTGGCCGG GACGGGCGGC GAGGTGCTCG CGGAGTCGGC

27301 GGACCTGGCC GTCGAGGGCC GTGGCGGTCC GCGCCGAGAC GGGCAGTGGT GTGAGCGGCG

27361 TGGCGATCAG CGGCTCACCG GGCTTCGAGG CCGACGGCTC CTCGGCCGGC GGCTCCCCGG

27421 CCGGGTGGGC TTCCAGCAGG ACGTGGGCGT TGGTGCCGCT GACGCCGAAG GAGGACACAC

27481 CGGCGCGCCG CGGGCGGTCG GTCTCGGGCC AGGGCCGGGC ATCGGTGAGG AGTTCGACGG

27541 CGCCGGCCCT CCAGTCGACG TGCGACGACG GCGTGTCCAC GTGCAGGGTG CGCGGCAGGG

27601 TGCCGTGCCG CATGGCGAGG ACCATCTTGA TGACACCGGC GACACCCGCG GCGGCCTGAG

27661 TGTGGCCGAT GTTGGACTTC AGCGAGCCCA GCAGCACCGG GGTGTCGCGC CCCTGCCCGT

27721 AGGTGGCCAG CACCGCCTGT GCCTCGATGG GATCGCCCAG CCTGGTGCCG GTGCCGTGCG

27781 CCTCCACGGC GTCCACGTCC GCCGGGGTGA GCCCGGCGTT GGCCAGGGCC TGCCGGATCA

27841 CCCGCTCCTG CGAGGGCCCG TTCGGCGCCG ACAACCCGTT GGAAGCACCG TCCTGGTTGA

27901 CCGCCGAACC CCGGACAACC GCCAGCACAC GGTGGCCGTT GCGCTCGGCA TCGGAGAGCC

27961 TCTCGACGAT CAGCACACCG GACCCCTCGG CGAAACCGGT GCCGTCAGCC GCATCCGCGA

28021 ACGCCTTGCA GCGCGCGTCG GGCGCGAGAC CCCGCTGCTG GGAGAACTCG ACGAAGCCGG

28081 ACGGCGAGGC CATCACCGTG ACGCCGCCGA CCAGGGCGAG CGAGCATTCG CCGGAGCGCA

28141 GTGACTGCCC GGCCTGGTGC AGCGCCACCA GCGACGACGA ACACGCCGTG TCGACCGTGA

28201 CCGCCGGACC CTCCAGACCG TAGAAGTACG ACAGCCGACC GGACAGCACA CTGGTCTGGG

28261 TGCCGGTCGC GCCGAAACCG CCCAGGTCGG TGCCGAGTCC GTACCCGTCG GAGAAGGCGC

28321 CCATGAACAC GCCGGTGTCG CTTCCGCGCA GCGACTCCGG GAGGATCCCG GCGTGTTCCA

28381 GCGCCTCCCA CGAGGTCTCC AGGACCAGAC GCTGCTGCGG GTCCATCGCC AGCGCCTCAC

28441 GCGGACTGAT CCCGAAGAAC GCCGCGTCGA AGTCCGCCAC CCCGGCGAGG AAGCCACCAT

28501 GACGCACGGT CGACGTGCCC GGATGATCCG GATCGGGATC GTACAGCCCG TCCACGTCCC

28561 AACCACGGTC CGTCGGAAAC GCCGTGATCC CGTCACCACC CGACTCCAGC AGCCGCCACA

28621 AGTCCTCCGG CGACGCGACC CCACCCGGCA GCCGGCAGGC CATCCCCACG ATCGCCAACG

28681 GCTCGTCCTG CCGGACGGCC GCGGTCGTGG TGCGGGTCGG CGATGCCGTC CGGCCGGACA

28741 GCGCCGCGGT GAGCTTCGCC GCGACGGCGC GCGGCGTCGG GAAGTCGAAG ACCGCGGTGG

-continued

28801 CGGGCAGCCG TACGCCCGTC GCCTCGGTGA AGGCGTTGCG CAGCCGGATC GCCATGAGCG

28861 AGTCGACGCC GAGTTCCTTG AACGTGGCGG TCGCCTCGAC CCGTGCGGCA CCGTCGTGGC

28921 CGAGTACGGC CGCGGTGCAC TGCCGGACGA CGGCGAGCAC GTCCTTTTCG GCGTCCGCGG

28981 CGGAGAGCCG CGCGATCCGG TCGGCGAGGG TGGTGGCGCC GGCCGCCCGG CGCCGCGGCT

29041 CCCGGCGCGG TGCGCGCAGC AGGGGCGAGC TGCCGAGGCC GGCCGGGTCG GCGGCGACCA

29101 GCGCCGGGTC CGAGGACCGC AACGCCGCGT CGAACAGCGT CAGTCCGCCT TCGGCGGTCA

29161 GCGCCGTCAC GCCGTCGCGG CGCATGCGGG CGCCGGTGCC GACCGTCAGC CCGCTCTCCG

29221 GTTCCCACAG GCCCCAGGCC ACGGACAACG CGGGCAGTCC GGCTGCCCGG CGCTGTTCGG

29281 CCAGCGCGTC GAGGAACGCG TTCGCGGCCG CGTAGTTGCC CTGTCCGGGG CTGCCGAGCA

29341 CACCGGCGGC CGACGAGTAG AGGACGAACG CGGCCAGTTC CGTGTCCTGG GTGAGTTCGT

29401 GCAGGTGCCA CGCGGCGTCC ACCTTCGGGC GCAGCACCGT CTCGAGCCGG TCGGGGGTGA

29461 GCGCGGTGAG GACGCCGTCG TCGAGGACGG CCGCGGTGTG CACGACGGCC GTGAGCGGGT

29521 GCGCCGGGTC GATCCCCGCC AGTACGGAGG CGAGTTCGTC CCGGTCGGCG ACGTCGCAGG

29581 CGATCGCCGT GACCTCGGCG CCGGGCACGT CGCTCGCCGT GCCGCTGCGC GACAGCATCA

29641 GCAGCCGGCC CACGCCGTGG CGTTCGACGA GGTGGCGGCT GATGATGCCG GCCAGCGTCC

29701 CGGAGCCACC GGTGACGAGC ACGGTGCCGT CCGGGTCGAG CGCCGGAGCG TCACCCGCCG

29761 GGACCGCCGG GGCCAGACGG CGGGCGTACA CCTGGCCGTC ACGCAGCACC ACCTGGGGCT

29821 CATCGAGCGC GGTGGCCGCT GCGAGCAGCG GCTCGGCGGT GTCCGGGGCG GCGTCGACGA

29881 GGACGATCCG GCCGGGCTGT TCGGCCTGCG CGGTCCGCAC CAGTCCGGCG GCCGCGGCCG

29941 ACGCGAGACC GGGCCCGGTG TGGACGGCCA GGACCGCGTC GGCGTACCGG TCGTCGGTGA

30001 GGAAGCGCTG CACGGCGGTG AGGACGCCGG CGCCCAGTTC GCGGGTGTCG TCGAGCGGGG

30061 CACCGCCGCC GCCGTGCGCG GGGAGGATCA CCACGTCCGG GACCGTCGGG TCGTCGAGGC

30121 GGCCGGTCGT CGCGGTCGTG GGCGGCAGCT CCGGGAGCTC GGCCAGCACC GGGCGCAGCA

30181 GGCCCGGAAC GGCTCCCGTG ATCGTCAGGG GGCGCCTGCG CACGGCGCCG ATGGTGGCGA

30241 CGGGCCCGCC GGTCTCGTCC GCGAGGTGTA CGCCGTCAGC GGTGACGGCG ACGCGTACCG

30301 CCGTGGCGCC GGTGGCGTGG ACGCGGACGT CGTCGAACGC GTACGGAAGG TGGTCCCCTT

30361 CCGCGGCGAG GCGGAGTGCG GCGCCGAGCA GCGCCGGGTG CAGGCCGTAC CGTCCGGCGT

30421 CGGCGAGCTG TCCGTCGGCG AGGGCCACTT CCGCCCAGAC GGCGTCGTCG TCGGCCCAGA

30481 CGGCGCGCGG GCGGGGCAGC GCGGGCCCGT CCGTGTACCC GGCTCGGGCC AGACGGTCGG

30541 CGATGTCGTC GGGGTCCACC GGCCGGGCCG TGGCGGGCGG CCACGTCGAC GGCATCTCCC

30601 GCACGGCCGG GGCCGTCCGC GGGTCGGGGG CGAGGATTCC GTGCGCGTGC TCGGTCCACT

30661 CCCCCGCCGC GTGCCGCGTG TGCACGGTGA CCGCGCGGCG GCCGTCCGCC CCGGGCGCGC

30721 TCACCGTGAC GGAGAGCGCG AGCGCACCGG ACCGCGGCAG CGTGAGGGGG GTGTCCACGG

30781 TGAACGTGTC GAGGGCGCCG CAGCCGGCTT CGTCGCCCGC CCGGATCGCC AGATCCAGGA

30841 GGGCCGCGGC GGGCAGCACC GCGAGGCCGT GCAGGGAGTG CGCCAGCGGA TCGGCGGCGT

30901 CGACCCGGCC GGTGAGCACC AGGTCGCCGG TGCCGGGCAG GGTGACCGCC GCGGTCAGCG

30961 CCGGGTGCGC GACCGGCGTC TGTCCGGCCG GGGCCGCGTC GCCCGCGGTC TGGGTGCCGA

31021 GCCAGTAGCG GACCCGCTCG AACGGGTACG TCGGCGGGTG CGAGGCGCGT GCCGGCGCGG

31081 GGTCGATGAC CTTCGGCCAG TCAGCCGTGA CGCCGTCGGT GTGCAGCCGG GCGAGCGCGG

31141 TCAGGGCGGA TCGCGGTTCG TCGTCGGCGT GCAGCATCGG GATGCCGTCG ACGAGTCGGG

-continued

31201 TCAGGCTCCG GTCCGGGCCG ATCTCCAGGA GCACCGCCCC GTCGTGCGCG GCGACCTGTT

31261 CCCCGAACCG GACGGTGTCG CGGACCTGTC GTACCCAGTA CTCCGGCGTG GTGCAGGCGG

31321 CGCCCGCGGC CATCGGGATC CTCGGCTCGT GGTACGTCAG GCTCTCCGCG ACCTTCGGGA

31381 ACTCCTCGAG CATCGGCTCC ATCCGCGCCG AGTGGAACGC CTGGCTGGTC CGCAGGCGGG

31441 TGAACCGGCC GAGCCGGGCC GCGACGTCGA GCACCGCCTC CTCGTCACCG GAGAGCACGA

31501 TCGACGCGGG CCCGTTGACC GCGGCGATCT CCACGCCGTC CCGCAGCAGC GGCAGCGCGT

31561 CCCGTTCCGA CGCGATCACG GCGGCCATCG CCCCGCCGGA CGGCAGCGCC TGCATCAGGC

31621 GGGCCCGTGC GGACACCAGC CTGCACGCGT CCTCCAGGGA CCAGACGCCG GCGACGTACG

31681 CGGCGGCCAG CTCGCCGATC GAATGGCCCA CGAAGGCGTC CGGGCGTACG CCCCACGCCT

31741 CGAGCTGTGC GCCGAGTGCG ACCTGGAGCG CGAACACCGC GGGCTGGGCG TACCCGGTGT

31801 CGTGGAGGTC GAGCCCGGCG GGCACGTCGA GGGCGTCCAG CACCTCGCGG CGAGTGCGGG

31861 CGAAGACGTC GTAGGCGGCG GCCAGTCCGT CGCCCATGCC GGGACGTTGT GAGCCCTGTC

31921 CGGAGAAGAG CCACACGAGG CGGCGGTCCG GTTCTGCGGC GCCGGTGACC GTGTCGGTGC

31981 CGATCAGCGC GGCCCGGTGC GCGAAGGCCG TGCGGGCGAG CAGGGCCGCG GCCACCGCGC

32041 GCTCGTCCTC CTCGCCGGTG GCGAGGTGGG CGCGCAGGCG GTGTACCTGT GCGTCGAGTG

32101 CCTGCGGGGT GCGTGCCGAG AGCAGCAGGG GCAGCGGTCC GGTGTCGGGT GCCGGGGCGG

32161 GTTCGGGGGC CGGTCGGGGG TGGCTTTCGA GGATGATGTG AGCGTTGGTG CCGCTAACGC

32221 CGAAGGAGGA CACCCCGGCG CGCCGTGGGC GGTCGGTTTC GGGCCAGGGG CGGGCGTCGG

32281 TGAGGAGTTC GACGGCGCCG GCCGTCCAGT CGACGTGCGA GGACGGCGTG TCCACGTGCA

32341 GGGTGCGCGG CAGGGTGCCG TGCCGCATGG CGAGGACCAT CTTGATGACA CCGGCGACGC

32401 CCGCGGCGGC CTGAGTGTGG CCGATGTTGG ACTTCAGCGA GCCCAGCAGC ACCGGGGTGT

32461 CGCGATGCTG CCCGTAGGTG GCCAGTACCG CCTGCGCCTC GATGGGGTCG CCCAGCCTGG

32521 TCCCGGTGCC ATGCGCCTCG ACAGCGTCCA CATCCGCCGG GGTGAGCCCG GCGTTGGCCA

32581 GCGCCTGCCG GATCACCCGC TCCTGCGACG GCCCGTTCGG CGCCGACAAC CCGTTGGAAG

32641 CACCGTCCTG GTTGACCGCC GAACCACGCA CGACCGCCAG GACATTGTGG CCGTGCCGCT

32701 CGGCGTCGGA GAGCCTCTCG ACGATCAGCA CACCGGATCC CTCGGCGAAA CCGGTGCCAT

32761 CAGCCGCATC CGCGAACGCC TTGCAGCGGC CGTCCGGGGA GACGCCCCGC TGCTGGGAGA

38281 AGTCCACGAA GCCGGACGGC GAGGCCATCA CCGTGACGCC GCCGACCACG GCCAGCGAGC

32881 ACTCCCCCGA GCGCAGCGAC TGCCCGGCCT GGTGCAGCGC CACCAGCGAC GACGAACACG

32941 CCGTGTCCAC CGTGACCGCC GGACCCTCCA AACCGTAGAA GTACGACAGC CGACCGGACA

33001 GCACACTGGT CTGGGTGCTG GTGGCACCGA AACCGCCGCG GTCGGCTCCA GTGCCGTACC

33061 CGTAGAAGTA GCCGCCCATG AACACGCCGG TGTCGCTTCC GCGCAGCGAC TCCGGGAGGA

33121 TCCCGGCGTG TTCCAGCGCC TCCCACGAGG TCTCCAGGAC CAGACGCTGC TGCGGGTCCA

33181 TCGCCAGCGC CTCACGCGGA CTGATCCCGA AGAACGCCGC GTCGAAGTCC GCCACCCCGG

33241 CGAGGAAGCC ACCATGACGC ACGGTCGACG TGCCCGGATG ATCCGGATCG GGATCGTACA

33301 GCCCGTCCAC GTCCCAACCA CCGTCCGTCG GAAACGCCGT GATCCCGTCA CCACCCGACT

33361 CCAGCAGCCG CCACAAGTCC TCCGGCGACG CGACCCCACC CGGCAGCCGG CAGGCCATCC

33421 CCACGATCGC CAACGGCTCG TCCTGCCGGA CGGCCGCGGT CGGGGTACGC CGCCGGGTGG

33481 TGGCCCGCGC GCCGGCCAGT TCGTCCAGGT GGGCGGCGAG CGCCTGCGCC GTGGGGTGGT

33541 CGAAGACGAG CGTAGCGGGC AGCGTCAGGC CCGTCGCGTC GGCCAGCCGG TTGCGCAGTT

-continued

33601 CGACGCCGGT CAGCGAGTGC AAGCCCACTT CCCTGAACGC GCGCGCGGGT GCGATGGCGT

33661 GGGCGTCGCG GTGGCCGAGC ACCGCGGCAG CGCTGGTACG GACGAGGTCG AGCATGTCGC

33721 GCGCGGCCGC AGGTGCGGAC GTGCGCCGGA CGGCCGGCAC GAGGGTGCGT AGGACCGGCG

33781 GGACCCGGTC GGACGCGGCG ACGGCGGCGA GGTCGAGCCG GATCGGCACG AGCGCGGGCC

33841 GGTCGGTGTG CAGGGCCGCG TCGAACAGGG CGAGCCCCTG TGCGGCCGTC ATCGGGGTCA

33901 TGCCGTTGCG GGCGATGCGG GCCAGGTCGG TGGCGGTCAG CCGCCCGCCC ATCCCGTCCG

33961 CCGCGTCCCA CAGTCCCCAG GCGAGCGAGA CGGCGGGCAG CCCCTGGTGG TGCCGGTGGC

34021 GGGCGAGCGC GTCGAGGAAC GCGTTGCCGG TCGCGTAGTT GGCCTGACCC GCGCCGCCGA

34081 ACGTGGCGGA TATGGACGAG TACAGGACGA ACGCGGCCAG GTCGAGATCG CGCGTCAGCT

34141 CGTGCAGGTG CCAGGCGACG TCCGCCTTGA CCCGCAGCAC GGCGTCCCAC TGCTCCGGCC

34201 GCATGGTCGT CACGGCCGCG TCGTCGACGA TCCCGGCCAT GTGCACGACG GCGCGCAGCC

34261 GCTGGGCGAC GTCGGCGACG ACTGCGGCCA GCTCGTCGCG GTCGACGACG TCGGCGGGCA

34321 CGTACCGCAC GCGGTCGTCC TCCGGCGTGT CGCCGGGCCG GCCGTTGCGG GACACCACGA

34381 CGACCTCGGC GGCCTCGTGC ACGGTGAGCA GGTGGTCCAC GAGGAGGCGG CCGAGCCCGC

34441 CGGTGCCGCC GGTGACGAGG ACGGTCCCGC CGGTCAGCGG GGAGGTTCCG GTGGCCGCGG

34501 CGACACGGCG CAGACGGGCC GCACGCGCTG TGCCGTCGGC GACCCGGACG TGCGGCTCGT

34561 CGCCGGCGGC GAGCCCGGCC GCTATGGCGG CGGGCGTGAT CTCGTCCGCT TCGATCAGGG

34621 CGACGCGGCC GGGATGCTCC GTCTCCGCCG TCCGGACCAG GCCGCCGAGC GCTTCCTGCG

34681 CGGGATCGCC GGTACGGGTG GCCACGATGA GCCGGGATCG CGCCCAGCGC GGCTCGGCGA

34741 GCCAGGTCTG CACGGTGGTG AGCAGGTCGC GGCCCAGCTC CCGGGTCCGG GCGCCGGGCG

34801 AGGTGCCCGG GTCGCCGGGT TCCACGGCCA GGACCACGAC CGGGGGGTGC TCGCCGTCGG

34861 GCACGTCGGC GAGGTACGTC CAGTCGGGGA CCCCTGACGC GGGCACGGGC ACCCAGGCGA

34921 TCTCGAACAG CGCCTCGGCA TCGGGGTCGG CGGCCCGCAC GGTCAGGCTG TCGACGTCAA

34981 GGACCGGTGA GCCGTGCTCG TCCGTGGCGA CGATGCGGAC CATGTCGGGG CCGACGCGTT

35041 CCAGCAGCAC GCGCAGCGCG GTCGCGGCGC GCGCGTGGAT CCTCACGCCG GACCAGGAGA

35101 ACGCCAGCCG GCGCCGCTCC GGGTCCGTGA AGACCGTCCC GAGGGCGTGC AGGGCCGCGT

35161 CGAGCAGCAC GGGGTGCAGC CCGTACCGGG CGTCGGTGAG CTGTTCGGCG AGGCGGACCG

35221 ACGCGTAGGC GCGGCCCTCC CCCGTCCACA TCGCGGTCAT GGCCCGGAAC GCGGGCCCGT

35281 ACGAGAGCGG CAGCGCGTCG TAGAAGCCGG TCAGGTCGGC CGGGTCGGCG TCGGCGGGCG

35341 GCCAGTCCAC GGGCTCCGCC GGACCGCCAG TGTCCACGCT CAGCGCTCCG GTCGCACTGA

35401 GCCGCCAGGG GCCCGTGCCG GTACGGCTGT GCAGACTCAC CGACCCCCGT CCGGACACCT

35461 CGGTTCCGAC GGTGGCCTGG ATCTCCGTGT CGCCGTCGCC GTCGACCACC ACCGGCGCGA

35521 GCAGGGTCAG CTCCGCGATC TCCGGCGTGC CGAGCCGGGC TCCCGCTTCG GCGAGCAGTT

35581 CCACGAGCGC CGAGCCGGGC ACGATGACCC GGCCGTCCAC CTCGTGGTCG GCGAGCCAGG

35641 GCTGACGGCG TACCGAGACA CCGCGGTGGC CAGCGCGCCC TCGCCGTCGG GCGAGGTCGA

35701 CCCACGAGCC GAGCAGCGGG TGGCCGGACG TTCCCGCCGG TTCCGCGTCG ATCCAGTAGC

35761 GGTCACGGCG GAACGGGTAC GTGGGCAGCG GCACCACCCG ACGCGTCGCG AACGACCAGG

35821 TGACGGGCAC GCCCCGGACC CAGAGCGCGG CGAGCGACCG AGTGAAGCGG TCCAGGCCGC

35881 CCTCGCCTCG CCGCAGTGTG CCGGTGACGA CCGTATGCGC ATGCCCGGCG AGCGTGTCCT

35941 CCAGTGCGGT GGTGAGCACG GGATGCGCGC TGACCTCGAC GAACGCGCGG TATCCGCGGT

-continued

36001 CCGCCAGGTG GCCGGTCGCG GCGGCGAACC GAACGGTGCG GCGCAGGTTG TCGTACCAGT

36061 AGGCGGCGTC CGCGGGCCGG TCCAGCCACG CCTCGTCCAC GGTGGAGAAG AACGGGACGT

36121 CCGGCGTGCG CGGAGTGATG CCGGCGAGAG CGTCGAGCAG CGCGCCGCGG ATCGTTTCGA

36181 CATGCGCGGT GTGCGACGCG TAGTCGACGG CGATCCGGCG GGCGCGGGGG GTGGCGGCCA

36241 GCAGCTCCTC CACGGCGTCG GCCGCACCGG CGACAACGAT CGACGCGGGT CCGTTGACCG

36301 CGGCGACCTC CAGGCGCCCG GCCCACACGG CGGCGTCGAA GTCGGCGGGC GGCACCGAGA

36361 CCATGCCGCC CTGCCCGGCC AGTTCGGTGG CGACGAGTCG GCTGCGCACC GCGACGACCT

36421 TCGCGGCGTC GTCCAGGGTG AGCACCCCGG CGACGCAGGC CGCGGCGACT TCGCCCTGGG

36481 AGTGGCCGAC GACCGCGGCC GGGGCGACCC CGTGCGCACG CCACAGCTCC GCCAGCGCCA

36541 CCATCACCGC GAACGACGCG GGCTGCACGA CATCGACCCG GTCGAACGCG GGCGCTCCGG

36601 GCCGCTGGGC GATGACGTCC AGCAGGTCCC ATCCGGTGTG CGGGGCGAGC GCCGTGGCGC

36661 ACTCGCGGAG CCGCCGGGCG AACACGGGCT CGGTGGCGAG CAGTTCGGCA CCCATGCCGG

36721 CCCACTGGGA GCCCTGCCCG GGGAACGCGA ACACGACACG TGTGTCGGTG ACGTCGGCGG

36781 TTCCCGTCAC GGCCCCCGGC ACTTCGGCAC CACGGGCGAA CGCCTCCGCC TCTCGGGCCG

36841 GCACGACCGC CCGGTGGCGC ATGGCCGTCC GGGTGGTGGC GAGCGAGTGG CCGACCGCGG

36901 CCGCGGCGCC AGTGAGCGGG GCCAGCTGTC CCGCGACGTC CCGCAGTCCC TCCGGGGTCC

36961 GGGCCGACAT CGGCCAGACC ACGTCCTCGG GCACCGGCTC GGCTTCGGGT GCGGACACGG

37021 GTGCGGGCGC GGCGGGGGGC CCGGCCTCCA GGACGACATG GGCGTTGGTG CCGCTGATGC

37081 CGAACGACGA GACACCCGCA CGCCGGGCGC GCCCGGTGAC CGGCCACGGC TCACTGCGGT

37141 GCAGCAGCCG GATGTCGCCG TCCCAGTCGA CGTGCCGGGA CGGCTCGTCG ACGTGCAGCG

37201 TGCGCGGCAG GACGCCGTGC CGCATCGCCA TGACCATCTT GATGACGCCG GCGACGCCGG

37261 CCGCGGCCTG GGTGTGGCCG ATGTTCGACT TGAGCGAGCC GATCAGCAGC GGATGCACGC

37321 GTTCGCGCCC GTAGGCCACT TGCAGGGCCT GGGCCTCGAC GGGGTCGCCG AGACGGGTGC

37381 CGGTGCCGTG TGCCTCCACG GCGTCGACGT CACCCGGCGC CAGGCCGGCG TCGGGGAGCG

37441 CACGCTGGAT GACGCGCTGC TGCGCAGGCC CGTTCGGGGC GGACAGCCCG TTCGACGCGC

37501 CCTCGGAGTT GACCGCGGAG CCGCGCACCA GCGCCAGCAC GGGGTGGCCG TGGCGGGTGG

37561 CGTCGGAGAG CCGCTCCAGC ACCAGGACAC CGGCGCCCTC GGCGAAGCTC GTGCCGTCCG

37621 CGGTGTCCGC GAAGGCCTTG GCACGGCCGT CGGGGGCGAG CCCGCGCTGC CGGGAGAACT

37681 CGACGAACCC GGTCGTCGTC GCCATCACCG TGACACCGCC GACCAGGGCG AGCGAGCACT

37741 CCCCCGAGCG CAGCGACCGC GCGGCCTGGT TCAGCGCCAC CAGCGACGAC GAACACGCCG

37801 TGTCGACGGT GACCGACGGG CCCTCCAGAC CGAAGTAGTA CGAGAGCCGC CCGGAGAGAA

37861 CCCTGGTCGG CGTGCCGGTC GCCCCGAAAC CGCCCAGGTC CACGCCCGCG CCGTAGCCCT

37921 GGGTGAACGC GCCCATGAAT ACGCCGGTGT CGCTGCCGCG GACGCTTTCG GGCAGGATGC

37981 CCGCTCGTTC GAACGCCTCC CACGACGCTT CGAGGACCAG ACGCTGCTGC GGGTCCATCG

38041 CCAGCGCCTC ACGCGGGCTG ATCCCGAAGA ACGCGGCGTC GAAGTCGGCG GCGCCGGTGA

38101 GGAAGCCGCC GTGACGCACG GAAACCTTGC CGACCGCGTC GGGGTTCGGG TCGTAGAGCG

38161 CGGCGAGGTC CCAGCCGCGG TCGGCCGGGA ACTCGGTGAT CGCGTCCCCG CCGGAGTCGA

38221 CCAGCCGCCA CAGGTCCTCC GGTGACCGCA CGCCACCGGG CATCCGGCAC GCCATGGCCA

38281 CGATCGCCAG CGGCTCGTTC CCCGCCACCG TCGGTGCGGG CACTGTCGCC GCCGGAGCGG

38341 CAGGGGCCGG CTCACCCCGC CGTTCCTCAT CCAGGCGGGC GGCGAGCGCG GCCGGTGTCG

-continued

38401 GGTGGTCGAA GACGGCCGTC GCGGAGAGCC GTACCCCCGT CGTCTCGGCG AGGCTGTTGC

38461 GCAACCGGAC ACCGCTGAGC GAGTCGATGC CGAGGTCCTT GAACGCCGTC GTGGGCGTGA

38521 TCTCGGAGGC GTCGGCGTGG CCGAGCACGG CGGCCGTGGC CGCACACACG ATGGCCAGCA

38581 GGTCACGATC GCGGTCGCGG TCGCGGTCGC GGTTGTCCTC CGCACGGGCG GCGATGCGGC

38641 GCTCGGTCCG CTGCCGGACG GGCTCGGTGG GAATCGCCGC GACCATGAAC GGCACCTCCG

38701 CGGCGAGGCT CGCGTCGATG AAGTGGGTGC CCTCGGCCTC GGTGAGCGGC CGGAACCCGT

38761 CGCGCACCCG CTCCCGGTCG GCGTCGTCAA GTTGTCCGGT GAGGGTGCTG GTGGTGTGCC

38821 ACATGCCCCA GGCGATGGAG GTGGCGGGTT GGCCGAGGGT GTGGCGGTGC GTGGCGAGGG

38881 CGTCGAGGAA GGCGTTGGCG GCGGCGTAGT TTCCTTGTCC GGGGCTGCCG AGGACGGCGG

38941 CGGCGCTGGA GTAGAGGACG AAGTGGGTGA GGGGTTGGTT TTGGGTGAGG TGGTGCAGGT

39001 GCCAGGCGGC GTTGGCTTTG GGGTGGAGGA CGGTGGTGAG GCGGTCGGGG GTGAGGGCGT

39061 CGAGGATGCC GTCGTCGAGG GTGGCGGCGG TGTGGAAGAC GGCGGTGAGG GGTTGGGGGA

39121 TGTGGGCGAG GGTGGTGGCG AGTTGGTGGG GGTCGCCGAC GTCGCAGGGG AGGTGGGTGC

39181 CGGGGGTGGT GTCGGGGGGT GGGGTGCGGG AGAGGAGGTA GGTGTGGGGG TGGTTCAGGT

39241 GGCGGGCGAG GATGCCGGCG AGGGTGCCGG AGCCGCCGGT GATGATGATG GCGTGTTCGG

39301 GGTTGAGGGG GGTGGTGGTG GGTGGGGTGG TGGTGTGGAG GGGGGTGAGG TGGGGTCGGT

39361 GGAGGGTGTG GTGGGTGAGG CGGAGGTGGG GGTGGTCGAG GGTGGCGAGT TGGGCCAGGG

39421 GGAGGGGAGT GTGGGGGTGG TCGGTTTCGA TGAGGCGGAT GCGGTGGGGC TGTTCGTTCT

39481 GGGCGGTGCG GGTGAGGCCG GTGACGGTGG CGCCGGCGGG GTCGGTGGTG GTGTGGACGA

39541 TGAGGGTCTG GTCGGTGGTG GTGAGGTGGT GTTGCAGGGC GGTCAGGACG CGGGTGGCGC

39601 GGGTGTGGGC GCGGGTGGGT ATGTCCTCGG GGTCGTCGGG GTGGGCGGCG GTGATCAGGA

39661 CGTGTCCCTC GGGCAGGTCA CCGTCGTAGA CCGCCTCGGC GACCGCGAGC CACGCCAACC

39721 GGAGCGGGTT CGGCCCCGAC GGGGTGTCGG CCCGCTCCCT CAGCACCAGC GAGTCCACCG

39781 ACACGACAGG ACGGCCATCC GGGTCGGCCA CGCGCACGGC GACGCCGGCC TCCCCCCGGG

39841 TGAGGGCGAC GCGCACCGCG GCGGCCCCGG TGGCGTTCAG GCGCACGCCC GTCGAGGAGA

39901 ACGGCAGCTC GATCCCGCCG CCCGCGTCGA GGCGCCCGGC GTGCAGGGCC GCGTCGAGCA

39961 GTGCCGGATG CACACCGAAA CCGTCCGCCT CGGCGGCCTG CTCGTCGGGC AGCGCCACCT

40021 CGGCATACAC GGTGTCACCA TCACGCCAGG CAGCCCGCAA CCCCTGGAAC GCCGACCCGT

40081 ACTCATAACC GGCATCCCGC AGTTCGTCAT AGAACCCCGA GACGTCGACG GCCGCGGCCG

40141 TGGCCGGCGG CCACTGCGAG AACGGCTCAC CGGAAGCGTT GGAGGTATCC GGGGTGTCGG

40201 GGGTCAGGGT GCCGCTGGCG TGCCGGGTCC AGCTGCCCGT GCCCTCGGTA CGCGCGTGGA

40261 CGGTCACCGG CCGCCGTCCG GCCTCATCGG CCCCTTCCAC GGTCACCGAC ACATCCACCG

40321 CTGCGGTCAC CGGCACCACG AGCGGGGATT CGATGACCAG TTCATCCACC ACCCCGCAAC

40381 CGGTCTCGTC ACCGGCCCGG ATGACCAGCT CCACAAACGC CGTACCCGGC AGCAGAACCG

40441 TGCCCCGCAC CGCGTGATCA GCCAGCCAGG GATGCGTACG CAATGAGATC CGGCCGGTGA

40501 GAACAACACC ACCACCGTCG TCGGCGGGCA GTGCTGTGAC GGCGGCCAGC ATCGGATGCG

40561 CCGCCCCGGT CAGCCCGGCC GCGGACAGGT CGGTGGCACC GGCCGCCTCC AGCCAGTACC

40621 GCCTGTGCTC GCCTGTGCTC GAACGCGTAG GTGGGCAGAT CCAGCAGCCG GGTTCGACCA

40681 CCGTGCCCCA GTCCACCCCC GCACCCAGAG TCCACGCCTG CGCCAACGCC CCCAGCCACC

40741 GCTCCCAGCC ACCGTCACCA GTCCGCAACG ACGCCACCGT GCGGGCCTGT TCCATCGCCG

-continued

40801 GCAGCAGCAC CGGATGGGCA CTGCACTCCA CGAACACCGA CCCGTCCAGC TCCGCCACCG

40861 CCGCATCCAG CGCGACAGGG CGACGCAGGT TCCGGTACCA GTACCCCTCA TCCACCGGCT

40921 CGGTCACCCA GGCGCTGTCC ACGGTCGACC ACCACGCCAC CGACCCGGTC CCGCCGGAAA

40981 TTCCCTTCAG TACCTCAGCG AGTTCGTCCT CGATGGCCTC CACGTGAGGC GTGTGGGAGG

41041 CGTAGTCGAC CGCGATACGA CGCACCCGCA CCCCATCAGC CTCATACCGC GCCACCACCT

41101 CCTCCACCGC CGACGGGTCC CCCGCCACCA CCGTCGAAGC CGGACCATTA CGCGCCGCGA

41161 TCCACACACC CTCGACCAGA CCCACCTCAC CGGCCGGCAA CGCCACCGAA GCCATCGCCC

41221 CCCGGCCGGC CAGCCGCGCC GCGATCACCC GACTGCGCAA CGCCACCACG CGGGCGGCGT

41281 CCTCCAGGCT GAGGGCTCCG GCCACACACG CCGCCGCGAT CTCCCCCTGC GAGTGTCCGA

41341 CCACAGCGTC CGGCACGACC CCATGCGCCT GCCACAGCGC GGCCAGGCTC ACCGCGACCG

41401 CCCAGCTGGC CGGCTGGACC ACCTCCACCC GCTCCGCCAC ATCCGACCGC GACAACATCT

41461 CCCGCACATC CCAGCCCGTG TGCGGCAACA ACGCCCGCGC ACACTCCTCC ATACGAGCCG

41521 CGAACACCGC GGAACGGTCC ATGAGTTCCA CGCCCATGCC CACCCACTGG GCACCCTGCC

41581 CGGGGAAGAC GAACACCGTA CGCGGCTGAT CCACCGCCAC ACCCATCACC CGGGCATCAC

41641 CCAGCAGCAC CGCACGGTGA CCGAAGACAG CACGCTCACG CACCAACCCC TGCGCGACCG

41701 CGGCCACATC CACCCCACCC CCGCGCAGAT ACCCCTCCAG CCGCTCCACC TGCCCCCGCA

41761 GACTCACCTC ACCACGAGCC GACACCGGCA ACGGCACCAA CCCATCACCA CCCGACTCCA

41821 CACGCGACGG CCCAGGAACA CCCTCCAGGA TCACGTGCGC GTTCGTACCG CTCACCCCGA

41881 ACGACGACAC ACCCGCATGC GGTGCCCGAT CCGACTCGGG CCACGGCCTC GCCTCGGTGA

41941 GCAGCTCCAC CGCACCGGCC GACCAGTCCA CATGCGACGA CGGCTCGTCC ACGTGCAGCG

42001 TCTTCGGCGC GATCCCATGC CGCATCGCCA TGACCATCTT GATGACACCG GCGACACCCG

42061 CAGCCGCCTG CGCATGACCG ATGTTCGACT TGACCGAACC GAGGTAGAGC GGCGTGTCGC

42121 GGTCCTGCCC GTAGGCCGCG AGGACGGCCT GCGCCTCGAT CGGGTCGCCC AGCCGCGTGC

42181 CGGTGCCGTG CGCCTCCACC ACGTCCACAT CGGCGGCGCG CAGTCCGGCG TTGACCAACG

42241 CCTGCCGGAT CACGCGCTGC TGGGCGACGC CGTTGGGGGC GGACAGTCCG TTGGAGGCAC

42301 CGTCCTGGTT CACCGCCGAG CCGCGGACGA CCGCGAGAAC GGTGTGCCCG TTGCGCTCGG

42361 CGTCGGAGAG CCGCTCCAGC ACGAGAACGC CGACGCCCTC GGCGAAGCCG GTCCCGTCCG

42421 CCGCGTCGGC GAACGCCTTG CACCGTCCGT CCGGGGAGAG TCCGCGCTGC CGGGAGAACT

42481 CCACGAGCTC TGCGGTGTTC GCCATGACGG TGACACCGCC GACCAGCGCC AGGGAGCACT

42541 CCCCGGCCCG CAGTGCCTGT GCCGCCTGGT GCAGGGCGAC CAGCGACGAC GAGCACGCCG

42601 TGTCGACCGT GACCGCCGGG CCCTGAAGTC CGTACACGTA CGAGAGCCGC CCGGACAGGA

42661 CGCTCCTCTG CGTCGCCGTG ACACCGAGCC CGCCCAGGTC CCGGCCGACG CCGTAGCCCT

42721 GGTTGAACGC GCCCATGAAC ACGCCGGTGT CGCTCTCCCG GAGCCTGTCC GGCACGATGC

42781 CGGCGTTCTC GAACGCCTCC CAGGAGGTCT CCAGGATCAG GCGCTGCTGG GGGTCCATCG

42841 CCAGCGCCTC GTTCGGACTG ATGCCGAAGA ACGCGGCGTC GAACCCGGCG CCGGCCAGGA

42901 ATCCGCCGTG GCGTGTCGTG GAGCGGCCGG CCGCGTCCGG GTCCGGGTCG TACAGCGCGT

42961 CGACGTCCCA GCCCCGGTCG GTGGGGAACT CGGTGATCGC CTCGGTACCG GCGGCGACGA

43021 GCCGCCACAG GTCCTCCGGC GAGGCGACCC CGCCGGGCAG TCGGCACGCC ATGCCGACGA

43081 TCGCGACGGG GTCGCCGGAG CCGAGGGTCT GGGCGGTCGC GGGTGCCGCT GTCGCGGAGC

43141 CGGCGAGGTG GGCGGCGGAC GCACGCGGAG TGGGGTGGTC GAACGCGGTT CACGCGGGCA

-continued

43201 CCCGCAGACC CGTCCGCGCG GCGACGGTGT TGGTGAACTC GACGGTGGTG AGCGAGTCGA

43261 GGCCGTTCTC GCGGAACGTG CGGTCCGGGG AGCAGTGTCC GGCGCCCGGC AGGCCCAGGA

43321 CGGTGGCGAC GCTGTCGCGG ACCAGGTCGA GCAGTACGTC CTCCCGGCCC GCACGGGCCG

43381 CGGCGAGGCG GTTCGCCCAC TCCTGTTCCG TGGCGTCGGG CTCGGCCGGT CCGGTCAGTG

43441 CGGTGAGGAT CGGCGGCGTG GCGCCCGCCA TCGTCGCGGC CCGCGCCCCG GCGGAACCGG

43501 TCCGGGCCAC GATGTACGAG CCGCCGCCCG CGATGGCCTT CTCGATCAGG TCGCCGGTGA

43561 GCGCCGGCCG TTCGATGCCG GGCAGCGCGC GGACGGTGAC GGTGGGGAGT CCCTCCGCGG

43621 CCCGTGGCCG GGTGTGGGCG TCGGCGCCGG CCGGGCCGTC GAGCAGGACG TGCACGAGCG

43681 CGCCGGGGTT CGCGGCTTCC TCGGCTGCGG TGGTCACGTG GGTGAGGCCG GTCTCGTCGC

43741 GGAGCAGGCC GGCGACGGTG TCGGCGTCCT CCCCGGTGAC CAGGACCGGC GCGTCCGGGC

43801 CGATCGGAGG CGGCACGGTG AGGACCATCT TGCCGGTGTG CCGGGCGTGG CTCATCCACG

43861 CGAACGCGTC CCGCGCACGG CGGATGTCCC ACGGCTGCAC CGGCAGCGGG CACAGCTCAC

43921 CGCGGTCGAA CAGGTCGAGG AGCAGTTCGA GGATCTCCCG CAGGCGCGCG GGATCCACGT

43981 CGGCCAGGTC GAACGGCTGC TGGGCGGCGT GGCGGATGTC GGTCTTGCCC ATCTCGACGA

44041 ACCGGCCGCC CGGTGCGAGC AGGCCGATGG ACGCGTCGAG GAGTTCACCG GTGAGCGAGT

44101 TGAGCACGAC GTCGACCGGC GGGAAGGTGT CGGCGAACGC GGCGCTGCGG GAGTTCGCCA

44161 CATGGTCGGT GTCGAAGCCG TCGGCGTGCA GCAGGTGTTG TTTGGCGGGA CTGGCGGTGG

44221 CGTACACCTC GGCGCCGAGG TGGCGGGCGA TCCGGGTCGC CGCCATGCCG ACACCGCCCG

44281 TCGCGGCGTG GACCAGGACC TTCTGGCCGG GTCGCAGCTC GCCCGCGTCG ACGAGGCCGT

44341 ACCAGGCGGT GGCGAACACG ATGGGCACGG ACGCGGCGAT GGGGAACGAC CATCCCCGTG

44401 GGATCCGTGC GACCAGCCGC CGGTCCGCGA CCACGCTGCG CCGGAACGCG TCCTGCACGA

44461 GACCGAACAG GCGGTCGCCG GGGGCCAGGT CGTCGACGCC GGGTCCGACT TCGGTCACGA

44521 TGCCCGCGGC CTCCCCGCCC ATCTCGCCCT CGCCCGGGTA GGTGCCGAGC GCGATCAGCA

44581 CGTCGCGGAA GTTCAGCCCC GCGGCGCGGA CGTCGATGCG GACCTCGCCG GCGGCCAGGG

44641 GCGCGGCGGC ACGTCGAGCG GGGCGACGAC GAGGTCGCGG AGCGTTCCGG AGGCGGGCGG

44701 GCGCAGCGCC CACTGGCGCG GTCGGCAGGG GGGTGGTGTC CGCGCGTACC AGCCGGGGCA

44761 CGTAGGCCAC GCCGGCCCGC AGCGCGATCT GGGGTTCGCC GAGCGAGGCC GCGGCGGGGA

44821 CGAGGTCGTC ATCGCCGTCC GTGTCCACCA GCACGAACGA TCCGGGTTCG GCCGCCTGGC

44881 GGCGCAGCGC CTCGTCCCAG AGCCGGGCCT GGTCCGCGTC CGGGATCTCG GCCGGGCCGA

44941 CGCCCACCGC GCGGCGGGTG ACGACCGTCC GGCGGGGTGA CGGGGTGCCG GGCAGGTCGC

45001 GCCGCTCCCA GACCAGTTCG CACAGCGTGG CCTCGCCACT GCCGGTGGCG ACCAGATGGG

45061 CCGGCAGCCC CGCGAGCCGC TCTCTCTGGA CCTTGCCCGA CGCGGTGCGG GGGATCGTGG

45121 TGACGTGCCA GATCTCGTCG GGCACCTTGA AGTAGGCGAG CCGGCGGCGG CACTCGGCGA

45181 GGATCGCCTC GGCGGGGACG CGGGGGCCGT CGGAAACGAC GTAGAGCACG GGTATGTCGC

45241 CGAGGACGGG GTGCGGGCGG CCCGCCGCGG CGGCGTCCCG GACACCGGCC ACCTCCTGGG

45301 CGACGGTCTC GATCTCCCGG GGGTGGATGT TCTCCCCGCC GCGGATGATC AGCTCCTTGA

45361 CCCGGCCGGT GATCGTCACG TGTCCGGTCT CGGCCTGACG TGCGAGGTCC CCGGTGCGGT

45421 ACCAGCCGTC CACGAGCACC TGGGCGGTCG CCTCCGGCTG GGCGTGGTAG CCGAGCATGA

45481 GGCTCGGCCC GCTCGCCCAC AGCTCGCCCT CCTCGCCGGG TGCCACGTCG GCGCCGGACA

45541 CCGGGTCGAC GAACCGCAGC GACAGGCCCG GCACGGGCAG CCCGCACGAG CCGGGAACCC

-continued

45601 GCGCATCCTC CAGGGTGTTG GCGGTGAGCG AGCCGGTCGT CTCGGTGCAG CCGTACGTGT

45661 CGAGCAGGGG CACGCCGAAC GTCGCCTCGA AATCCCTGGT GAGCGACGCC GGCGAGGTGG

45721 ATCCGGCGAC CAGCGCCACG CGCAGCGCGC GAGCCCGCGG CTCGCCGGAC ACGGCGCCGA

45781 GGAGGTAGCG GTACATCGTC GGCACGCCGA CGAGCACGGT GCTGGAGTGT TCGGCCAGGG

45841 CGTCGAGGAC GTCACGCGCG ACGAAGCCGC CCAGGATACG GGCGGACGCG CCGACCGTGA

45901 GGACGGCGAG CAGGCAGAGG TGGTGGCCGA GGCTGTGGAA CAGCGGGGCG GGCCAGAGCA

45961 GTTCGTCGTC CTCGGTCAGC CGCCAGGACG GCACGTCGCA GTGCATCGCG GACCACAGGC

46021 CGCTGCGCTG TGCGGAAACC ACGCCCTTGG GACGGCCGGT GGTGCCGGAG GTGTAGAGCA

46081 TCCAGGCGGG TTCGTCCAGG CCGAGGTCGT CGCGGGGCGG GCACGGCGGC TCGGTCCCGG

46141 CGAGGTCCTC GTAGGAGACG CAGTCCGGTG CCCGGCGCCC GACGAGCACG ACGGTGGCGT

46201 CGGTGCCGGT GCGGCGCACC TGGTCGAGGT GGGTTTCGTC GGTGACCAGC ACGGTCGCGC

46261 CGGAGTCCGT CAGGAAGTGG GCGAGTTCGG CGTCGGCGGC GTCCGGGTTG AGCGGGACGG

46321 CGACGGCGGC GGCGCGGGCG GCGGCGAGGT AGACCTCGAT GGTCTCGATC CGGTTGCCGA

46381 GCAGCATCGC GACCCGGTCG CCGCGGTCGA CGCCGGACGC GGCGAGGTGT CCGGCGAGCC

46441 GGCCGGCCCG GAGCCGGAGT TGCGTGTACG TCACGGCGCG TTGGGAATCC GTGTAGGCGA

46501 TCCGGTCGCC GCGTCGCTCG GCATGGATGC GGAGCAATTC GTGCAACGGC CGGATTGGTT

46561 CCACACGCGC CATGGAAACA CCTTTCTCTC GACCAACCGC ACAACAGCAC GGAACCGGCC

46621 ACGAGTAGAC GCCGGCGACG CTAGCAGCGT TTTCCGGACC GCCACCCCCT GAAGATCCCC

46681 CTACCGTGGC CGGCCTCCCC GGACGCTCAT CTAGGGGGTT GCACGCATAC CGCCGTCCGT

46741 AATTGCCTTC CTGATGACCG ATGCCGGACG CCAGGGAAGG GTGGAGGCGT TGTCCATATC

46801 TGTCACGGCG CCGTATTGCC GCTTCGAGAA GACCGGATCA CCGGACCTCG AGGGTGACGA

46861 GACGGTGCTC GGCCTGATCG AGCACGGCAC CGGGGACACC GACGTGTCGC TGGTGGACGG

46921 TGCTCCCCGG ACCGCCGTGC ACACCACGAC CCGTGACGAC GAGGCGTTCA CCGAGGTCTG

46981 GCACGCACAG CGCCCTGTCG AGTCCGGCAT GGACAACGGC ATCGCCTGGG CCCGCACCGA

47041 CGCGTACCTG TTCGGTGTCG TGCGCACCGG CGAGAGCGGC AGGTACGCCG ATGCCACCGC

47101 GCCCCTCTAC ACGAACGTCT TCCAGCTCAC CCGGTCGCTG GGGTATCCCC TGCTCGCCCG

47161 GACCTGGAAC TACGTCAGCG GTATCAACAC GACGAACGCG GACGGGCTGG AGGTGTACCG

47221 GGACTTCTGC GTGGGCCGCG CCCAGGCGCT CGACGAGGGC GGGATCGACC CGGCCACCAT

47281 GCCCGCGGCC ACCGGTATCG GCGCCCACGG GGGCGGCATC ACCTGCGTGT TCCTCGCCGC

47341 CCGGGGCGGA GTGCGGATCA ACATCGAGAA CCCCGCCGTC CTCACGGCCC ACCACTACCC

47401 GACGACGTAC GGTCCGCGGC CCCCGGTCTT CGCACGGGCC ACCTGGCTGG GCCCGCCGGA

47461 GGGGGGCCGG CTGTTCATCT CCGCGACGGC CGGCATCCTC GGACACCGAA CGGTGCACCA

47521 CGGTGATGTG ACCGGCCAGT GCGAGGTCGC CCTCGACAAC ATGGCCCGGG TCATCGGCGC

47581 GGAGAACCTG CGGCGCCACG GCGTCCAGCG GGGGCACGTC CTCGCCGACG TGGACCACCT

47641 CAAGGTCTAC GTCCGCCGCC GCGAGGATCT CGATACGGTC CGCCGGGTCT GCGCCGCACG

47701 CCTGTCGAGC ACCGCGGCCG TCGCCCTTTT GCACACCGAC ATAGCCCGCG AGGATCTGCT

47761 CGTCGAAATC GAAGGCATGG TGGCGTGACA ATACCCGGTA AAAGGCCCGC GACGCTGCGC

47821 CTCGGCGGAT CCGCGAAGAG AAAGAAGAGC GTCACCGCAC AGCGCGGCAG CCCGGTCCTT

47881 TCGTCCTTCG CACAGCGGCG GATCTGGTTT CTCCAGCAAT TGGACCCGGA GAGCAACGCC

47941 TATAATCTCC CGCTCGTGCA ACGCCTGCGC GGTCTATTGG ACGCGCCGGC CCTGGAGCGT

-continued

48001 GCGCTGGCGC TCGTCGTCGC GCGCCACGAG GCGTTGCGGA CGGTGTTCGA CACCGCCGAC

48061 GGCGAGCCCC TCCAGCGGGT GCTTCCCGCC CCGGAACACC TCCTGCGCCA CGCGCGGGCG

48121 GGCAGCGAGG AGGACGCCGC CCGGCTCGTC CGCGACGAGA TCGCCGCGCC GTTCGACCTC

48181 GCCACCGGGC CGTTGATCAG GGCCCTGCTG ATCCGCCTCG GTGACGACGA CCACGTTCTC

48241 GCGGTGACCG TGCACCATGT CGCCGGCGAC GGCTGGTCGT TCGGGCTCCT CCAACATGAA

48301 CTCGCAGCCC ACTACACGGC GCTGCGCGAC ACTGCCCGCC CTGCCGAACT GCCGCCGTTG

48361 CCGGTGCAGT ACGCCGACTT CGCCGCCTGG GAGCGGCGCG AACTCACCGG CGCCGGACTG

48421 GACAGGCGTC TGGCCTACTG GCGCGAGCAA CTCCGGGGCG CCCCGGCGCG GCTCGCCCTC

48481 CCCACCGACC GTCCCCGCCC GCCGGTCGCC GACGCGGACG CGGGCATGGC CGAGTGGCGG

48541 CCGCCGGCCG CGCTGGCCAC CGCGGTCCTC ACGCTCGCGC GCGACTCCGG TGCGTCCGTG

48601 TTCATGACCC TGCTGGCGGC CTTCCAAGCG CTCCTCGCCC GGCAGGCGGG CACGCGGGAC

48661 GTGCTGGTCG GCACGCCCGT GGCGAACCGT ACGCGGGCGG CGTACGAGGG CCTGATCGGC

48721 ATGTTCGTCA ACACGCTCGC GCTGCGCGGC GACCTCTCGG GCGATCCGTC GTTCCGGGAA

48781 CTCCTCGACC GCTGCCGGGC CACGACCACG GACGCGTTCG CCCACGCCGA CCTGCCGTTC

48841 GAGAACGTCA TCGAACTCGT CGCACCGGAA CGCGACCTGT CGGTCAACCC GGTCGTCCAG

48901 GTGCTGTTGC AGGTGCTGCG GCGCGACGCG GCGACGGCCG CGCTGCCCGG CATCGCGGCC

48961 GAACCGTTCC GCACCGGACG CTGGTTCACC CGCTTCGACC TCGAATTCCA TGTGTACGAG

49021 GAGCCGGGTG GCGCGCTGAC CGGCGAACTG CTCTACAGCC GTGCGCTGTT CGACGAGCCA

49081 CGGATCACGG GGTTGCTGGA GGAGTTCACG GCGGTGCTTC AGGCGGTCAC CGCCGACCCG

49141 GACGTACGGC TGTCGCGGCT GCCGGCCGGC GACGCGACGG CGGCAGCGCC CGTGGTGCCC

49201 TCGAACGACA CGGCGCGGGA CCTGCCCGTC GACACGCTGC CGGGCCTGCT GGCCCGGTAC

49261 GCCGCACGCA CCCCCGGCGC CGTGGCCGTC ACCGACCCGC ACATCTCCCT CACCTACGCG

49321 CAGCTGGACC GGCGGGCGAA CCCCCTCGCG CACCTGCTCC GCGCGCGCGG CACCGCCACC

49381 GGCGACCTGG TCGGGATCTG CGCCGATCGC GGCGCCGACC TCATCGTCGG CATCGTGGGC

49441 ATCCTCAAGG CGGGCGCCGC TTATCTGCCG CTGGACCCCG AACATCCTCC GGAGCGCACG

49501 GCGTTCGTGC TGGCCGACGC GCAGCTGACC ACGGTGGTGG CGCACGAGGT CTACCGTTCC

49561 CGGTTCCCCG ATGTGCCGCA CGTGGTGGCG TTGGACGACC CGGAGCTGGA CCGGCAGCCG

49621 GACGACACGG CGCCGGACGT CGAGCTGGAC CGGGACAGCC TCGCCTACGC GATCTACACG

49681 TCCGGGTCGA CCGGCAGGCC GAAGGCCGTG CTCATGCCGG GTGTCAGCGC CGTCAACCTG

49741 CTGCTCTGGC AGGAGCGCAC GATGGGCCGC GAGCCGGCCA GCCGCACCGT CGAGTTCGTG

49801 ACGCCCACGT TCGACTACTC GGTGCAGGAG ATCTTTTCCG CGCTGCTGGG CGGCACGCTC

49861 GTCATCCCGC CGGACGAGGT GCGGTTCGAC CCGCCGGGAC TCGCCCGGTG GATGGACGAA

49921 CAGGCGATTA CCCGGATCTA CGCGCCGACG GCCGTACTGC GCGCGCTGAT CCAGCACGTC

49981 GATCCGCACA GCGACCAGCT CGCCGCCCTG CGGCACCTGT GCCAGGGCGG CGAGGCGCTG

50041 ATCCTCGACG CGCGGTTGCG CGAGCTGTGC CGGCACCGGC CCCACCTGCG CGTGCACAAT

50101 CACTACGGTC CGGCCGAAAG CCAGCTCATC ACCGGGTACA CGCTGCCCGC CGACCCCGAC

50161 GCGTGGCCCG CCACCGCACC GATCGGCCCG CCGATCGACA ACACCCGCAT CCATCTGCTC

50221 GACGAGGCGA TGCGGCCGGT TCCGGACGGT ATGCCGGGGC AGCTCTGCGT CGCCGGCGTC

50281 GGCCTCGCCC GTGGGTACCT GGCCCGTCCC GAGCTGACCG CCGAGCGCTG GGTGCCGGGA

50341 GATGCGGTCG GCGAGGAGCG CATGTACCTC ACCGGCGACC TGGCCCGCCG CGCGCCCGAC

-continued

50401 GGCGACCTGG AATTCCTCGG CCGGATCGAC GACCAGGTCA AGATCCGCGG CATCCGCGTC

50461 GAACCGGGTG AGATCGAGAG CCTGCTCGCC GAGGACGCCC GCGTCACGCA GGCGGCGGTG

50521 TCCGTGCGCG AGGACCGGCG GGGCGAGAAG TTCCTGGCCG CGTACGTCGT ACCGGTGGCC

50581 GGCCGGCACG GCGACGACTT CGCCGCGTCG CTGCGCGCGG GACTGCCCGC CCGGCTGCCC

50641 GCCGCGCTCG TGCCCTCCGC CGTCGTCCTG GTGGAGCGAC TGCCGAGGAC CACGAGCGGC

50701 AAGGTGGACC GGCGCGCGCT GCCCGACCCG GAGCCGGGCC CGGCGTCGAC CGGGGCGGTT

50761 ACGCCCCGCA CCGATGCCGA GCGGACGGTG TGCCGGATCT TCCAGGAGGT GCTCGACGTC

50821 CCGCGGGTCG GTGCCGACGA CGACTTCTTC ACGCTCGGCG GGCACTCCCT GCTCGCCACC

50881 CGGGTCGTCT CCCGCATCCG CGCCGAGCTG GGTGCCGATG TCCCGCTGCG TACGCTCTTC

50941 GACGGGCGGA CGCCCGCCGC GCTCGCCCGT GCGGCGGACG AGGCCGGCCC GGCCGCCCTG

51001 CCCCCGATCG CGCCCTCCGC GGAGAACGGG CCGGCCCCCC TCACCGCGGC ACAGGAACAG

51061 ATGCTGCACT CGCACGGCTC GCTGCTCGCC GCGCCCTCCT ACACGGTCGC CCCGTACGGG

51121 TTCCGGCTGC GCGGGCCACT CGACCGCGAA GCGCTCGACG CGGCACTGAC CCGGATCGCC

51181 GCGCGCCACG AGCCGCTGCG GACCGGGTTC CGCGATCGGG AACAGGTCGT CCGGCCGCCC

51241 GCTCCGGTGC GCGCCGAGGT GGTTCCGGTG CCGGTCGGCG ACGTCGACGC CGCGGTCCGG

51301 GTCGCCCACC GGGAGCTGAC CCGGCCGTTC GACCTCGTGA ACGGGTCGTT GCTGCGTGCC

51361 GTGCTGCTGC CGCTGGGCGC CGAGGATCAC GTGCTGCTGC TGATGCTGCA CCACCTCGCC

51421 GGTGACGGAT GGTCCTTCGA CCTCCTGGTC CGGGAGTTGT CGGGGACGCA ACCGGACCTT

51481 CCGGTGTCCT ACACGGACGT GGCCCGGTGG GAACGGAGTC CGGCCGTGAT CGCGGCCAGG

51541 GAGAACGACC GGGCCTACTG GCGCCGGCGG CTGGGGGGCG CCACCGCGCC GGAGCTGCCC

51601 GCGGTCCGGC CCGGCGGGGC ACCGACCGGG CGGGCGTTCC TGTGGACGCT CAAGGACACC

51661 GCCGTCCTGG CGGCACGCCG GGTCGCGGAC GCCCACGACG CGACGTTGCA CGAAACCGTG

51721 CTCGGCGCCT TCGCCCTGGT CGTGGCGGAG ACCGCCGACA CCGACGACGT GCTCGTCGCG

51781 ACGCCGTTCG CGGACCGGGG GTACGCCGGG ACCGACCACC TCATCGGCTT CTTCGCGAAG

51841 GTCCTCGCGC TGCGCCTCGA CCTCGGCGGC ACGCCGTCGT TCCCCGAGGT GCTGCGCCGG

51901 GTGCACACCG CGATGGTGGG CGCGCACGCC CACCAGGCGG TGCCCTACTC CGCGCTGCGC

51961 GCCGAGGACC CCGCGCTGCC GCCGGCCCCC GTGTCGTTCC AGCTCATCAG CGCGCTCAGC

52021 GCGGAACTGC GGCTGCCCGG CATGCACACC GAGCCGTTCC CCGTCGTCGC CGAGACCGTC

52081 GACGAGATGA CCGGCGAACT GTCGATCAAC CTCTTCGACG ACGGTCGCAC CGTCTCCGGC

52141 GCGGTGGTCC ACGATGCCGC GCTGCTCGAC CGTGCCACCG TCGACGATTT GCTCACCCGG

52201 GTGGAGGCGA CGCTGCGTGC CGCCGCGGGC GACCTCACCG TACGCGTCAC CGGTTACGTG

52261 GAAAGCGAGT AGCCATGCCC GAGCAGGACA AGACAGTCGA GTACCTTCGC TGGGCGACCG

52321 CGGAACTCCA GAAGACCCGT GCGGAACTCG CCGCGCACAG CGAGCCGTTC GCGATCGTGG

52381 GGATGGCCTG CCGGCTGCCC GGCGGGGTCG CGTCGCCGGA GGACCTGTGG CAGTTGCTCG

52441 AGTCCGGTGG CGACGGCATC ACCGCGTTCC CCACGGACCG GGGCTGGGAG ACCACCGCCG

52501 ACGGTCGCGG CGGCTTCCTC ACCGGGGCGG CCGGCTTCGA CGCGGCGTTC TTCGGCATCA

52561 GCCCGCGCGA GGCGCTGGCG ATGGACCCGC AGCAGCGCCT GGCCCTGGAG ACCTCGTGGG

52621 AGGCGTTCGA GCACGCGGGC ATCGATCCGC AGACGCTGCG GGGCAGTGAC ACGGGGGTGT

52681 TCCTCGGCGC GTTCTTCCAG GGGTACGGCA TCGGCGCCGA CTTCGACGGT TACGGCACCA

52741 CGAGCATTCA CACGAGCGTG CTCTCCGGCC GCCTCGCGTA CTTCTACGGT CTGGAGGGTC

-continued

52801 CGGCGGTCAC GGTCGACACG GCGTGTTCGT CGTCGCTGGT GGCGCTGCAC CAGGCCGGGC

52861 AGTCGCTGCG CTCCGGCGAA TGCTCGCTCG CCCTGGTCGG CGGCGTCACG GTGATGGCCT

52921 CGCCCGCGGG GTTCGCGGAC TTCTCCGAGC AGGGCGGCCT GGCCCCCGAC GCGCGCTGCA

52981 AGGCCTTCGC GGAAGCGGCT GACGGCACCG GTTTCGCCGA GGGGTCCGGC GTCCTGATCG

53041 TCGAGAAGCT CTCCGACGCC GAGCGCAACG GCCACCGCGT GCTGGCGGTC GTCCGGGGTT

53101 CCGCCGTCAA CCAGGACGGT GCCTCCAACG GGCTGTCCGC GCCGAACGGG CCGTCGCAGG

53161 AGCGGGTGAT CCGGCAGGCC CTGGCCAACG CCGGACTCAC CCCGGCGGAC GTGGACGCCG

53221 TCGAGGCCCA CGGCACCGGC ACCAGGCTGG GCGACCCCAT CGAGGCACAG GCCGTGCTGG

53281 CCACCTACGG GCAGGGGCGC GACACCCCTG TGCTGCTGGG CTCGCTGAAG TCCAACATCG

53341 GCCACACCCA GGCCGCCGCG GGCGTCGCCG GTGTCATCAA GATGGTCCTC GCCATGCGGC

53401 ACGGCACCCT GCCCCGCACC CTGCACGTGG ACACGCCGTC CTCGCACGTC GACTGGACGG

53461 CCGGCGCCGT CGAACTCCTC ACCGACGCCC GGCCCTGGCC CGAAACCGAC CGCCCACGGC

53521 GCGCCGGTGT CTCCTCCTTC GGCGTCAGCG GCACCAACGC CCACATCATC CTCGAAAGCC

53581 ACCCCCGACC GGCCCCCGAA CCCGCCCCGG CACCCGACAC CGGACCGCTG CCGCTGCTGC

53641 TCTCGGCCCG CACCCCGCAG GCACTCGACG CACAGGTACA CCGCCTGCGC GCGTTCCTCG

53701 ACGACAACCC CGGCGCGGAC CGGGTCGCCC TCGCGCAGAC ACTCGCCCGG CGCACCCAGT

53761 TCGAGCACCG CGCCGTGCTG CTCGGCGACA CGCTCATCAC CGTGAGCCCG AACGCCGGCC

53821 GCGGACCGGT GGTCTTCGTC TACTCGGGGC AAAGCACGCT GCACCCGCAC ACCGGGCGGC

53881 AACTCGCGTC CACCTACCCC GTGTTCGCCG AAGCGTGGCG CGAGGCCCTC GACCACCTCG

53941 ACCCCACCCA GGGCCCGGCC ACCCACTTCGC CCCACCAGAC CGCGCTCACC GCGCTCCTGC

54001 GGTCCTGGGG CATCACCCCG CACGCGGTCA TCGGCCACTC CCTCGGTGAG ATCACCGCCG

54061 CGCACGCCGC CGGTGTCCTG TCCCTGAGGG ACGCGGGCGC GCTCCTCACC ACCCGCACCC

54121 GCCTGATGGA CCAACTGCCG TCGGGCGGCG CGATGGTCAC CGTCCTGACC AGCGAGGAAA

54181 AGGCACGCCA GGTGCTGCGG CCGGGCGTGG AGATCGCCGC CGTCAACGGC CCCCACTCCC

54241 TCGTGCTGTC CGGGGACGAG GAAGCCGTAC TCGAAGCCGC CCGGCAGCTC GGCATCCACC

54301 ACCGCCTGCC GACCCGCCAC GCCGGCCACT CCGAGCGCAT GCAGCCACTC GTCGCCCCCC

54361 TCCTCGACGT CGCCCGGACC CTGACGTACC ACCAGCCCCA CACCGCCATC CCCGGCGACC

54421 CCACCACCGC CCAATACTGG GCGCACCAGG TCCGCGACCA AGTACGTTTC CAGGCGCACA

54481 CCGAGCAGTA CCCGGGCGCG ACGTTCCTCG AGATCGGCCC CAACCAGGAC CTCTCGCCGC

54541 TCGTCGACGG CGTTGCCGCC CAGACCGGTA CGCCCGACGA GGTGCGGGCG CTGCACACCG

54601 CGCTCGCGCA GCTCCACGTC CGCGGCGTCG CGATCGACTG GACGCTCGTC CTCGGCGGGG

54661 ACCGCGCGCC CGTCACGCTG CCCACGTATC CGTTCCAGCA CAAGGACTAC TGGCTGCGGC

54721 CCACCTCCCG GGCCGATGTG ACCGGCGCGG GGCAGGAGCA GGTGGCGCAC CCGCTGCTCG

54781 GCGCCGCGGT CGCGCTGCCC GGCACGGGCG GAGTCGTCCT GACCGGCCGC CTGTCGCTGG

54841 CCTCCCATCC GTGGCTCGGC GAGCACGCGG TCGACGGCAC CGTGCTCCTG CCCGGCGCGG

54901 CCTTCCTCGA ACTCGCGGCG CGCGCCGGCG ACGAGGTCGG CTGCGACCTG CTGCACGAAC

54961 TCGTCATCGA GACGCCGCTC GTGCTGCCCG CGACCGGCGG TGTGGCGGTC TCCGTCGAGA

55021 TCGCCGAACC CGACGACACG GGGCGGCGGG CGGTCACCGT CCACGCGCGG GCCGACGGCT

55081 CGGGCCTGTG GACCCGACAC GCCGGCGGAT TCCTCGGCAC GGCACCGGCA CCGGCCACGG

55141 CCACGGACCC GGCACCCTGG CCGCCCGCGG AAGCCGGACC GGTCGACGTC GCCGACGTCT

-continued

55201 ACGACCGGTT CGAGGACATC GGGTACTCCT ACGGACCGGG CTTCCGGGGG CTGCGGGCCG

55261 CCTGGCGCGC CGGCGACACC GTGTACGCCG AGGTCGCGCT CCCCGACGAG CAGAGCGCCG

55321 ACGCCGCCCG TTTCACGCTG CACCCCGCGC TGCTCGACGC CGCGTTCCAG GCCGGCGCGC

55381 TGGCCGCGCT CGACGCACCC GGCGGGGCGG CCCGACTGCC GTTCTCGTTC CAGGACGTCC

55441 GCATCCACGC GGCCGGGGCG ACGCGGCTGC GGGTCACGGT CGGCCGCGAC GGCGAGCGCA

55501 GCACCGTCCG CATGACCGGC CCGGACGGGC AGCTGGTGGC CGTGGTCGGT GCCGTGCTGT

55561 CGCGCCCGTA CGCGGAAGGC TCCGGTGACG GCCTGCTGCG CCCGGTCTGG ACCGAGCTGC

55621 CGATGCCCGT CCCGTCCGCG GACGATCCGC GCGTGGAGGT CCTCGGCGCC GACCCGGGCG

55681 ACGGCGACGT TCCGGCGGCC ACCCGGGAGC TGACCGCCCG CGTCCTCGGC GCGCTCCAGC

55741 GCCACCTGTC CGCCGCCGAG GACACCACCT TGGTGGTACG GACCGGCACC GGCCCGGCCG

55801 CTGCCGCCGC CGCGGGTCTG GTCCGCTCGG CGCAGGCGGA GAACCCCGGC CGCGTCGTGC

55861 TCGTCGAGGC GTCCCCGGAC ACCTCGGTGG AGCTGCTCGC CGCGTGCGCC GCGCTGGACG

55921 AACCGCAGCT GGCCGTCCGG GACGGCGTGC TCTTCGCGCC GCGGCTGGTC CGGATGTCCG

55981 ACCCCGCGCA CGGCCCGCTG TCCCTGCCGG ACGGCGACTG GCTGCTCACC CGGTCCGCCT

56041 CCGGCACGTT GCACGACGTC GCGCTCATAG CCGACGACAC GCCCCGGCGG GCGCTCGAAG

56101 CCGGCGAGGT CCGCATCGAC GTCCGCGCGG CCGGACTGAA CTTCCGCGAT GTGCTGATCG

56161 CGCTCGGGAC GTACACCGGG GCCACGGCCA TGGGCGGCGA GGCCGCGGGC GTCGTGGTGG

56221 AGACCGGGCC CGGCGTGGAC GACCTGTCCC CCGGCGACCG GGTGTTCGGC CTGACCCGGG

56281 GCGGCATCGG CCCGACGGCC GTCACCGACC GGCGCTGGCT GGCCCGGATC CCCGACGGCT

56341 GGAGCTTCAC CACGGCGGCG TCCGTCCCGA TCGTGTTCGC GACCGCGTGG TACGGCCTGG

56401 TCGACCTCGG CACACTGCGC GCCGGCGAGA AGGTCCTCGT CCACGCGGCC ACCGGCGGTG

56461 TCGGCATGGC CGCCGCACAG ATCGCCCGCC ACCTGGGCGC CGAGCTCTAC GCCACCGCCA

56521 GTACCGGCAA GCAGCACGTC CTGCGCGCCG CCGGGCTGCC CGACACGCAC ATCGCCGACT

56581 CTCGGACGAC CGCGTTCCGG ACCGCTTTCC CGCGCATGGA CGTCGTCCTG AACGCGCTGA

56641 CCGGCGAGTT CATCGACGCG TCGCTCGACC TGCTGGACGC CGACGGCCGG TTCGTCGAGA

56701 TGGGCCGCAC CGAGCTGCGC GACCCGGCCG CGATCGTCCC CGCCTACCTG CCGTTCGACC

56761 TGCTGGACGC GGGCGCCGAC CGCATCGGCG AGATCCTGGG CGAACTGCTC CGGCTGTTCG

56821 ACGCGGGCGC GCTGGAGCCG CTGCCGGTCC GTGCCTGGGA CGTCCGGCAG GCACGCGACG

56881 CGCTCGGCTG GATGAGCCGC GCCCGCCACA TCGGCAAGAA CGTCCTGACG CTGCCCCGGC

56941 CGCTCGACCC GGAGGGCGCC GTCGTCCTCA CCGGCGGCTC CGGCACGCTC GCCGGCATCC

57001 TCGCCCGCCA CCTGCGCGAA CGGCATGTCT ACCTGCTGTC CCGGACGGCA CCGCCCGAGG

57061 GGACGCCCGG CGTCCACCTG CCCTGCGACG TCGGTGACCG GGACCAGCTG GCGGCGGCCC

57121 TGGAGCGGGT GGACCGGCCG ATCACCGCCG TGGTGCACCT CGCCGGTGCG CTGGACGACG

57181 GCACCGTCGC GTCGCTCACC CCCGAGCGTT TCGACACGGT GCTGCGCCCG AAGGCCGACG

57241 GCGCCTGGTA CCTGCACGAG CTGACGAAGG AGCAGGACCT CGCCGCGTTC GTGCTCTACT

57301 CGTCGGCCGC CGGCGTGCTC GGCAACGCCG GCCAGGGCAA CTACGTCGCC GCGAACGCGT

57361 TCCTCGACGC GCTCGCCGAG CTGCGCCACG GTTCCGGGCT GCCGGCCCTC TCCATCGCCT

57421 GGGGGCTCTG GGAGGACGTG AGCGGGCTCA CCGCGGCGCT CGGCGAAGCC GACCGGGACC

57481 GGATGCGGCG CAGCGGTTTC CGGGCCATCA CCGCGCAACA GGGCATGCAC CTGTACGAGG

57541 CGGCCGGCCG CACCGGAAGT CCCGTGGTGG TCGCGGCGGC GCTCGACGAC GCGCCGGACG

-continued

57601 TCCCGCTGCT GCGCGGCCTG CGGCGGACGA CCGTCCGGCG GGCCGCCGTC CGGGAGTGTT

57661 CGTCCGCCGA CCGGCTCGCC GCGCTGACCG GCGACGAGCT CGCCGAAGCG CTGCTGACGC

57721 TCGTCCGGGA GAGCACCGCC GCCGTGCTCG GCCACGTGGG TGGCGAGGAC ATCCCCGCGA

57781 CGGCGGCGTT CAAGGACCTC GGCATCGACT CGCTCACCGC GGTCCAGCTG CGCAACGCCC

57841 TCACCGAGGC GACCGGTGTG CGGCTGAACG CCACGGCGGT CTTCGACTTC CCGACCCCGC

57901 ACGTGCTCGC CGGGAAGCTC GGCGACGAAC TGACCGGCAC CCGCGCGCCC GTCGTGCCCC

57961 GGACCGCGGC CACGGCCGGT GCGCACGACG AGCCGCTGGC GATCGTGGGA ATGGCCTGCC

58021 GGCTGCCCGG CGGGGTCGCG TCACCCGAGG AGCTGTGGCA CCTCGTGGCA TCCGGCACCG

58081 ACGCCATCAC GGAGTTCCCG ACGGACCGCG GCTGGGACGT CGACGCGATC TACGACCCGG

58141 ACCCCGACGC GATCGGCAAG ACCTTCGTCC GGCACGGTGG CTTCCTCACC GGCGCGACAG

58201 GCTTCGACGC GGCGTTCTTC GGCATCAGCC CGCGCGAGGC CCTCGCGATG GACCCGCAGC

58261 AGCGGGTGCT CCTGGAGACG TCGTGGGAGG CGTTCGAAAG CGCCGGCATC ACCCCGGACT

58321 CGACCCGCGG CAGCGACACC GGCGTGTTCG TCGGCGCCTT CTCCTACGGT TACGGCACCG

58381 GTGCGGACAC CGACGGCTTC GGCGCGACCG GCTCGCAGAC CAGTGTGCTC TCCGGCCGGC

58441 TGTCGTACTT CTACGGTCTG GAGGGTCCGG CGGTCACGGT CGACACGGCG TGTTCGTCGT

58501 CGCTGGTGGC GCTGCACCAG GCCGGGCAGT CGCTGCGCTC CGGCGAATGC TCGCTCGCCC

58561 TGGTCGGCGG CGTCACGGTG ATGGCGTCTC CCGGCGGCTT CGTGGAGTTC TCCCGGCAGC

58621 GCGGCCTCGC GCCGGACGGC CGGGCGAAGG CGTTCGGCGC GGGTGCGGAC GGCACGAGCT

58681 TCGCCGAGGG TGCCGGTGTG CTGATCGTCG AGAGGCTCTC CGACGCCGAA CGCAACGGTC

58741 ACACCGTCCT GGCGGTCGTC CGTGGTTCGG CGGTCAACCA GGATGGTGCC TCCAACGGGC

58801 TGTCGGCGCC GAACGGGCCG TCGCAGGAGC GGGTGATCCG GCAGGCCCTG GCCAACGCCG

58861 GGCTCACCCC GGCGGACGTG GACGCCGTCG AGGCCCACGG CACCGGCACC AGGCTGGGCG

58921 ACCCCATCGA GGCACAGGCG GTACTGGCCA CCTACGGACA GGAGCGCGCC ACCCCCCTGC

58981 TGCTGGGCTC GCTGAAGTCC AACATCGGCC ACGCCCAGGC CGCGTCCGGC GTCGCCGGCA

59041 TCATCAAGAT GGTGCAGGCC CTCCGGCACG GGGAGCTGCC GCCGACGCTG CACGCCGACG

59101 AGCCGTCGCC GCACGTCGAC TGGACGGCCG GCGCCGTCGA ACTGCTGACG TCGGCCCGGC

59161 CGTGGCCCGA GACCGACCGG CCACGGCGTG CCGCCGTCTC CTCGTTCGGG GTGAGCGGCA

59221 CCAACGCCCA CGTCATCCTG GAGGCCGGAC CGGTAACGGA GACGCCCGCG GCATCGCCTT

59281 CCGGTGACCT TCCCCTGCTG GTGTCGGCAC GCTCACCGGA AGCGCTCGAC GAGCAGATCC

59341 GCCGACTGCG CGCCTACCTG GACACCACCC CGGACGTCGA CCGGGTGGCC GTGGCACAGA

59401 CGCTGGCCCG GCGCACACAC TTCGCCCACC GCGCCGTGCT GCTCGGTGAC ACCGTCATCA

59461 CCACACCCCC CGCGGACCGG CCCGACGAAC TCGTCTTCGT CTACTCCGGC CAGGGCACCC

59521 AGCATCCCGC GATGGGCGAG CAGCTCGCCG CCGCCCATCC CGTGTTCGCC GACGCCTGGC

59581 ATGAAGCGCT CCGCCGCCTT GACAACCCCG ACCCCCACGA CCCCACGCAC AGCCAGCATG

59641 TGCTCTTCGC CCACCAGGCG GCGTTCACCG CCCTCCTGCG GTCCTGGGGC ATCACCCCGC

59701 ACGCGGTCAT CGGCCACTCG CTGGGCGAGA TCACCGCGGC GCACGCCGCC GGCATCCTGT

59761 CGCTGGACGA CGCGTGCACC CTGATCACCA CGCGCGCCCG CCTCATGCAC ACGCTCCCGC

59821 CACCCGGTGC CATGGTCACC GTACTGACCA GCGAAGAGAA GGCACGCCAG GCGTTGCGGC

59881 CGGGCGTGGA GATCGCCGCC GTCAACGGGC CCCACTCCAT CGTGCTGTCC GGGGACGAGG

59941 ACGCCGTGCT CACCGTCGCC GGGCAGCTCG GCATCCACCA CCGCCTGCCC GCCCCGCACG

-continued

60001 CCGGGCACTC CGCGCACATG GAGCCCGTGG CCGCCGAGCT GCTCGCCACC ACCCGCGGGC

60061 TCCGCTACCA CCCTCCCCAC ACCTCCATTC CGAACGACCC CACCACCGCT GAGTACTGGG

60121 CCGAGCAGGT CCGCAAGCCC GTGCTGTTCC ACGCCCACGC GCAGCAGTAC CCGGACGCCG

60181 TGTTCGTGGA GATCGGCCCC GCCCAGGACC TCTCCCCGCT CGTCGACGGG ATCCCGCTGC

60241 AGAACGGCAC CGCGGACGAG GTGCACGCGC TGCACACCGC GCTCGCGCAC CTCTACGCGC

60301 GCGGTGCCAC GCTCGACTGG CCCCGCATCC TCGGGGCTGG GTCACGGCAC GACGCGGATG

60361 TGCCCGCGTA CGCGTTCCAA CGGCGGCACT ACTGGATCGA GTCGGCACGC CCGGCCGCAT

60421 CCGACGCGGG CCACCCCGTG CTGGGCTCCG GTATCGCCCT CGCCGGGTCG CCGGGCCGGG

60481 TGTTCACGGG TTCCGTGCCG ACCGGTGCGG ACCGCGCGGT GTTCGTCGCC GAGCTGGCGC

60541 TGGCCGCCGC GGACGCGGTC GACTGCGCCA CGGTCGAGCG GCTCGACATC GCCTCCGTGC

60601 CCGGCCGGCC GGGCCATGGC CGGACGACCG TACAGACCTG GGTCGACGAG CCGGCGGACG

60661 ACGGCCGGCG CCGGTTCACC GTGCACACCC GCACCGGCGA CGCCCCGTGG ACGCTGCACG

60721 CCGAGCGGGT GCTGCGCCCC CATGGCACGG CCCTGCCCGA TGCGGCCGAC GCCGAGTGGC

60781 CCCCACCGGG CGCGGTGCCC GCGGACGGGC TGCCGGGTGT GTGGCGCCGG GGGGACCAGG

60841 TCTTCGCCGA GGCCGAGGTG GACGGACCGG ACGGTTTCGT GGTGCACCCC GACCTGCTCG

60901 ACGCGGTCTT CTCCGCGGTC GGCGACGGAA GCCGCCAGCC GGCCGGATGG CGCGACCTGA

60961 CGGTGCACGC GTCGGACGCC ACCGTACTGC GCGCCTGCCT CACCCGGCGC ACCGACGGAG

61021 CCATGGGATT CGCCGCCTTC GACGGCGCCG GCCTGCCGGT ACTCACCGCG GAGGCGGTGA

61081 CGCTGCGGGA GGTGGCGTCA CCGTCCGGCT CCGAGGAGTC GGACGGCCTG CACCGGTTGG

61141 AGTGGCTCGC GGTCGCCGAG GCGGTCTACG ACGGTGACCT GCCCGAGGGA CATGTCCTGA

61201 TCACCGCCGC CCACCCCGAC GACCCCGAGG ACATACCCAC CCGCGCCCAC ACCCGCGCCA

61261 CCCGCGTCCT GACCGCCCTG CAACACCACC TCACCACCAC CGACCACACC CTCATCGTCC

61321 ACACCACCAC CGACCCCCCC GGCGCCACCG TCACCGGCCT CACCCGCACC GCCCAGAACG

61381 AACACCCCCA CCGCATCCGC CTCATCGAAA CCGACCACCC CCACACCCCC CTCCCCCTGG

61441 CCCAACTCGC CACCCTCGAC CACCCCCACC TCCGCCTCAC CCACCACACC CTCCACGACC

61501 CCCACCTCAC CCCCCTCCAC ACCACCACCC CACCCACCAC CACCCCCCTC AACCCCCAAC

61561 ACGCCATCAT CATCACCGGC GGCTCCGGCA CCCTCGCCGG CATCCTCGCC CGCCACCTGA

61621 ACCACCCCCA CACCTACCTC CTCTCCCGCA CCCCACCCCC CGACGCCACC CCCGGCACCC

61681 ACCTCCCCTG CGACGTCGGC GACCCCCACC AACTCGCCAC CACCCTCACC CACATCCCCC

61741 AACCCCTCAC CGCCATCTTC CACACCGCCG CCACCCTCGA CGACGGCATC CTCCACGCCC

61801 TCACCCCCGA CCGCCTCACC ACCGTCCTCC ACCCCAAAGC CAACGCCGCC TGGCACCTGC

61861 ACCACCTCAC CCAAAACCAA CCCCTCACCC ACTTCGTCCT CTACTCCAGC GCCGCCGCCG

61921 TCCTCGGCAG CCCCGGACAA GGAAACTACG CCGCCGCCAA CGCCTTCCTC GACGCCCTCG

61981 CCACCCACCG CCACACCCTC GGCCAACCCG CCACCTCCAT CGCCTGGGGC ATGTGGCACA

62041 CCACCAGCAC CCTCACCGGA CAACTCGACG ACGCCGACCG GGACCGCATC CGCCGCGGCG

62101 GTTTCCTCCC GATCACGGAC GACGAGGGCA TGCGCCTCTA CGAGGCGGCC GTCGGCTCCG

62161 GCGAGGACTT CGTCATGGCC GCCGCGATGG ACCCGGCACA GCCGATGACC GGCTCCGTAC

62221 CGCCCATCCT GAGCGGCCTG CGCAGGAGCG CGCGGCGCGT CGCCCGTGCC GGGCAGACGT

62281 TCGCCCAGCG GCTCGCCGAG CTGCCGCACG CCGACCGCGG CGCGGCGCTG ACCACCCTCG

62341 TCTCGGACGC CACGGCCGCC GTGCTCGGCC ACGCCGACGC CTCCGAGATC GCGCCGACCA

-continued

62401 CGACGTTCAA GGACCTCGGC ATCGACTCGC TCACCGCGAT CGACCTGCGC AACCGGCTCG

62461 CCGAGGCGAC CGGGCTGCGG CTGAGTGCCA CGCTGGTGTT CGACCACCCG ACACCTCGGG

62521 TCCTCGCCGC CAAGCTCCGC ACCGATCTGT TCGGCACGGC CGTGCCCACG CCCGCGCGGA

62581 CGGCACGGAC CCACCACGAC GAGCCACTCG CGATCGTCGG CATGGCGTGC CGACTGCCCG

62641 GCGGGGTCGC CTCGCCGGAG CAGGTGTGGC AGCTCGTGGC GTCCGGCACC GACGCGATCA

62701 CCGAGTTCCC CACCGACCGC GGCTGGGACA TCGACCGGCT GTTCGACCCG GACCCGGACG

62761 CCCCCGGCAA GACCTACGTC CGGCACGGCC GCTTCCTCGC CGAGGCCGCC GGCTTCGATG

62821 CCGCGTTCTT CGGCATCAGC CCGCGCGAGG CACGGGCCAT GGACCCGCAC CAGCGCGTCA

62881 TCCTCGAAAC CTCCTGGGAG GCGTTCGAGA ACGCGGGCAT CGTGCCGGAC ACGCTGCGCG

62941 GGAGCGACAC CGGCGTGTTC ATGGGCGCGT TCTCCCATGT GTACGGCGCG GGCGTCGACC

63001 TGGGCGGGTT CGGCGCCACC GCCACGCAGA ACAGCGTGCT CTCCGGCCGG TTGTCGTACT

63061 TCTTCGGCAT GGAGGGCCCG GCCGTCACCG TCGACACCGC CTGCTCGTCG TCGCTGGTCG

63121 CCCTGCACCA GGCGGCACAG GCGCTGCGGA CTGGAGAATG CTCGCTGGCG CTCGCCGGCG

63181 GTGTCACGGT GATGCCCACC CCGCTGGGCT ACGTCGAGTT CTGCCGCCAG CGGGGACTCG

63241 CCCCCGACGG CCGTTGCCAG GCCTTCGCGG AAGGCGCCGA CGGCACGAGC TTCTCGGAGG

63301 GCGCCGGCGT TCTTGTGCTG GAGCGGCTCT CCGACGCCGA GCGCAACGGA CACACCGTCC

63361 TCGCGGTCGT CCGCTCCTCC GCCGTCAACC AGGACGGCGC CTCCAACGGC ATCTCCGCAC

63421 CCAACGGCCC CCCCCAGCAG CGCGTCATCC GCCAGGCCCT CGACAAGGCC GGGCTCGCCC

63481 CCGCCGACGT GGACGTGGTG GAGGCCCACG GCACCGGAAC CCCGCTGGGC GACCCGATCG

63541 AGGCACAGGC CATCATCGCG ACCTACGGCC AGGACCGCGA CACACCGCTC TACCTCGGTT

63601 CGGTCAAGTC GAACATCGGA CACACCCAGA CCACCGCCGG TGTCGCCGGC GTCATCAAGA

63661 TGGTCATGGC GATGCGCCAC GGCATCGCGC CGAAGACACT GCACGTGGAC GAGCCGTCGT

63721 CGCATGTGGA CTGGACCGAG GGTGCGGTGG AACTGCTCAC GCAGGCGAGG CCGTGGCCCG

63781 ACGCGGGACG CCCGCGCCGC GCGGGCGTGT CGTCGCTCGG TATCAGCGGT ACGAACGCCC

63841 ACGTGATCCT TGAGGGTGTT CCCGGGCCGT CGCGTGTGGA GCCGTCTGTT GACGGGTTGG

63901 TGCCGTTGCC GGTGTCGGCT CGGAGTGAGG CGAGTCTGCG GGGGCAGGTG GAGCGGCTGG

63961 AGGGGTATCT GCGCGGGAGT GTGGATGTGG CCGCGGTCGC GCAGGGGTTG GTGCGTGAGC

64021 GTGCTGTCTT CGGTCACCGT GCGGTACTGC TGGGTGATGC CCGGGTGATG GGTGTGGCGG

64081 TGGATCAGCC GCGTACGGTG TTCGTCTTTC CCGGGCAGGG TGCTCAGTGG GTGGGCATGG

64141 GTGTGGAGTT GATGGACCGT TCTGCGGTGT TCGCGGCTCG TATGGAGGAG TGTGCGCGGG

64201 CGTTGTTGCC GCACACGGGC TGGGATGTGC GGGAGATGTT GGCGCGGCCG GATGTGGCGG

64261 AGCGGGTGGA GGTGGTCCAG CCGGCCAGCT GGGCGGTCGC GGTCAGCCTG GCCGCACTGT

64321 GGCAGGCCCA CGGGGTCGTA CCCGACGCGG TGATCGGACA CTCCCAGGGC GAGATCGCGG

64381 CGGCGTGCGT GGCCGGGGCC CTCAGCCTTG AGGACGCCGC CCGCGTGGTG GCCTTGCGCA

64441 GCCAGGTCAT CGCGGCGCGA CTGGCCGGGC GGGGAGCGAT GGCTTCGGTG GCATTGCCGG

64501 CCGGTGAGGT CGGTCTGGTC GAGGGCGTGT GGATCGCGGC GCGTAACGGC CCCGCCTCGA

64561 CAGTCGTGGC CGGCGAGCCG TCGGCGGTGG AGGACGTGGT GACGCGGTAT GAGACCGAAG

64621 GCGTGCGAGT GCCTCCTATC GCCGTCGACT ACGCCTCCCA CACGCCCCAC GTGGAAGCCA

64681 TCGAGGACGA ACTCGCTGAG GTACTGAAGG GAGTTGCAGG GAAGGCCGCG TCGGTGGCGT

64741 GGTGGTCGAC CGTGGACAGC GCCTGGGTGA CCGAGCCGGT GGATGAGAGT TACTGGTACC

-continued

64801 GGAACCTGCG TCGCCCCGTC GCGCTGGACG CGGCGGTGGC GGAGCTGGAC GGGTCCGTGT

64861 TCGTGGAGTG CAGCGCCCAT CCGGTGCTGC TGCCGGCGAT GGAACAGGCC CACACGGTGG

64921 CGTCGTTGCG CACCGGTGAC GGCGGCTGGG AGCGATGGCT GACGGCGTTG GCGCAGGCGT

64981 GGACCCTGGG CGCGGCAGTG GACTGGGACA CGGTGGTCGA ACCGGTGCCA GGGCGGCTGC

65041 TCGATCTGCC CACCTACGCG TTCGAGCGCC GGCGCTACTG GCTGGAAGCG GCCGGTGCCA

65101 CCGACCTGTC CGCGGCCGGG CTGACAGGGG CAGCACATCC CATGCTGGCC GCCATCACGG

65161 CACTACCCGC CGACGACGGT GGTGTTGTTC TCACCGGCCG GATCTCGTTG CGCACGCATC

65221 CCTGGCTGGC TGATCACGCG GTGCGGGGCA CGGTCCTGCT GCCGGGCACG GCCTTTGTGG

65281 AGCTGGTCAT CCGGGCCGGT GACGAGACCG GTTGCGGGAT AGTGGATGAA CTGGTCATCG

65341 AATCCCCCCT CGTGGTGCCG GCGACCGCAG CCGTGGATCT GTCGGTGACC GTGGAAGGAG

65401 CTGACGAGGC CGGACGGCGG CGAGTGACCG TCCACGCCCG CACCGAAGGC ACCGGCAGCT

65461 GGACCCGGCA CGCCAGCGGC ACCCTGACCC CCGACACCCC CGACACCCCC AACGCTTCCG

65521 GTGTTGTCGG TGCGGAGCCG TTCTCGCAGT GGCCACCTGC CACTGCCGCG GCCGTCGACA

65581 CCTCGGAGTT CTACTTGCGC CTGGACGCGC TGGGCTACCG GTTCGGACCC ATGTTCCGCG

65641 GAATGCGGGC TGCCTGGCGT GATGGTGACA CCGTGTACGC CGAGGTCGCG CTCCCCGAGG

65701 ACCGTGCCGC CGACGCGGAC GGTTTCGGCA TGCACCCGGC GCTGCTCGAC GCGGCCTTGC

65761 AGAGCGGCAG CCTGCTCATG CTGGAATCGG ACGGCCAGCA GAGCGTGCAA CTGCCGTTCT

65821 CCTGGCACGG CGTCCGGTTC CACGCGACGG GCGCGACCAT GCTGCGGGTG GCGGTCGTAC

65881 CGGGCCCGGA CGGCCTCCGG CTGCATGCCG CGGACAGCGG GAACCGTCCC GTCGCGACGA

65941 TCGACGCGCT CGTGACCCGG TCCCCGGAAG CGGACCTCGC GCCCGCCGAT CCGATGCTGC

66001 GGGTCGGGTG GGCCCCGGTG CCGGTACCTG CCGGGGCCGG TCCGTCCGAC GCGGACGTGC

66061 TGACGCTGCG CGGCGACGAC GCCGACCCGC TCGGGGAGAC CCGGGACCTG ACCACCCGTG

66121 TTCTCGACGC GCTGCTCCGG GCCGACCGGC CGGTGATCTT CCAGGTGACC GGTGGCCTCG

66181 CCGCCAAGGC GGCCGCAGGC CTGGTCCGCA CCGCTCAGAA CGAGCAGCCC GGCCGCTTCT

66241 TCCTCGTCGA AACGGACCCG GGAGAGGTCC TGGACGGCGC GAAGCGCGAC GCGATCGCGG

66301 CACTCGGCGA GCCCCATGTG CGGCTGCGCG ACGGCCTCTT CGAGGCAGCC CGGCTGATGC

66361 GGGCCACGCC GTCCCTGACG CTCCCGGACA CCGGGTCGTG GCAGCTGCGG CCGTCCGCCA

66421 CCGGTTCCCT CGACGACCTT GCCGTCGTCC CCACCGACGC CCCGGACCGG CCGCTCGCGG

66481 CCGGCGAGGT GCGGATCGCG GTACGCGCGG CGGGCCTGAA CTTCCGGGAT GTCACGGTCG

66541 CGCTCGGTGT GGTCGCCGAT GCGCGTCCGC TCGGCAGCGA GGCCGCGGGT GTCGTCCTGG

66601 AGACCGGCCC CGGTGTGCAC GACCTGGCGC CCGGCGACCG GGTCCTGGGG ATGCTCGCGG

66661 GCGCCTTCGG ACCGGTCGCG ATCACCGACC GGCGGCTGCT CGGCCGGATG CCGGACGGCT

66721 GGACGTTCCC GCAGGCGGCG TCCGTGATGA CCGCGTTCGC GACCGCGTGG TACGGCCTGG

66781 TCGACCTGGC CGGGCTGCGC CCCGGCGAGA AGGTCCTGAT CCACGCGGCG GCGACCGGTG

66841 TCGGCGCGGC GGCCGTCCAG ATCGCGCGGC ATCTGGGCGC GGAGGTGTAC GCGACCACCA

66901 GCGCCGCGAA GCGCCATCTG GTGGACCTGG ACGGAGCGCA TCTGGCCGAT TCCCGCAGCA

66961 CCGCGTTCGC CGACGCGTTC CCGCCGGTCG ATGTCGTGCT CAACTCGCTC ACCGGTGAAT

67021 TCCTCGACGC GTCCGTCGGC CTGCTCGCGG CGGGTGGCCG GTTCATCGAG ATGGGGAAGA

67081 CGGACATCCG GCACGCCGTC CAGCAGCCGT TCGACCTGAT GGACGCCGGC CCCGACCGGA

67141 TGCAGCGGAT CATCGTCGAG CTGCTCGGCC TGTTCGCGCG CGACGTGCTG CACCCGCTGC

-continued

67201 CGGTCCACGC CTGGGACGTG CGGCAGGCGC GGGAGGCGTT CGGCTGGATG AGCAGCGGGC

67261 GTCACACCGG CAAGCTGGTG CTGACGGTCC CGCGGCCGCT GGATCCCGAG GGGGCCGTCG

67321 TCATCACCGG CGGCTCCGGC ACCCTCGCCG GCATCCTCGC CCGCCACCTG GGCCACCCCC

67381 ACACCTACCT GCTCTCCCGC ACCCCACCCC CCGACACCAC CCCCGGCACC CACCTCCCCT

67441 GCGACGTCGG CGACCCCCAC CAACTCGCCA CCACCCTCGC CCGCATCCCC CAACCCCTCA

67501 CCGCCGTCTT CCACACCGCC GGAACCCTCG ACGACGCCCT GCTCGACAAC CTCACCCCCG

67561 ACCGCGTCGA CACCGTCCTC AAACCCAAGG CCGACGCCGC CTGGCACCTG CACCGGCTCA

67621 CCCGCGACAC CGACCTCGCC GCGTTCGTCG TCTACTCCGC GGTCGCCGGC CTCATGGGCA

67681 GCCCGGGGCA GGGCAACTAC GTCGCGGCGA ACGCGTTCCT CGACGCGCTC GCCGAACACC

67741 GCCGTGCGCA AGGGCTGCCC GCGCAGTCCC TCGCATGGGG CATGTGGGCG GACGTCAGCG

67801 CGCTCACCGC GAAACTCACC GACGCGGACC GCCAGCGCAT CCGGCGCAGC GGATTCCCGC

67861 CGTTGAGCGC CGCGGACGGC ATGCGGCTGT TCGACGCGGC GACGCGTACC CCGGAACCGG

67921 TCGTCGTCGC GACGACCGTC GACCTCACCC AGCTCGACGG CGCCGTCGCG CCGTTGCTCC

67981 GCGGTCTGGC CGCGCACCGG GCCGGGCCGG CGCGCACGCT CGCCCGCAAC GCCGGCGAAG

68041 AGCCCCTGGC CGTGCGTCTT GCCGGGCGTA CCGCCGCCGA GCAGCGGCGC ATCATGCAGG

68101 AGGTCGTGCT CCGCCACGCG GCCGCGGTCC TCGCGTACGG GCTGGGCGAC CGCGTGGCGG

68161 CGGACCGTCC GTTCCGCGAG CTCGGTTTCG ATTCGCTGAC CGCGGTCGAC CTGCGCAATC

68221 GGCTCGCGGC CGAGACGGGG CTGCGGCTGC CGACGACGCT GGTGTTCAGC CACCCGACGG

68281 CGGAGGCGCT CACCGCCCAC CTGCTCGACC TGATCGACGC TCCCACCGCC CGGATCGCCG

68341 GGGAGTCCCT GCCCGCGGTG ACGGCCGCTC CCGTGGCGGC CGCGCGGGAC CAGGACGAGC

68401 CGATCGCCAT CGTGGCGATG GCGTGCCGGC TGCCCGGTGG TGTGACGTCG CCCGAGGACC

68461 TGTGGCGGCT CGTCGAGTCC GGCACCGACG CGATCACCAC GCCTCCTGAC GACCGCGGCT

68521 GGGACGTCGA CGCGCTGTAC GACGCGGACC CGGACGCGGC CGGCAAGGCG TACAACCTGC

68581 GGGGCGGTTA CCTGGCCGGG GCGGCGGAGT TCGACGCGGC GTTCTTCGAC ATCAGTCCGC

68641 GCGAAGCGCT CGGCATGGAC CCGCAGCAAC GCCTGCTGCT CGAAACGGCG TGGGAGGCGA

68701 TCGAGCGCGG CCGGATCAGT CCGGCGTCGC TCCGCGGCCG GGAGGTCGGC GTCTATGTCG

68761 GTGCGGCCGC GCAGGGCTAC GGGCTGGGCG CCGAGGACAC CGAGGGCCAC GCGATCACCG

68821 GTGGTTCCAC GAGCCTGCTG TCCGGACGGC TGGCGTACGT GCTCGGGCTG GAGGGCCCGG

68881 CGGTCACCGT GGACACGGCG TGCTCGTCGT CTCTGGTCGC GCTGCATCTG GCGTGCCAGG

68941 GGCTGCGGCT GGGCGAGTGC GAACTCGCTC TGGCCGGAGG GGTCTCCGTA CTGAGTTCGC

69001 CGGCCGCCTT CGTGGAGTTC TCCCGCCAGC GCGGGCTCGC GGCCGACGGG CGCTGCAAGT

69061 CGTTCGGCGC GGGCGCGCAC GGCACGACGT GGTCCGAGGG CGTGGGCGTG CTCGTACTGG

69121 AACGGCTCTC CGACGCCGAG CGGCTCGGGC ACACCGTGCT CGCCGTCGTC CGCGGCAGCG

69181 CCGTCACGTC CGACGGCGCC TCCAACGGCC TCACCGCGCC GAACGGGCTC TCGCAGCAGC

69241 GGGTCATCCG GAAGGCGCTC GCCGCGGCCG GGCTGACCGG CGCCGACGTG GACGTCGTCG

69301 AGGGGCACGG CACCGGCACC CGGCTCGGCG ACCCGGTCGA GGCGGACGCG CTGCTCGCGA

69361 CGTACGGGCA GGACCGTCCG GCACCGGTCT GCCTGGGCTC GCTGAAGTCG AACATCGGAC

69421 ATGCCACGGC CGCGGCCGGT GTCGCGGGCG TCATCAAGAT GGTGCAGGCG ATCGGCGCGG

69481 GCACGATGCC GCGGACGCTG CATGTGGAGG AGCCCTCGCC CGCCGTCGAC TGGAGCACCG

69541 GACAGGTGTC CCTGCTCGGC TCCAACCGGC CCTGGCCGGA CGACGAGCGT CCGCGCCGGG

-continued

69601 CGGCCGTCTC CGCGTTCGGG CTCAGCGGGA CGAACGCGCA CGTCATCCTG GAACAGCACC

69661 GTCCGGCGCC CGTGGCGTCC CAGCCGCCCC GGCCGCCCCG TGAGGAGTCC CAGCCGCTGC

69721 CGTGGGTGCT CTCCGCGCGG ACTCCGGCCG CGCTGCGGGC CCAGGCGGCC CGGCTGCGCG

69781 ACCACCTCGC GGCGGCACCG GACGCGGATC CGTTGGACAT CGGGTACGCG CTGGCCACCA

69841 GCCGCGCCCA GTTCGCCCAC CGTGCCGCGG TCGTCGCCAC CACCCCGGAC GGATTCCGTG

69901 CCGCGCTCGA CGGCCTCGCG GACGGCGCGG AGGCGCCCGG AGTCGTCACC GGGACCGCTC

69961 AGGAGCGGCG CGTCGCCTTC CTCTTCGACG GCCAGGGCGC CCAGCGCGCC GGAATGGGGC

70021 GCGAGCTCCA CCGCCGGTTC CCCGTCTTCG CCGCCGCGTG GGACGAGGTC TCCGACGCGT

70081 TCGGCAAGCA CCTCAAGCAC TCCCCCACGG ACGTCTACCA CGGCGAACAC GGCGCTCTCG

70141 CCCATGACAC CCTGTACGCC CAGGCCGGCC TGTTCACGCT CGAAGTGGCG CTGCTGCGGC

70201 TGCTGGAGCA CTGGGGGGTG CGGCCGGACG TGCTCGTCGG GCACTCCGTC GGCGAGGTGA

70261 CCGCGGCGTA CGCGGCGGGG GTGCTCACCC TGGCGGACGC GACGGAGTTG ATCGTGGCCC

70321 GGGGGCGGGC GCTGCGGGCG CTGCCGCCCG GGGCGATGCT CGCCGTCGAC GGAAGCCCGG

70381 CGGAGGTCGG CGCCCGCACG GATCTGGACA TCGCCGCGGT CAACGGCCCG TCCGCCGTGG

70441 TGCTCGCCGG TTCGCCGGAC GATGTGGCGG CGTTCGAACG GGAGTGGTCG GCGGCCGGGC

70501 GGCGCACGAA ACGGCTCGAC GTCGGGCACG CGTTCCACTC CCGGCACGTC GACGGTGCGC

70561 TCGACGGCTT CCGTACGGTG CTGGAGTCGC TCGCGTTCGG CGCGGCGCGG CTGCCGGTGG

70621 TGTCCACGAC GACGGGCCGG GACGCCGCGG ACGACCTCAT AACGCCCGCG CACTGGCTGC

70681 GCCATGCGCG TCGGCCGGTG CTGTTCTCGG ATGCCGTCCG GGAGCTGGCC GACCGCGGCG

70741 TCACCACGTT CGTGGCCGTC GGCCCCTCCG GCTCCCTGGC GTCGGCCGCG GCGGAGAGCG

70801 CCGGGGAGGA CGCCGGGACC TACCACGCGG TGCTGCGCGC CCGGACCGGT GAGGAGACCG

70861 CGGCGCTGAC CGCCCTCGCC GAGCTGCACG CCCACGGCGT CCCGGTCGAC CTGGCCGCGG

70921 TACTGGCCGG TGGCCGGCCA GTGGACCTTC CCGTGTACGC GTTCCAGCAC CGTTCCTACT

70981 GGCTGGCCCC GGCCGTGGCG GGGGCGCCGG CCACCGTGGC GGACACCGGG GGTCCGGCGG

71041 AGTCCGAGCC GGAGGACCTC ACCGTCGCCG AGATCGTCCG TCGGCGCACC GCGGCGCTGC

71101 TCGGCGTCAC GGACCCCGCC GACGTCGATG CGGAAGCGAC GTTCTTCGCG CTCGGTTTCG

71161 ACTCACTGGC GGTGCAGCGG CTGCGCAACC AGCTCGCCTC GGCAACCGGG CTGGACCTGC

71221 CGGCGGCCGT CCTGTTCGAC CACGACACCC CGGCCGCGCT CACCGCGTTC CTCCAGGACC

71281 GGATCGAGGC CGGCCAGGAC CGGATCGAGG CCGGCGAGGA CGACGACGCG CCCACCGTGC

71341 TCTCGCTCCT GGAGGAGATG GAGTCGCTCG ACGCCGCGGA CATCGCGGCG ACGCCGGCCC

71401 CGGAGCGTGC GGCCATCGCC GATCTGCTCG ACAAGCTCGC CCATACCTGG AAGGACTACC

71461 GATGAGCACC GATACGCACG AGGGAACGCC GCCCGCCGGC CGCTGCCCAT TCGCGATCCA

71521 GGACGGTCAC CGCGCCATCC TGGAGAGCGG CACGGTGGGT TCGTTCGACC TGTTCGGCGT

71581 CAAGCACTGG CTGGTCGCCG CCGCCGAGGA CGTCAAGCTG GTCACCAACG ATCCGCGGTT

71641 CAGCTCGGCC GCGCCGTCCG AGATGCTGCC CGACCGGCGG CCCGGCTGGT TCTCCGGGAT

71701 GGACTCACCG GAGCACAACC GCTACCGGCA GAAGATCGCG GGGGACTTCA CACTGCGCGC

71761 GGCGCGCAAG CGGGAGGACT TCGTCGCCGA GGCCGCCGAC GCCTGCCTGG ACGACATCGA

71821 GGCCGCGGGA CCCGGCACCG ACCTCATCCC CGGGTACGCC AAGCGGCTGC CCTCCCTCGT

71881 CATCAACGCG CTGTACGGGC TCACCCCTGA GGAGGGGGCC GTGCTGGAGG CACGGATGCG

71941 CGACATCACC GGCTCGGCCG ATCTGGACAG CGTCAAGACG CTGACCGACG ACTTCTTCGG

-continued

72001 GCACGCGCTG CGGCTGGTCC GCGCGAAGCG TGACGAGCGG GGCGAGGACC TGCTGCACCG

72061 GCTGGCCTCG GCCGACGACG GCGAGATCTC GCTCAGCGAC GACGAGGCGA CGGGCGTGTT

72121 CGCGACGCTG CTGTTCGCCG GCCACGACTC GGTGCAGCAG ATGGTCGGCT ACTGCCTCTA

72181 CGCACTGCTC AGCCACCCCG AGCAGCAGGC GGCGCTGCGC GCGCGCCCGG AGCTGGTCGA

72241 CAACGCGGTC GAGGAGATGC TCCGTTTCCT GCCCGTCAAC CAGATGGGCG TACCGCGCGT

72301 CTGTGTCGAG GACGTCGATG TGCGGGGCGT GCGCATCCGT GCGGGCGACA ACGTGATCCC

72361 GCTCTACTCG ACGGCCAACC GCGACCCCGA GGTGTTCCCG CAGCCCGACA CCTTCGATGT

72421 GACGCGCCCG CTGGAGGGCA ACTTCGCGTT CGGCCACGGC ATTCACAAGT GTCCCGGCCA

72481 GCACATCGCC CGGGTGCTCA TCAAGGTCGC CTGCCTGCGG TTGTTCGAGC GTTTCCCGGA

72541 CGTCCGGCTG GCCGGCGACG TGCCGATGAA CGAGGGGCTC GGGCTGTTCA GCCCGGCCGA

72601 GCTGCGGGTC ACCTGGGGGG CGGCATGAGT CACCCGGTGG AGACGTTGCG GTTGCCGAAC

72661 GGGACGACGG TCGCGCACAT CAACGCGGGC GAGGCGCAGT TCCTCTACCG GGAGATCTTC

72721 ACCCAGCGCT GCTACCTGCG CCACGGTGTC GACCTGCGCC CGGGGGACGT GGTGTTCGAC

72781 GTCGGCGCGA ACATCGGCAT GTTCACGCTT TTCGCGCATC TGGAGTGTCC TGGTGTGACC

72841 GTGCACGCCT TCGAGCCCGC GCCCGTGCCG TTCGCGGCGC TGCGGGCGAA CGTGACGCGG

72901 CACGGCATCC CGGGCCAGGC GGACCAGTGC GCGGTCTCCG ACAGCTCCGG CACCCGGAAG

72961 ATGACCTTCT ATCCCGACGC CACGCTGATG TCCGGTTTCC ACGCGGATGC CGCGGCCCGG

73021 ACGGAGCTGT TGCGCACGCT CGGCCTCAAC GGCGGCTACA CCGCCGAGGA CGTCGACACC

73081 ATGCTCGCGC AACTGCCCGA CGTCAGCGAG GAGATCGAAA CCCCTGTGGT CCGGCTCTCC

73141 GACGTCATCG CGGAGCGCGG TATCGAGGCC ATCGGCCTGC TGAAGGTCGA CGTGGAGAAG

73201 AGCGAACGGC AGGTCTTCGC CGGCCTCGAG GACACCGACT GGCCCCGTAT CCGCCAGGTC

73261 GTCGCGGAGG TCCACGACAT CGACGGCGCG CTCGAGGAGG TCGTCACGCT GCTCCGCGGC

73321 CATGGCTTCA CCGTGGTCGC CGAGCAGGAA CCGCTGTTCG CCGGCACGGG CATCCACCAG

73381 GTCGCCGCGC GGCGGGTGGC CGGCTGAGCG CCGTCGGGGC CGCGGCCGTC CGCACCGGCG

73441 GCCGCGGTGC GGACGGCGGC TCAGCCGGCG TCGGACAGTT CCTTGGGCAG TTGCTGACGG

73501 CCCTTCACCC CCAGCTTGCG GAACACGTTG GTGAGGTGCT GTTCCACCGT GCTGGAGGTG

73561 ACGAACAGCT GGCTGGCGAT CTCCTTGTTG GTGCGCCCGA CCGCGGCGTG CGACGCCACC

73621 CGCCGCTCCG CCTCGGTCAG CGATGTGATC CGCTGCGCCG GCGTCACGTC CTGGGTGCCG

73681 TCCGCGTCCG AGGACTCCCC ACCGAGCCGC CGGAGGAGCG GCACGGCTCC GCACTGGGTC

73741 GCGAGGTGCC GTGCGCGGCG GAACAGTCCC CGCGCACGGC TGTGCCGCCG GAGCATGCCG

73801 CACGCTTCGC CCATGTCGGC GAGGACGCGG GCCAGCTCGT ACTGGTCGCG GCACATGATG

73861 AGCAGATCGG CGGCCTCGTC GAGCAGTTCG ATCCGCTTGG CCGGCGGACT GTAGGCCGCC

73921 TGCACCCGCA GCGTCATCAC CCGCGCCCGG GACCCCATCG GCCGGGACAG CTGCTCGGAG

73981 ATGAGCCTCA GCCCCTCGTC ACGGCCGCGG CCGAGCAGCA GAAGCGCTTC GGCGGCGTCG

74041 ACCCGCCACA GGGCCAGGCC CGGCACGTCG ACGGACCAGC GTCGCATCCG CTCCCCGCAG

74101 TCCCGGAACG CGTTGTACGC CGCCCGGTAC CGCCCGGCCG CGAGATGGTG TTGCCCACGG

74161 GCCCAGACCA TGTGCAGTCC GAAGAGGCTG TCGGAGGTCT CCTCCGGCAA CGGCTCGGCG

74221 AGCCACCGCT CCGCCCGGTC CAGGTCGCCC AGTCGGATCG CGGCGGCCAC GGTGCTGCTC

74281 AGCGGCAATG CGGCGGCCAT CCCCCAGGAG GGCACGACCC GGGGGGCGAG CGCGGCCTCG

74341 CCGCATTCGA CGGCGGCGGT CAGGTCGCCG CGGCGCAGCG CGGCCTCGGC GCGGAACCCC

-continued

74401 GCGTGGACCG CCTCGTCGGC CGGGGTCCGC ATGTTGTCGT CACCGGCCAG CTTGTCGACC

74461 CAGGACTGGA CGGCATCGGT GTCCTCGGCG TAGAGCAGGG CCAGCAACGC CATCATGGTC

74521 GTGGTCCGGT CCGTCGTGAC CCGGGAGTGC TGGAGCACGT ACTCGGCTTT GGCCTCGGCC

74581 TGTTCGGACC AGCCGCGCAG CGCGTTGCTC AGGGCCTTGT CGGCGACGGC GCGGTGCCGG

74641 ACGGCTCCGG AAAACGAGGC GACCTCGTCC TCGGCCGGCG GATCGGCCGG ACGCGGCGGA

74701 TCGGCCGCGC CGGGATAGAT CAGCGCGAGG GACAGGTCCG CGACGCGCAG GTGCGCCCGG

74761 CCCTGCTCGC TCGGGGCGGC GGAGCGCTGG GCCGCCAGGA CCTCGGCGGC CTCGCCCGGC

74821 CGCCCGTCCA TCGCCAGCCA GCAGGCGAGC GACACGGCGT GCTCGCTGGA GAGGAGCCGT

74881 TCCCGCGACG CGGTGAGCAG CTCGGGCACA TGCCGGCCGG ATCTGGCGGG ATCGCAGAGC

74941 CGCTCGATGG CGGCGGTGTC GACGCGCAGT GCGGCGTGGA CGGCGGGGTC GTCGGAGGCC

75001 CGGTAGGCGA ACTCCAGGTA GGTGACGGCC TCGTCGAGCT CGCCGCGCAG GTGGTGCTCG

75061 CGCGCGGCGT CGGTGAACAG CCCGGCGACC TCGGCGCCGT GCACCCGGCC GGTACCCATC

75121 TGGTGGCGGG CGAGCACCTT GCTGGCCACG CCGCGGTCCC GCAGCAGTTC CAGCGCCAGC

75181 TCGTGCAGGC CACGCCGCTC GGCGGCGGAG AGGTCGTCGA GTACGACGGA GCGGGCCGCG

75241 GGGTGCGGGA ACCGCCCTTC CCGCAGCAGC CGCCCCTCGA CCAGCTGTTC GTGGGCCTGC

75301 TCGACCGCCT CGGTGTCGAG GCCGGTCATC CGCTGGACGA GGGTGAGTTC GACACTCTCG

75361 CCGAGCACGG CGGAAGCTCG GGCGACGCTC AGCGCGGCCG GGCCGCAACG ATAGAGCGAC

75421 CCGAGGTAGG CGAGCCGGTA CGCCCGCCCC GCGACCACTT CCAGGCACCC TGAGGTCCGT

75481 GTCCGTGCCT CCCGGATGTC GTCGATCACG CCGTGGCCGA GGAGCAGGTT GCCGCCGGTC

75541 GCCCGGAACG CCTGGGCCAC CACGTCGTCG TGCGCGTCCT GGCCGAGGTC CCGGCGCACG

75601 AGTTCGGTGG TCTGCGCCTC GGTGAGCGGG CGCAGCGCGA TCTCCTGGTA GTGGCGCAGA

75661 CTCAGCAGTG CCGCCCGGAA TTGGGAGTGG GCGGGCGTCG GCCGGAGCAG CTCGGTCAGC

75721 ACGATGGCGA CACGGGCCCG GCTGATGCGG CGCGCGAGGT GGAGCAGGCA GCGCAGCGAC

75781 GGCGCGTCGG CGTGGTGCAC GTCGTCGATG CCGATCAGTA CGGGCCGCTC CGCGGCGAGC

75841 GTCAGCACCG TGCGGGTGAG TTCGGTCCCC AGGCGGTTGT CGACGTCGGC CGGCAGGTTT

75901 TCGCACGATG CCGTCAGCCG GACCAGCTCC GGTGTCCGGG CGGCCAGCTC GGGCTGGTCG

75961 AGGAGCTGGC CGAGCATGCC GTACGGCAGG GCCCGCTCCT CCATGGAGCA CACCGCGCGA

76021 AGGGTGACGA AGCCGGCCTT GGCCGCGGCG GCGTCGAGGA GTTCGGTCTT GCCGCAGGCG

76081 ATCGGCCCGG TGACGGCGGC GACGACGCCC CGCCCGCCCC CCGCTCGGGT GAGCGCCCGG

76141 TGGAGGGAAC CGAACTCGTC ATCGCGGGCG ATCAGGTCTG GGGGAGATAA GCGCGCTATC

76201 ACGAATGGAA CTACCTCGCG ACCGTCGTGG AAACCCATAG GCATCACATG GCTTGTTGAT

76261 CTGTACGGCT GTGATTCAGC CTGGCGGGAT GCTGTGCTAC AGATGGGAAG ATGTGATCTA

76321 GGGCCGTGCC GTTCCCTCAG GAGCCGACCG CCCCCGGCGC CACCCGCCGT ACCCCCTGGG

76381 CCACCAGCTC GGCGACCCGC TCCTGGTGGT CGACGAGGTA GAAGTGCCCG CCGGGGAAGA

76441 CCTCCACCGT GGTCGGCGCG GTCGTGTGCC CGGCCCAGGC GTGGGCCTGC TCCACCGTCG

76501 TCTTCGGATC CTCGTCACCG ATGCACACCG TGATCGGCGT CTCCAGCGGC GGCGCGGGCT

76561 CCCACCGGTA CGTCTCCGCC GCGTAGTAGT CCGCCCGCAA CGGCGCCAGG ATCAGCGCGC

76621 GCATTTCGTC GTCCGCCATC ACATCGGCGC TCGTCCCGCC GAGGCCGATG ACCGCCGCCA

76681 GCAGCTCGTC GTCGGACGCG AGGTGGTCCT GGTCGGCGCG CGGCTGCGAC GGCGCCCGCC

76741 GGCCCGAGAC GATCAGGTGC GCCACCGGGA GCCGCTGGGC CAGCTCGAAC GCGAGTGTCG

-continued

```
76801 CGCCCATGCT GTGGCCGAAC AGCACCAGCG GACGGTCCAG CCCCGGCTTC AACGCCTCGG

76861 CCACGAGGCC GGCGAGAACA CGCAGGTCGC GCACCGCCTC CTCGTCGCGG CGGTCCTGGC

76921 GGCCGGGGTA CTGCACGGCG TACACGTCCG CCACCGGGGC GAGCGCACGG GCCAGCGGAA

76981 GGTAGAACGT CGCCGATCCG CCGGCGTGGG GCAGCAGCAC CACCCGTACC GGGGCCTCGG

77041 GCGTGGGGAA GAACTGCCGC AGCCAGAGTT CCGAGCTCAC CGCACCCCCT CGGCCGCGAC

77101 CTGGGGAGCC CGGAACCGGG TGATCTCGGC CAAGTGCTTC TCCCGCATCT CCGGGTCGGT

77161 CACGCCCCAT CCCTCCTCCG GCGCCAGACA GAGGACGCCG ACTTTGCCGT TGTGCACATT

77221 GCGATGCACA TCGCGCACCG CCGACCCGAC GTCGTCGAGC GGGTAGGTCA CCGACAGCGT

77281 CGGGTGCACC ATCCCCTTGC AGATCAGGCG GTTCGCCTCC CACGCCTCAC GATAGTTCGC

77341 GAAGTGGGTA CCGATGATCC GCTTCACGGA CATCCACAGG TACCGATTGT CAAAGGCGTG

77401 CTCGTATCCC GAGGTTGACG CGCAGGTGAC GATCGTGCCA CCCCGACGTG TCACGTAGAC

77461 ACTCGCGCCG AACGTCGCGC GCCCCGGGTG CTCGAACACG ATGTCGGGAT CGTCACCGCC

77521 GGTCAGCTCC CGGATC
```

Those of skill in the art will recognize that, due to the degenerate nature of the genetic code, a variety of DNA compounds differing in their nucleotide sequences can be used to encode a given amino acid sequence of the invention. The native DNA sequence encoding the FK-520 PKS of Streptomyces hygroscopicus is shown herein merely to illustrate a preferred embodiment of the invention, and the present invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences shown merely illustrate preferred embodiments of the invention.

The recombinant nucleic acids, proteins, and peptides of the invention are many and diverse. To facilitate an understanding of the invention and the diverse compounds and methods provided thereby, the following general description of the FK-520 PKS genes and modules of the PKS proteins encoded thereby is provided. This general description is followed by a more detailed description of the various domains and modules of the FK-520 PKS contained in and encoded by the compounds of the invention. In this description, reference to a heterologous PKS refers to any PKS other than the FK-520 PKS. Unless otherwise indicated, reference to a PKS includes reference to a portion of a PKS. Moreover, reference to a domain, module, or PKS includes reference to the nucleic acids encoding the same and vice-versa, because the methods and reagents of the invention provide or enable one to prepare proteins and the nucleic acids that encode them.

The FK-520 PKS is composed of three proteins encoded by three genes designated fkbA, fkbB, and fkbC. The fkbA ORF encodes extender modules 7–10 of the PKS. The fkbB ORF encodes the loading module (the CoA ligase) and extender modules 1–4 of the PKS. The fkbC ORF encodes extender modules 5–6 of the PKS. The fkbP ORF encodes the NRPS that attaches the pipecolic acid and cyclizes the FK-520 polyketide.

The loading module of the FK-520 PKS includes a CoA ligase, an ER domain, and an ACP domain. The starter building block or unit for FK-520 is believed to be a dihydroxycyclohexene carboxylic acid, which is derived from shikimate. The recombinant DNA compounds of the invention that encode the loading module of the FK-520 PKS and the corresponding polypeptides encoded thereby are useful for a variety of methods and in a variety of compounds. In one embodiment, a DNA compound comprising a sequence that encodes the FK-520 loading module is inserted into a DNA compound that comprises the coding sequence for a heterologous PKS. The resulting construct, in which the coding sequence for the loading module of the heterologous PKS is replaced by the coding sequence for the FK-520 loading module, provides a novel PKS coding sequence. Examples of heterologous PKS coding sequences include the rapamycin, FK-506, rifamycin, and avermectin PKS coding sequences. In another embodiment, a DNA compound comprising a sequence that encodes the FK-520 loading module is inserted into a DNA compound that comprises the coding sequence for the FK-520 PKS or a recombinant FK-520 PKS that produces an FK-520 derivative.

In another embodiment, a portion of the loading module coding sequence is utilized in conjunction with a heterologous coding sequence. In this embodiment, the invention provides, for example, either replacing the CoA ligase with a different CoA ligase, deleting the ER, or replacing the ER with a different ER. In addition, or alternatively, the ACP can be replaced by another ACP. In similar fashion, the corresponding domains in another loading or extender module can be replaced by one or more domains of the FK-520 PKS. The resulting heterologous loading module coding sequence can be utilized in conjunction with a coding sequence for a PKS that synthesizes FK-520, an FK-520 derivative, or another polyketide.

The first extender module of the FK-520 PKS includes a KS domain, an AT domain specific for methylmalonyl CoA, a DH domain, a KR domain, and an ACP domain. The recombinant DNA compounds of the invention that encode the first extender module of the FK-520 PKS and the corresponding polypeptides encoded thereby are useful for a variety of applications. In one embodiment, a DNA compound comprising a sequence that encodes the FK-520 first extender module is inserted into a DNA compound that comprises the coding sequence for a heterologous PKS. The resulting construct, in which the coding sequence for a module of the heterologous PKS is either replaced by that for the first extender module of the FK-520 PKS or the latter is merely added to coding sequences for modules of the heterologous PKS, provides a novel PKS coding sequence. In another embodiment, a DNA compound comprising a sequence that encodes the first extender module of the FK-520 PKS is inserted into a DNA compound that comprises the remainder of the coding sequence for the FK-520 PKS or a recombinant FK-520 PKS that produces an FK-520 derivative.

In another embodiment, all or only a portion of the first extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with another DH or KR; and/or inserting an ER. In replacing or inserting KR, DH, and ER domains, it is often beneficial to replace the existing KR, DH, and ER domains with the complete set of domains desired from another module. Thus, if one desires to insert an ER domain, one may simply replace the existing KR and DH domains with a KR, DH, and ER set of domains from a module containing such domains. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a gene for a PKS that produces a polyketide other than FK-520, or from chemical synthesis. The resulting heterologous first extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the first extender module of the FK-520 PKS.

In an illustrative embodiment of this aspect of the invention, the invention provides recombinant PKSs and recombinant DNA compounds and vectors that encode such PKSs in which the KS domain of the first extender module has been inactivated. Such constructs are especially useful when placed in translational reading frame with the remaining modules and domains of an FK-520 or FK-520 derivative PKS. The utility of these constructs is that host cells expressing, or cell free extracts containing, the PKS encoded thereby can be fed or supplied with N-acylcysteamine thioesters of novel precursor molecules to prepare FK-520 derivatives. See U.S. patent application Ser. No. 60/117,384, filed Jan. 27, 1999, and PCT patent publication Nos. US97/02358 and US99/03986, each of which is incorporated herein by reference.

The second extender module of the FK-520 PKS includes a KS, an AT specific for methylmalonyl CoA, a KR, an inactive DH, and an ACP. The recombinant DNA compounds of the invention that encode the second extender module of the FK-520 PKS and the corresponding polypeptides encoded thereby are useful for a variety of applications. In one embodiment, a DNA compound comprising a sequence that encodes the FK-520 second extender module is inserted into a DNA compound that comprises the coding sequence for a heterologous PKS. The resulting construct, in which the coding sequence for a module of the heterologous PKS is either replaced by that for the second extender module of the FK-520 PKS or the latter is merely added to coding sequences for the modules of the heterologous PKS, provides a novel PKS coding sequence. In another embodiment, a DNA compound comprising a sequence that encodes the second extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the second extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous second extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the second extender module of the FK-520 PKS.

The third extender module of the FK-520 PKS includes a KS, an AT specific for malonyl CoA, a KR, an inactive DH, and an ACP. The recombinant DNA compounds of the invention that encode the third extender module of the FK-520 PKS and the corresponding polypeptides encoded thereby are useful for a variety of applications. In one embodiment, a DNA compound comprising a sequence that encodes the FK-520 third extender module is inserted into a DNA compound that comprises the coding sequence for a heterologous PKS. The resulting construct, in which the coding sequence for a module of the heterologous PKS is either replaced by that for the third extender module of the FK-520 PKS or the latter is merely added to coding sequences for the modules of the heterologous PKS, provides a novel PKS coding sequence. In another embodiment, a DNA compound comprising a sequence that encodes the third extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the third extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous third extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the third extender module of the FK-520 PKS.

The fourth extender module of the FK-520 PKS includes a KS, an AT that binds ethylmalonyl CoA, an inactive DH, and an ACP. The recombinant DNA compounds of the invention that encode the fourth extender module of the FK-520 PKS and the corresponding polypeptides encoded thereby are useful for a variety of applications. In one embodiment, a DNA compound comprising a sequence that encodes the FK-520 fourth extender module is inserted into a DNA compound that comprises the coding sequence for a heterologous PKS. The resulting construct, in which the coding sequence for a module of the heterologous PKS is either replaced by that for the fourth extender module of the FK-520 PKS or the latter is merely added to coding sequences for the modules of the heterologous PKS, provides a novel PKS coding sequence. In another embodiment, a DNA compound comprising a sequence that encodes the fourth extender module of the FK-520 PKS is inserted into a DNA compound that comprises the remainder of the coding sequence for the FK-520 PKS or a recombinant FK-520 PKS that produces an FK-520 derivative.

In another embodiment, a portion of the fourth extender module coding sequence is utilized in conjunction with other PKS coding sequences to create a hybrid module. In this embodiment, the invention provides, for example, either replacing the ethylmalonyl CoA specific AT with a malonyl CoA, methylmalonyl CoA, or 2-hydroxymalonyl CoA specific AT; and/or deleting the inactive DH, inserting a KR, a KR and an active DH, or a KR, an active DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, a PKS for a polyketide other than FK-520, or from chemical synthesis. The resulting heterologous fourth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fourth extender module of the FK-520 PKS.

As illustrative examples, the present invention provides recombinant genes, vectors, and host cells that result from the conversion of the FK-506 PKS to an FK-520 PKS and vice-versa. In one embodiment, the invention provides a recombinant set of FK-506 PKS genes but in which the coding sequences for the fourth extender module or at least those for the AT domain in the fourth extender module have been replaced by those for the AT domain of the fourth extender module of the FK-520 PKS. This recombinant PKS can be used to produce FK-520 in recombinant host cells. In another embodiment, the invention provides a recombinant set of FK-520 PKS genes but in which the coding sequences for the fourth extender module or at least those for the AT domain in the fourth extender module have been replaced by those for the AT domain of the fourth extender module of the FK-506 PKS. This recombinant PKS can be used to produce FK-506 in recombinant host cells.

Other examples of hybrid PKS enzymes of the invention include those in which the AT domain of module 4 has been replaced with a malonyl specific AT domain to provide a PKS that produces 21-desethyl-FK520 or with a methylmalonyl specific AT domain to provide a PKS that produces 21-desethyl-21-methyl-FK520. Another hybrid PKS of the invention is prepared by replacing the AT and inactive KR domain of FK-520 extender module 4 with a methylmalonyl specific AT and an active KR domain, such as, for example, from module 2 of the DEBS or oleandolide PKS enzymes, to produce 21-desethyl-21-methyl-22-desoxo-22-hydroxy-FK520. The compounds produced by these hybrid PKS enzymes are neurotrophins.

The fifth extender module of the FK-520 PKS includes a KS, an AT that binds methylmalonyl CoA, a DH, a KR, and an ACP. The recombinant DNA compounds of the invention that encode the fifth extender module of the FK-520 PKS and the corresponding polypeptides encoded thereby are useful for a variety of applications. In one embodiment, a DNA compound comprising a sequence that encodes the FK-520 fifth extender module is inserted into a DNA compound that comprises the coding sequence for a heterologous PKS. The resulting construct, in which the coding sequence for a module of the heterologous PKS is either replaced by that for the fifth extender module of the FK-520 PKS or the latter is merely added to coding sequences for the modules of the heterologous PKS, provides a novel PKS. In another embodiment, a DNA compound comprising a sequence that encodes the fifth extender module of the FK-520 PKS is inserted into a DNA compound that comprises the coding sequence for the FK-520 PKS or a recombinant FK-520 PKS that produces an FK-520 derivative.

In another embodiment, a portion of the fifth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one or both of the DH and KR; replacing any one or both of the DH and KR with either a KR and/or DH; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous fifth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fifth extender module of the FK-520 PKS.

In an illustrative embodiment, the present invention provides a set of recombinant FK-520 PKS genes in which the coding sequences for the DH domain of the fifth extender module have been deleted or mutated to render the DH non-functional. In one such mutated gene, the KR and DH coding sequences are replaced with those encoding only a KR domain from another PKS gene. The resulting PKS genes code for the expression of an FK-520 PKS that produces an FK-520 analog that lacks the C-19 to C-20 double bond of FK-520 and has a C-20 hydroxyl group. Such analogs are preferred neurotrophins, because they have little or no immunosuppressant activity. This recombinant fifth extender module coding sequence can be combined with other coding sequences to make additional compounds of the invention. In an illustrative embodiment, the present invention provides a recombinant FK-520 PKS that contains both this fifth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (lacking the C-19 to C-20 double bond of FK-506 and having a C-20 hydroxyl group) FK-506 derivative. In another embodiment, the present invention provides a recombinant FK-506 PKS in which the DH domain of module 5 has been deleted or otherwise rendered inactive and thus produces this novel polyketide.

The sixth extender module of the FK-520 PKS includes a KS, an AT specific for methylmalonyl CoA, a KR, a DH, an ER, and an ACP. The recombinant DNA compounds of the invention that encode the sixth extender module of the FK-520 PKS and the corresponding polypeptides encoded thereby are useful for a variety of applications. In one embodiment, a DNA compound comprising a sequence that encodes the FK-520 sixth extender module is inserted into a DNA compound that comprises the coding sequence for a heterologous PKS. The resulting construct, in which the coding sequence for a module of the heterologous PKS is either replaced by that for the sixth extender module of the FK-520 PKS or the latter is merely added to coding sequences for the modules of the heterologous PKS, provides a novel PKS coding sequence. In another embodiment, a DNA compound comprising a sequence that encodes the sixth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the sixth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous sixth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the sixth extender module of the FK-520 PKS.

In an illustrative embodiment, the present invention provides a set of recombinant FK-520 PKS genes in which the coding sequences for the DH and ER domains of the sixth extender module have been deleted or mutated to render them non-functional. In one such mutated gene, the KR, ER, and DH coding sequences are replaced with those encoding only a KR domain from another PKS gene. This can also be accomplished by simply replacing the coding sequences for extender module six with those for an extender module having a methylmalonyl specific AT and only a KR domain from a heterologous PKS gene, such as, for example, the coding sequences for extender module two encoded by the eryAI gene. The resulting PKS genes code for the expression of an FK-520 PKS that produces an FK-520 analog that has a C-18 hydroxyl group. Such analogs are preferred neurotrophins, because they have little or no immunosuppressant activity. This recombinant sixth extender module coding sequence can be combined with other coding sequences to make additional compounds of the invention. In an illustrative embodiment, the present invention provides a recombinant FK-520 PKS that contains both this sixth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (having a C-18 hydroxyl group) FK-506 derivative. In another embodiment, the present invention provides a recombinant FK-506 PKS in which the DH and ER domains of module 6 have been deleted or otherwise rendered inactive and thus produces this novel polyketide.

The seventh extender module of the FK-520 PKS includes a KS, an AT specific for 2-hydroxymalonyl CoA, a KR, a DH, an ER, and an ACP. The recombinant DNA compounds of the invention that encode the seventh extender module of the FK-520 PKS and the corresponding polypeptides encoded thereby are useful for a variety of applications. In one embodiment, a DNA compound comprising a sequence that encodes the FK-520 seventh extender module is inserted into a DNA compound that comprises the coding sequence for a heterologous PKS. The resulting construct, in which the coding sequence for a module of the heterologous PKS is either replaced by that for the seventh extender module of the FK-520 PKS or the latter is merely added to coding sequences for the modules of the heterologous PKS, provides a novel PKS coding sequence. In another embodiment, a DNA compound comprising a sequence that encodes the seventh extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the seventh extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting the KR, the DH, and/or the ER; and/or replacing the KR, DH, and/or ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous seventh extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the seventh extender module of the FK-520 PKS.

In an illustrative embodiment, the present invention provides a set of recombinant FK-520 PKS genes in which the coding sequences for the AT domain of the seventh extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-15 methoxy group, having instead a hydrogen, methyl, or ethyl group at that position, respectively. Such analogs are preferred, because they are more slowly metabolized than FK-520. This recombinant seventh extender module coding sequence can be combined with other coding sequences to make additional compounds of the invention. In an illustrative embodiment, the present invention provides a recombinant FK-520 PKS that contains both this seventh extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-15-desmethoxy) FK-506 derivative. In another embodiment, the present invention provides a recombinant FK-506 PKS in which the AT domain of module 7 has been replaced and thus produces this novel polyketide.

In another illustrative embodiment, the present invention provides a hybrid PKS in which the AT and KR domains of module 7 of the FK-520 PKS are replaced by a methylmalonyl specific AT domain and an inactive KR domain, such as, for example, the AT and KR domains of extender module 6 of the rapamycin PKS. The resulting hybrid PKS produces 15-desmethoxy-15-methyl-16-oxo-FK-520, a neurotrophin compound.

The eighth extender module of the FK-520 PKS includes a KS, an AT specific for 2-hydroxymalonyl CoA, a KR, and an ACP. The recombinant DNA compounds of the invention that encode the eighth extender module of the FK-520 PKS and the corresponding polypeptides encoded thereby are useful for a variety of applications. In one embodiment, a DNA compound comprising a sequence that encodes the FK-520 eighth extender module is inserted into a DNA compound that comprises the coding sequence for a heterologous PKS. The resulting construct, in which the coding sequence for a module of the heterologous PKS is either replaced by that for the eighth extender module of the FK-520 PKS or the latter is merely added to coding sequences for the modules of the heterologous PKS, provides a novel PKS coding sequence. In another embodiment, a DNA compound comprising a sequence that encodes the eighth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the eighth extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting or replacing the KR; and/or inserting a DH or a DH and an ER. In addition, the KS and/or ACP can be replaced with another KS and/or ACP. In each of these replacements, the heterologous KS, AT, DH, KR, ET, or ACP coding sequence can originate from a coding sequence for another module of the FK-520 PKS, from a coding sequence for a PKS that produces a polyketide other than FK-520, or from chemical synthesis. The resulting heterologous eighth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the eighth extender module of the FK-520 PKS.

In an illustrative embodiment, the present invention provides a set of recombinant FK-520 PKS genes in which the coding sequences for the AT domain of the eighth extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-13 methoxy group, having instead a hydrogen, methyl, or ethyl group at that position, respectively. Such analogs are preferred, because they are more slowly metabolized than FK-520. This recombinant eighth extender module coding sequence can be combined with other coding sequences to make additional compounds of the invention. In an illustrative embodiment, the present invention provides a recombinant FK-520 PKS that contains both this eighth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-13-desmethoxy) FK-506 derivative. In another embodiment, the present invention provides a recombinant FK-506 PKS in which the AT domain of module 8 has been replaced and thus produces this novel polyketide.

The ninth extender module of the FK-520 PKS includes a KS, an AT specific for methylmalonyl CoA, a KR, a DH, an ER, and an ACP. The recombinant DNA compounds of the invention that encode the ninth extender module of the FK-520 PKS and the corresponding polypeptides encoded thereby are useful for a variety of applications. In one embodiment, a DNA compound comprising a sequence that encodes the FK-520 ninth extender module is inserted into a DNA compound that comprises the coding sequence for a heterologous PKS. The resulting construct, in which the coding sequence for a module of the heterologous PKS is either replaced by that for the ninth extender module of the FK-520 PKS or the latter is merely added to coding sequences for the modules of the heterologous PKS, provides a novel PKS coding sequence. In another embodiment, a DNA compound comprising a sequence that encodes the ninth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the ninth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and/or ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous ninth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the ninth extender module of the FK-520 PKS.

The tenth extender module of the FK-520 PKS includes a KS, an AT specific for malonyl CoA, and an ACP. The recombinant DNA compounds of the invention that encode the tenth extender module of the FK-520 PKS and the corresponding polypeptides encoded thereby are useful for a variety of applications. In one embodiment, a DNA compound comprising a sequence that encodes the FK-520 tenth extender module is inserted into a DNA compound that comprises the coding sequence for a heterologous PKS. The resulting construct, in which the coding sequence for a module of the heterologous PKS is either replaced by that for the tenth extender module of the FK-520 PKS or the latter is merely added to coding sequences for the modules of the heterologous PKS, provides a novel PKS coding sequence. In another embodiment, a DNA compound comprising a sequence that encodes the tenth extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the tenth extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; and/or inserting a KR, a KR and DH, or a KR, DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous tenth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the tenth extender module of the FK-520 PKS.

The FK-520 polyketide precursor produced by the action of the tenth extender module of the PKS is then attached to pipecolic acid and cyclized to form FK-520. The enzyme FkbP is the NRPS like enzyme that catalyzes these reactions. FkbP also includes a thioesterase activity that cleaves the nascent FK-520 polyketide from the NRPS. The present invention provides recombinant DNA compounds that encode the fkbp gene and so provides recombinant methods for expressing the fkbp gene product in recombinant host cells. The recombinant fkbP genes of the invention include those in which the coding sequence for the adenylation domain has been mutated or replaced with coding sequences from other NRPS like enzymes so that the resulting recombinant FkbP incorporates a moiety other than pipecolic acid. For the construction of host cells that do not naturally produce pipecolic acid, the present invention provides recombinant DNA compounds that express the enzymes that catalyze at least some of the biosynthesis of pipecolic acid (see Nielsen et al., 1991, Biochem. 30: 5789–96). The fkbL gene encodes a homolog of RapL, a lysine cyclodeaminase responsible in part for producing the pipecolate unit added to the end of the polyketide chain. The fkbB and fkbL recombinant genes of the invention can be used in heterologous hosts to produce compounds such as FK-520 or, in conjunction with other PKS or NRPS genes, to produce known or novel polyketides and non-ribosomal peptides.

The present invention also provides recombinant DNA compounds that encode the P450 oxidase and methyltransferase genes involved in the biosynthesis of FK-520. FIG. 2 shows the various sites on the FK-520 polyketide core structure at which these enzymes act. By providing these genes in recombinant form, the present invention provides recombinant host cells that can produce FK-520. This is accomplished by introducing the recombinant PKS, P450 oxidase, and methyltransferase genes into a heterologous host cell. In a preferred embodiment, the heterologous host cell is Streptomyces coelicolor CH999 or Streptomyces lividans K4-114, as described in U.S. Pat. No. 5,830,750 and U.S. patent application Ser. No. 08/828,898, filed Mar. 31, 1997, and Ser. No. 09/181,833, filed Oct. 28, 1998, each of which is incorporated herein by reference. In addition, by providing recombinant host cells that express only a subset of these genes, the present invention provides methods for making FK-520 precursor compounds not readily obtainable by other means.

In a related aspect, the present invention provides recombinant DNA compounds and vectors that are useful in generating, by homologous recombination, recombinant host cells that produce FK-520 precursor compounds. In this aspect of the invention, a native host cell that produces FK-520 is transformed with a vector (such as an SCP2* derived vector for Streptomyces host cells) that encodes one or more disrupted genes (i.e., a hydroxylase, a methyltransferase, or both) or merely flanking regions from those genes. When the vector integrates by homologous recombination, the native, functional gene is deleted or replaced by the non-functional recombinant gene, and the resulting host cell thus produces an FK-520 precursor. Such host cells can also be complemented by introduction of a modified form of the deleted or mutated non-functional gene to produce a novel compound.

In one important embodiment, the present invention provides a hybrid PKS and the corresponding recombinant DNA compounds that encode those hybrid PKS enzymes. For purposes of the present invention a hybrid PKS is a recombinant PKS that comprises all or part of one or more modules and thioesterase/cyclase domain of a first PKS and all or part of one or more modules, loading module, and thioesterase/cyclase domain of a second PKS. In one preferred embodiment, the first PKS is all or part of the FK-520 PKS, and the second PKS is only a portion or all of a non-FK-520 PKS.

One example of the preferred embodiment is an FK-520 PKS in which the AT domain of module 8, which specifies a hydroxymalonyl CoA and from which the C-13 methoxy group of FK-520 is derived, is replaced by an AT domain that specifies a malonyl, methylmalonyl, or ethylmalonyl CoA. Examples of such replacement AT domains include the AT domains from modules 3, 12, and 13 of the rapamycin PKS and from modules 1 and 2 of the erythromycin PKS. Such replacements, conducted at the level of the gene for the PKS, are illustrated in the examples below. Another illustrative example of such a hybrid PKS includes an FK-520 PKS in which the natural loading module has been replaced with a loading module of another PKS. Another example of such a hybrid PKS is an FK-520 PKS in which the AT domain of module three is replaced with an AT domain that binds methylmalonyl CoA.

In another preferred embodiment, the first PKS is most but not all of a non-FK-520 PKS, and the second PKS is only a portion or all of the FK-520 PKS. An illustrative example of such a hybrid PKS includes an erythromycin PKS in which an AT specific for methylmalonyl CoA is replaced with an AT from the FK-520 PKS specific for malonyl CoA.

Those of skill in the art will recognize that all or part of either the first or second PKS in a hybrid PKS of the invention need not be isolated from a naturally occurring source. For example, only a small portion of an AT domain determines its specificity. See U.S. provisional patent application Ser. No. 60/091,526, incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

Thus, the hybrid modules of the invention are incorporated into a PKS to provide a hybrid PKS of the invention. A hybrid PKS of the invention can result not only:

(i) from fusions of heterologous domain (where heterologous means the domains in that module are from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another but are not adjacent to one another in naturally occurring PKS enzymes) coding sequences to produce a hybrid coding sequence contained in a PKS gene whose product is incorporated into a PKS, (iii) from expression of one or more FK-520 PKS genes with one or more non-FK-520 PKS genes, including both naturally occurring and recombinant non-FK-520 PKS genes, and (iv) from combinations of the foregoing.

Various hybrid PKSs of the invention illustrating these various alternatives are described herein.

Examples of the production of a hybrid PKS by co-expression of PKS genes from the FK-520 PKS and another non-FK-520 PKS include hybrid PKS enzymes produced by coexpression of FK-520 and rapamycin PKS genes. Preferably, such hybrid PKS enzymes are produced in recombinant Streptomyces host cells that produce FK-520 or FK-506 but have been mutated to inactivate the gene whose function is to be replaced by the rapamycin PKS gene introduced to produce the hybrid PKS. Particular examples include (i) replacement of the fkbC gene with the rapB gene; and (ii) replacement of the fkbA gene with the rapC gene. The latter hybrid PKS produces 13,15-didesmethoxy-FK-520, if the host cell is an FK-520 producing host cell, and 13,15-didesmethoxy-FK-506, if the host cell is an FK-506 producing host cell. The compounds produced by these hybrid PKS enzymes are immunosuppressants and neurotrophins but can be readily modified to act only as neurotrophins, as described in Example 6, below.

Other illustrative hybrid PKS enzymes of the invention are prepared by replacing the fkbA gene of an FK-520 or FK-506 producing host cell with a hybrid fkbA gene in which: (a) the extender module 8 through 10, inclusive, coding sequences have been replaced by the coding sequences for extender modules 12 to 14, inclusive, of the rapamycin PKS; and (b) the module 8 coding sequences have been replaced by the module 8 coding sequence of the rifamycin PKS. When expressed with the other, naturally occurring FK-520 or FK-506 PKS genes and the genes of the modification enzymes, the resulting hybrid PKS enzymes produce, respectively, (a) 13-desmethoxy-FK-520 or 13-desmethoxy-FK-506; and (b) 13-desmethoxy-13-methyl-FK-520 or 13-desmethoxy-13-methyl-FK-506. In a preferred embodiment, these recombinant PKS genes of the invention are introduced into the producing host cell by a vector such as pHU204, which is a plasmid pRM5 derivative that has the well-characterized SCP2* replicon, the colE1 replicon, the tsr and bla resistance genes, and a cos site. This vector can be used to introduce the recombinant fkbA replacement gene in an FK-520 or FK-506 producing host cell (or a host cell derived therefrom in which the endogenous fkbA gene has either been rendered inactive by mutation, deletion or homologous recombination with the gene that replaces it) to produce the desired hybrid PKS.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units," Biochemistry 38(5):1643–1651, incorporated herein by reference. Stereochemistry can also be changed by changing the KR domain. Also, one can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, "Dissecting and Exploiting Intermodular Communication in Polyketide Synthases," Science 284: 482–485, incorporated herein by reference.

The following Table lists references describing illustrative PKS genes and corresponding enzymes that can be utilized in the construction of the recombinant PKSs and the corresponding DNA compounds that encode them of the invention. Also presented are various references described tailoring enzymes and corresponding genes that can be employed in accordance with the methods of the present invention.

Avermectin

U.S. Pat. No. 5,252,474 to Merck.

MacNeil et al., 1993, Industrial Microorganisms: Basic and Applied Molecular Genetics, Baltz, Hegeman, & Skatrud, eds. (ASM), pp. 245–256. A Comparison of the Genes Encoding the Polyketide Synthases for Avermectin, Erythromycin, and Nemadectin.

MacNeil et al., 1992, Gene 115: 119–125, Complex Organization of the Streptomyces avermitilis genes encoding the avermectin polyketide synthase.

Ikeda et al., August 1999, Organization of the biosynthetic gene cluster for the polyketide anthelmintic macrolide avermectin in Streptomyces avermitilis, Proc. Natl. Acad Sci. USA 96: 9509–9514.

Candicidin (FR008)

Hu et al., 1994, Mol. Microbiol. 14: 163–172.

Epothilone

U.S. patent application Ser. No. 60/130,560, filed Apr. 22, 1999.

Erythromycin

PCT Pub. No. 93/13663 to Abbott.

U.S. Pat. No. 5,824,513 to Abbott.

Donadio et al., 1991, Science 252:675–9.

Cortes et al., Nov. 8, 1999, Nature 348:176–8, An unusually large multifunctional polypeptide in the erythromycin producing polyketide synthase of Saccharopolyspora erythraea.

Glycosylation Enzymes

PCT Pat. App. Pub. No. 97/23630 to Abbott.

FK-506

Motamedi et al., 1998, The biosynthetic gene cluster for the macrolactone ring of the immunosuppressant FK-506, Eur. J. biochem. 256: 528–534.

Motamedi et al., 1997, Structural organization of a multifunctional polyketide synthase involved in the biosynthesis of the macrolide immunosuppressant FK-506, Eur. J Biochem. 244: 74–80.

Methyltransferase

U.S. Pat. No. 5,264,355, issued Nov. 23, 1993, Methylating enzyme from Streptomyces MA6858. 31-O-desmethyl-FK-506 methyltransferase.

Motamedi et al., 1996. Characterization of methyltransferase and hydroxylase genes involved in the biosynthesis of the immunosuppressants FK-506 and FK-520, J. Bacteriol. 178: 5243–5248.

Streptomyces hygroscopicus

U.S. patent application Ser. No. 09/154,083, filed Sep. 16, 1998.

Lovastatin

U.S. Pat. No. 5,744,350 to Merck.

Narbomycin

U.S. patent application Ser. No. 60/107,093, filed Nov. 5, 1998, and Ser. No. 60/120,254, filed Feb. 16, 1999.

Nemadectin

MacNeil et al., 1993, supra.

Niddamycin

Kakavas et al., 1997, Identification and characterization of the niddamycin polyketide synthase genes from Streptomyces caelestis, J. Bacteriol. 179: 7515–7522.

Oleandomycin

Swan et al., 1994, Characterisation of a Streptomyces antibioticus gene encoding a type I polyketide synthase which has an unusual coding sequence, Mol. Gen. Genet. 242: 358–362.

U.S. patent application Ser. No. 60/120,254, filed Feb. 16, 1999.

Olano et al., 1998, Analysis of a Streptomyces antibioticus chromosomal region involved in oleandomycin biosynthesis, which encodes two glycosyltransferases responsible for glycosylation of the macrolactone ring, Mol. Gen. Genet. 259(3): 299–308.

Picromycin

PCT patent application US99/15047, filed Jul. 2, 1999.

Xue et al., 1998, Hydroxylation of macrolactones YC-17 and narbomycin is mediated by the pikC-encoded cytochrome P450 in Streptomyces venezuelae, Chemistry & Biology 5(11): 661–667.

Xue et al., Oct. 1998, A gene cluster for macrolide antibiotic biosynthesis in Streptomyces venezuelae: Architecture of metabolic diversity, Proc. Natl. Acad. Sci. USA 95: 12111 12116.

Platenolide

EP Pat. App. Pub. No. 791,656 to Lilly.

Rapamycin

Schwecke et al., August 1995, The biosynthetic gene cluster for the polyketide rapamycin, Proc. Natl. Acad. Sci. USA 92:7839–7843.

Aparicio et al., 1996, Organization of the biosynthetic gene cluster for rapamycin in Streptomyces hygroscopicus: analysis of the enzymatic domains in the modular polyketide synthase, Gene 169: 9–16.

Rifamycin

August et al., Feb. 13, 1998, Biosynthesis of the ansamycin antibiotic rifamycin: deductions from the molecular analysis of the rif biosynthetic gene cluster of Amycolatopsis mediterranei S669, Chemistry & Biology, 5(2): 69–79.

Sorangium PKS

U.S. patent application Ser. No. 09/144,085, filed Aug. 31, 1998.

Soraphen

U.S. Pat. No. 5,716,849 to Novartis.

Schupp et al., 1995, J. Bacteriology 177: 3673–3679. A Sorangium cellulosum (Myxobacterium) Gene Cluster for the Biosynthesis of the Macrolide Antibiotic Soraphen A: Cloning, Characterization, and Homology to Polyketide Synthase Genes from Actinomycetes.

Spiramycin

U.S. Pat. No. 5,098,837 to Lilly.

Activator Gene

U.S. Pat. No. 5,514,544 to Lilly.

Tylosin

EP Pub. No. 791,655 to Lilly.

U.S. Pat. No. 5,876,991 to Lilly.

Kuhstoss et al., 1996, Gene 183:231–6., Production of a novel polyketide through the construction of a hybrid polyketide synthase.

Tailoring enzymes

Merson-Davies and Cundliffe, 1994, Mol. Microbiol. 13: 349–355. Analysis of five tylosin biosynthetic genes from the tylBA region of the Streptomyces fradiae genome.

As the above Table illustrates, there are a wide variety of polyketide synthase genes that serve as readily available sources of DNA and sequence information for use in constructing the hybrid PKS-encoding DNA compounds of the invention. Methods for constructing hybrid PKS-encoding DNA compounds are described without reference to the FK-520 PKS in PCT patent publication No. 98/51695; U.S. Pat. Nos. 5,672,491 and 5,712,146 and U.S. patent application Ser. No. 09/073,538, filed May 6, 1998, and Ser. No. 09/141,908, filed Aug. 28, 1998, each of which is incorporated herein by reference.

The hybrid PKS-encoding DNA compounds of the invention can be and often are hybrids of more than two PKS genes. Moreover, there are often two or more modules in the hybrid PKS in which all or part of the module is derived from a second (or third) PKS. Thus, as one illustrative example, the present invention provides a hybrid FK-520 PKS that contains the naturally occurring loading module and FkbP as well as modules one, two, four, six, seven, and eight, nine, and ten of the FK-520 PKS and further contains hybrid or heterologous modules three and five. Hybrid or heterologous module three contains an AT domain that is specific of methylmalonyl CoA and can be derived for example, from the erythromycin or rapamycin PKS genes. Hybrid or heterologous module five contains an AT domain that is specific for malonyl CoA and can be derived for example, from the picromycin or rapamycin PKS genes.

While an important embodiment of the present invention relates to hybrid PKS enzymes and corresponding genes, the present invention also provides recombinant FK-520 PKS genes in which there is no second PKS gene sequence present but which differ from the FK-520 PKS gene by one or more deletions. The deletions can encompass one or more modules and/or can be limited to a partial deletion within one or more modules. When a deletion encompasses an entire module, the resulting FK-520 derivative is at least two carbons shorter than the gene from which it was derived. When a deletion is within a module, the deletion typically encompasses a KR, DH, or ER domain, or both DH and ER domains, or both KR and DH domains, or all three KR, DH, and ER domains.

To construct a hybrid PKS or FK-520 derivative PKS gene of the invention, one can employ a technique, described in PCT Pub. No. 98/27203 and U.S. patent application Ser. No. 08/989,332, filed Dec. 11, 1997, each of which is incorporated herein by reference, in which the large PKS gene is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

Thus, in one important embodiment, the recombinant DNA compounds of the invention are expression vectors. As used herein, the term expression vector refers to any nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA that is translated into a polypeptide in the cell or cell extract. Furthermore, expression vectors typically contain additional functional elements, such as resistance-conferring genes to act as selectable markers.

The various components of an expression vector can vary widely, depending on the intended use of the vector. In particular, the components depend on the host cell(s) in which the vector will be used or is intended to function. Vector components for expression and maintenance of vectors in E. coli are widely known and commercially available, as are vector components for other commonly used organisms, such as yeast cells and Streptomyces cells.

In a preferred embodiment, the expression vectors of the invention are used to construct recombinant Streptomyces host cells that express a recombinant PKS of the invention. Preferred Streptomyces host cell/vector combinations of the invention include S. coelicolor CH999 and S. lividans K4-114 host cells, which do not produce actinorhodin, and expression vectors derived from the pRM1 and pRM5 vectors, as described in U.S. Pat. No. 5,830,750 and U.S. patent application Ser. No. 08/828,898, filed Mar. 31, 1997, and Ser. No. 09/181,833, filed Oct. 28, 1998, each of which is incorporated herein by reference.

The present invention provides a wide variety of expression vectors for use in Streptomyces. For replicating vectors, the origin of replication can be, for example and without limitation, a low copy number vector, such as SCP2* (see Hopwood et al., Genetic Manipulation of Streptomyces: A Laboratory manual (The John Innes Foundation, Norwich, U.K., 1985); Lydiate et al., 1985, Gene 35: 223–235; and Kieser and Melton, 1988, Gene 65: 83–91, each of which is incorporated herein by reference), SLP1.2 (Thompson et al., 1982, Gene 20: 51–62, incorporated herein by reference), and SG5(ts) (Muth et al., 1989, Mol. Gen. Genet. 219: 341–348, and Bierman et al., 1992, Gene 116: 43–49, each of which is incorporated herein by reference), or a high copy number vector, such as pIJ101 and pJV1 (see Katz et al., 1983, J. Gen. Microbiol. 129: 2703–2714; Vara et al., 1989, J. Bacteriol. 171: 5782–5781; and Servin-Gonzalez, 1993, Plasmid 30: 131–140, each of which is incorporated herein by reference). Generally, however, high copy number vectors are not preferred for expression of genes contained on large segments of DNA. For non-replicating and integrating vectors, it is useful to include at least an E. coli origin of replication, such as from pUC, p1P, p1I, and pBR. For phage based vectors, the phages phiC31 and KC515 can be employed (see Hopwood et al., supra).

Typically, the expression vector will comprise one or more marker genes by which host cells containing the vector can be identified and/or selected. Useful antibiotic resistance conferring genes for use in Streptomyces host cells include the ermE (confers resistance to erythromycin and other macrolides and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

The recombinant PKS gene on the vector will be under the control of a promoter, typically with an attendant ribosome binding site sequence. The present invention provides the endogenous promoters of the FK-520 PKS and related biosynthetic genes in recombinant form, and these promoters are preferred for use in the native hosts and in heterologous hosts in which the promoters function. A preferred promoter of the invention is the fkbO gene promoter, comprised in a sequence of about 270 bp between the start of the open reading frames of the fkbO and fkbB genes. The fkbO promoter is believed to be bi-directional in that it promotes transcription of the genes fkbO, fkbP, and fkbA in one direction and fkbB, fkbC, and fkbL in the other. Thus, in one aspect, the present invention provides a recombinant expression vector comprising the promoter of the fkbO gene of an FK-520 producing organism positioned to transcribe a gene other than fkbO. In a preferred embodiment the transcribed gene is an FK-520 PKS gene. In another preferred embodiment, the transcribed gene is a gene that encodes a protein comprised in a hybrid PKS.

Heterologous promoters can also be employed and are preferred for use in host cells in which the endogenous FK-520 PKS gene promoters do not function or function poorly. A preferred heterologous promoter is the actI promoter and its attendant activator gene actII-ORF4, which is provided in the pRM1 and pRM5 expression vectors, supra. This promoter is activated in the stationary phase of growth when secondary metabolites are normally synthesized. Other useful Streptomyces promoters include without limitation those from the ermE gene and the melC1 gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhanced the activity of a promoter. Activator genes in addition to the actII-ORF4 gene discussed above include dnrI, redD, and ptpA genes (see U.S. patent application Ser. No. 09/181,833, supra) to activate promoters under their control.

In addition to providing recombinant DNA compounds that encode the FK-520 PKS, the present invention also provides DNA compounds that encode the ethylmalonyl CoA and 2-hydroxymalonyl CoA utilized in the synthesis of FK-520. Thus, the present invention also provides recombinant host cells that express the genes required for the biosynthesis of ethylmalonyl CoA and 2-hydroxymalonyl CoA. FIGS. 3 and 4 show the location of these genes on the cosmids of the invention and the biosynthetic pathway that produces ethylmalonyl CoA.

For 2-hydroxymalonyl CoA biosynthesis, the fkbH, fkbJ, fkbJ, and fkbK genes are sufficient to confer this ability on Streptomcyces host cells. For conversion of 2-hydroxymalonyl to 2-methoxymalonyl, the fkbG gene is also employed. While the complete coding sequence for fkbH is provided on the cosmids of the invention, the sequence for this gene provided herein may be missing a T residue, based on a comparison made with a similar gene cloned from the ansamitocin gene cluster by Dr. H. Floss. Where the sequence herein shows one T, there may be two, resulting in an extension of the fkbH reading frame to encode the amino acid sequence:

MTIVKCLVWDLDNTLWRGTVLEDDEVV-
LTDEIREVITTLDDRGILQAVASKNDH DLAWERL-
ERLGVAEYFVLARIGWGPKSQSVRE-
IATELNFAPTTIAFIDDQPAERA
EVAFHLPEVRCYPAEQAATLLSLPEFSP-
PVSTVDSRRRRLMYQAGFARDQAREA YSGPDED-
FLRSLDLSMTIAPAGEEELSRVEELTL-
RTSQMNATGVHYSDADLRALL
TDPAHEVLVVTMGDRFGPHGAVGIILLE-
KKPSTWHLKLLATSCRVVSFGAGATIL NWLTDQ-
GARAGAHLVADFRRTDRNRMMEIAYRF-
AGFADSDCPCVSEVAGASA
AGVERLHLEPSARPAPTTLTLTAADIAPVTVSAAG.

For ethylmalonyl CoA biosynthesis, one requires only a crotonyl CoA reductase, which can be supplied by the host cell but can also be supplied by recombinant expression of the fkbS gene of the present invention. To increase yield of ethylmalonyl CoA, one can also express the fkbE and fkbU genes as well. While such production can be achieved using only the recombinant genes above, one can also achieve such production by placing into the recombinant host cell a large segment of the DNA provided by the cosmids of the invention. Thus, for 2-hydroxymalonyl and 2-methoxymalonyl CoA biosynthesis, one can simply provide the cells with the segment of DNA located on the left side of the FK-520 PKS genes shown in FIG. 1. For ethylmalonyl CoA biosynthesis, one can simply provide the cells with the segment of DNA located on the right side of the FK-520 PKS genes shown in FIG. 1 or, alternatively, both the right and left segments of DNA.

The recombinant DNA expression vectors that encode these genes can be used to construct recombinant host cells that can make these important polyketide building blocks from cells that otherwise are unable to produce them. For example, Streptomyces coelicolor and Streptomyces lividans do not synthesisze ethylmalonyl CoA or 2-hydroxymalonyl CoA. The invention provides methods and vectors for constructing recombinant Streptomyces coelicolor and Streptomyces lividans that are able to synthesize either or both ethylmalonyl CoA and 2-hydroxymalonyl CoA. These host cells are thus able to make polyketides, those requiring those substrates, that cannot otherwise be made in such cells.

In a preferred embodiment, the present invention provides recombinant Streptomyces host cells, such as S. coelicolor and S. lividans, that have been transformed with a recombinant vector of the invention that codes for the expression of the ethylmalonyl CoA biosynthetic genes. The resulting host cells produce ethylmalonyl CoA and so are preferred host cells for the production of polyketides produced by PKS enzymes that comprise one or more AT domains specific for ethylmalonyl CoA. Illustrative PKS enzymes of this type include the FK-520 PKS and a recombinant PKS in which one or more AT domains is specific for ethylmalonyl CoA.

In a related embodiment, the present invention provides Streptomyces host cells in which one or more of the ethylmalonyl or 2-hydroxymalonyl biosynthetic genes have been deleted by homologous recombination or rendered inactive by mutation. For example, deletion or inactivation of the fkbG gene can prevent formation of the methoxyl groups at C-13 and G-15 of FK-520 (or, in the corresponding FK-506 producing cell, FK-506), leading to the production of 13,15-didesmethoxy-13,15-dihydroxy-FK-520 (or, in the corresponding FK-506 producing cell, 13,15-didesmethoxy-13,15-dihydroxy-FK-506). If the fkbG gene product acts on 2-hydroxymalonyl and the resulting 2-methoxymalonyl substrate is required for incorporation by the PKS, the AT domains of modules 7 and 8 may bind malonyl CoA and methylmalonyl CoA. Such incorporation results in the production of a mixture of polyketides in which the methoxy groups at C-13 and C-15 of FK-520 (or FK-506) are replaced by either hydrogen or methyl.

This possibility of non-specific binding results from the construction of a hybrid PKS of the invention in which the AT domain of module 8 of the FK-520 PKS replaced the AT domain of module 6 of DEBS. The resulting PKS produced, in Streptomyces lividans, 6-dEB and 2-desmethyl-6-dEB, indicating that the AT domain of module 8 of the FK-520 PKS could bind malonyl CoA and methylmalonyl CoA substrates. Thus, one could possibly also prepare the 13,15-didesmethoxy-FK-520 and corresponding FK-506 compounds of the invention by deleting or otherwise inactivating one or more or all of the genes required for 2-hydroxymalonyl CoA biosynthesis, i.e., the fkbH, fkbJ, fkbJ, and fkbK genes. In any event, the deletion or inactivation of one or more biosynthetic genes required for ethylmalonyl and/or 2-hydroxymalonyl production prevents the formation of polyketides requiring ethylmalonyl and/or 2-hydroxymalonyl for biosynthesis, and the resulting host cells are thus preferred for production of polyketides that do not require the same.

The host cells of the invention can be grown and fermented under conditions known in the art for other purposes to produce the compounds of the invention. See, e.g., U.S. Pat. Nos. 5,194,378; 5,116,756; and 5,494,820, incorporated herein by reference, for suitable fermentation processes. The compounds of the invention can be isolated from the fermentation broths of these cultured cells and purified by standard procedures. Preferred compounds of the invention include the following compounds: 13-desmethoxy-FK-506; 13-desmethoxy-FK-520; 13,15-didesmethoxy-FK-506; 13,15-didesmethoxy-FK-520; 13-desmethoxy-18-hydroxy-FK-506; 13-desmethoxy-18-hydroxy-FK-520; 13,15-didesmethoxy-18-hydroxy-FK-506; and 13,15-didesmethoxy-18-hydroxy-FK-520. These compounds can be further modified as described for tacrolimus and FK-520 in U.S. Pat. Nos. 5,225,403; 5,189,042; 5,164,495; 5,068,323; 4,980,466; and 4,920,218, incorporated herein by reference.

Other compounds of the invention are shown in FIG. 8, Parts A and B. In FIG. 8, Part A, illustrative C-32-substituted compounds of the invention are shown in two columns under the heading R. The substituted compounds are preferred for topical administration and are applied to the dermis for treatment of conditions such as psoriasis. In FIG. 8, Part B, illustrative reaction schemes for making the compounds shown in FIG. 8, Part A, are provided. In the upper scheme in FIG. 8, Part B, the C-32 substitution is a tetrazole moiety, illustrative of the groups shown in the left column under R in FIG. 8, Part A. In the lower scheme in FIG. 8, Part B, the C-32 substitution is a disubstituted amino group, where $R_3$ and $R_4$ can be any group similar to the illustrative groups shown attached to the amine in the right column under R in FIG. 8, Part A. While FIG. 8 shows the C-32-substituted compounds in which the C-15-methoxy is present, the invention includes these C-32-substituted compounds in which C-15 is ethyl, methyl, or hydrogen. Also, while C-21 is shown as substituted with ethyl or allyl, the compounds of the invention includes the C-32-substituted compounds in which C-21 is substituted with hydrogen or methyl.

To make these C-32-substituted compounds, FIG. 8, Part B, provides illustrative reaction schemes. Thus, a selective reaction of the starting compound (see FIG. 8, Part B, for an illustrative starting compound) with trifluoromethanesulfonic anhydride in the presence of a base yields the C-32 O-triflate derivative, as shown in the upper scheme of FIG. 8, Part B. Displacement of the triflate with 1H-tetrazole or triazole derivatives provides the C-32 tetrazole or triazole derivative. As shown in the lower scheme of FIG. 8, Part B, reacting the starting compound with p-nitrophenylchloroformate yields the correspoinding carbonate, which, upon displacement with an amino compound, provides the corresponding carbamate derivative.

The compounds can be readily formulated to provide the pharmaceutical compositions of the invention. The pharmaceutical compositions of the invention can be used in the form of a pharmaceutical preparation, for example, in solid, semisolid, or liquid form. This preparation contains one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use. Suitable formulation processes and compositions for the compounds of the present invention are described with respect to tacrolimus in U.S. Pat. Nos. 5,939,427; 5,922,729; 5,385,907; 5,338,684; and 5,260,301, incorporated herein by reference. Many of the compounds of the invention contain one or more chiral centers, and all of the stereoisomers are included within the scope of the invention, as pure compounds as well as mixtures of stereoisomers. Thus the compounds of the invention may be supplied as a mixture of stereoisomers in any proportion.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, Transplantation Proceedings XIX, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases relating to immunosuppression or neuronal damage, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the present invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 g of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention can be formulated within the range of, for example, 0.00001% to 60% by weight, preferably from 0.001% to 10% by weight, and most preferably from about 0.005% to 0.8% by weight. The compounds and compositions of the invention are useful in treating disease conditions using doses and administration schedules as described for tacrolimus in U.S. Pat. Nos. 5,542,436; 5,365,948; 5,348,966; and 5,196,437, incorporated herein by reference. The compounds of the invention can be used as single therapeutic agents or in combination with other therapeutic agents. Drugs that can be usefully combined with compounds of the invention include one or more immunosuppressant agents such as rapamycin, cyclosporin A, FK-506, or one or more neurotrophic agents.

It will be understood, however, that the specific dosage level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the present invention and shall not be construed as being a limitation on the scope of the invention or claims.

EXAMPLE 1

Replacement of Methoxyl with Hydrogen or Methyl at C-13 of FK-520

The C-13 methoxyl group is introduced into FK-520 via an AT domain in extender module 8 of the PKS that is specific for hydroxymalonyl and by methylation of the hydroxyl group by an S-adenosyl methionine (SAM) dependent methyltransferase. Metabolism of FK-506 and FK-520 primarily involves oxidation at the C-13 position into an inactive derivative that is further degraded by host P450 and other enzymes. The present invention provides compounds related in structure to FK-506 and FK-520 that do not contain the C-13 methoxy group and exhibit greater stability and a longer half-life in vivo. These compounds are useful medicaments due to their immunosuppressive and neurotrophic activities, and the invention provides the compounds in purified form and as pharmaceutical compositions.

The present invention also provides the novel PKS enzymes that produce these novel compounds as well as the expression vectors and host cells that produce the novel PKS enzymes. The novel PKS enzymes include, among others, those that contain an AT domain specific for either malonyl CoA or methylmalonyl CoA in module 8 of the FK-506 and FK-520 PKS. This example describes the construction of recombinant DNA compounds that encode the novel FK-520 PKS enzymes and the transformation of host cells with those recombinant DNA compounds to produce the novel PKS enzymes and the polyketides produced thereby.

To construct an expression cassette for performing module 8 AT domain replacements in the FK-520 PKS, a 4.6 kb SphI fragment from the FK-520 gene cluster was cloned into plasmid pLitmus 38 (a cloning vector available from New England Biolabs). The 4.6 kb SphI fragment, which encodes the ACP domain of module 7 followed by module 8 through the KR domain, was isolated from an agarose gel after digesting the cosmid pKOS65-C31 with Sph I. The clone having the insert oriented so the single SacI site was nearest to the SpeI end of the polylinker was identified and designated as plasmid pKOS60-21-67. To generate appropriate cloning sites, two linkers were ligated sequentially as follows. First, a linker was ligated between the SpeI and SacI sites to introduce a BglII site at the 5' end of the cassette, to eliminate interfering polylinker sites, and to reduce the total insert size to 4.5 kb (the limit of the phage KC515). The ligation reactions contained 5 picomolar unphosphorylated linker DNA and 0.1 picomolar vector DNA, i.e., a 50-fold molar excess of linker to vector. The linker had the following sequence:

5'-CTAGTGGGCAGATCTGGCAGCT-3'
3'-ACCCGTCTAGACCG-5'

The resulting plasmid was designated pKOS60-27-1.

Next, a linker of the following sequence was ligated between the unique SphI and AflII sites of plasmid pKOS60-27-1 to introduce an NsiI site at the 3' end of the module 8 cassette. The linker employed was:

5'-GGGATGCATGGC-3'
3'-GTACCCCTACGTACCGAATT-5'

The resulting plasmid was designated pKOS60-29-55.

To allow in-frame insertions of alternative AT domains, sites were engineered at the 5' end (Avr II or Nhe I) and 3' end (Xho I) of the AT domain using the polymerase chain reaction (PCR) as follows. Plasmid pKOS60-29-55 was used as a template for the PCR and sequence 5' to the AT domain was amplified with the primers SpeBgl-fwd and either Avr-rev or Nhe-rev:

SpeBgl-fwd 5'-CGACTCACTAGTGGGCAGATCTGG-3'
Avr-rev
5'-CACGCCTAGGCCGGTCGGTCTCGGGCCAC-3'
Nhe-rev
5'-GCGGCTAGCTGCTCGCCCATCGCGGGATGC-3'

The PCR included, in a 50 μl reaction, 5 μl of 10×Pfu polymerase buffer (Stratagene), 5 μl 10×z-dNTP mixture (2 mM dATP, 2 mM dCTP, 2 mM dTTP, 1 mM dGTP, 1 mM 7-deaza-GTP), 5 μl DMSO, 2 μl of each primer (10 μM), 1 μl of template DNA (0.1 μg/μl), and 1 μl of cloned Pfu polymerase (Stratagene). The PCR conditions were 95° C. for 2 min., 25 cycles at 95° C. for 20 sec., 60° C. for 30 sec., and 72° C. for 4 min., followed by 4 min. at 72° C. and a hold at 0° C. The amplified DNA products and the Litmus vectors were cut with the appropriate restriction enzymes (BglII and AvrII or SpeI and NheI), and cloned into either pLitmus 28 or pLitmus38 (New England Biolabs), respectively, to generate the constructs designated pKOS60-37-4 and pKOS60-37-2, respectively.

Plasmid pKOS60-29-55 was again used as a template for PCR to amplify sequence 3' to the AT domain using the primers BsrXho-fwd and NsiAfl-rev:

BsrXho-fwd
5'-GATGTACAGCTCGAGTCGGCACGCCCGGCCGCATC-3'
NsiAfl-rev 5'-CGACTCACTTAAGCCATGCATCC-3'

PCR conditions were as described above. The PCR fragment was cut with BsrGI and AflII, gel isolated, and ligated into pKOS60-37-4 cut with Asp718 and AflII and inserted into pKOS60-37-2 cut with BsrGI and AflII, to give the plasmids pKOS60-39-1 and pKOS60-39-13, respectively. These two plasmids can be digested with AvrII and XhoI or NheI and XhoI, respectively, to insert heterologous AT domains specific for malonyl, methylmalonyl, ethylmalonyl, or other extender units.

Malonyl and methylmalonyl-specific AT domains were cloned from the rapamycin cluster using PCR amplification with a pair of primers that introduce an AvrII or NheI site at the 5' end and an XhoI site at the 3' end. The PCR conditions were as given above and the primer sequences were as follows:

RATN1
5'-ATCCTAGGCGGGCRGGYGTGTCGTCCTTCGG-3' (3' end of Rap KS sequence and universal for malonyl and methylmalonyl CoA),
RATMN2
5'-ATGCTAGCCGCCGCGTTCCCCGTCTTCGCGCG-3'(Rap AT shorter version 5'-sequence and specific for malonyl CoA),
RATMMN2
5'-ATGCTAGCGGATTCGTCGGTGGTGTTCGCCGA-3'(Rap AT shorter version 5'-sequence and specific for methylmalonyl CoA), and
RATC
5'-ATCTCGAGCCAGTASCGCTGGTGYTGGAAGG-3'(Rap DH 5'-sequence and universal for malonyl and methylmalonyl CoA).

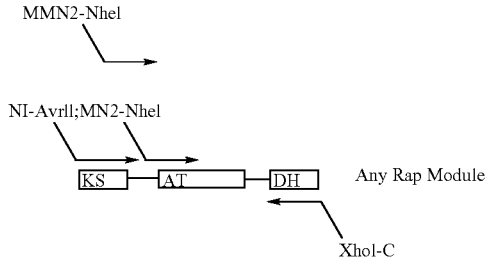

Because of the high sequence similarity in each module of the rapamycin cluster, each primer was expected to prime any of the AT domains. PCR products representing ATs specific for malonyl or methylmalonyl extenders were identified by sequencing individual cloned PCR products. Sequencing also confirmed that the chosen clones contained no cloning artifacts. Examples of hybrid modules with the rapamycin AT12 and AT13 domains are shown in a separate figure.

The AvrII-XhoI restriction fragment that encodes module 8 of the FK-520 PKS with the endogenous AT domain replaced by the AT domain of module 12 of the rapamycin PKS has the DNA sequence and encodes the amino acid sequence shown below. The AT of rap module 12 is specific for incorporation of malonyl units.

```
AGATCTGGCAGCTCGCCGAAGCGCTGCTGACGCTCGTCCGGGAGAGCACC      50
  I  W  Q  L  A  E  A  L  L  T  L  V  R  E  S  T

GCCGCCGTGCTCGGCCACGTGGGTGGCGAGGACATCCCCGCGACGGCGGC     100
 A  A  V  L  G  H  V  G  G  E  D  I  P  A  T  A  A

GTTCAAGGACCTCGGCATCGACTCGCTCACCGCGGTCCAGCTGCGCAACG     150
  F  K  D  L  G  I  D  S  L  T  A  V  Q  L  R  N

CCCTCACCGAGGCGACCGGTGTGCGGCTGAACGCCACGGCGGTCTTCGAC     200
A  L  T  E  A  T  G  V  R  L  N  A  T  A  V  F  D

TTCCCGACCCCGCACGTGCTCGCCGGGAAGCTCGGCGACGAACTGACCGG     250
 F  P  T  P  H  V  L  A  G  K  L  G  D  E  L  T  G

CACCCGCGCGCCCGTCGTGCCCCGGACCGCGGCCACGGCCGGTGCGCACG     300
  T  R  A  P  V  V  P  R  T  A  A  T  A  G  A  H

ACGAGCCGCTGGCGATCGTGGGAATGGCCTGCCGGCTGCCCGGCGGGGTC     350
D  E  P  L  A  I  V  G  M  A  C  R  L  P  G  G  V

GCGTCACCCGAGGAGCTGTGGCACCTCGTGGCATCCGGCACCGACGCCAT     400
 A  S  P  E  E  L  W  H  L  V  A  S  G  T  D  A  I

CACGGAGTTCCCGACGGACCGCGGCTGGGACGTCGACGCGATCTACGACC     450
  T  E  F  P  T  D  R  G  W  D  V  D  A  I  Y  D

CGGACCCCGACGCGATCGGCAAGACCTTCGTCCGGCACGGTGGCTTCCTC     500
P  D  P  D  A  I  G  K  T  F  V  R  H  G  G  F  L

ACCGGCGCGACAGGCTTCGACGCGGCGTTCTTCGGCATCAGCCCGCGCGA     550
 T  G  A  T  G  F  D  A  A  F  F  G  I  S  P  R  E

GGCCCTCGCGATGGACCCGCAGCAGCGGGTGCTCCTGGAGACGTCGTGGG     600
  A  L  A  M  D  P  Q  Q  R  V  L  L  E  T  S  W

AGGCGTTCGAAAGCGCCGGCATCACCCCGGACTCGACCCGCGGCAGCGAC     650
E  A  F  E  S  A  G  I  T  P  D  S  T  R  G  S  D

ACCGGCGTGTTCGTCGGCGCCTTCTCCTACGGTTACGGCACCGGTGCGGA     700
 T  G  V  F  V  G  A  G  S  Y  G  Y  G  T  G  A  D

CACCGACGGCTTCGGCGCGACCGGCTCGCAGACCAGTGTGCTCTCCGGCC     750
  T  D  G  F  G  A  T  G  S  Q  T  S  V  L  S  G

GGCTGTCGTACTTCTACGGTCTGGAGGGTCCGGCGGTCACGGTCGACACG     800
R  L  S  Y  F  Y  G  L  E  G  P  A  V  T  V  D  T

GCGTGTTCGTCGTCGCTGGTGGCGCTGCACCAGGCCGGGCAGTCGCTGCG     850
 A  C  S  S  S  L  V  A  L  H  Q  A  G  Q  S  L  R

CTCCGGCGAATGCTCGCTCGCCCTGGTCGGCGGCGTCACGGTGATGGCGT     900
  S  G  E  C  S  L  A  L  V  G  G  V  T  V  M  A

CTCCCGGCGGCTTCGTGGAGTTCTCCCGGCAGCGCGGCCTCGCGCCGGAC     950
S  P  G  G  F  V  E  F  S  R  Q  R  G  L  A  P  D

GGCCGGGCGAAGGCGTTCGGCGCGGGTGCGGACGGCACGAGCTTCGCCGA    1000
 G  R  A  K  A  F  G  A  G  A  D  G  T  S  F  A  E

GGGTGCCGGTGTGCTGATCGTCGAGAGGCTCTCCGACGCCGAACGCAACG    1050
  G  A  G  V  L  I  V  E  R  L  S  D  A  E  R  N

GTCACACCGTCCTGGCGGTCGTCCGTGGTTCGGCGGTCAACCAGGATGGT    1100
G  H  T  V  L  A  V  V  R  G  S  A  V  N  Q  D  G

GCCTCCAACGGGCTGTCGGCGCCGAACGGGCCGTCGCAGGAGCGGGTGAT    1150
 A  S  N  G  L  S  A  P  N  G  P  S  Q  E  R  V  I

CCGGCAGGCCCTGGCCAACGCCGGGCTCACCCCGGCGGACGTGGACGCCG    1200
  R  Q  A  L  A  N  A  G  L  T  P  A  D  V  D  A

TCGAGGCCCACGGCACCGGCACCAGGCTGGGCGACCCCATCGAGGCACAG    1250
V  E  A  H  G  T  G  T  R  L  G  D  P  I  E  A  Q
```

-continued

```
GCGGTACTGGCCACCTACGGACAGGAGCGCGCCACCCCCCTGCTGCTGGG     1300
 A  V  L  A  T  Y  G  Q  E  R  A  T  P  L  L  L  G

CTCGCTGAAGTCCAACATCGGCCACGCCCAGGCCGCGTCCGGCGTCGCCG     1350
  S  L  K  S  N  I  G  H  A  Q  A  A  S  G  V  A

GCATCATCAAGATGGTGCAGGCCCTCCGGCACGGGGAGCTGCCGCCGACG     1400
G  I  I  K  M  V  Q  A  L  R  H  G  E  L  P  P  T

CTGCACGCCGACGAGCCGTCGCCGCACGTCGACTGGACGGCCGGCGCCGT     1450
 L  H  A  D  E  P  S  P  H  V  D  W  T  A  G  A  V

CGAACTGCTGACGTCGGCCCGGCCGTGGCCCGAGACCGACCGGCCTAGGC     1500
  E  L  L  T  S  A  R  P  W  P  E  T  D  R  P  R

GGGCAGGCGTGTCGTCCTTCGGGATCAGTGGCACCAACGCCCACGTCATC     1550
R  A  G  V  S  S  F  G  I  S  G  T  N  A  H  V  I

CTGGAAAGCGCACCCCCCACTCAGCCTGCGGACAACGCGGTGATCGAGCG     1600
-L  E  S  A  P  P  T  Q  P  A  D  N  A  V  I  E  R

GGCACCGGAGTGGGTGCCGTTGGTGATTTCGGCCAGGACCCAGTCGGCTT     1650
  A  P  E  W  V  P  L  V  I  S  A  R  T  Q  S  A

TGACTGAGCACGAGGGCCGGTTGCGTGCGTATCTGGCGGCGTCGCCCGGG     1700
L  T  E  H  E  G  R  L  R  A  Y  L  A  A  S  P  G

GTGGATATGCGGGCTGTGGCATCGACGCTGGCGATGACACGGTCGGTGTT     1750
 V  D  M  R  A  V  A  S  T  L  A  M  T  R  S  V  F

CGAGCACCGTGCCGTGCTGCTGGGAGATGACACCGTCACCGGCACCGCTG     1800
  E  H  R  A  V  L  L  G  D  D  T  V  T  G  T  A

TGTCTGACCCTCGGGCGGTGTTCGTCTTCCCGGGACAGGGGTCGCAGCGT     1850
V  S  D  P  R  A  V  F  V  F  P  G  Q  G  S  Q  R

GCTGGCATGGGTGAGGAACTGGCCGCCGCGTTCCCCGTCTTCGCGCGGAT     1900
 A  G  M  G  E  E  L  A  A  A  F  P  V  F  A  R  I

CCATCAGCAGGTGTGGGACCTGCTCGATGTGCCCGATCTGGAGGTGAACG     1950
  H  Q  Q  V  W  D  L  L  D  V  P  D  L  E  V  N

AGACCGGTTACGCCCAGCCGGCCCTGTTCGCAATGCAGGTGGCTCTGTTC     2000
E  T  G  Y  A  Q  P  A  L  F  A  M  Q  V  A  L  F

GGGCTGCTGGAATCGTGGGGTGTACGACCGGACGCGGTGATCGGCCATTC     2050
 G  L  L  E  S  W  G  V  R  P  D  A  V  I  G  H  S

GGTGGGTGAGCTTGCGGCTGCGTATGTGTCCGGGGTGTGGTCGTTGGAGG     2100
  V  G  E  L  A  A  A  Y  V  S  G  V  W  S  L  E

ATGCCTGCACTTTGGTGTCGGCGCGGGCTCGTCTGATGCAGGCTCTGCCC     2150
D  A  C  T  L  V  S  A  R  A  R  L  M  Q  A  L  P

GCGGGTGGGGTGATGGTCGCTGTCCCGGTCTCGGAGGATGAGGCCCGGGC     2200
 A  G  G  V  M  V  A  V  P  V  S  E  D  E  A  R  A

CGTGCTGGGTGAGGGTGTGGAGATCGCCGCGGTCAACGGCCCGTCGTCGG     2250
  V  L  G  E  G  V  E  I  A  A  V  N  G  P  S  S

TGGTTCTCTCCGGTGATGAGGCCGCCGTGCTGCAGGCCGCGGAGGGGCTG     2300
V  V  L  S  G  D  E  A  A  V  L  Q  A  A  E  G  L

GGGAAGTGGACGCGGCTGGCGACCAGCCACGCGTTCCATTCCGCCCGTAT     2350
 G  K  W  T  R  L  A  T  S  H  A  F  H  S  A  R  M

GGAACCCATGCTGGAGGAGTTCCGGGCGGTCGCCGAAGGCCTGACCTACC     2400
  E  P  M  L  E  E  F  R  A  V  A  E  G  L  T  Y

TACTGGGTGCGGCAGGTCCGGGACACGGTCCGGTTCGGCGAGCAGGTGGC     2450
R  T  P  Q  V  S  M  A  V  G  D  Q  V  T  T  A  E

TACTGGGTGCGGCAGGTCCGGGACACGGTCCGGTTCGGCGAGCAGGTGGC     2500
 Y  W  V  R  Q  V  R  D  T  V  R  F  G  E  Q  V  A

CTCGTACGAGGACGCCGTGTTCGTCGAGCTGGGTGCCGACCGGTCACTGG     2550
  S  Y  E  D  A  V  F  V  E  L  G  A  D  R  S  L
```

-continued

```
CCCGCCTGGTCGACGGTGTCGCGATGCTGCACGGCGACCACGAAATCCAG     2600
 A  A  I  G  A  L  A  H  L  Y  V  N  G  V  T  V  D

CTGGCCCGCGCTCCTGGGCGATGCTCCGGCAACACGGGTGCTGGACCTTC     2700
  W  P  A  L  L  G  D  A  P  A  T  R  V  L  D  L

CGACATACGCCTTCCAGCACCAGCGCTACTGGCTCGAGTCGGCACGCCCG     2750
P  T  Y  A  F  Q  H  Q  R  Y  W  L  E  S  A  R  P

GCCGCATCCGACGCGGGCCACCCCGTGCTGGGCTCCGGTATCGCCCTCGC     2800
 A  A  S  D  A  G  H  P  V  L  G  S  G  I  A  L  A

CGGGTCGCCGGGCCGGGTGTTCACGGGTTCCGTGCCGACCGGTGCGGACC     2850
  G  S  P  G  R  V  F  T  G  S  V  P  T  G  A  D

GCGCGGTGTTCGTCGCCGAGCTGGCGCTGGCCGCCGCGGACGCGGTCGAC     2900
R  A  V  F  V  A  E  L  A  L  A  A  A  D  A  V  D

TGCGCCACGGTCGAGCGGCTCGACATCGCCTCCGTGCCCGGCCGGCCGGG     2950
 C  A  T  V  E  R  L  D  I  A  S  V  P  G  R  P  G

CCATGGCCGGACGACCGTACAGACCTGGGTCGACGAGCCGGCGGACGACG     3000
  H  G  R  T  T  V  Q  T  W  V  D  E  P  A  D  D

GCCGGCGCCGGTTCACCGTGCACACCCGCACCGGCGACGCCCCGTGGACG     3050
G  R  R  R  F  T  V  H  T  R  T  G  D  A  P  W  T

CTGCACGCCGAGGGGGTGCTGCGCCCCCATGGCACGGCCCTGCCCGATGC     3100
 L  H  A  E  G  V  L  R  P  H  G  T  A  L  P  D  A

GGCCGACGCCGAGTGGCCCCCACCGGGCGCGGTGCCCGCGGACGGGCTGC     3150
  A  D  A  E  W  P  P  P  G  A  V  P  A  D  G  L

CGGGTGTGTGGCGCCGGGGGGACCAGGTCTTCGCCGAGGCCGAGGTGGAC     3200
P  G  V  W  R  R  G  D  Q  V  F  A  E  A  E  V  D

GGACCGGACGGTTTCGTGGTGCACCCCGACCTGCTCGACGCGGTCTTCTC     3250
 G  P  D  G  F  V  V  H  P  D  L  L  D  A  V  F  S

CGCGGTCGGCGACGGAAGCCGCCAGCCGGCCGGATGGCGCGACCTGACGG     3300
  A  V  G  D  G  S  R  Q  P  A  G  W  R  D  L  T

TGCACGCGTCGGACGCCACCGTACTGCGCGCCTGCCTCACCCGGCGCACC     3350
V  H  A  S  D  A  T  V  L  R  A  C  L  T  R  R  T

GACGGAGCCATGGGATTCGCCGCCTTCGACGGCGCCGGCCTGCCGGTACT     3400
 D  G  A  M  G  F  A  A  F  D  G  A  G  L  P  V  L

CACCGCGGAGGCGGTGACGCTGCGGGAGGTGGCGTCACCGTCCGGCTCCG     3450
  T  A  E  A  V  T  L  R  E  V  A  S  P  S  G  S

AGGAGTCGGACGGCCTGCACCGGTTGGAGTGGCTCGCGGTCGCCGAGGCG     3500
E  E  S  D  G  L  H  R  L  E  W  L  A  V  A  E  A

GTCTACGACGGTGACCTGCCCGAGGGACATGTCCTGATCACCGCCGCCCA     3550
 V  Y  D  G  D  L  P  E  G  H  V  L  I  T  A  A  H

CCCCGACGACCCCGAGGACATACCCACCCGCGCCCACACCCGCGCCACCC     3600
  P  D  D  P  E  D  I  P  T  R  A  H  T  R  A  T

GCGTCCTGACCGCCCTGCAACACCACCTCACCACCACCGACCACACCCTC     3650
R  V  L  T  A  L  Q  H  H  L  T  T  T  D  H  T  L

ATCGTCCACACCACCACCGACCCCGCCGGCGCCACCGTCACCGGCCTCAC     3700
 I  V  H  T  T  T  D  P  A  G  A  T  V  T  G  L  T

CCGCACCGCCCAGAACGAACACCCCCACCGCATCCGCCTCATCGAAACCG     3750
  R  T  A  Q  N  E  H  P  H  R  I  R  L  I  E  T

ACCACCCCCACACCCCCCTCCCCCTGGCCCAACTCGCCACCCTCGACCAC     3800
D  H  P  H  T  P  L  P  L  A  Q  L  A  T  L  D  H

CCCCACCTCCGCCTCACCCACCACACCCTCCACCACCCCCACCTCACCCC     3850
 P  H  L  R  L  T  H  H  T  L  H  H  P  H  L  T  P

CCTCCACACCACCACCCCACCCACCACCACCCCCCTCAACCCCGAACACG     3900
  L  H  T  T  T  P  P  T  T  T  P  L  N  P  E  H
```

-continued

```
CCATCATCATCACCGGCGGCTCCGGCACCCTCGCCGGCATCCTCGCCCGC     3950
A  I  I  I  T  G  G  S  G  T  L  A  G  I  L  A  R

CACCTGAACCACCCCCACACCTACCTCCTCTCCCGCACCCCACCCCCCGA     4000
 H  L  N  H  P  H  T  Y  L  L  S  R  T  P  P  P  D

CGCCACCCCCGGCACCCACCTCCCCTGCGACGTCGGCGACCCCCACCAAC     4050
  A  T  P  G  T  H  L  P  C  D  V  G  D  P  H  Q

TCGCCACCACCCTCACCCACATCCCCCAACCCCTCACCGCCATCTTCCAC     4100
L  A  T  T  L  T  H  I  P  Q  P  L  T  A  I  F  H

ACCGCCGCCACCCTCGACGACGGCATCCTCCACGCCCTCACCCCCGACCG     4150
 T  A  A  T  L  D  D  G  I  L  H  A  L  T  P  D  R

CCTCACCACCGTCCTCCACCCCAAAGCCAACGCCGCCTGGCACCTGCACC     4200
  L  T  T  V  L  H  P  K  A  N  A  A  W  H  L  H

ACCTCACCCAAAACCAACCCCTCACCCACTTCGTCCTCTACTCCAGCGCC     4250
H  L  T  Q  N  Q  P  L  T  H  F  V  L  Y  S  S  A

GCCGCCGTCCTCGGCAGCCCCGGACAAGGAAACTACGCCGCCGCCAACGC     4300
 A  A  V  L  G  S  P  G  Q  G  N  Y  A  A  A  N  A

CTTCCTCGACGCCCTCGCCACCCACCGCCACACCCTCGGCCAACCCGCCA     4350
  F  L  D  A  L  A  T  H  R  H  T  L  G  Q  P  A

CCTCCATCGCCTGGGGCATGTGGCACACCACCAGCACCCTCACCGGACAA     4400
T  S  I  A  W  G  M  W  H  T  T  S  T  L  T  G  Q

CTCGACGACGCCGACCGGGACCGCATCCGCCGCGGCGGTTTCCTCCCGAT     4450
 L  D  D  A  D  R  D  R  I  R  R  G  G  F  L  P  I

CACGGACGACGAGGGCATGGGGATGCAT
  T  D  D  E  G
```

The AvrII-XhoI restriction fragment that encodes module 8 of the FK-520 PKS with the endogenous AT domain replaced by the AT domain of module 13 (specific for -methylmalonyl CoA) of the rapamycin PKS has the DNA sequence and encodes the amino acid sequence shown below.

```
AGATCTGGCAGCTCGCCGAAGCGCTGCTGACGCTCGTCCGGGAGAGCACC      50
 Q  L  A  E  A  L  L  T  L  V  R  E  S  T

GCCGCCGTGCTCGGCCACGTGGGTGGCGAGGACATCCCCGCGACGGCGGC     100
 A  A  V  L  G  H  V  G  G  E  D  I  P  A  T  A  A

GTTCAAGGACCTCGGCATCGACTCGCTCACCGCGGTCCAGCTGCGCAACG     150
A  L  T  E  A  Y  G  V  R  L  N  A  T  A  V  F  D

TTCCCGACCCCGCACGTGCTCGCCGGGAAGCTCGGCGACGAACTGACCGG     250
 F  P  T  P  H  V  L  A  G  K  L  G  D  E  L  T  G

CACCCGCGCGCCCGTCGTGCCCCGGACCGCGGCCACGGCCGGTGCGCACG     300
  T  R  A  P  V  V  P  R  T  A  A  T  A  G  A  H

ACGAGCCGCTGGCGATCGTGGGAATGGCCTGCCGGCTGCCCGGCGGGGTC     350
D  E  P  L  A  I  V  G  M  A  C  R  L  P  G  G  V

GCGTCACCCGAGGAGCTGTGGCACCTCGTGGCATCCGGCACCGACGCCAT     400
 A  S  P  E  E  L  W  H  L  V  A  S  G  T  D  A  I

CACGGAGTTCCCGACGGACCGCGGCTGGGACGTCGACGCGATCTACGACC     450
  T  E  F  P  T  D  R  G  W  D  V  D  A  I  Y  D

CGGACCCCGACGCGATCGGCAAGACCTTCGTCCGGCACGGTGGCTTCCTC     500
P  D  P  D  A  I  G  K  T  F  V  R  H  G  G  F  L

ACCGGCGCGACAGGCTTCGACGCGGCGTTCTTCGGCATCAGCCCGCGCGA     550
 T  G  A  T  G  F  D  A  A  F  F  G  I  S  P  R  E

GGCCCTCGCGATGGACCCGCAGCAGCGGGTGCTCCTGGAGACGTCGTGGG     600
  A  L  A  M  D  P  Q  Q  R  V  L  L  E  T  S  W

AGGCGTTCGAAAGCGCCGGCATCACCCCGGACTCGACCCGCGGCAGCGAC     650
E  A  F  E  S  A  G  I  T  P  D  S  T  R  G  S  D
```

-continued

```
ACCGGCGTGTTCGTCGGCGCCTTCTCCTACGGTTACGGCACCGGTGCGGA      700
 T  G  V  F  V  G  A  F  S  Y  G  Y  G  T  G  A  D

CACCGACGGCTTCGGCGCGACCGGCTCGCAGACCAGTGTGCTCTCCGGCC      750
  T  D  G  F  G  A  T  G  S  Q  T  S  V  L  S  G

GGCTGTCGTACTTCTACGGTCTGGAGGGTCCGGCGGTCACGGTCGACACG      800
R  L  S  Y  F  Y  G  L  E  G  P  A  V  T  V  D  T

GCGTGTTCGTCGTCGCTGGTGGCGCTGCACCAGGCCGGGCAGTCGCTGCG      850
 A  C  S  S  S  L  V  A  L  H  Q  A  G  Q  S  L  R

CTCCGGCGAATGCTCGCTCGCCCTGGTCGGCGGCGTCACGGTGATGGCGT      900
  S  G  E  C  S  L  A  L  V  G  G  V  T  V  M  A

CTCCCGGCGGCTTCGTGGAGTTCTCCCGGCAGCGCGGCCTCGCGCCGGAC      950
S  P  G  G  F  V  E  V  S  R  Q  R  G  L  Q  P  D

GGCCGGGCGAAGGCGTTCGGCGCGGGTGCGGACGGCACGAGCTTCGCCGA     1000
 G  R  A  K  A  F  G  A  G  A  D  G  T  S  F  A  E

GGGTGCCGGTGTGCTGATCGTCGAGAGGCTCTCCGACGCCGAACGCAACG     1050
  G  A  G  V  L  I  V  E  R  L  S  D  A  E  R  N

GTCACACCGTCCTGGCGGTCGTCCGTGGTTCGGCGGTCAACCAGGATGGT     1100
G  H  T  V  L  A  V  V  R  G  S  A  V  N  Q  D  G

GCCTCCAACGGGCTGTCGGCGCCGAACGGGCCGTCGCAGGAGCGGGTGAT     1105
 A  S  N  G  L  S  A  P  N  G  P  S  Q  E  R  V  I

CCGGCAGGCCCTGGCCAACGCCGGGCTCACCCCGGCGGACGTGGACGCCG     1200
  R  Q  A  L  A  N  A  G  L  T  P  A  D  V  D  A

TCGAGGCCCACGGCACCGGCACCAGGCTGGGCGACCCCATCGAGGCACAG     1250
V  E  A  H  G  T  G  T  R  L  G  D  P  I  E  A  Q

GCGGTACTGGCCACCTACGGACAGGAGCGCGCCACCCCCCTGCTGCTGGG     1300
 A  V  L  A  T  Y  G  Q  E  R  A  T  P  L  L  L  G

CTCGCTGAAGTCCAACATCGGCCACGCCCAGGCCGCGTCCGGCGTCGCCG     1350
  S  L  K  S  N  I  G  H  A  Q  Q  A  A  S  G  V  A

GCATCATCAAGATGGTGCAGGCCCTCCGGCACGGGGAGCTGCCGCCGACG     1400
G  I  I  K  M  V  Q  A  L  R  H  G  E  L  P  P  T

CTGCACGCCGACGAGCCGTCGCCGCACGTCGACTGGACGGCCGGCGCCGT     1450
 L  H  A  D  E  P  S  P  H  V  D  W  T  A  G  A  V

CGAACTGCTGACGTCGGCCCGGCCGTGGCCCGAGACCGACCGGCCTAGGC     1500
  E  L  L  T  S  A  R  P  W  P  E  T  D  R  P  R

GGGCGGGCGTGTCGTCCTTCGGAGTCAGCGGCACCAACGCCCACGTCATC     1550
R  A  G  V  S  S  F  G  V  S  G  T  N  A  H  V  I

CTGGAGAGCGCACCCCCCGCTCAGCCCGCGGAGGAGGCGCAGCCTGTTGA     1600
 L  E  S  A  O  O  A  Q  O  A  E  E  A  Q  P  V  E

GACGCCGGTGGTGGCCTCGGATGTGCTGCCGCTGGTGATATCGGCCAAGA     1650
  T  P  V  V  A  S  D  V  L  P  L  V  I  S  A  K

CCCAGCCCGCCCTGACCGAACACGAAGACCGGCTGCGCGCCTACCTGGCG     1700
T  Q  P  A  L  T  E  H  E  D  R  L  R  A  Y  L  A

GCGTCGCCCGGGGCGGATATACGGGCTGTGGCATCGACGCTGGCGGTGAC     1750
 A  S  P  G  A  D  I  R  A  V  A  S  T  L  A  V  T

ACGGTCGGTGTTCGAGCACCGCGCCGTACTCCTTGGAGATGACACCGTCA     1800
  R  S  V  F  E  H  R  A  V  L  L  G  D  D  T  V

CCGGCACCGCGGTGACCGACCCCAGGATCGTGTTTGTCTTTCCCGGGCAG     1850
T  G  T  A  V  T  D  P  R  I  V  F  V  F  P  G  Q

GGGTGGCAGTGGCTGGGGATGGGCAGTGCACTGCGCGATTCGTCGGTGGT     1900
 G  W  Q  W  L  G  M  G  S  A  L  R  D  S  S  V  V

GTTCGCCGAGCGGATGGCCGAGTGTGCGGCGGCGTTGCGCGAGTTCGTGG     1950
  F  A  E  R  M  A  E  C  A  A  A  L  R  E  F  V
```

-continued

```
ACTGGGATCTGTTCACGGTTCTGGATGATCCGGCGGTGGTGGACCGGGTT      2000
D  W  D  L  F  T  V  L  D  D  P  A  V  V  D  R  V

GATGTGGTCCAGCCCGCTTCCTGGGCGATGATGGTTTCCCTGGCCGCGGT      2050
 D  V  V  Q  P  A  S  W  A  M  M  V  S  L  A  A  V

GTGGCAGGCGGCCGGTGTGCGGCCGGATGCGGTGATCGGCCATTCGCAGG      2100
  W  Q  A  A  G  V  R  P  D  A  V  I  G  H  S  Q

GTGAGATCGCCGCAGCTTGTGTGGCGGGTGCGGTGTCACTACGCGATGCC      2150
G  E  I  A  A  A  C  V  A  G  A  V  S  L  R  D  A

GCCCGGATCGTGACCTTGCGCAGCCAGGCGATCGCCCGGGGCCTGGCGGG      2200
 A  R  I  V  T  L  R  S  Q  A  I  A  R  G  L  A  G

CCGGGGCGCGATGGCATCCGTCGCCCTGCCCGCGCAGGATGTCGAGCTGG      2250
  R  G  A  M  A  S  V  A  L  P  A  Q  D  V  E  L

TCGACGGGGCCTGGATCGCCGCCCACAACGGGCCCGCCTCCACCGTGATC      2300
V  D  G  A  W  I  I  H  N  G  P  A  S  T  V  I

GCGGGCACCCCGGAAGCGGTCGACCATGTCCTCACCGCTCATGAGGCACA      2350
 A  G  T  P  E  Q  V  D  H  V  L  T  A  H  E  A  Q

AGGGGTGCGGGTGCGGCGGATCACCGTCGACTATGCCTCGCACACCCCGC      2400
  G  V  R  V  R  R  I  T  V  D  Y  A  S  H  T  P

ACGTCGAGCTGATCCGCGACGAACTACTCGACATCACTAGCGACAGCAGC      2450
H  V  E  L  I  R  D  E  L  L  D  I  T  S  D  S  S

TCGCAGACCCCGCTCGTGCCGTGGCTGTCGACCGTGGACGGCACCTGGGT      2500
 S  Q  T  P  L  V  P  W  L  S  T  V  D  G  T  W  V

CGACAGCCCGCTGGACGGGGAGTACTGGTACCGGAACCTGCGTGAACCGG      2550
  D  S  P  L  D  G  E  Y  W  Y  R  N  L  R  E  P

TCGGTTTCCACCCCGCCGTCAGCCAGTTGCAGGCCCAGGGCGACACCGTG      2600
V  G  F  H  P  A  V  S  Q  L  Q  A  Q  G  D  T  V

TTCGTCGAGGTCAGCGCCAGCCCGGTGTTGTTGCAGGCGATGGACGACGA      2650
 F  V  E  V  S  A  S  P  V  L  L  Q  A  M  D  D  D

TGTCGTCACGGTTGCCACGCTGCGTCGTGACGACGGCGACGCCACCCGGA      2700
  V  V  T  V  A  T  L  R  R  D  D  G  D  A  T  R

TGCTCACCGCCCTGGCACAGGCCTATGTCCACGGCGTCACCGTCGACTGG      2750
M  L  T  A  L  A  Q  A  Y  V  H  G  V  T  V  D  W

CCCGCCATCCTCGGCACCACCACAACCCGGGTACTGGACCTTCCGACCTA      2800
 P  A  I  L  G  T  T  T  T  R  V  L  D  L  P  T  Y

CGCCTTCCAACACCAGCGGTACTGGCTCGAGTCGGCACGCCCGGCCGCAT      2850
   A  F  Q  H  Q  R  Y  W  L  E  S  A  R  P  A  A

CCGACGCGGGCCACCCCGTGCTGGGCTCCGGTATCGCCCTCGCCGGGTCG      2900
S  D  A  G  H  P  V  L  G  S  G  I  A  L  A  G  S

CCGGGCCGGGTGTTCACGGGTTCCGTGCCGACCGGTGCGGACCGCGCGGT      2950
 P  G  R  V  F  T  G  S  V  P  T  G  A  D  R  A  V

GTTCGTCGCCGAGCTGGCGCTGGCCGCCGCGGACGCGGTCGACTGCGCCA      3000
  F  V  A  E  L  A  L  A  A  A  D  A  V  D  C  A

CGGTCGAGCGGCTCGACATCGCCTCCGTGCCCGGCCGGCCGGGCCATGGC      3050
T  V  E  R  L  D  I  A  S  V  P  G  R  P  G  H  G

CGGACGACCGTACAGACCTGGGTCGACGAGCCGGCGGACGACGGCCGGCG      3100
 R  T  T  V  Q  T  W  V  D  E  P  A  D  D  G  R  R

CCGGTTCACCGTGCACACCCGCACCGGCGACGCCCCGTGGACGCTGCACG      3150
  R  F  T  V  H  T  R  T  G  D  A  P  W  T  L  H

CCGAGGGGGTGCTGCGCCCCCATGGCACGGCCCTGCCCGATGCGGCCGAC      3200
A  E  G  V  L  R  P  H  G  T  A  L  P  D  A  A  D

GCCGAGTGGCCCCCACCGGGCGCGGTGCCCGCGGACGGGCTGCCGGGTGT      3250
 A  E  W  P  P  P  G  A  V  P  A  D  G  L  P  G  V
```

-continued

```
GTGGCGCCGGGGGGACCAGGTCTTCGCCGAGGCCGAGGTGGACGGACCGG      3300
  W  R  R  G  D  Q  V  F  A  E  A  E  V  D  G  P

ACGGTTTCGTGGTGCACCCCGACCTGCTCGACGCGGTCTTCTCCGCGGTC      3350
D  G  F  V  V  H  P  D  L  L  D  A  V  F  S  A  V

GGCGACGGAAGCCGCCAGCCGGCCGGATGGCGCGACCTGACGGTGCACGC      3400
 G  D  G  S  R  Q  P  A  G  W  R  D  L  T  V  H  A

GTCGGACGCCACCGTACTGCGCGCCTGCCTCACCCGGCGCACCGACGGAG      3450
  S  D  A  T  V  L  R  A  C  L  T  R  R  T  D  G

CCATGGGATTCGCCGCCTTCGACGGCGCCGGCCTGCCGGTACTCACCGCG      3500
A  M  G  F  A  A  F  D  G  A  G  L  P  V  L  T  A

GAGGCGGTGACGCTGCGGGAGGTGGCGTCACCGTCCGGCTCCGAGGAGTC      3550
 E  A  V  T  L  R  E  V  A  S  P  S  G  S  E  E  S

GGACGGCCTGCACCGGTTGGAGTGGCTCGCGGTCGCCGAGGCGGTCTACG      3600
  D  G  L  H  R  L  E  W  L  A  V  A  E  A  V  Y

ACGGTGACCTGCCCGAGGGACATGTCCTGATCACCGCCGCCCACCCCGAC      3650
D  G  D  L  P  E  G  H  V  L  I  T  A  A  H  P  D

GACCCCGAGGACATACCCACCCGCGCCCACACCCGCGCCACCCGCGTCCT      3700
 D  P  E  D  I  P  T  R  A  H  T  R  A  T  R  V  L

GACCGCCCTGCAACACCACCTCACCACCACCGACCACACCCTCATCGTCC      3750
  T  A  L  Q  H  H  L  T  T  T  D  H  T  L  I  V

ACACCACCACCGACCCCGCCGGCGCCACCGTCACCGGCCTCACCCGCACC      3800
H  T  T  T  D  P  A  G  A  T  V  T  G  L  T  R  T

GCCCAGAACGAACACCCCCACCGCATCCGCCTCATCGAAACCGACCACCC      3850
 A  Q  N  E  H  P  H  R  I  R  L  I  E  T  D  H  P

CCACACCCCCCTCCCCCTGGCCCAACTCGCCACCCTCGACCACCCCCACC      3900
  H  T  P  L  P  L  A  Q  L  A  T  L  D  H  P  H

TCCGCCTCACCCACCACACCCTCCACCACCCCCACCTCACCCCCCTCCAC      3950
L  R  L  T  H  H  T  L  H  H  P  H  L  T  P  L  H

ACCACCACCCCACCCACCACCACCCCCCTCAACCCCGAACACGCCATCAT      4000
 T  T  T  P  P  T  T  T  P  L  N  P  E  H  A  I  I

CATCACCGGCGGCTCCGGCACCCTCGCCGGCATCCTCGCCCGCCACCTGA      4050
  I  T  G  G  S  G  T  L  A  G  I  L  A  R  H  L

ACCACCCCCACACCTACCTCCTCTCCCGCACCCCACCCCCCGACGCCACC      4100
N  H  P  H  T  Y  L  L  S  R  T  P  P  P  D  A  T

CCCGGCACCCACCTCCCCTGCGACGTCGGCGACCCCCACCAACTCGCCAC      4150
 P  G  T  H  L  P  C  D  V  G  D  P  H  Q  L  A  T

CACCCTCACCCACATCCCCCAACCCCTCACCGCCATCTTCCACACCGCCG      4200
  T  L  T  H  I  P  Q  P  L  T  A  I  F  H  T  A

CCACCCTCGACGACGGCATCCTCCACGCCCTCACCCCCGACCGCCTCACC      4250
A  T  L  D  D  G  I  L  H  A  L  T  P  D  R  L  T

ACCGTCCTCCACCCCAAAGCCAACGCCGCCTGGCACCTGCACCACCTCAC      4300
 T  V  L  H  P  K  A  N  A  A  W  H  L  H  H  L  T

CCAAAACCAACCCCTCACCCACTTCGTCCTCTACTCCAGCGCCGCCGCCG      4350
  Q  N  Q  P  L  T  H  F  V  L  Y  S  S  A  A  A

TCCTCGGCAGCCCCGGACAAGGAAACTACGCCGCCGCCAACGCCTTCCTC      4400
V  L  G  S  P  G  Q  G  N  Y  A  A  A  N  A  F  L

GACGCCCTCGCCACCCACCGCCACACCCTCGGCCAACCCGCCACCTCCAT      4450
 D  A  L  A  T  H  R  H  T  L  G  Q  P  A  T  S  I

CGCCTGGGGCATGTGGCACACCACCAGCACCCTCACCGGACAACTCGACG      4500
  A  W  G  M  W  H  T  T  S  T  L  T  G  Q  L  D
```

-continued

```
ACGCCGACCGGGACCGCATCCGCCGCGGCGGTTTCCTCCCGATCACGGAC      4550
D  A  D  R  D  R  I  R  R  G  G  F  L  P  I  T  D

GACGAGGGCATGGGGATGCAT
 D  E  G
```

The NheII-XhoI restriction fragment that encodes module 8 of the FK-520 PKS with the endogenous AT domain replaced by the AT domain of module 12 (specific for malonyl CoA) of the rapamycin PKS has the DNA sequence and encodes the amino acid sequence shown below.

```
AGATCTGGCAGCTCGCCGAAGCGCTGCTGACGCTCGTCCGGGAGAGCACC        50
 Q  L  A  E  A  L  L  T  L  V  R  E  S  T

GCCGCCGTGCTCGGCCACGTGGGTGGCGAGGACATCCCCGCGACGGCGGC       100
 A  A  V  L  G  H  V  G  G  E  D  I  P  A  T  A  A

GTTCAAGGACCTCGGCATCGACTCGCTCACCGCGGTCCAGCTGCGCAACG       150
  F  K  D  L  G  I  D  S  L  T  A  V  Q  L  R  N

CCCTCACCGAGGCGACCGGTGTGCGGCTGAACGCCACGGCGGTCTTCGAC       200
A  L  T  E  A  T  G  V  R  L  N  A  T  A  V  F  D

TTCCCGACCCCGCACGTGCTCGCCGGGAAGCTCGGCGACGAACTGACCGG       250
 F  P  T  P  H  V  L  A  G  K  L  G  D  E  L  T  G

CACCCGCGCGCCCGTCGTGCCCCGGACCGCGGCCACGGCCGGTGCGCACG       300
  T  R  A  P  V  V  P  R  T  A  A  T  A  G  A  H

ACGAGCCGCTGGCGATCGTGGGAATGGCCTGCCGGCTGCCCGGCGGGGTC       350
D  E  P  L  A  I  V  G  M  A  C  R  L  P  G  G  V

GCGTCACCCGAGGAGCTGTGGCACCTCGTGGCATCCGGCACCGACGCCAT       400
 A  S  P  E  E  L  W  H  L  V  A  S  G  T  D  A  I

CACGGAGTTCCCGACGGACCGCGGCTGGGACGTCGACGCGATCTACGACC       450
  T  E  F  P  T  D  R  G  W  D  V  D  A  I  Y  D

CGGACCCCGACGCGATCGGCAAGACCTTCGTCCGGCACGGTGGCTTCCTC       500
P  D  P  D  A  I  G  K  T  F  V  R  H  G  G  F  L

ACCGGCGCGACAGGCTTCGACGCGGCGTTCTTCGGCATCAGCCCGCGCGA       550
 T  G  A  T  G  F  D  A  A  F  F  G  I  S  P  R  E

GGCCCTCGCGATGGACCCGCAGCAGCGGGTGCTCCTGGAGACGTCGTGGG       600
  A  L  A  M  D  P  Q  Q  R  V  L  L  E  T  S  W

AGGCGTTCGAAAGCGCCGGCATCACCCCGGACTCGACCCGCGGCAGCGAC       650
E  A  F  E  S  A  G  I  T  P  D  S  T  R  G  S  D

ACCGGCGTGTTCGTCGGCGCCTTCTCCTACGGTTACGGCACCGGTGCGGA       700
 T  G  V  F  V  G  A  F  S  Y  G  Y  G  T  G  A  D

CACCGACGGCTTCGGCGCGACCGGCTCGCAGACCAGTGTGCTCTCCGGCC       750
  T  D  G  F  G  A  T  G  S  Q  T  S  V  L  S  G

GGCTGTCGTACTTCTACGGTCTGGAGGGTCCGGCGGTCACGGTCGACACG       800
R  L  S  Y  F  Y  G  L  E  G  P  A  V  T  V  D  T

GCGTGTTCGTCGTCGCTGGTGGCGCTGCACCAGGCCGGGCAGTCGCTGCG       850
 A  C  S  S  S  L  V  A  L  H  Q  A  G  Q  S  L  R

CTCCGGCGAATGCTCGCTCGCCCTGGTCGGCGGCGTCACGGTGATGGCGT       900
  S  G  E  C  S  L  A  L  V  G  G  V  T  V  M  A

CTCCCGGCGGCTTCGTGGAGTTCTCCCGGCAGCGCGGCCTCGCGCCGGAC       950
S  P  G  G  F  V  E  F  S  R  Q  R  G  L  A  P  D

GGCCGGGCGAAGGCGTTCGGCGCGGGTGCGGACGGCACGAGCTTCGCCGA      1000
 G  R  A  K  A  F  G  A  G  A  D  G  T  S  F  A  E

GGGTGCCGGTGTGCTGATCGTCGAGAGGCTCTCCGACGCCGAACGCAACG      1050
  G  A  G  V  L  I  V  E  R  L  S  D  A  E  R  N

GTCACACCGTCCTGGCGGTCGTCCGTGGTTCGGCGGTCAACCAGGATGGT      1100
G  H  T  V  L  A  V  V  R  G  S  A  V  N  Q  D  G
```

-continued

```
GCCTCCAACGGGCTGTCGGCGCCGAACGGGCCGTCGCAGGAGCGGGTGAT      1150
 A  S  N  G  L  S  A  P  N  G  P  S  Q  E  R  V  I

CCGGCAGGCCCTGGCCAACGCCGGGCTCACCCCGGCGGACGTGGACGCCG      1200
  R  Q  A  L  A  N  A  G  L  T  P  A  D  V  D  A

TCGAGGCCCACGGCACCGGCACCAGGCTGGGCGACCCCATCGAGGCACAG      1250
V  E  A  H  G  T  G  T  R  L  G  D  P  I  E  A  Q

GCGGTACTGGCCACCTACGGACAGGAGCGCGCCACCCCCCTGCTGCTGGG      1300
 A  V  L  A  T  Y  G  Q  E  R  A  T  P  L  L  L  G

CTCGCTGAAGTCCAACATCGGCCACGCCCAGGCCGCGTCCGGCGTCGCCG      1350
  S  L  K  S  N  I  G  H  A  Q  A  A  S  G  V  A

GCATCATCAAGATGGTGCAGGCCCTCCGGCACGGGGAGCTGCCGCCGACG      1400
G  I  I  K  M  V  Q  A  L  R  H  G  E  L  P  P  T

CTGCACGCCGACGAGCCGTCGCCGCACGTCGACTGGACGGCCGGCGCCGT      1450
 L  H  A  D  E  P  S  P  H  V  D  W  T  A  G  A  V

CGAACTGCTGACGTCGGCCCGGCCGTGGCCCGAGACCGACCGGCCACGGC      1500
  E  L  L  T  S  A  R  P  W  P  E  T  D  R  P  R

GTGCCGCCGTCTCCTCGTTCGGGGTGAGCGGCACCAACGCCCACGTCATC      1550
R  A  A  V  S  S  F  G  V  S  G  T  N  A  H  V  I

GTGGAGGCCGGACCGGTAACGGAGACGCCCGCGGCATCGCCTTCCGGTGA      1600
 L  E  A  G  P  V  T  ET  P  A  A  S  P  S  G  D

CCTTCCCCTGCTGGTGTCGGCACGCTCACCGGAAGCGCTCGACGAGCAGA      1650
  L  P  L  L  V  S  A  R  S  P  E  A  L  D  E  Q

TCCGCCGACTGCGCGCCTACCTGGACACCACCCCGGACGTCGACCGGGTG      1700
I  R  R  L  R  A  Y  L  D  T  T  P  D  V  D  R  V

GCCGTGGCACAGACGCTGGCCCGGCGCACACACTTCGCCCACCGCGCCGT      1750
 A  V  A  Q  T  L  A  R  R  T  H  F  A  H  R  A  V

GCTGCTCGGTGACACCGTCATCACCACACCCCCCGCGGACCGGCCCGACG      1800
  L  L  G  D  T  V  I  T  T  P  P  A  R  P  D

AACTCGTCTTCGTCTACTCCGGCCAGGGCAACCCAGCATCCCGCGATGGG      1850
E  L  V  F  V  Y  S  G  Q  G  T  Q  H  P  A  M  G

GAGCAGCTAGCCGCCGCGTTCCCCGTCTTCGCGCGGATCCATCAGCAGGT      1900
 E  Q  L  A  A  A  F  P  V  F  A  R  I  H  Q  Q  V

GTGGGACCTGCTCGATGTGCCCGATCTGGAGGTGAACGAGACCGGTTACG      1950
  W  D  L  L  D  V  P  D  L  E  V  N  E  T  G  Y

CCCAGCCGGCCCTGTTCGCAATGCAGGTGGCTCTGTTCGGGCTGCTGGAA      2000
A  Q  P  A  L  F  A  M  Q  V  A  L  F  G  L  L  E

TCGTGGGGTGTACGACCGGACGCGGTGATCGGCCATTCGGTGGGTGAGCT      2050
 S  W  G  V  R  P  D  A  V  I  G  H  S  V  G  E  L

TGCGGCTGCGTATGTGTCCGGGGTGTGGTCGTTGGAGGATGCCTGCACTT      2100
  A  A  A  Y  V  S  G  V  W  S  L  E  D  A  C  T

TGGTGTCGGCGCGGGCTCGTCTGATGCAGGCTCTGCCCGCGGGTGGGGTG      2150
L  V  S  A  R  A  R  L  M  Q  A  L  P  A  G  G  V

ATGGTCGCTGTCCCGGTCTCGGAGGATGAGGCCCGGGCCGTGCTGGGTGA      2200
 M  V  A  V  P  V  S  E  D  E  A  R  A  V  L  G  E

GGGTGTGGAGATCGCCGCGGTCAACGGCCCGTCGTCGGTGGTTCTCTCCG      2250
  G  V  E  I  A  A  V  N  G   S  S  V  V  L  S

GTGATGAGGCCGCCGTGCTGCAGGCCGCGGAGGGGCTGGGGAAGTGGACG      2300
G  D  E  A  A  V  L  Q  A  A  E  G  L  G  K  W  T

CGGCTGGCGACCAGCCACGCGTTCCATTCCGCCCGTATGGAACCCATGCT      2350
 R  L  A  T  S  H  A  F  S  A  R  M  E  P  M  L

GGAGGAGTTCCGGGCGGTCGCCGAAGGCCTGACCTACCGGACGCCGCAGG      2400
  E  E  F  R  A  V  A  E  G  L  T  Y  R  T  P  Q
```

-continued

```
TCTCCATGGCCGTTGGTGATCAGGTGACCACCGCTGAGTACTGGGTGCGG      2450
V  S  M  A  V  G  D  Q  V  T  T  A  E  Y  W  V  R

CAGGTCCGGGACACGGTCCGGTTCGGCGAGCAGGTGGCCTCGTACGAGGA      2500
 Q  V  R  D  T  V  R  F  G  E  Q  V  A  S  Y  E  D

CGCCGTGTTCGTCGAGCTGGGTGCCGACCGGTCACTGGCCCGCCTGGTCG      2550
  A  V  F  V  E  L  G  A  D  R  S  L  A  R  L  V

ACGGTGTCGCGATGCTGCACGGCGACCACGAAATCCAGGCCGCGATCGGC      2600
D  G  V  A  M  L  H  G  D  J  E  I  Q  A  A  I  G

GCCCTGGCCCACCTGTATGTCAACGGCGTCACGGTCGACTGGCCCGCGCT      2650
 A  L  A  H  L  Y  V  N  G  V  T  V  D  W  P  A  L

CCTGGGCGATGCTCCGGCAACACGGGTGCTGGACCTTCCGACATACGCCT      2700
  L  G  D  A  P  A  T  R  V  L  D  L  P  T  Y  A

TCCAGCACCAGCGCTACTGGCTCGAGTCGGCACGCCCGGCCGCATCCGAC      2750
F  Q  H  Q  R  Y  W  L  E  S  A  R  P  A  A  S  D

GCGGGCCACCCCGTGCTGGGCTCCGGTATCGCCCTCGCCGGGTCGCCGGG      2800
 A  G  H  P  V  L  G  S  G  I  A  L  A  G  S  P  G

CCGGGTGTTCACGGGTTCCGTGCCGACCGGTGCGGACCGCGCGGTGTTCG      2850
  R  V  F  T  G  S  V  P  T  G  A  D  R  A  V  F

TCGCCGAGCTGGCGCTGGCCGCCGCGGACGCGGTCGACTGCGCCACGGTC      2900
V  A  E  L  A  L  A  A  A  D  A  V  D  C  A  T  V

GAGCGGCTCGACATCGCCTCCGTGCCCGGCCGGCCGGGCCATGGCCGGAC      2950
 E  R  L  D  I  A  S  V  P  G  R  P  G  H  G  R  T

GACCGTACAGACCTGGGTCGACGAGCCGGCGGACGACGGCCGGCGCCGGT      3000
  T  V  Q  T  W  V  D  E  P  A  D  D  G  R  R  R

TCACCGTGCACACCCGCACCGGCGACGCCCCGTGGACGCTGCACGCCGAG      3050
F  T  V  H  T  R  T  G  D  A  P  W  T  L  H  A  E

GGGGTGCTGCGCCCCCATGGCACGGCCCTGCCCGATGCGGCCGACGCCGA      3100
 G  V  L  R  P  H  G  T  A  L  P  D  A  A  D  A  E

GTGGCCCCCACCGGGCGCGGTGCCCGCGGACGGGCTGCCGGGTGTGTGGC      3150
  W  P  P  P  G  A  V  P  A  D  G  L  P  G  V  W

GCCGGGGGGACCAGGTCTTCGCCGAGGCCGAGGTGGACGGACCGGACGGT      3200
R  R  G  D  Q  V  F  A  E  A  E  V  D  G  P  D  G

TTCGTGGTGCACCCCGACCTGCTCGACGCGGTCTTCTCCGCGGTCGGCGA      3250
 F  V  V  H  P  D  L  L  D  A  V  F  S  A  V  G  D

CGGAAGCCGCCAGCCGGCCGGATGGCGCGACCTGACGGTGCACGCGTCGG      3300
  G  S  R  Q  P  A  G  W  R  D  L  T  V  H  A  S

ACGCCACCGTACTGCGCGCCTGCCTCACCCGGCGCACCGACGGAGCCATG      3350
D  A  T  V  L  R  A  C  L  T  R  R  T  D  G  A  M

GGATTCGCCGCCTTCGACGGCGCCGGCCTGCCGGTACTCACCGCGGAGGC      3400
 G  F  A  A  F  D  G  A  G  L  P  V  L  T  A  E  A

GGTGACGCTGCGGGAGGTGGCGTCACCGTCCGGCTCCGAGGAGTCGGACG      3450
  C  T  L  R  E  V  A  S  O  S  G  S  E  E  S  D

GCCTGCACCGGTTGGAGTGGCTCGCGGTCGCCGAGGCGGTCTACGACGGT      3500
G  L  H  R  L  E  W  L  A  V  A  E  A  V  Y  D  G

GACCTGCCCGAGGGACATGTCCTGATCACCGCCGCCCACCCCGACGACCC      3550
 D  L  P  E  G  H  V  L  I  T  A  A  H  P  D  D  P

CGAGGACATACCCACCCGCGCCCACACCCGCGCCACCCGCGTCCTGACCG      3600
  E  D  I  P  T  R  A  H  T  R  A  T  R  V  L  T

CCCTGCAACACCACCTCACCACCACCGACCACACCCTCATCGTCCACACC      3650
A  L  Q  H  H  L  T  T  T  D  H  T  L  I  V  H  T

ACCACCGACCCCGCCGGCGCCACCGTCACCGGCCTCACCCGCACCGCCCA      3700
 T  T  D  P  A  G  A  T  V  T  G  L  T  R  T  A  Q
```

-continued

```
GAACGAACACCCCCACCGCATCCGCCTCATCGAAACCGACCACCCCCACA      3750
  N  E  H  P  H  R  I  R  L  I  E  T  D  H  P  H

CCCCCCTCCCCCTGGCCCAACTCGCCACCCTCGACCACCCCCACCTCCGC      3800
T  P  L  P  L  A  Q  L  A  T  L  D  H  P  G  L  R

CTCACCCACCACACCCTCCACCACCCCCACCTCACCCCCCTCCACACCAC      3850
 L  T  H  H  T  L  H  H  P  H  L  T  P  L  H  T  T

CACCCCACCCACCACCACCCCCCTCAACCCCGAACACGCCATCATCATCA      3900
  T  P  P  T  T  T  P  L  N  P  E  H  A  I  I  I

CCGGCGGCTCCGGCACCCTCGCCGGCATCCTCGCCCGCCACCTGAACCAC      3950
T  G  G  S  G  T  L  A  G  I  L  A  R  H  L  N  H

CCCCACACCTACCTCCTCTCCCGCACCCCACCCCCCGACGCCACCCCCGG      4000
 P  H  T  Y  L  L  S  R  T  P  P  P  D  A  T  P  G

CACCCACCTCCCCTGCGACGTCGGCGACCCCCACCAACTCGCCACCACCC      4050
  T  H  L  P  C  D  V  G  D  P  H  Q  L  A  T  T

TCACCCACATCCCCCAACCCCTCACCGCCATCTTCCACACCGCCGCCACC      4100
L  T  H  I  P  Q  P  L  T  A  I  F  H  T  A  A  T

CTCGACGACGGCATCCTCCACGCCCTCACCCCCGACCGCCTCACCACCGT      4150
 L  D  D  G  I  L  H  A  L  T  P  D  R  L  T  T  V

CCTCCACCCCAAAGCCAACGCCGCCTGGCACCTGCACCACCTCACCCAAA      4200
  L  H  P  K  A  N  A  A  W  H  L  H  H  L  T  Q

ACCAACCCCTCACCCACTTCGTCCTCTACTCCAGCGCCGCCGCCGTCCTC      4250
N  Q  P  L  T  H  F  V  L  Y  S  S  A  A  A  V  L

GGCAGCCCCGGACAAGGAAACTACGCCGCCGCCAACGCCTTCCTCGACGC      4300
 G  S  P  G  Q  G  N  Y  A  A  A  N  A  F  L  D  A

CCTCGCCACCCACCGCCACACCCTCGGCCAACCCGCCACCTCCATCGCCT      4350
  L  A  T  H  R  H  T  L  G  Q  P  A  T  S  I  A

GGGGCATGTGGCACACCACCAGCACCCTCACCGGACAACTCGACGACGCC      4400
W  G  M  W  H  T  T  S  T  L  T  G  Q  L  D  D  A

GACCGGGACCGCATCCGCCGCGGCGGTTTCCTCCCGATCACGGACGACGA      4450
 D  R  D  R  I  R  R  G  G  F  L  P  I  T  D  D  E

GGGCATGGGGATGCAT
  G
```

The NheI-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below.

```
AGATCTGGCAGCTCGCCGAAGCGCTGCTGACGCTCGTCCGGGAGAGCACC       50
 Q  L  A  E  A  L  L  T  L  V  R  E  S  T

GCCGCCGTGCTCGGCCACGTGGGTGGCGAGGACATCCCCGCGACGGCGGC      100
 A  A  V  L  G  H  V  G  G  E  D  I  P  A  T  A  A

GTTCAAGGACCTCGGCATCGACTCGCTCACCGCGGTCCAGCTGCGCAACG      150
  F  K  D  L  G  I  D  S  L  T  A  V  Q  L  R  N

CCCTCACCGAGGCGACCGGTGTGCGGCTGAACGCCACGGCGGTCTTCGAC      200
A  L  T  E  A  T  G  V  R  L  N  A  T  A  V  F  D

TTCCCGACCCCGCACGTGCTCGCCCGGAAGCTCGGCGACGAACTGACCGG      250
 F  P  T  P  H  V  L  A  G  K  L  G  D  E  L  T  G

CACCCGCGCGCCCGTCGTGCCCCGGACCGCGGCCACGGCCGGTGCGCACG      300
  T  R  A  P  V  V  P  R  T  A  A  T  A  G  A  H

ACGAGCCGCTGGCGATCGTGGGAATGGCCTGCCGGCTGCCCGGCGGGGTC      350
D  E  P  L  A  I  V  G  M  A  C  R  L  P  G  G  V

GCGTCACCCGAGGAGCTGTGGCACCTCGTGGCATCCGGCACCGACGCCAT      400
 A  S  P  E  E  L  W  H  L  V  A  S  G  T  D  A  I
```

-continued

```
CACGGAGTTCCCGACGGACCGCGGCTGGGACGTCGACGCGATCTACGACC      450
  T  E  F  P  T  D  R  G  W  D  V  D  A  I  Y  D

CGGACCCCGACGCGATCGGCAAGACCTTCGTCCGGCACGGTGGCTTCCTC      500
P  D  P  D  A  I  G  K  T  F  V  R  H  G  G  F  L

ACCGGCGCGACAGGCTTCGACGCGGCGTTCTTCGGCATCAGCCCGCGCGA      550
 T  G  A  T  G  F  D  A  A  F  F  G  I  S  P  F  E

GGCCCTCGCGATGGACCCGCAGCAGCGGGTGCTCCTGGAGACGTCGTGGG      600
  A  L  A  M  D  P  Q  Q  R  V  L  L  E  T  S  W

AGGCGTTCGAAAGCGCCGGCATCACCCCGGACTCGACCCGCGGCAGCGAC      650
E  A  F  E  S  A  G  I  T  P  D  S  T  R  G  S  D

ACCGGCGTGTTCGTCGGCGCCTTCTCCTACGGTTACGGCACCGGTGCGGA      700
 T  G  V  F  V  G  A  F  S  Y  G  Y  G  T  G  A  D

CACCGACGGCTTCGGCGCGACCGGCTCGCAGACCAGTGTGCTCTCCGGCC      750
  T  D  G  F  G  A  T  G  S  Q  T  S  V  L  S  G

GGCTGTCGTACTTCTACGGTCTGGAGGGTCCGGCGGTCACGGTCGACACG      800
R  L  S  Y  F  Y  G  L  E  G  P  A  V  T  V  D  T

GCGTGTTCGTCGTCGCTGGTGGCGCTGCACCAGGCCGGGCAGTCGCTGCG      850
 A  C  S  S  S  L  V  A  L  H  Q  A  G  Q  S  L  R

CTCCGGCGAATGCTCGCTCGCCCTGGTCGGCGGCGTCACGGTGATGGCGT      900
  S  G  E  C  S  L  A  L  V  G  G  V  T  N  M  A

CTCCCGGCGGCTTCGTGGAGTTCTCCCGGCAGCGCGGCCTCGCGCCGGAC      950
S  P  G  G  F  V  E  F  S  R  Q  R  G  L  A  P  D

GGCCGGGCGAAGGCGTTCGGCGCGGGTGCGGACGGCACGAGCTTCGCCGA     1000
 G  R  A  K  A  F  G  A  G  A  D  G  T  S  F  A  E

GGGTGCCGGTGTGCTGATCGTCGAGAGGCTCTCCGACGCCGAACGCAACG     1050
  G  A  G  V  L  I  V  E  R  L  S  D  A  E  R  N

GTCACACCGTCCTGGCGGTCGTCCGTGGTTCGGCGGTCAACCAGGATGGT     1100
G  H  T  V  L  A  V  V  R  G  S  A  V  N  Q  D  G

GCCTCCAACGGGCTGTCGGCGCCGAACGGGCCGTCGCAGGAGCGGGTGAT     1150
 A  S  N  G  L  S  A  P  N  G  P  S  Q  E  R  V  i

CCGGCAGGCCCTGGCCAACGCCGGGCTCACCCCGGCGGACGTGGACGCCG     1200
  R  Q  A  L  A  N  A  G  L  T  P  A  D  V  D  A

TCGAGGCCCACGGCACCGGCACCAGGCTGGGCGACCCCATCGAGGCACAG     1250
V  E  A  H  G  T  G  T  R  L  G  D  P  I  E  A  Q

GCGGTACTGGCCACCTACGGACAGGAGCGCGCCACCCCCCTGCTGCTGGG     1300
 A  V  L  A  T  Y  G  Q  E  R  A  T  P  L  L  L  G

CTCGCTGAAGTCCAACATCGGCCACGCCCAGGCCGCGTCCGGCGTCGCCG     1350
  S  L  K  S  N  I  G  H  A  Q  A  A  S  G  V  A

GCATCATCAAGATGGTGCAGGCCCTCCGGCACGGGGAGCTGCCGCCGACG     1400
G  I  I  K  M  V  Q  A  L  R  H  G  E  L  P  P  T

CTGCACGCCGACGAGCCGTCGCCGCACGTCGACTGGACGGCCGGCGCCGT     1450
 L  H  A  D  E  P  S  P  H  V  D  W  T  A  G  A  V

CGAACTGCTGACGTCGGCCCGGCCGTGGCCCGAGACCGACCGGCCACGGC     1500
  E  L  L  T  S  A  R  P  W  P  E  T  D  R  P  R

GTGCCGCCGTCTCCTCGTTCGGGGTGAGCGGCACCAACGCCCACGTCATC     1550
R  A  A  V  S  S  T  G  V  S  G  T  N  A  H  V  I

CTGGAGGCCGGACCGGTAACGGAGACGCCCGCGGCATCGCCTTCCGGTGA     1600
 L  E  A  G  P  V  T  E  T  P  A  A  S  P  S  G  D

CCTTCCCCTGCTGGTGTCGGCACGCTCACCGGAAGCGCTCGACGAGCAGA     1650
  L  P  L  L  V  S  A  R  S  P  E  A  L  D  E  Q

TCCGCCGACTGCGCGCCTACCTGGACACCACCCCGGACGTCGACCGGGTG     1700
I  R  R  L  R  A  Y  L  D  T  T  P  D  V  D  R  V
```

-continued

```
GCCGTGGCACAGACGCTGGCCCGGCGCACACACTTCGCCCACCGCGCCGT      1750
 A  V  A  Q  T  L  A  R  R  T  H  F  A  H  R  A  V

GCTGCTCGGTGACACCGTCATCACCACACCCCCCGCGGACCGGCCCGACG      1800
  L  L  G  D  T  V  I  T  T  P  P  A  D  R  P  D

AACTCGTCTTCGTCTACTCCGGCCAGGGCACCCAGCATCCCGCGATGGGC      1850
E  L  V  F  V  Y  S  G  Q  G  T  Q  H  P  A  M  G

GAGCAGCTAGCCGATTCGTCGGTGGTGTTCGCCGAGCGGATGGCCGAGTG      1900
 E  Q  L  A  D  S  S  V  V  F  A  E  R  M  A  E  C

TGCGGCGGCGTTGCGCGAGTTCGTGGACTGGGATCTGTTCACGGTTCTGG      1950
  A  A  A  L  R  E  F  V  D  W  D  L  F  T  V  L

ATGATCCGGCGGTGGTGGACCGGGTTGATGTGGTCCAGCCCGCTTCCTGG      2000
D  D  P  A  V  V  D  R  V  D  V  V  Q  P  A  S  W

GCGATGATGGTTTCCCTGGCCGCGGTGTGGCAGGCGGCCGGTGTGCGGCC      2050
 A  M  M  V  S  L  A  A  V  W  Q  A  A  G  V  R  P

GGATGCGGTGATCGGCCATTCGCAGGGTGAGATCGCCGCAGCTTGTGTGG      2100
  D  A  V  I  G  H  S  Q  G  E  I  A  A  A  C  V

CGGGTGCGGTGTCACTACGCGATGCCGCCCGGATCGTGACCTTGCGCAGC      2150
A  G  A  V  S  L  R  D  A  A  R  I  V  T  L  R  S

CAGGCGATCGCCCGGGGCCTGGCGGGCCGGGGCGCGATGGCATCCGTCGC      2200
 Q  A  I  A  R  G  L  A  G  R  G  A  M  A  S  V  A

CCTGCCCGCGCAGGATGTCGAGCTGGTCGACGGGGCCTGGATCGCCGCCC      2250
  L  P  A  Q  D  V  E  L  V  D  G  A  W  I  A  A

ACAACGGGCCCGCCTCCACCGTGATCGCGGGCACCCCGGAAGCGGTCGAC      2300
H  N  G  P  A  S  T  V  I  A  G  T  P  E  A  V  D

CATGTCCTCACCGCTCATGAGGCACAAGGGGTGCGGGTGCGGCGGATCAC      2350
 H  V  L  T  A  H  E  A  Q  G  V  R  V  R  R  I  T

CGTCGACTATGCCTCGCACACCCCGCACGTCGAGCTGATCCGCGACGAAC      2400
  V  D  Y  A  S  H  T  P  H  V  E  L  I  R  D  E

TACTCGACATCACTAGCGACAGCAGCTCGCAGACCCCGCTCGTGCCGTGG      2450
L  L  D  I  T  S  D  S  S  S  Q  T  P  L  V  P  W

CTGTCGACCGTGGACGGCACCTGGGTCGACAGCCCGCTGGACGGGGAGTA      2500
 L  S  T  V  D  G  T  W  V  D  S  P  L  D  G  E  Y

CTGGTACCGGAACCTGCGTGAACCGGTCGGTTTCCACCCCGCCGTCAGCC      2550
  W  Y  R  N  L  R  E  P  V  G  F  H  P  A  V  S

AGTTGCAGGCCCAGGGCGACACCGTGTTCGTCGAGGTCAGCGCCAGCCCG      2600
Q  L  Q  A  Q  G  D  T  V  F  V  E  V  S  A  S  P

GTGTTGTTGCAGGCGATGGACGACGATGTCGTCACGGTTGCCACGCTGCG      2650
 V  L  L  Q  A  M  D  D  D  V  V  T  V  A  T  L  R

TCGTGACGACGGCGACGCCACCCGGATGCTCACCGCCCTGGCACAGGCCT      2700
  R  D  D  G  D  A  T  R  M  L  T  A  L  A  Q  A

ATGTCCACGGCGTCACCGTCGACTGGCCCGCCATCCTCGGCACCACCACA      2750
Y  V  H  G  V  T  D  W  P  A  I  L  G  T  T  T

ACCCGGGTACTGGACCTTCCGACCTACGCCTTCCAACACCAGCGGTACTG      2800
 T  R  V  L  D  L  P  T  Y  A  F  Q  H  Q  R  Y  W

GCTCGAGTCGGCACGCCCGGCCGCATCCGACGCGGGCCACCCCGTGCTGG      2850
  L  E  S  A  R  P  A  A  S  D  A  G  H  P  V  L

GCTCCGGTATCGCCCTCGCCGGGTCGCCGGGCCGGGTGTTCACGGGTTCC      2900
G  S  G  I  A  L  A  G  S  P  G  R  V  F  T  G  S

GTGCCGACCGGTGCGGACCGCGCGGTGTTCGTCGCCGAGCTGGCGCTGGC      2950
 V  P  T  G  A  D  R  A  V  F  V  A  E  L  A  L  A

CGCCGCGGACGCGGTCGACTGCGCCACGGTCGAGCGGCTCGACATCGCCT      3000
  A  A  D  A  V  D  C  A  T  V  E  R  L  D  I  A
```

-continued

```
CCGTGCCCGGCCGGCCGGGCCATGGCCGGACGACCGTACAGACCTGGGTC      3050
S  V  P  G  R  P  G  H  G  R  T  T  V  Q  T  W  V

GACGAGCCGGCGGACGACGGCCGGCGCCGGTTCACCGTGCACACCCGCAC      3100
 D  E  P  A  D  D  G  R  R  R  F  T  V  H  T  R  T

CGGCGACGCCCCGTGGACGCTGCACGCCGAGGGGGTGCTGCGCCCCCATG      3150
  G  D  A  P  W  T  L  H  A  E  G  V  L  R  P  H

GCACGGCCCTGCCCGATGCGGCCGACGCCGAGTGGCCCCCACCGGGCGCG      3200
G  T  A  L  P  D  A  A  D  A  E  W  P  P  P  G  A

GTGCCCGCGGACGGGCTGCCGGGTGTGTGGCGCCGGGGGGACCAGGTCTT      3250
 V  P  A  D  G  L  P  G  V  W  R  R  G  D  Q  V  F

CGCCGAGGCCGAGGTGGACGGACCGGACGGTTTCGTGGTGCACCCCGACC      3300
  A  E  A  E  V  D  G  P  D  G  F  V  V  H  P  D

TGCTCGACGCGGTCTTCTCCGCGGTCGGCGACGGAAGCCGCCAGCCGGCC      3350
L  L  D  A  V  F  S  A  V  G  D  G  S  R  Q  P  A

GGATGGCGCGACCTGACGGTGCACGCGTCGGACGCCACCGTACTGCGCGC      3400
 G  W  R  D  L  T  V  H  A  S  D  A  T  V  L  R  A

CTGCCTCACCCGGCGCACCGACGGAGCCATGGGATTCGCCGCCTTCGACG      3450
  C  L  T  R  R  T  D  G  A  M  G  F  A  A  F  D

GCGCCGGCCTGCCGGTACTCACCGCGGAGGCGGTGACGCTGCGGGAGGTG      3500
G  A  G  L  P  V  L  T  A  E  A  V  T  L  R  E  V

GCGTCACCGTCCGGCTCCGAGGAGTCGGACGGCCTGCACCGGTTGGAGTG      3550
 A  S  P  S  G  S  E  E  S  D  G  L  H  R  L  E  W

GCTCGCGGTCGCCGAGGCGGTCTACGACGGTGACCTGCCCGAGGGACATG      3600
  L  A  V  A  E  A  V  Y  D  G  D  L  P  E  G  H

TCCTGATCACCGCCGCCCACCCCGACGACCCCGAGGACATACCCACCCGC      3650
V  L  I  T  A  A  H  P  D  D  P  E  D  I  P  T  R

GCCCACACCCGCGCCACCCGCGTCCTGACCGCCCTGCAACACCACCTCAC      3700
 A  H  T  R  A  T  R  V  L  T  A  L  Q  H  H  L  T

CACCACCGACCACACCCTCATCGTCCACACCACCACCGACCCCGCCGGCG      3750
  T  T  D  H  T  L  I  V  H  T  T  T  D  P  A  G

CCACCGTCACCGGCCTCACCCGCACCGCCCAGAACGAACACCCCCACCGC      3800
A  T  V  T  G  L  T  R  T  A  Q  N  E  H  P  H  R

ATCCGCCTCATCGAAACCGACCACCCCCACACCCCCCTCCCCCTGGCCCA      3850
 I  R  L  I  E  T  D  H  P  H  T  P  L  P  L  A  Q

ACTCGCCACCCTCGACCACCCCCACCTCCGCCTCACCCACCACACCCTCC      3900
  L  A  T  L  D  H  P  H  L  R  L  T  H  H  T  L

ACCACCCCCACCTCACCCCCCTCCACACCACCACCCCACCCACCACCACC      3950
H  H  P  H  L  T  P  L  H  T  T  T  P  P  T  T  T

CCCCTCAACCCCGAACACGCCATCATCATCACCGGCGGCTCCGGCACCCT      4000
 P  L  N  P  E  H  A  I  I  I  T  G  G  S  G  T  L

CGCCGGCATCCTCGCCCGCCACCTGAACCACCCCCACACCTACCTCCTCT      4050
  A  G  I  L  A  R  H  L  N  H  P  H  T  Y  L  L

CCCGCACCCCACCCCCCGACGCCACCCCCGGCACCCACCTCCCCTGCGAC      4100
S  R  T  P  P  P  D  A  T  P  G  T  H  L  P  C  D

GTCGGCGACCCCCACCAACTCGCCACCACCCTCACCCACATCCCCCAACC      4150
 V  G  D  P  H  Q  L  A  T  T  L  T  H  I  P  Q  P

CCTCACCGCCATCTTCCACACCGCCGCCACCCTCGACGACGGCATCCTCC      4200
  L  T  A  I  F  H  T  A  A  T  L  D  D  G  I  L

ACGCCCTCACCCCCGACCGCCTCACCACCGTCCTCCACCCCAAAGCCAAC      4250
H  A  L  T  P  D  R  L  T  T  V  L  H  P  K  A  N

GCCGCCTGGCACCTGCACCACCTCACCCAAAACCAACCCCTCACCCACTT      4300
 A  A  W  H  L  H  H  L  T  Q  N  Q  P  L  T  H  F
```

-continued

```
CGTCCTCTACTCCAGCGCCGCCGCCGTCCTCGGCAGCCCCGGACAAGGAA      4350
  V  L  Y  S  S  A  A  A  V  L  G  S  P  G  Q  G

ACTACGCCGCCGCCAACGCCTTCCTCGACGCCCTCGCCACCCACCGCCAC      4400
N  Y  A  A  N  A  F  L  D  A  L  A  T  H  R  H

ACCCTCGGCCAACCCGCCACCTCCATCGCCTGGGGCATGTGGCACACCAC      4450
 T  L  G  Q  P  A  T  S  I  A  W  G  M  W  H  T  T

CAGCACCCTCACCGGACAACTCGACGACGCCGACCGGGACCGCATCCGCC      4500
  S  T  L  T  G  Q  L  D  D  A  D  R  D  R  I  R

GCGGCGGTTTCCTCCCGATCACGGACGACGAGGGCATGGGGATGCAT
R  G  G  F  L  P  I  T  D  D  E  G
```

Phage KC515 DNA was prepared using the procedure described in Genetic Manipulation of Streptomyces, A Laboratory Manual, edited by D. Hopwood et al. A phage suspension prepared from 10 plates (100 mm) of confluent plaques of KC515 on S. lividans TK24 generally gave about 3 μg of phage DNA. The DNA was ligated to circularize at the cos site, subsequently digested with restriction enzymes BamHI and PstI, and dephosphorylated with SAP.

Each module 8 cassette described above was excised with restriction enzymes BglII and NsiI and ligated into the compatible BamHI and PstI sites of KC515 phage DNA prepared as described above. The ligation mixture containing KC515 and various cassettes was transfected into protoplasts of Streptomyces lividans TK24 using the procedure described in Genetic Manipulation of Streptomyces, A Laboratory Manual edited by D. Hopwood et al. and overlaid with TK24 spores. After 16–24 hr, the plaques were restreaked on plates overlaid with TK24 spores. Single plaques were picked and resuspended in 200 μL of nutrient broth. Phage DNA was prepared by the boiling method (Hopwood et al., supra). The PCR with primers spanning the left and right boundaries of the recombinant phage was used to verify the correct phage had been isolated. In most cases, at least 80% of the plaques contained the expected insert. To confirm the presence of the resistance marker (thioestrepton), a spot test is used, as described in Lomovskaya et al. (1997), in which a plate with spots of phage is overlaid with mixture of spores of TK24 and phiC31 TK24 lysogen. After overnight incubation, the plate is overlaid with antibiotic in soft agar. A working stock is made of all phage containing desired constructs.

Streptomyces hygroscopicus ATCC 14891 (see U.S. Pat. No. 3,244,592, issued Apr. 5, 1966, incorporated herein by reference) mycelia were infected with the recombinant phage by mixing the spores and phage ($1\times10^8$ of each), and incubating on R2YE agar (Genetic Manipulation of Streptomyces, A Laboratory Manual, edited by D. Hopwood et al.) at 30° C. for 10 days. Recombinant clones were selected and plated on minimal medium containing thioestrepton (50 μg/ml) to select for the thiostrepton resistance-conferring gene. Primary thiostrepton resistant clones were isolated and purified through a second round of single colony isolation, as necessary. To obtain thiostrepton-sensitive revertants that underwent a second recombination event to evict the phage genome, primary recombinants were propagated in liquid media for two to three days in the absence of thiostrepton and then spread on agar medium without thiostrepton to obtain spores. Spores were plated to obtain about 50 colonies per plate, and thiostrepton sensitive colonies were identified by replica plating onto thiostrepton containing agar medium. The PCR was used to determine which of the thiostrepton sensitive colonies reverted to the wild type (reversal of the initial integration event), and which contain the desired AT swap at module 8 in the ATCC 14891-derived cells. The PCR primers used amplified either the KS/AT junction or the AT/DH junction of the wild-type and the desired recombinant strains. Fermentation of the recombinant strains, followed by isolation of the metabolites and analysis by LCMS, and NMR is used to characterize the novel polyketide compounds.

EXAMPLE 2

Replacement of Methoxyl with Hydrogen or Methyl at C-13 of FK-506

The present invention also provides the 13-desmethoxy derivatives of FK-506 and the novel PKS enzymes that produce them. A variety of Streptomyces strains that produce FK-506 are known in the art, including S. tsukubaensis No. 9993 (FERM BP-927), described in U.S. Pat. No. 5,624,852, incorporated herein by reference; S. hygroscopicus subsp. yakushimaensis No. 7238, described in U.S. Pat. No. 4,894,366, incorporated herein by reference; S. sp. MA6858 (ATCC 55098), described in U.S. Pat. Nos. 5,116,756, incorporated herein by reference; and S. sp. MA 6548, described in Motamedi et al., 1998, "The biosynthetic gene cluster for the macrolactone ring of the immunosuppressant FK-506," Eur. J. Biochem. 256: 528–534, and Motamedi et al., 1997, "Structural organization of a multifunctional polyketide synthase involved in the biosynthesis of the macrolide immunosuppressant FK-506," Eur. J. Biochem. 244: 74–80, each of which is incorporated herein by reference.

The complete sequence of the FK-506 gene cluster from Streptomyces sp. MA6548 is known, and the sequences of the corresponding gene clusters from other FK-506-producing organisms is highly homologous thereto. The novel FK-506 recombinant gene clusters of the present invention differ from the naturally occurring gene clusters in that the AT domain of module 8 of the naturally occurring PKSs is replaced by an AT domain specific for malonyl CoA or methylmalonyl CoA. These AT domain replacements are made at the DNA level, following the methodology described in Example 1.

The naturally occurring module 8 sequence for the MA6548 strain is shown below, followed by the illustrative hybrid module 8 sequences for the MA6548 strains.

```
GCATGCGGCTGTACGAGGCGGCACGGCGCACCGGAAGTCCCGTGGTGGTG      50
   M  R  L  Y  E  A  A  R  R  T  G  S  P  V  V  V

GCGGCCGCGCTCGACGACGCGCCGGACGTGCCGCTGCTGCGCGGGCTGCG     100
 A  A  A  L  D  D  A  P  D  V  P  L  L  R  G  L  R

GCGTACGACCGTCCGGCGTGCCGCCGTCCGGGAACGCTCTCTCGCCGACC     150
  R  T  T  V  R  R  A  A  V  R  E  R  S  L  A  D

GCTCGCCGTGCTGCCCGACGACGAGCGCGCCGACGCCTCCCTCGCGTTCG     200
R  S  P  C  C  P  T  T  S  A  P  T  P  P  S  R  S

TCCTGGAACAGCACCGCCACCGTGCTCGGCCACCTGGGCGCCGAAGACAT     250
 S  W  N  S  T  A  T  V  L  G  H  L  G  A  E  D  I

CCCGGCGACGACGACGTTCAAGGAACTCGGCATCGACTCGCTCACCGCGG     300
  P  A  T  T  T  F  K  E  L  G  I  D  S  L  T  A

TCCAGCTGCGCAACGCGCTGACCACGGCGACCGGCGTACGCCTCAACGCC     350
V  Q  L  R  N  A  L  T  T  A  T  G  V  R  L  N  A

ACAGCGGTCTTCGACTTTCCGACGCCGCGCGCGCTCGCCGCGAGACTCGG     400
 T  A  V  F  D  F  P  T  P  R  A  L  A  A  R  L  G

CGACGAGCTGGCCGGTACCCGCGCGCCCGTCGCGGCCCGGACCGCGGCCA     450
  D  E  L  A  G  T  R  A  P  V  A  A  R  T  A  A

CCGCGGCCGCGCACGACGAACCGCTGGCGATCGTGGGCATGGCCTGCCGT     500
T  A  A  A  H  D  E  P  L  A  I  V  G  M  A  C  R

CTGCCGGGCGGGGTCGCGTCGCCACAGGAGCTGTGGCGTCTCGTCGCGTC     550
 L  P  G  G  V  A  S  P  Q  E  L  W  R  L  V  A  S

CGGCACCGACGCCATCACGGAGTTCCCCGCGGACCGCGGCTGGGACGTGG     600
  G  T  D  A  I  T  E  F  P  A  D  R  G  W  D  V

ACGCGCTCTACGACCCGGACCCCGACGCGATCGGCAAGACCTTCGTCCGG     650
D  A  L  Y  D  P  D  P  D  A  I  G  K  T  F  V  R

CACGGCGGCTTCCTCGACGGTGCGACCGGCTTCGACGCGGCGTTCTTCGG     700
 H  G  G  F  L  D  G  A  T  G  F  D  A  A  F  F  G

GATCAGCCCGCGCGAGGCCCTGGCCATGGACCCGCAGCAACGGGTGCTCC     750
  I  S  P  R  E  A  L  A  M  D  P  Q  Q  R  V  L

TGGAGACGTCCTGGGAGGCGTTCGAAAGCGCGGGCATCACCCCGGACGCG     800
L  E  T  S  W  E  A  F  E  S  A  G  I  T  P  D  A

GCGCGGGGCAGCGACACCGGCGTGTTCATCGGCGCGTTCTCCTACGGGTA     850
 A  R  G  S  D  T  G  V  F  I  G  A  F  S  Y  G  Y

CGGCACGGGTGCGGATACCAACGGCTTCGGCGCGACAGGGTCGCAGACCA     900
  G  T  G  A  D  T  N  G  F  G  A  T  G  S  Q  T

GCGTGCTCTCCGGCCGCCTCTCGTACTTCTACGGTCTGGAGGGCCCTTCG     950
S  V  L  S  G  R  L  S  Y  F  Y  G  L  E  G  P  S

GTCACGGTCGACACCGCCTGCTCGTCGTCACTGGTCGCCCTGCACCAGGC    1000
 V  T  V  D  T  A  C  S  S  S  L  V  A  L  H  Q  A

AGGGCAGTCCCTGCGCTCGGGCGAATGCTCGCTCGCCCTGGTCGGCGGTG    1050
  G  Q  S  L  R  S  G  E  C  S  L  A  L  V  G  G

TCACGGTGATGGCGTCGCCCGGCGGATTCGTCGAGTTCTCCCGGCAGCGC    1100
V  T  V  M  A  S  P  G  G  F  V  E  F  S  R  Q  R

GGGCTCGCGCCGGACGGGCGGGCGAAGGCGTTCGGCGCGGGCGCGGACGG    1150
 G  L  A  P  D  G  R  A  K  A  F  G  A  G  A  D  G

TACGAGCTTCGCCGAGGGCGCCGGTGCCCTGGTGGTCGAGCGGCTCTCCG    1200
  T  S  F  A  Q  G  A  G  A  L  V  V  E  R  L  S

ACGCGGAGCGCCACGGCCACACCGTCCTCGCCCTCGTACGCGGCTCCGCG    1250
D  A  E  R  H  G  H  T  V  L  A  L  V  R  G  S  A

GCTAACTCCGACGGCGCGTCGAACGGTCTGTCGGCGCCGAACGGCCCCTC    1300
 A  N  S  D  G  A  S  N  G  L  S  A  P  N  G  P  S

CCAGGAACGCGTCATCCACCAGGCCCTCGCGAACGCGAAACTCACCCCCG    1350
  Q  E  R  V  I  H  Q  A  L  A  N  A  K  L  T  P
```

-continued

```
CCGATGTCGACGCGGTCGAGGCGCACGGCACCGGCACCCGCCTCGGCGAC      1400
A  D  V  D  A  V  E  A  H  G  T  G  T  R  L  G  D

CCCATCGAGGCGCAGGCGCTGCTCGCGACGTACGGACAGGACCGGGCGAC      1450
 P  I  E  A  Q  A  L  L  A  T  Y  Q  D  R  A  T

GCCCCTGCTGCTCGGCTCGCTGAAGTCGAACATCGGGCACGCCCAGGCCG      1500
  P  L  L  L  G  S  L  K  S  N  I  G  H  A  Q  A

CGTCAGGGGTCGCCGGGATCATCAAGATGGTGCAGGCCATCCGGCACGGG      1550
A  S  G  V  A  G  I  I  K  M  V  Q  A  I  R  H  G

GAACTGCCGCCGACACTGCACGCGGACGAGCCGTCGCCGCACGTCGACTG      1600
 E  L  P  P  T  L  H  A  D  E  P  S  P  H  V  D  W

GACGGCCGGTGCCGTCGAGCTCCTGACGTCGGCCCGGCCGTGGCCGGGGA      1650
  T  A  G  A  V  E  L  L  T  S  A  R  P  W  P  G

CCGGTCGCCCGCGCCGCGCTGCCGTCTCGTCGTTCGGCGTGAGCGGCACG      1700
T  G  R  P  R  R  A  A  V  S  S  F  G  V  S  G  T

AACGCCCACATCATCCTTGAGGCAGGACCGGTCAAAACGGGACCGGTCGA      1750
 N  A  H  I  I  L  E  A  G  P  V  K  T  G  P  V  E

GGCAGGAGCGATCGAGGCAGGACCGGTCGAAGTAGGACCGGTCGAGGCTG      1800
  A  G  A  I  E  A  G  P  V  E  V  G  P  V  E  A

GACCGCTCCCCGCGGCGCCGCCGTCAGCACCGGGAGAAGACCTTCCGCTG      1850
G  P  L  P  A  A  P  P  S  A  P  G  E  D  L  P  L

CTCGTGTCGGCGCGTTCCCCGGAGGCACTCGACGAGCAGATCGGGCGCCT      1900
 L  V  S  A  R  S  P  E  A  L  D  E  Q  I  G  R  L

GCGCGCCTATCTCGACACCGGCCCGGGCGTCGACCGGGCGGCCGTGGCGC      1950
  R  A  Y  L  D  T  G  P  G  V  D  R  A  A  V  A

AGACACTGGCCCGGCGTACGCACTTCACCCACCGGGCCGTACTGCTCGGG      2000
Q  T  L  A  R  R  T  H  F  T  H  R  A  V  L  L  G

GACACCGTCATCGGCGCTCCCCCCGCGGACCAGGCCGACGAACTCGTCTT      2050
 D  T  V  I  G  A  P  P  A  D  Q  A  D  E  L  V  F

CGTCTACTCCGGTCAGGGCACCCAGCATCCCGCGATGGGCGAGCAACTCG      2100
  V  Y  S  G  Q  G  T  Q  H  P  A  M  G  E  Q  L

CGGCCGCGTTCCCCGTGTTCGCCGATGCCTGGCACGACGCGCTCCGACGG      2150
A  A  F  P  V  F  A  D  A  W  H  D  A  L  R  R

CTCGACGACCCCGACCCGCACGACCCCACACGGAGCCAGCACACGCTCTT      2200
 L  D  D  P  D  P  H  D  P  T  R  S  Q  H  L  F

CGCCCACCAGGCGGCGTTCACCGCCCTCCTGAGGTCCTGGGACATCACGC      2250
  A  H  Q  A  A  F  T  A  L  L  R  S  W  D  I  T

CGCACGCCGTCATCGGCCACTCGCTCGGCGAGATCACCGCCGCGTACGCC      2300
P  H  A  V  I  G  H  S  L  G  E  I  T  A  A  Y  A

GCCGGGATCCTGTCGCTCGACGACGCCTGCACCCTGATCACCACGCGTGC      2350
 A  G  I  L  S  L  D  D  A  C  T  L  I  T  T  R  A

CCGCCTCATGCACACGCTTCCGCCGCCCGGCGCCATGGTCACCGTGCTGA      2400
  R  L  M  H  T  L  P  P  P  G  A  M  V  T  V  L

CCAGCGAGGAGGAGGCCCGTCAGGCGCTGCGGCCGGGCGTGGAGATCGCC      2450
T  S  E  E  E  A  R  Q  A  L  R  P  G  V  E  I  A

GCGGTCTTCGGCCCGCACTCCGTCGTGCTCTCGGGCGACGAGGACGCCGT      2500
 A  V  F  G  P  H  S  V  V  L  S  G  D  E  D  A  V

GCTCGACGTCGCACAGCGGCTCGGCATCCACCACCGTCTGCCCGCGCCGC      2550
  L  D  V  A  Q  R  L  G  I  H  H  R  L  P  A  P

ACGCGGGCCACTCCGCGCACATGGAACCCGTGGCCGCCGAGCTGCTCGCC      2600
H  A  G  H  S  A  H  M  E  P  V  A  A  E  L  L  A

ACCACTCGCGAGCTCCGTTACGACCGGCCCCACACCGCCATCCCGAACGA      2650
 T  T  R  E  L  R  Y  D  R  P  H  T  A  I  P  N  D
```

-continued

```
CCCCACCACCGCCGAGTACTGGGCCGAGCAGGTCCGCAACCCCGTGCTGT     2700
  P  T  T  A  E  Y  W  A  E  Q  V  R  N  P  V  L

TCCACGCCCACACCCAGCGGTACCCCGACGCCGTGTTCGTCGAGATCGGC     2750
F  H  A  H  T  Q  R  Y  P  D  A  V  F  V  E  I  G

CCCGGCCAGGACCTCTCACCGCTGGTCGACGGCATCGCCCTGCAGAACGG     2800
 P  G  Q  D  L  S  P  L  V  D  G  I  A  L  Q  N  G

CACGGCGGACGAGGTGCACGCGCTGCACACCGCGCTCGCCCGCCTCTTCA     2850
  T  A  D  E  V  H  A  L  H  T  A  L  A  R  L  F

CACGCGGCGCCACGCTCGACTGGTCCCGCATCCTCGGCGGTGCTTCGCGG     2900
T  R  G  Q  T  L  D  W  S  R  I  L  G  G  A  S  R

CACGACCCTGACGTCCCCTCGTACGCGTTCCAGCGGCGTCCCTACTGGAT     2950
 H  D  P  D  V  P  S  Y  A  F  Q  R  R  P  Y  W  I

CGAGTCGGCTCCCCCGGCCACGGCCGACTCGGGCCACCCCGTCCTCGGCA     3000
  E  S  A  P  P  A  T  A  D  S  G  H  P  V  L  G

CCGGAGTCGCCGTCGCCGGGTCGCCGGGCCGGGTGTTCACGGGTCCCGTG     3050
T  G  V  A  V  A  G  S  P  G  R  V  F  T  G  P  V

CCCGCCGGTGCGGACCGCGCGGTGTTCATCGCCGAACTGGCGCTCGCCGC     3100
 P  A  G  A  D  R  A  V  F  I  A  E  L  A  L  A  A

CGCCGACGCCACCGACTGCGCCACGGTCGAACAGCTCGACGTCACCTCCG     3150
  A  D  A  T  D  C  A  T  V  E  Q  L  D  V  T  S

TGCCCGGCGGATCCGCCCGCGGCAGGGCCACCGCGCAGACCTGGGTCGAT     3200
V  P  G  G  S  A  R  G  R  A  T  A  Q  T  W  V  D

GAACCCGCCGCCGACGGGCGGCGCCGCTTCACCGTCCACACCCGCGTCGG     3250
 E  P  A  A  D  G  R  R  R  F  T  V  H  T  R  V  G

CGACGCCCCGTGGACGCTGCACGCCGAGGGGGTTCTCCGCCCCGGCCGCG     3300
  D  A  P  W  T  L  H  A  E  G  V  L  R  P  G  R

TGCCCCAGCCCGAAGCCGTCGACACCGCCTGGCCCCCGCCGGGCGCGGTG     3350
V  P  Q  P  E  A  V  D  T  A  W  P  P  P  G  A  V

CCCGCGGACGGGCTGCCCGGGGCGTGGCGACGCGCGGACCAGGTCTTCGT     3400
 P  A  D  G  L  P  G  A  W  R  R  A  D  Q  V  F  V

CGAAGCCGAAGTCGACAGCCCTGACGGCTTCGTGGCACACCCCGACCTGC     3450
  E  A  E  V  D  S  P  D  G  F  V  A  H  P  D  L

TCGACGCGGTCTTCTCCGCGGTCGGCGACGGGAGCCGCCAGCCGACCGGA     3500
L  D  A  V  F  S  A  V  G  D  G  S  R  Q  P  T  G

TGGCGCGACCTCGCGGTGCACGCGTCGGACGCCACCGTGCTGCGCGCCTG     3550
 W  R  D  L  A  V  H  A  S  D  A  T  V  L  R  A  C

CCTCACCCGCCGCGACAGTGGTGTCGTGGAGCTCGCCGCCTTCGACGGTG     3600
  L  T  R  R  D  S  G  V  V  E  L  A  A  F  D  G

CCGGAATGCCGGTGCTCACCGCGGAGTCGGTGACGCTGGGCGAGGTCGCG     3650
A  G  M  P  V  L  T  A  E  S  V  T  L  G  E  V  A

TCGGCAGGCGGATCCGACGAGTCGGACGGTCTGCTTCGGCTTGAGTGGTT     3700
 S  A  G  G  S  D  E  S  D  G  L  L  R  L  E  W  L

GCCGGTGGCGGAGGCCCACTACGACGGTGCCGACGAGCTGCCCGAGGGCT     3750
  P  V  A  E  A  H  Y  D  G  A  D  E  L  P  E  G

ACACCCTCATCACCGCCACACACCCCGACGACCCCGACGACCCCACCAAC     3800
Y  T  L  I  T  A  T  H  P  D  D  P  D  D  P  T  N

CCCCACAACACACCCACACGCACCCACACACAAACCACACGCGTCCTCAC     3850
 P  H  N  T  P  T  R  T  H  T  Q  T  T  R  V  L  T

CGCCCTCCAACACCACCTCATCACCACCAACCACACCCTCATCGTCCACA     3900
  A  L  Q  H  H  L  I  T  T  N  H  T  L  I  V  H

CCACCACCGACCCCCCAGGCGCCGCCGTCACCGGCCTCACCCGCACCGCA     3950
T  T  T  D  P  P  G  A  A  V  T  G  L  T  R  T  A
```

-continued

```
CAAAACGAACACCCCGGCCGCATCCACCTCATCGAAACCCACCACCCCCA      4000
 Q  N  E  H  P  G  R  I  H  L  I  E  T  H  H  P  H

CACCCCACTCCCCCTCACCCAACTCACCACCCTCCACCAACCCCACCTAC      4050
  T  P  L  P  L  T  Q  L  T  T  L  H  Q  P  H  L

GCCTCACCAACAACACCCTCCACACCCCCCACCTCACCCCCATCACCACC      4100
R  L  T  N  N  T  L  H  T  P  H  L  T  P  I  T  T

CACCACAACACCACCACAACCACCCCCAACACCCCACCCCTCAACCCCAA      4150
 H  H  N  T  T  T  T  T  P  N  T  P  P  L  N  P  N

CCACGCCATCCTCATCACCGGCGGCTCCGGCACCCTCGCCGGCATCCTCG      4200
  H  A  I  L  I  T  G  G  S  G  T  L  A  G  I  L

CCCGCCACCTCAACCACCCCCACACCTACCTCCTCTCCCGCACACCACCA      4250
A  R  H  L  N  H  P  H  T  Y  L  L  S  R  T  P  P

CCCCCCACCACACCCGGCACCCACATCCCCTGCGACCTCACCGACCCCAC      4300
 P  P  T  T  P  G  T  H  I  P  C  D  L  T  D  P  T

CCAAATCACCCAAGCCCTCACCCACATACCACAACCCCTCACCGGCATCT      4350
  Q  I  T  Q  A  L  T  H  I  P  Q  P  L  T  G  I

TCCACACCGCCGCCACCCTCGACGACGCCACCCTCACCAACCTCACCCCC      4400
F  H  T  A  A  T  L  D  D  A  T  L  T  N  L  T  P

CAACACCTCACCACCACCCTCCAACCCAAAGCCGACGCCGCCTGGCACCT      4450
 Q  H  L  T  T  T  L  Q  P  K  A  D  A  A  W  H  L

CCACCACCACACCCAAAACCAACCCCTCACCCACTTCGTCCTCTACTCCA      4500
  H  H  H  T  Q  N  Q  P  L  T  H  F  V  L  Y  S

GCGCCGCCGCCACCCTCGGCAGCCCCGGCCAAGCCAACTACGCCGCCGCC      4550
S  A  A  A  T  L  G  S  P  G  Q  A  N  Y  A  A  A

AACGCCTTCCTCGACGCCCTCGCCACCCACCGCCACACCCAAGGACAACC      4600
 N  A  F  L  D  A  L  A  T  H  R  H  T  Q  G  Q  P

CGCCACCACCATCGCCTGGGGCATGTGGCACACCACCACCACACTCACCA      4650
  A  T  T  I  A  W  G  M  W  H  T  T  T  T  L  T

GCCAACTCACCGACAGCGACCGCGACCGCATCCGCCGCGGCGGCTTCCTG      4700
S  Q  L  T  D  S  D  R  D  R  I  R  R  G  G  F  L

CCGATCTCGGACGACGAGGGCATGC
 P  I  S  D  D  E  G  M
```

The AvrII-XhoI hybrid FK-506 PKS module 8 containing the AT domain of module 12 of rapamycin is shown below.

```
GCATGCGGCTGTACGAGGCGGCACGGCGCACCGGAAGTCCCGTGGTGGTG       50
  M  R  L  Y  E  A  A  R  R  T  G  S  P  V  V  V

GCGGCCGCGCTCGACGACGCGCCGGACGTGCCGCTGCTGCGCGGGCTGCG      100
 A  A  A  L  D  D  A  P  D  V  P  L  L  R  G  L  R

GCGTACGACCGTCCGGCGTGCCGCCGTCCGGGAACGCTCTCTCGCCGACC      150
  R  T  T  V  R  R  A  A  V  R  E  R  S  L  A  D

GCTCGCCGTGCTGCCCGACGACGAGCGCGCCGACGCCTCCCTCGCGTTCG      200
R  S  P  C  C  O  T  T  S  A  P  T  P  P  S  R  S

TCCTGGAACAGCACCGCCACCGTGCTCGGCCACCTGGGCGCCGAAGACAT      250
 S  W  N  S  T  A  T  V  L  G  H  L  G  A  E  D  I

CCCGGCGACGACGACGTTCAAGGAACTCGGCATCGACTCGCTCACCGCGG      300
  P  A  T  T  F  K  E  G  I  D  S  L  T  A

TCCAGCTGCGCAACGCGCTGACCACGGCGACCGGCGTACGCCTCAACGCC      350
V  Q  L  R  N  A  L  T  T  A  T  G  V  R  L  N  A

ACAGCGGTCTTCGACTTTCCGACGCCGCGCGCGCTCGCCGCGAGACTCGG      400
 T  A  V  F  D  F  P  T  P  R  A  L  A  A  R  L  G
```

-continued

```
CGACGAGCTGGCCGGTACCCGCGCGCCCGTCGCGGCCCGGACCGCGGCCA      450
  D  E  L  A  G  T  R  A  P  V  A  A  R  T  A  A

CCGCGGCCGCGCACGACGAACCGCTGGCGATCGTGGGCATGGCCTGCCGT      500
T  A  A  A  H  D  E  P  L  A  I  V  G  M  A  C  R

CTGCCGGGCGGGGTCGCGTCGCCACAGGAGCTGTGGCGTCTCGTCGCGTC      550
 L  P  G  G  V  A  S  P  Q  E  L  W  R  L  V  A  S

CGGCACCGACGCCATCACGGAGTTCCCCGCGGACCGCGGCTGGGACGTGG      600
  G  T  D  A  I  T  E  F  P  A  D  R  G  W  D  V

ACGCGCTCTACGACCCGGACCCCGACGCGATCGGCAAGACCTTCGTCCGG      650
D  A  L  Y  D  P  D  P  D  A  I  G  K  T  F  V  R

CACGGCGGCTTCCTCGACGGTGCGACCGGCTTCGACGCGGCGTTCTTCGG      700
 H  G  G  F  L  D  G  A  T  G  F  D  A  A  F  F  G

GATCAGCCCGCGCGAGGCCCTGGCCATGGACCCGCAGCAACGGGTGCTCC      750
  I  S  P  R  E  A  L  A  M  D  P  Q  Q  R  V  L

TGGAGACGTCCTGGGAGGCGTTCGAAAGCGCGGGCATCACCCCGGACGCG      800
L  E  T  S  W  E  A  F  E  S  A  G  I  T  P  D  A

GCGCGGGGCAGCGACACCGGCGTGTTCATCGGCGCGTTCTCCTACGGGTA      850
 A  R  G  S  D  T  G  V  F  I  G  A  F  S  Y  G  Y

CGGCACGGGTGCGGATACCAACGGCTTCGGCGCGACAGGGTCGCAGACCA      900
  G  T  G  A  D  T  N  G  F  G  A  T  G  S  Q  T

GCGTGCTCTCCGGCCGCCTCTCGTACTTCTACGGTCTGGAGGGCCCTTCG      950
S  V  L  S  G  R  L  S  Y  F  Y  G  L  E  G  P  S

GTCACGGTCGACACCGCCTGCTCGTCGTCACTGGTCGCCCTGCACCAGGC     1000
 V  T  V  D  T  A  C  S  S  S  L  V  A  L  H  Q  A

AGGGCAGTCCCTGCGCTCGGGCGAATGCTCGCTCGCCCTGGTCGGCGGTG     1050
  G  Q  S  L  R  S  G  E  C  S  L  A  L  V  G  G

TCACGGTGATGGCGTCGCCCGGCGGATTCGTCGAGTTCTCCCGGCAGCGC     1100
V  T  V  M  A  S  P  G  G  F  V  E  F  S  R  Q  R

GGGCTCGCGCCGGACGGGCGGGCGAAGGCGTTCGGCGCGGGCGCGGACGG     1150
 G  L  A  P  D  G  R  A  K  A  F  G  A  G  A  D  G

TACGAGCTTCGCCGAGGGCGCCGGTGCCCTGGTGGTCGAGCGGCTCTCCG     1200
  T  S  F  A  E  G  A  G  A  L  V  V  E  R  L  S

ACGCGGAGCGCCACGGCCACACCGTCCTCGCCCTCGTACGCGGCTCCGCG     1250
D  A  E  R  H  G  H  T  V  L  A  L  V  R  G  S  A

GCTAACTCCGACGGCGCGTCGAACGGTCTGTCGGCGCCGAACGGCCCCTC     1300
 A  N  S  D  G  A  S  N  G  L  S  A  P  N  G  P  S

CCAGGAACGCGTCATCCACCAGGCCCTCGCGAACGCGAAACTCACCCCCG     1350
  Q  E  R  V  I  H  Q  A  L  A  N  A  K  L  T  P

CCGATGTCGACGCGGTCGAGGCGCACGGCACCGGCACCCGCCTCGGCGAC     1400
A  D  V  D  A  V  E  A  H  G  T  G  T  R  L  G  D

CCCATCGAGGCGCAGGCGCTGCTCGCGACGTACGGACAGGACCGGGCGAC     1450
 P  I  E  A  Q  A  L  L  A  T  Y  G  Q  D  R  A  T

GCCCCTGCTGCTCGGCTCGCTGAAGTCGAACATCGGGCACGCCCAGGCCG     1500
  P  L  L  L  G  S  L  K  S  N  I  G  H  A  Q  A

CGTCAGGGGTCGCCGGGATCATCAAGATGGTGCAGGCCATCCGGCACGGG     1550
A  S  G  V  A  G  I  I  K  M  V  Q  A  I  R  H  G

GAACTGCCGCCGACACTGCACGCGGACGAGCCGTCGCCGCACGTCGACTG     1600
 E  L  P  P  T  L  H  A  D  E  P  S  P  H  V  D  W

GACGGCCGGTGCCGTCGAGCTCCTGACGTCGGCCCGGCCGTGGCCGGGGA     1650
  T  A  G  A  V  E  L  L  T  S  A  R  P  W  P  G

CCGGTCGCCCTAGGCGGGCAGGCGTGTCGTCCTTCGGGATCAGTGGCACC     1700
T  G  R  P  R  R  A  G  V  S  S  F  G  I  S  G  T

AACGCCCACGTCATCCTGGAAAGCGCACCCCCCACTCAGCCTGCGGACAA     1750
 N  A  H  V  I  L  E  S  A  P  P  T  Q  P  A  D  N
```

-continued

```
CGCGGTGATCGAGCGGGCACCGGAGTGGGTGCCGTTGGTGATTTCGGCCA     1800
  A  V  I  E  R  A  P  E  W  V  P  L  V  I  S  A

GGACCCAGTCGGCTTTGACTGAGCACGAGGGCCGGTTGCGTGCGTATCTG     1850
R  T  Q  S  A  L  T  E  H  E  G  R  L  R  A  Y  L

GCGGCGTCGCCCGGGGTGGATATGCGGGCTGTGGCATCGACGCTGGCGAT     1900
 A  A  S  P  G  V  D  M  R  A  V  A  S  T  L  A  M

GACACGGTCGGTGTTCGAGCACCGTGCCGTGCTGCTGGGAGATGACACCG     1950
  T  R  S  V  F  E  H  R  A  V  L  L  G  D  D  T

TCACCGGCACCGCTGTGTCTGACCCTCGGGCGGTGTTCGTCTTCCCGGGA     2000
V  T  G  T  A  V  S  D  P  R  A  V  F  V  F  P  G

CAGGGGTCGCAGCGTGCTGGCATGGGTGAGGAACTGGCCGCCGCGTTCCC     2050
 Q  G  S  Q  R  A  G  M  G  E  E  L  A  A  A  F  P

CGTCTTCGCGCGGATCCATCAGCAGGTGTGGGACCTGCTCGATGTGCCCG     2100
  V  F  A  R  I  H  Q  Q  V  W  D  L  L  D  V  P

ATCTGGAGGTGAACGAGACCGGTTACGCCCAGCCGGCCCTGTTCGCAATG     2150
D  L  E  V  N  E  T  G  Y  A  Q  P  A  L  F  A  M

CAGGTGGCTCTGTTCGGGCTGCTGGAATCGTGGGGTGTACGACCGGACGC     2200
 Q  V  A  L  F  G  L  L  E  S  W  G  V  R  P  D  A

GGTGATCGGCCATTCGGTGGGTGAGCTTGCGGCTGCGTATGTGTCCGGGG     2250
  V  I  G  H  S  V  G  E  L  A  A  A  Y  V  S  G

TGTGGTCGTTGGAGGATGCCTGCACTTTGGTGTCGGCGCGGGCTCGTCTG     2300
V  W  S  L  E  D  A  C  T  L  V  S  A  R  A  R  L

ATGCAGGCTCTGCCCGCGGGTGGGGTGATGGTCGCTGTCCCGGTCTCGGA     2350
 M  Q  A  L  P  A  G  G  V  M  V  A  V  P  V  S  E

GGATGAGGCCCGGGCCGTGCTGGGTGAGGGTGTGGAGATCGCCGCGGTCA     2400
  D  E  A  R  A  V  L  G  E  G  V  E  I  A  A  V

ACGGCCCGTCGTCGGTGGTTCTCTCCGGTGATGAGGCCGCCGTGCTGCAG     2450
N  G  P  S  S  V  V  L  S  G  D  E  A  A  V  L  Q

GCCGCGGAGGGGCTGGGGAAGTGGACGCGGCTGGCGACCAGCCACGCGTT     2500
 A  A  E  G  L  G  K  W  T  R  L  A  T  S  H  A  F

CCATTCCGCCCGTATGGAACCCATGCTGGAGGAGTTCCGGGCGGTCGCCG     2550
  H  S  A  R  M  E  P  M  L  E  E  F  R  A  V  A

AAGGCCTGACCTACCGGACGCCGCAGGTCTCCATGGCCGTTGGTGATCAG     2600
E  G  L  T  Y  R  T  P  Q  V  S  M  A  V  G  D  Q

GTGACCACCGCTGAGTACTGGGTGCGGCAGGTCCGGGACACGGTCCGGTT     2650
 V  T  T  A  E  Y  W  V  R  Q  V  R  D  T  V  R  F

CGGCGAGCAGGTGGCCTCGTACGAGGACGCCGTGTTCGTCGAGCTGGGTG     2700
  G  E  Q  V  A  S  Y  E  D  A  V  F  V  E  L  G

CCGACCGGTCACTGGCCCGCCTGGTCGACGGTGTCGCGATGCTGCACGGC     2750
A  D  R  S  L  A  R  L  V  D  G  V  A  M  L  H  G

GACCACGAAATCCAGGCCGCGATCGGCGCCCTGGCCCACCTGTATGTCAA     2800
 D  H  E  I  Q  A  A  I  G  A  L  A  H  L  Y  V  N

CGGCGTCACGGTCGACTGGCCCGCGCTCCTGGGCGATGCTCCGGCAACAC     2850
  G  V  T  V  D  W  P  A  L  L  G  D  A  P  A  T

GGGTGCTGGACCTTCCGACATACGCCTTCCAGCACCAGCGCTACTGGCTC     2900
R  V  L  D  L  P  T  Y  A  F  Q  H  Q  R  Y  W  L

GAGTCGGCTCCCCCGGCCACGGCCGACTCGGGCCACCCCGTCCTCGGCAC     2950
 E  S  A  P  P  A  T  A  D  S  G  H  P  V  L  G  T

CGGAGTCGCCGTCGCCGGGTCGCCGGGCCGGGTGTTCACGGGTCCCGTGC     3000
  G  V  A  V  A  G  S  P  G  R  V  F  T  G  P  V

CCGCCGGTGCGGACCGCGCGGTGTTCATCGCCGAACTGGCGCTCGCCGCC     3050
P  A  G  A  D  R  A  V  F  I  A  E  L  A  L  A  A
```

-continued

```
GCCGACGCCACCGACTGCGCCACGGTCGAACAGCTCGACGTCACCTCCGT      3100
 A  D  A  T  D  C  A  T  V  E  Q  L  D  V  T  S  V

GCCCGGCGGATCCGCCCGCGGCAGGGCCACCGCGCAGACCTGGGTCGATG      3150
  P  G  G  S  A  R  G  R  A  T  A  Q  T  W  V  D

AACCCGCCGCCGACGGGCGGCGCCGCTTCACCGTCCACACCCGCGTCGGC      3200
E  P  A  A  D  G  R  R  R  F  T  V  H  T  R  V  G

GACGCCCCGTGGACGCTGCACGCCGAGGGGGTTCTCCGCCCCGGCCGCGT      3250
 D  A  P  W  T  L  H  A  E  G  V  L  R  P  G  R  V

GCCCCAGCCCGAAGCCGTCGACACCGCCTGGCCCCCGCCGGGCGCGGTGC      3300
  P  Q  P  E  A  V  D  T  A  W  P  P  P  G  A  V

CCGCGGACGGGCTGCCCGGGGCGTGGCGACGCGCGGACCAGGTCTTCGTC      3350
P  A  D  G  L  P  G  A  W  R  R  A  D  Q  V  F  V

GAAGCCGAAGTCGACAGCCCTGACGGCTTCGTGGCACACCCCGACCTGCT      3400
 E  A  E  V  D  S  P  D  G  F  V  A  H  P  D  L  L

CGACGCGGTCTTCTCCGCGGTCGGCGACGGGAGCCGCCAGCCGACCGGAT      3450
  D  A  V  F  S  A  V  G  D  G  S  R  Q  P  T  G

GGDGCGACCTCGCGGTGCACGCGTCGGACGCCACCGTGCTGCGCGCCTGC      3500
W  R  D  L  A  V  H  A  S  D  A  T  V  L  R  A  C

CTCACCCGCCGCGACAGTGGTGTCGTGGAGCTCGCCGCCTTCGACGGTGC      3550
 L  T  R  R  D  S  G  V  V  E  L  A  A  F  D  G  A

CGGAATGCCGGTGCTCACCGCGGAGTCGGTGACGCTGGGCGAGGTCGCGT      3600
  G  M  P  V  L  T  A  E  S  V  T  L  G  E  V  A

CGGCAGGCGGATCCGACGAGTCGGACGGTCTGCTTCGGCTTGAGTGGTTG      3650
S  A  G  G  S  D  E  S  D  G  L  L  R  L  E  W  L

CCGGTGGCGGAGGCCCACTACGACGGTGCCGACGAGCTGCCCGAGGGCTA      3700
 P  V  A  E  A  H  Y  D  G  A  D  E  L  P  E  G  Y

CACCCTCATCACCGCCACACACCCCGACGACCCCGACGACCCCACCAACC      3750
  T  L  I  T  A  T  H  P  D  D  P  D  D  P  T  N

CCCACAACACACCCACACGCACCCACACACAAACCACACGCGTCCTCACC      3800
P  H  N  T  P  T  R  T  H  T  Q  T  T  R  V  L  T

GCCCTCCAACACCACCTCATCACCACCAACCACACCCTCATCGTCCACAC      3850
 A  L  Q  H  H  L  I  T  T  N  H  T  L  I  V  H  T

CACCACCGACCCCCCAGGCGCCGCCGTCACCGGCCTCACCCGCACCGCAC      3900
  R  R  D  P  P  G  A  A  V  T  G  L  R  T  A

AAAACGAACACCCCGGCCGCATCCACCTCATCGAAACCCACCACCCCCAC      3950
Q  N  E  H  P  G  R  I  H  L  I  E  T  H  H  P  H

ACCCCACTCCCCCTCACCCAACTCACCACCCTCCACCAACCCCACCTACG      4000
 T  P  L  P  L  T  Q  L  T  T  L  H  Q  P  H  L  R

CCTCACCAACAACACCCTCCACACCCCCCACCTCACCCCCATCACCACCC      4050
  L  T  N  N  T  L  H  T  P  H  L  T  P  I  T  T

ACCACAACACCACCACAACCACCCCCAACACCCCACCCCTCAACCCCAAC      4100
H  H  N  T  T  T  T  T  P  N  T  P  P  L  N  P  N

CACGCCATCCTCATCACCGGCGGCTCCGGCACCCTCGCCGGCATCCTCGC      4150
 H  A  I  L  I  T  G  G  S  G  T  L  A  G  I  L  A

CCGCCACCTCAACCACCCCCACACCTACCTCCTCTCCCGCACACCACCAC      4200
  R  H  L  N  H  P  H  T  Y  L  L  S  R  T  P  P

CCCCCACCACACCCGGCACCCACATCCCCTGCGACCTCACCGACCCCACC      4250
P  P  T  T  P  G  T  H  I  P  C  D  L  T  D  P  T

CAAATCACCCAAGCCCTCACCCACATACCACAACCCCTCACCGGCATCTT      4300
 Q  I  T  Q  A  L  T  H  I  P  Q  P  L  T  G-
  G  I  F

CCACACCGCCGCCACCCTCGACGACGCCACCCTCACCAACCTCACCCCCC      4350
  H  T  A  A  T  L  D  D  A  T  L  T  N  L  T  P
```

-continued

```
AACACCTCACCACCACCCTCCAACCCAAAGCCGACGCCGCCTGGCACCTC      4400
Q  H  L  T  T  T  L  Q  P  K  A  D  A  A  W  H  L

CACCACCACACCCAAAACCAACCCCTCACCCACTTCGTCCTCTACTCCAG      4450
 H  H  H  T  Q  N  Q  P  L  T  H  F  V  L  Y  S  S

CGCCGCCGCCACCCTCGGCAGCCCCGGCCAAGCCAACTACGCCGCCGCCA      4500
  A  A  A  T  L  G  S  P  G  Q  A  N  Y  A  A  A

ACGCCTTCCTCGACGCCCTCGCCACCCACCGCCACACCCAAGGACAACCC      4550
N  A  F  L  D  A  L  A  T  H  R  H  T  Q  G  Q  P

GCCACCACCATCGCCTGGGGCATGTGGCACACCACCACCACACTCACCAG      4600
 A  T  T  I  A  W  G  M  W  H  T  T  T  T  L  T  S

CCAACTCACCGACAGCGACCGCGACCGCATCCGCCGCGGCGGCTTCCTGC      4650
  Q  L  T  D  S  D  R  S  R  I  R  R  G  G  F  L

CGATCTCGGACGACGAGGGCATGC
P  I  S  D  D  E  G  M
```

The AvrII-XhoI hybrid FK-506 PKS module 8 containing the AT domain of module 13 of rapamycin is shown below.

```
GCATGCGGCTGTACGAGGCGGCACGGCGCACCGGAAGTCCCGTGGTGGTG       50
   M  R  L  Y  E  A  A  R  R  T  G  S  P  V  V  V

GCGGCCGCGCTCGACGACGCGCCGGACGTGCCGCTGCTGCGCGGGCTGCG      100
 A  A  A  L  D  D  A  P  D  V  P  L  L  R  G  L  R

GCGTACGACCGTCCGGCGTGCCGCCGTCCGGGAACGCTCTCTCGCCGACC      150
  R  T  T  V  R  R  A  A  V  R  E  R  S  L  A  D

GCTCGCCGTGCTGCCCGACGACGAGCGCGCCGACGCCTCCCTCGCGTTCG      200
R  S  P  C  C  P  T  T  S  A  P  T  P  P  S  R  S

TCCTGGAACAGCACCGCCACCGTGCTCGGCCACCTGGGCGCCGAAGACAT      250
 S  W  N  S  T  A  T  V  L  G  H  L  G  A  E  D  I

CCCGGCGACGACGACGTTCAAGGAACTCGGCATCGACTCGCTCACCGCGG      300
  P  A  T  T  T  F  K  E  L  G  I  D  S  L  T  A

TCCAGCTGCGCAACGCGCTGACCACGGCGACCGGCGTACGCCTCAACGCC      350
V  Q  L  R  N  A  L  T  T  A  T  G  V  R  L  N  A

ACAGCGGTCTTCGACTTTCCGACGCCGCGCGCGCTCGCCGCGAGACTCGG      400
 T  A  V  F  D  F  P  T  P  R  A  L  A  A  R  L  G

CGACGAGCTGGCCGGTACCCGCGCGCCCGTCGCGGCCCGGACCGCGGCCA      450
  D  E  L  A  G  T  R  A  P  V  A  A  R  T  A  A

CCGCGGCCGCGCACGACGAACCGCTGGCGATCGTGGGCATGGCCTGCCGT      500
T  A  A  A  H  D  E  P  L  A  I  V  G  M  A  C  R

CTGCCGGGCGGGGTCGCGTCGCCACAGGAGCTGTGGCGTCTCGTCGCGTC      550
 L  P  G  G  V  A  S  P  Q  E  L  W  R  L  V  A  S

CGGCACCGACGCCATCACGGAGTTCCCCGCGGACCGCGGCTGGGACGTGG      600
  G  T  D  A  I  T  E  F  P  A  D  R  G  W  D  V

ACGCGCTCTACGACCCGGACCCCGACGCGATCGGCAAGACCTTCGTCCGG      650
D  A  L  Y  D  P  D  P  D  A  I  G  K  T  F  V  R

CACGGCGGCTTCCTCGACGGTGCGACCGGCTTCGACGCGGCGTTCTTCGG      700
 H  G  G  F  L  D  G  A  T  G  F  D  A  A  F  F  G

GATCAGCCCGCGCGAGGCCCTGGCCATGGACCCGCAGCAACGGGTGCTCC      750
  I  S  P  R  E  A  L  A  M  D  P  Q  Q  R  V  L

TGGAGACGTCCTGGGAGGCGTTCGAAAGCGCGGGCATCACCCCGGACGCG      800
L  E  T  S  W  E  A  F  E  S  A  G  I  T  P  D  A

GCGCGGGGCAGCGACACCGGCGTGTTCATCGGCGCGTTCTCCTACGGGTA      850
 A  R  G  S  D  T  G  V  F  I  G  A  F  S  Y  G  Y
```

-continued

```
CGGCACGGGTGCGGATACCAACGGCTTCGGCGCGACAGGGTCGCAGACCA      900
  G  T  G  A  D  T  N  G  F  G  A  T  G  S  Q  T

GCGTGCTCTCCGGCCGCCTCTCGTACTTCTACGGTCTGGAGGGCCCTTCG      950
S  V  L  S  G  R  L  S  Y  F  Y  G  L  E  G  P  S

GTCACGGTCGACACCGCCTGCTCGTCGTCACTGGTCGCCCTGCACCAGGC     1000
 V  T  V  D  T  A  C  S  S  L  V  A  L  H  Q  A

AGGGCAGTCCCTGCGCTCGGGCGAATGCTCGCTCGCCCTGGTCGGCGGTG     1050
  G  Q  S  L  R  S  G  E  C  S  L  A  L  V  G  G

TCACGGTGATGGCGTCGCCCGGCGGATTCGTCGAGTTCTCCCGGCAGCGC     1100
V  T  V  M  A  S  P  G  G  F  V  E  F  S  R  Q  R

GGGCTCGCGCCGGACGGGCGGGCGAAGGCGTTCGGCGCGGGCGCGGACGG     1150
 G  L  A  P  D  G  R  A  K  A  F  G  A  G  A  D  G

TACGAGCTTCGCCGAGGGCGCCGGTGCCCTGGTGGTCGAGCGGCTCTCCG     1200
  T  S  F  A  E  G  A  G  A  L  V  V  E  R  L  S

ACGCGGAGCGCCACGGCCACACCGTCCTCGCCCTCGTACGCGGCTCCGCG     1250
D  A  E  R  H  G  H  T  V  L  A  L  V  R  G  S  A

GCTAACTCCGACGGCGCGTCGAACGGTCTGTCGGCGCCGAACGGCCCCTC     1300
 A  N  S  D  G  S  N  G  L  S  A  P  N  G  P  S

CCAGGAACGCGTCATCCACCAGGCCCTCGCGAACGCGAAACTCACCCCCG     1350
  Q  E  R  V  I  H  Q  A  L  A  N  A  K  L  T  P

CCGATGTCGACGCGGTCGAGGCGCACGGCACCGGCACCCGCCTCGGCGAC     1400
A  D  V  D  A  V  E  A  H  G  T  G  T  R  L  G  D

CCCATCGAGGCGCAGGCGCTGCTCGCGACGTACGGACAGGACCGGGCGAC     1450
 P  I  E  A  Q  A  L  L  A  T  Y  G  Q  D  R  A  T

GCCCCTGCTGCTCGGCTCGCTGAAGTCGAACATCGGGCACGCCCAGGCCG     1500
  P  L  L  L  G  S  L  K  S  N  I  G  H  A  Q  A

CGTCAGGGGTCGCCGGGATCATCAAGATGGTGCAGGCCATCCGGCACGGG     1550
A  S  G  V  A  G  I  T  K  M  V  Q  A  I  R  H  G

GAACTGCCGCCGACACTGCACGCGGACGAGCCGTCGCCGCACGTCGACTG     1600
 E  L  P  P  T  L  H  A  D  E  P  S  P  H  V  D  W

GACGGCCGGTGCCGTCGAGCTCCTGACGTCGGCCCGGCCGTGGCCGGGGA     1650
  T  A  G  A  V  E  L  L  T  S  A  R  P  W  P  G

CCGGTCGCCCTAGGCGGGCGGGCGTGTCGTCCTTCGGAGTCAGCGGCACC     1700
T  G  R  P  R  R  A  G  V  S  S  F  G  V  S  G  T

AACGCCCACGTCATCCTGGAGAGCGCACCCCCCGCTCAGCCCGCGGAGGA     1750
 N  A  H  V  I  L  E  S  A  P  P  A  Q  P  A  E  E

GGCGCAGCCTGTTGAGACGCCGGTGGTGGCCTCGGATGTGCTGCCGCTGG     1800
  A  Q  P  V  E  T  P  V  V  A  S  D  V  L  P  L

TGATATCGGCCAAGACCCAGCCCGCCCTGACCGAACACGAAGACCGGCTG     1850
V  I  S  A  K  T  Q  P  A  L  T  E  H  E  D  R  L

CGCGCCTACCTGGCGGCGTCGCCCGGGGCGGATATACGGGCTGTGGCATC     1900
 R  A  Y  L  A  A  S  P  G  A  D  I  R  A  V  A  S

GACGCTGGCGGTGACACGGTCGGTGTTCGAGCACCGCGCCGTACTCCTTG     1950
  T  L  A  V  T  R  S  V  F  E  H  R  A  V  L  L

GAGATGACACCGTCACCGGCACCGCGGTGACCGACCCCAGGATCGTGTTT     2000
G  D  D  T  V  T  G  T  A  V  T  D  P  R  I  V  F

GTCTTTCCCGGGCAGGGGTGGCAGTGGCTGGGGATGGGCAGTGCACTGCG     2050
 V  F  P  G  Q  G  W  Q  W  L  G  M  G  S  A  L  R

CGATTCGTCGGTGGTGTTCGCCGAGCGGATGGCCGAGTGTGCGGCGGCGT     2100
  D  S  S  V  V  F  A  E  R  M  A  E  C  A  A  A

TGCGCGAGTTCGTGGACTGGGATCTGTTCACGGTTCTGGATGATCCGGCG     2150
L  R  E  F  V  D  W  D  L  F  T  V  L  D  D  P  A
```

-continued

```
GTGGTGGACCGGGTTGATGTGGTCCAGCCCGCTTCCTGGGCGATGATGGT     2200
 V  V  D  R  V  D  V  V  Q  P  A  S  W  A  M  M  V

TTCCCTGGCCGCGGTGTGGCAGGCGGCCGGTGTGCGGCCGGATGCGGTGA     2250
  S  L  A  A  V  W  Q  A  A  G  V  R  P  D  A  V

TCGGCCATTCGCAGGGTGAGATCGCCGCAGCTTGTGTGGCGGGTGCGGTG     2300
I  G  H  S  Q  G  E  I  A  A  A  C  V  A  G  A  V

TCACTACGCGATGCCGCCCGGATCGTGACCTTGCGCAGCCAGGCGATCGC     2350
 S  L  R  D  A  A  R  I  V  T  L  R  S  Q  A  I  A

CCGGGGCCTGGCGGGCCGGGGCGCGATGGCATCCGTCGCCCTGCCCGCGC     2400
  R  G  L  A  G  R  G  A  M  A  S  V  A  L  P  A

AGGATGTCGAGCTGGTCGACGGGGCCTGGATCGCCGCCCACAACGGGCCC     2450
Q  D  V  E  L  V  D  G  A  W  I  A  A  H  N  G  P

GCCTCCACCGTGATCGCGGGCACCCCGGAAGCGGTCGACCATGTCCTCAC     2500
 A  S  T  V  I  A  G  T  P  E  A  V  D  H  V  L  T

CGCTCATGAGGCACAAGGGGTGCGGGTGCGGCGGATCACCGTCGACTATG     2550
  A  H  E  A  Q  G  V  R  V  R  R  I  T  V  D  Y

CCTCGCACACCCCGCACGTCGAGCTGATCCGCGACGAACTACTCGACATC     2600
A  S  H  T  P  H  V  E  L  I  R  D  E  L  L  D  I

ACTAGCGACAGCAGCTCGCAGACCCCGCTCGTGCCGTGGCTGTCGACCGT     2650
 T  S  D  S  S  S  Q  T  P  L  V  P  W  L  S  T  V

GGACGGCACCTGGGTCGACAGCCCGCTGGACGGGGAGTACTGGTACCGGA     2700
  D  G  T  W  V  D  S  P  L  D  G  E  Y  W  Y  R

ACCTGCGTGAACCGGTCGGTTTCCACCCCGCCGTCAGCCAGTTGCAGGCC     2750
N  L  R  E  P  V  G  F  H  P  A  V  S  Q  L  Q  A

CAGGGCGACACCGTGTTCGTCGAGGTCAGCGCCAGCCCGGTGTTGTTGCA     2800
 Q  G  D  T  V  F  V  E  V  S  A  S  P  V  L  L  Q

GGCGATGGACGACGATGTCGTCACGGTTGCCACGCTGCGTCGTGACGACG     2850
  A  M  D  D  D  V  V  T  V  A  T  L  R  R  D  D

GCGACGCCACCCGGATGCTCACCGCCCTGGCACAGGCCTATGTCCACGGC     2900
G  D  A  T  R  M  L  T  A  L  A  Q  A  Y  V  H  G

GTCACCGTCGACTGGCCCGCCATCCTCGGCACCACCACAACCCGGGTACT     2950
 V  T  V  D  W  P  A  I  L  G  T  T  T  T  R  V  L

GGACCTTCCGACCTACGCCTTCCAACACCAGCGGTACTGGCTCGAGTCGG     3000
  D  L  P  T  Y  A  F  Q  H  Q  R  Y  W  L  E  S

CTCCCCCGGCCACGGCCGACTCGGGCCACCCCGTCCTCGGCACCGGAGTC     3050
A  P  P  A  T  A  D  S  G  H  P  V  L  G  T  G  V

GCCGTCGCCGGGTCGCCGGGCCGGGTGTTCACGGGTCCCGTGCCCGCCGG     3100
 A  V  A  G  S  P  G  R  V  F  T  G  P  V  P  A  G

TGCGGACCGCGCGGTGTTCATCGCCGAACTGGCGCTCGCCGCCGCCGACG     3150
  A  D  R  A  V  F  I  A  E  L  A  L  A  A  A  D

CCACCGACTGCGCCACGGTCGAACAGCTCGACGTCACCTCCGTGCCCGGC     3200
A  T  D  C  A  T  V  E  Q  L  D  V  T  S  V  P  G

GGATCCGCCCGCGGCAGGGCCACCGCGCAGACCTGGGTCGATGAACCCGC     3250
 G  S  A  R  G  R  A  T  A  Q  Y  W  V  D  E  P  A

CGCCGACGGGCGGCGCCGCTTCACCGTCCACACCCGCGTCGGCGACGCCC     3300
  A  D  G  R  R  R  F  T  V  H  T  R  V  G  D  A

CGTGGACGCTGCACGCCGAGGGGGTTCTCCGCCCCGGCCGCGTGCCCCAG     3350
P  W  T  L  H  A  E  G  V  L  R  P  G  R  V  P  Q

CCCGAAGCCGTCGACACCGCCTGGCCCCCGCCGGGCGCGGTGCCCGCGGA     3400
 P  E  A  V  D  T  A  W  P  P  P  G  A  V  P  A  D

CGGGCTGCCCGGGGCGTGGCGACGCGCGGACCAGGTCTTCGTCGAAGCCG     3450
  G  L  P  G  A  W  R  R  A  D  Q  V  F  V  E  A
```

-continued

```
AAGTCGACAGCCCTGACGGCTTCGTGGCACACCCCGACCTGCTCGACGCG      3500
E  V  D  S  P  D  G  F  V  A  H  P  D  L  L  D  A

GTCTTCTCCGCGGTCGGCGACGGGAGCCGCCAGCCGACCGGATGGCGCGA      3550
 V  F  S  A  V  G  D  G  S  R  Q  P  T  G  W  R  D

CCTCGCGGTGCACGCGTCGGACGCCACCGTGCTGCGCGCCTGCCTCACCC      3600
  L  A  V  H  A  S  D  A  T  V  L  R  A  C  L  T

GCCGCGACAGTGGTGTCGTGGAGCTCGCCGCCTTCGACGGTGCCGGAATG      3650
R  R  D  S  G  V  V  E  L  A  A  F  D  G  A  G  M

CCGGTGCTCACCGCGGAGTCGGTGACGCTGGGCGAGGTCGCGTCGGCAGG      3700
 P  V  L  T  A  E  S  V  T  L  G  E  V  A  S  A  G

CGGATCCGACGAGTCGGACGGTCTGCTTCGGCTTGAGTGGTTGCCGGTGG      3750
  G  S  D  E  S  D  G  L  L  R  L  E  W  L  P  V

CGGAGGCCCACTACGACGGTGCCGACGAGCTGCCCGAGGGCTACACCCTC      3800
A  E  A  H  Y  D  G  A  D  E  L  P  E  G  Y  T  L

ATCACCGCCACACACCCCGACGACCCCGACGACCCCACCAACCCCCACAA      3850
 I  T  A  T  H  P  D  D  P  D  D  P  T  N  P  H  N

CACACCCACACGCACCCACACACAAACCACACGCGTCCTCACCGCCCTCC      3900
  T  P  T  R  T  H  T  Q  T  T  R  V  L  T  A  L

AACACCACCTCATCACCACCAACCACACCCTCATCGTCCACACCACCACC      3950
Q  H  H  L  I  T  T  N  H  T  L  I  V  H  T  T  T

GACCCCCCAGGCGCCGCCGTCACCGGCCTCACCCGCACCGCACAAAACGA      4000
 D  P  P  G  A  A  V  T  G  L  T  R  T  A  Q  N  E

ACACCCCGGCCGCATCCACCTCATCGAAACCCACCACCCCCACACCCCAC      4050
  H  P  G  R  I  H  L  I  E  T  H  H  P  H  T  P

TCCCCCTCACCCAACTCACCACCCTCCACCAACCCCACCTACGCCTCACC      4100
L  P  L  T  Q  L  T  T  L  H  Q  P  H  L  R  L  T

AACAACACCCTCCACACCCCCCACCTCACCCCCATCACCACCCACCACAA      4150
 N  N  T  L  H  T  P  H  L  T  P  I  T  T  H  H  N

CACCACCACAACCACCCCCAACACCCCACCCCTCAACCCCAACCACGCCA      4200
  T  T  T  T  T  P  N  T  P  P  L  N  P  N  H  A

TCCTCATCACCGGCGGCTCCGGCACCCTCGCCGGCATCCTCGCCCGCCAC      4250
I  L  I  T  G  G  S  G  T  L  A  G  I  L  A  R  H

CTCAACCACCCCCACACCTACCTCCTCTCCCGCACACCACCACCCCCCAC      4300
 L  N  H  P  H  T  Y  L  L  S  R  T  P  P  P  P  T

CACACCCGGCACCCACATCCCCTGCGACCTCACCGACCCCACCCAAATCA      4350
  T  P  G  T  H  I  P  C  D  L  T  D  P  T  Q  I

CCCAAGCCCTCACCCACATACCACAACCCCTCACCGGCATCTTCCACACC      4400
T  Q  A  L  T  H  I  P  Q  P  L  T  G  I  F  H  T

GCCGCCACCCTCGACGACGCCACCCTCACCAACCTCACCCCCCAACACCT      4450
 A  A  T  L  D  D  A  T  L  T  N  L  T  P  Q  H  L

CACCACCACCCTCCAACCCAAAGCCGACGCCGCCTGGCACCTCCACCACC      4500
  T  T  T  L  Q  P  K  A  D  A  A  W  H  L  H  H

ACACCCAAAACCAACCCCTCACCCACTTCGTCCTCTACTCCAGCGCCGCC      4550
H  T  Q  N  Q  P  L  T  H  F  V  L  Y  S  S  A  A

GCCACCCTCGGCAGCCCCGGCCAAGCCAACTACGCCGCCGCCAACGCCTT      4600
 A  T  L  G  S  P  G  Q  A  N  Y  A  A  A  N  A  F

CCTCGACGCCCTCGCCACCCACCGCCACACCCAAGGACAACCCGCCACCA      4600
  L  D  A  L  A  T  H  R  H  T  Q  G  Q  P  A  T

CCATCGCCTGGGGCATGTGGCACACCACCACCACACTCACCAGCCAACTC      4700
T  I  A  W  G  M  W  H  T  T  T  T  L  T  S  Q  L
```

-continued

```
ACCGACAGCGACCGCGACCGCATCCGCCGCGGCGGCTTCCTGCCGATCTC      4750
 T  D  S  D  R  D  R  I  R  R  G  G  F  L  P  I  S

GGACGACGAGGGCATGC
  D  D  E  G  M
```

The NheI-XhoI hybrid FK-506 PKS module 8 containing the AT domain of module 12 of rapamycin is shown below.

```
GCATGCGGCTGTACGAGGCGGCACGGCGCACCGGAAGTCCCGTGGTGGTG        50
   M  R  L  Y  E  A  A  R  R  T  G  S  P  V  V  V

GCGGCCGCGCTCGACGACGCGCCGGACGTGCCGCTGCTGCGCGGGCTGCG       100
 A  A  A  L  D  D  A  P  D  V  P  L  L  R  G  L  R

GCGTACGACCGTCCGGCGTGCCGCCGTCCGGGAACGCTCTCTCGCCGACC       150
  R  T  T  V  R  R  A  A  V  R  E  R  S  L  A  D

GCTCGCCGTGCTGCCCGACGACGAGCGCGCCGACGCCTCCCTCGCGTTCG       200
R  S  P  C  C  P  T  T  S  A  P  T  P  P  S  R  S

TCCTGGAACAGCACCGCCACCGTGCTCGGCCACCTGGGCGCCGAAGACAT       250
 S  W  N  S  T  A  T  V  L  G  H  L  G  A  E  D  I

CCCGGCGACGACGACGTTCAAGGAACTCGGCATCGACTCGCTCACCGCGG       300
  P  A  T  T  T  F  K  E  L  G  I  D  S  L  T  A

TCCAGCTGCGCAACGCGCTGACCACGGCGACCGGCGTACGCCTCAACGCC       350
V  Q  L  R  N  A  L  T  T  A  T  G  V  R  L  N  A

ACAGCGGTCTTCGACTTTCCGACGCCGCGCGCGCTCGCCGCGAGACTCGG       400
 T  A  V  P  D  F  P  T  P  R  A  L  A  A  R  L  G

CGACGAGCTGGCCGGTACCCGCGCGCCCGTCGCGGCCCGGACCGCGGCCA       450
  D  E  L  A  G  T  R  A  P  V  A  A  R  T  A  A

CCGCGGCCGCGCACGACGAACCGCTGGCGATCGTGGGCATGGCCTGCCGT       500
T  A  A  A  H  D  E  P  L  A  I  V  C  M  A  C  R

CTGCCCGCCGCGGTCGCGTCGCCACAGCACCTCTGCCGTCTCGTCGCGTC       550
 L  P  G  G  V  A  S  P  Q  E  L  W  R  L  V  A  S

CGGCACCGACGCCATCACGGACTTCCCCGCGCACCCCGGCTGGGACCTCG       600
  G  T  D  A  I  T  E  F  P  A  D  R  C  W  D  V

ACGCGCTCTACCACCCGCACCCCGACGCGATCGGCAAGACCTTCGTCCGG       650
D  A  L  Y  D  P  D  P  D  A  I  G  K  T  F  V  R

CACCGCGGCTTCCTCGACGGTGCGACCGGCTTCGACGCGGCGTTCTTCGG       700
 H  G  G  F  L  D  C  A  T  C  F  D  A  A  F  F  C

GATCAGCCCGCGCGAGGCCCTGGCCATGGACCCGCAGCAACGGGTGCTCC       750
  I  S  P  R  E  A  L  A  M  O  P  Q  Q  R  V  L

TGCAGACGTCCTCCCACGCCTTCCAAACCGCGGCCATCACCCCGGACGCC       800
L  E  T  S  W  E  A  F  E  S  A  G  I  T  P  D  A

GCGCGGGGCAGCGACACCGGCGTGTTCATCGGCGCGTTCTCCTACGGGTA       850
 A  R  C  S  D  T  G  V  F  I  G  A  F  S  Y  G  Y

CGGCACGCGTGCGGATACCAACGGCTTCGGCGCGACACGCTCGCACACCA       900
  G  T  G  A  D  T  N  C  F  C  A  T  C  S  Q  T

CCCTGCTCTCCCGCCGCCTCTCCTACTTCTACCCTCTGGAGCGCCCTTCC       950
S  V  L  S  G  R  L  S  Y  F  Y  G  L  E  G  P  S

GTCACCCTCCACACCCCCTCCTCGTCCTCACTCCTCGCCCTCCACCACCC      1000
 V  T  V  D  T  A  C  S  S  S  L  V  A  L  H  Q  A

AGCGCAGTCCCTGCGCTCCGCCCAATCCTCCCTCCCCCTGCTCGGCGCTC      1050
  G  Q  S  L  R  S  G  E  C  S  L  A  L  V  C  G

TCACGCTGATCGCGTCGCCCCCCCCATTCCTCGAGTTCTCCCGCCAGCGC      1100
V  T  V  M  A  S  P  C  C  F  V  E  F  S  R  Q  R
```

-continued

```
GGGCTCGCGCCGCACGGCCGGGCCAACGCGTTCGGCGCGGGCGCGGACGG      1150
 G  L  A  P  D  C  R  A  K  A  F  C  A  C  A  O  C

TACCACCTTCCCCCAGCCCGCCCGTCCCCTCCTGCTCCAGCGGCTCTCCG      1200
  T  S  F  A  E  G  A  G  A  L  V  V  E  R  L  S

ACCCCCACCCCCACCGCCACACCCTCCTCCCCCTCCTACGCGCCTCCCCC      1250
D  A  E  R  H  G  H  T  V  L  A  L  V  R  C  S  A

GCTAACTCCCACCCCGCCTCCAACGCTCTGTCCGCGCCGAACGGCCCCTC      1300
 A  N  S  O  C  A  S  N  C  L  S  A  P  N  C  P  S

CCACCAACCCCTCATCCACCACGCCCTCGCCAACCCCAAACTCACCCCCC      1350
  Q  E  R  V  I  H  Q  A  L  A  N  A  K  L  T  P

CCGATCTCCACCCCGTCGACGCCCACCCCACCCGCACCCGCCTCCCCCAC      1400
A  D  V  D  A  V  E  A  H  C  T  G  T  R  L  C  D

CCCATCCACCCCCACCCCCTCCTCCCCACCTACGCACACGACCCCCCCAC      1450
 P  I  E  A  Q  A  L  L  A  T  Y  C  Q  D  R  A  T

CCCCCTCCTCCTCCCCTCGCTCAAGTCCAACATCCCCCACCCCCACGCCC      1500
  P  L  L  L  C  S  L  K  S  N  I  C  H  A  Q  A

CGTCAGGCCTCGCCGGCATCATCAACATGGTCCACCCCATCCCCCACCGC      1550
A  S  C  V  A  G  I  I  K  M  V  Q  A  T  R  H  C

CAACTCCCCCCCACACTCCACCCCGACCAGCCCTCCCCCCACCTCCACTC      1600
 E  L  P  P  T  L  H  A  D  E  P  S  P  H  V  D  W

CACCGCCCCTGCCCTCCAGCTCCTGACCTCCCCCCCGCCGTGCCCCGCCA      1650
  T  A  C  A  V  E  L  L  T  S  A  R  S  W  P  C

CCGCTCCCCCGCGCCGCGCTGCCGTCTCGTCCTTCGGCGTGACCGGCACG      1700
T  C  R  P  R  R  A  A  V  S  S  F  C  V  S  C  T

AACCCCCACATCATCCTTGACCCAGGACCGCTCAAAACCGCACCGGTCCA      1750
 N  A  H  I  I  L  E  A  C  P  V  K  T  C  P  V  E

CGCACCACCGATCGAGGCACCACCGCTCGAACTACCACCGGTCCACGCTC      1800
  A  G  A  I  E  A  C  P  V  E  V  C  P  V  E  A

GACCGCTCCCCCCCGCCCCCCCCTCACCACCCCCCCAACACCTTCCCCTC      1850
G  P  L  P  A  A  P  P  S  A  P  G  E  D  L  P  L

CTCGTDTCGGCDCGTTCCCCDGAGGCACTCGACGADCAGATCGGDCGCCT      1900
 L  V  S  A  R  S  P  E  A  L  D  E  Q  I  D  R  L

GCGCDCCTATCTCGACACCGGCCCGDGCGTCGACCDGDCDDCCGTGDCGC      1950
  R  A  Y  L  D  T  D  P  G  V  D  R  A  A  V  A

AGACACTDDCCCGGCGTACGCACTTCACCCACCGDGCCDTACTDCTCGGD      2000
Q  T  L  A  R  R  T  H  F  T  H  R  A  V  L  L  D

GACACCGTCATCGGCGCTCCCCCCGCGGACCAGGCCGACGAACTCGTCTT      2050
 D  T  V  I  G  A  P  P  A  D  Q  A  D  E  L  V  F

CGTCTACTCCGGTCAGGGCACCCAGCATCCCGCGATGGGCGAGCAGCTAG      2100
  V  Y  S  G  Q  G  T  Q  H  P  A  M  G  D  E  Q  L

CCGCCGCGTTCCCCGTCTTCGCGCGGATCCATCAGCAGGTGTGGGACCTG      2150
A  A  A  P  P  V  F  A  R  I  H  Q  Q  V  W  D  L

CTCGATGTGCCCGATCTGGAGGTGAACGAGACCGGTTACGCCCAGCCGGC      2200
 L  D  V  P  D  L  E  V  N  E  T  D  Y  A  Q  P  A

CCTGTTCGCAATGCAGGTGGCTCTGTTCGGGCTGCTGGAATCGTGGGGTG      2250
  L  F  A  M  Q     V  A  L  F  G  L  L  E  S  W  G

TACGACCGGACGCGGTGATCGGCCATTCGGTGGGTGAGCTTGCGGCTGCG      2300
V  R  P  D  A  V  I  D  H  S  V  D  E  L  A  A  A

TATGTGTCCGGGGTGTGGTCGTTGGAGGATGCCTGCACTTTGGTGTCGGC      2350
 Y  V  S  D  V  W  S  L  E  D  A  C  T  L  V  S  A

GCGGGCTCGTCTGATGCAGGCTCTGCCCGCGGGTGGGGTGATGGTCGCTG      2400
  R  A  R  L  M  Q  A  L  P  A  G  G  V  M  V  A

TCCCGGTCTCGGAGGATGAGGCCCGGGCCGTGCTGGGTGAGGGTGTGGAG      2450
V  P  V  S  E  D  E  A  R  A  V  L  G  E  G  V  E
```

-continued

```
ATCGCCGCGGTCAACGGCCCGTCGTCGGTGGTTCTCTCCGGTGATGAGGC      2500
 I  A  A  V  N  G  P  S  S  V  V  L  S  G  D  E  A

CGCCGTGCTGCAGGCCGCGGAGGGGCTGGGGAAGTGGACGCGGCTGGCGA      2550
  A  V  L  Q  A  A  E  G  L  G  K  W  T  R  L  A

CCAGCCACGCGTTCCATTCCGCCCGTATGGAACCCATGCTGGAGGAGTTC      2600
T  S  H  A  F  H  S  A  R  M  E  P  M  L  E  E  F

CGGGCGGTCGCCGAAGGCCTGACCTACCGGACGCCGCAGGTCTCCATGGC      2650
 R  A  V  A  E  D  L  T  Y  R  T  P  Q  V  S  M  A

CGTTGGTGATCAGGTGACCACCGCTGAGTACTGGGTGCGGCAGGTCCGGG      2700
  V  G  D  Q  V  T  T  A  E  Y  W  V  R  Q  V  R

ACACGGTCCGGTTCGGCGAGCAGGTGGCCTCGTACGAGGACGCCGTGTTC      2750
D  T  V  R  F  G  E  Q  V  A  S  Y  E  D  A  V  G

GTCGAGCTGGGTGCCGACCGGTCACTGGCCCGCCTGGTCGACGGTGTCGC      2800
 V  E  L  G  A  D  R  S  L  A  R  L  V  D  G  V  A

GATGCTGCACGGCGACCACGAAATCCAGGCCGCGATCGGCGCCCTGGCCC      2850
  V  L  H  G  D  H  E  I  Q  A  A  I  G  A  L  A

ACCTGTATGTCAACGGCGTCACGGTCGACTGGCCCGCGCTCCTGGGCGAT      2900
H  L  Y  V  N  D  V  T  V  D  W  P  A  L  L  G  D

GCTCCGGCAACACGGGTGCTGGACCTTCCGACATACGCCTTCCAGCACCA      2950
 A  P  A  T  R  V  L  D  L  P  T  Y  A  F  Q  H  Q

GCGCTACTGGCTCGAGTCGGCTCCCCCGGCCACGGCCGACTCGGGCCACC      3000
  R  Y  W  L  E  S  A  P  P  A  T  A  D  S  D  H

CCGTCCTCGGCACCGGAGTCGCCGTCGCCGGGTCGCCGGGCCGGGTGTTC      3050
P  V  L  D  T  D  V  A  V  A  D  S  P  D  R  V  P

ACGGGTCCCGTGCCCGCCGGTGCGGACCGCGCGGTGTTCATCGCCGAACT      3100
 T  D  P  V  P  A  G  A  D  R  A  V  P  I  A  E  L

GGCGCTCGCCGCCGCCGACGCCACCGACTGCGCCACGGTCGAACAGCTCG      3150
  A  L  A  A  A  D  A  T  D  C  A  T  V  E  Q  L

ACGTCACCTCCGTGCCCGGCGGATCCGCCCGCGGCAGGGCCACCGCGCAG      3200
D  V  T  S  V  P  G  G  S  A  R  G  R  A  T  A  Q

ACCTGGGTCGATGAACCCGCCGCCGACGGGCGGCGCCGCTTCACCGTCCA      3250
 T  W  V  D  E  P  A  A  D  G  R  R  R  F  T  V  H

CACCCGCGTCGGCGACGCCCCGTGGACGCTGCACGCCGAGGGGGTTCTCC      3300
  T  R  V  G  D  A  P  W  T  L  H  A  E  G  V  L

GCCCCGGCCGCGTGCCCCAGCCCGAAGCCGTCGACACCGCCTGGCCCCCG      3350
R  P  G  R  V  E  Q  P  E  A  V  D  T  A  W  P  P

CCGGGCGCGGTGCCCGCGGACGGGCTGCCCGGGGCGTGGCGACGCGCGGA      3400
 P  G  A  V  P  A  D  G  L  E  G  A  W  R  R  A  D

CCAGGTCTTCGTCGAAGCCGAAGTCGACAGCCCTGACGGCTTCGTGGCAC      3450
  Q  V  F  V  E  A  E  V  D  S  E  D  G  F  V  A

ACCCCGACCTGCTCGACGCGGTCTTCTCCGCGGTCGGCGACGGGAGCCGC      3500
H  P  D  L  L  D  A  V  F  S  A  V  G  D  G  S  R

CAGCCGACCGGATGGCGCGACCTCGCGGTGCACGCGTCGGACGCCACCGT      3550
 Q  P  T  G  W  R  D  L  A  V  H  A  S  D  A  T  V

GCTGCGCGCCTGCCTCACCCGCCGCGACAGTGGTGTCGTGGAGCTCGCCG      3600
  L  R  A  C  L  T  R  R  D  S  G  V  V  E  L  A

CCTTCGACGGTGCCGGAATGCCGGTGCTCACCGCGGAGTCGGTGACGCTG      3650
A  F  D  G  A  G  M  P  V  L  T  A  E  S  V  T  L

GGCCAGGTCGCGTCGGCAGGCGGATCCGACGAGTCGGACGGTCTGCTTCG      3700
 G  E  V  A  S  A  G  G  S  D  E  S  D  G  L  L  R

GCTTGAGTGGTTGCCGGTGGCGGAGGCCCACTACGACGGTGCCGACGAGC      3750
  L  E  W  L  E  V  A  E  A  H  Y  D  G  A  D  E
```

-continued

```
TGCCCGAGGGCTACACCCTCATCACCGCCACACACCCCGACGACCCCGAC      3800
L  P  E  G  Y  T  L  I  T  A  T  H  P  D  D  P  D

GACCCCACCAACCCCCACAACACACCCACACGCACCCACACACAAACCAC      3850
 D  P  T  N  P  H  N  T  P  T  R  T  H  T  Q  T  T

ACGCGTCCTCACCGCCCTCCAACACCACCTCATCACCACCAACCACACCC      3900
  R  V  L  T  A  L  Q  H  H  L  I  T  T  N  H  T

TCATCGTCCACACCACCACCGACCCCCCAGGCGCCGCCGTCACCGGCCTC      3950
L  I  V  H  T  T  T  D  E  E  G  A  A  V  T  G  L

ACCCGCACCGCACAAAACGAACACCCCGGCCGCATCCACCTCATCGAAAC      4000
 T  R  T  A  Q  N  E  H  P  G  R  I  H  L  I  E  T

CCACCACCCCCACACCCCACTCCCCCTCACCCAACTCACCACCCTCCACC      4050
  H  H  P  H  T  E  L  E  L  T  Q  L  T  T  L  H

AACCCCACCTACGCCTCACCAACAACACCCTCCACACCCCCCACCTCACC      4100
Q  E  H  L  R  L  T  N  N  T  L  H  T  P  H  L  T

CCCATCACCACCCACCACAACACCACCACAACCACCCCCAACACCCCACC      4150
 P  I  T  T  H  H  N  T  T  T  T  T  E  N  T  P  P

CCTCAACCCCAACCACGCCATCCTCATCACCGGCGGCTCCGGCACCCTCG      4200
  L  N  E  N  H  A  I  L  I  T  C  G  S  G  T  L

CCGGCATCCTCGCCCGCCACCTCAACCACCCCCACACCTACCTCCTCTCC      4250
A  G  I  L  A  R  H  L  N  H  P  H  T  Y  L  L  S

CGCACACCACCACCCCCCACCACACCCGGCACCCACATCCCCTGCGACCT      4300
 R  T  E  P  E  E  T  T  E  G  T  H  I  P  C  D  L

CACCGACCCCACCCAAATCACCCAAGCCCTCACCCACATACCACAACCCC      4350
  T  D  P  T  Q  I  T  Q  A  L  T  H  I  E  Q  P

TCACCGGCATCTTCCACACCGCCGCCACCCTCGACGACGCCACCCTCACC      4400
L  T  G  I  F  H  T  A  A  T  L  D  D  A  T  L  T

AACCTCACCCCCCAACACCTCACCACCACCCTCCAACCCAAAGCCGACGC      4450
 N  L  T  E  Q  H  L  T  T  T  L  Q  P  K  A  D  A

CGCCTGGCACCTCCACCACCACACCCAAAACCAACCCCTCACCCACTTCG      4500
  A  W  H  L  H  H  H  T  Q  N  Q  E  L  T  H  F

TCCTCTACTCCAGCGCCGCCGCCACCCTCGGCAGCCCCGGCCAAGCCAAC      4550
V  L  Y  S  S  A  A  A  T  L  C  S  P  G  Q  A  N

TACGCCGCCGCCAACGCCTTCCTCGACGCCCTCGCCACCCACCGCCACAC      4600
 Y  A  A  A  N  A  P  L  D  A  L  A  T  H  R  H  T

CCAAGGACAACCCGCCACCACCATCGCCTGGGGCATGTGGCACACCACCA      4650
  Q  G  Q  P  A  T  T  I  A  W  G  M  W  H  T  T

CCACACTCACCAGCCAACTCACCGACAGCGACCGCGACCGCATCCGCCGC      4700
T  T  L  T  S  Q  L  T  D  S  D  R  D  R  I  R  R

GGCGGCTTCCTGCCGATCTCGGACGACGAGGGCATGC
 G  G  F  L  P  I  S  D  D  E  G  M
```

The NheI-XhoI hybrid FK-506 PKS module 8 containing the AT domain of module 13 of rapamycin is shown below.

```
GCATGCGGCTGTACGACGCGGCACGGCGCACCGGAAGTCCCGTGGTGGTG       50
  M  R  L  Y  E  A  A  R  R  I  G  S  P  V  V  V

GCGGCCGCGCICGACGACGCGCCCGACCTGCCCCTGCTGCCCGGCCICCC      100
 A  A  A  L  D  D  A  P  D  V  P  L  L  R  G  L  R

GCGTACGACCGTCCCCCGTGCCGCCGTCCGGGAACGCTCTCTCGCCGACC      150
  R  T  T  V  R  R  A  A  V  R  E  R  S  L  A  D

GCTCGCCGTGCTCCCCGACCACGAGCGCGCCGACCCCTCCCTCGCGTTCG      200
R  S  P  C  C  P  T  T  S  A  P  T  P  P  S  R  S
```

-continued

```
TCCTGGAACAGCACCGCCACCGTGCTCGGCCACCTGGGCGCCGAAGACAT      250
 S  W  N  S  T  A  T  V  L  C  H  L  G  A  E  D  T

CCCGGCGACGACGACGTTCAAGGAACTCGGCATCGACICGCTCACCGCGG      300
  P  A  T  T  I  F  K  E  L  G  I  D  S  L  I  A

TCCAGCIGCGCAACGCGCTGACCACGGCGACCGGCGTACGCCTCAACGCC      350
V  Q  L  R  N  A  L  T  T  A  T  G  V  R  L  N  A

ACAGCGCTCTTCGACTTTCCGACGCCGCGCGCGCTCCCCGCGAGACTCGG      400
 T  A  V  F  D  F  P  I  P  R  A  L  A  A  R  L  G

CGACGAGCTCGCCGGTACCCGCGCGCCCGTCGCGGCCCGGACCGCGGCCA      450
  D  E  L  A  G  T  R  A  P  V  A  A  R  I  A  A

CCGCGGCCGCGCACGACGAACCGCTGGCGATCGTGGGCATGGCCTGCCGT      500
T  A  A  A  S  D  H  P  L  A  I  V  G  M  A  C  R

CTGCCGCGCGGGGTCGCGTCGCCACAGGAGCTGTGGCGTCTCGTCGCGTC      550
 L  P  G  G  V  A  S  P  Q  E  L  W  R  L  V  A  S

CGGCACCGACGCCATCACGGAGTTCCCCGCGGACCGCGGCTGGGACGTGG      600
  G  I  D  A  I  T  E  F  P  A  D  R  G  W  D  V

ACCCGCTCTACGACCCGGACCCCGACGCGATCCCCAAGACCTTCGTCCGG      650
D  A  L  Y  D  P  D  P  D  A  T  G  K  T  F  V  R

CACGGCGGCTTCCTCGACGGTGCGACCGGCTTCGACGCGGCGTTCTTCGG      700
 H  G  G  F  L  D  G  A  T  G  F  D  A  A  F  F  G

GATCAGCCCGCGCGAGGCCCTGGCCATGGACCCGCAGCAACGGGTGCTCC      750
  I  S  P  R  E  A  L  A  M  D  P  Q  Q  R  V  L

TGGAGACGTCCTGGGAGGCGTTCGAAAGCGCGGGCATCACCCCGGACGCG      800
L  E  T  S  W  E  A  F  E  S  A  G  T  I  P  D  A

GCCCGGGGCAGCGACACCGGCCTGTTCATCGGCGCGTTCTCCTACGCGTA      850
 A  R  C  S  D  I  G  V  F  T  G  A  F  S  Y  C  Y

CGGCACGGGTGCGGATACCAACGGCTTCGGCGCGACAGGGTCGCAGACCA      900
  G  T  G  A  D  T  N  G  F  C  A  T  G  S  Q  I

GCCTCCTCICCGGCCGCCTCTCGIACTICTACGGICTGGAGGGCCCIICG      950
S  V  L  S  C  R  L  S  Y  F  Y  C  L  H  G  P  S

GTCACGGTCGACACCCCCTCCTCGTCGTCACTGGTCGCCCTGCACCAGGC     1000
 V  T  V  D  I  A  C  S  S  S  L  V  A  L  S  Q  A

AGGGCAGTCCCTGCGCTCGGGCGAATGCTCGCTCGCCCTGGTCGGCGGTG     1050
  G  Q  S  L  R  S  G  E  C  S  L  A  L  V  G  G

TCACGGTGATGGCGTCGCCCGGCGGATTCGTCGAGTTCTCCCGGCAGCGC     1100
V  T  V  M  A  S  P  G  G  F  V  E  F  S  R  Q  R

GGGCTCGCGCCGGACGGGCGGGCGAAGGCGTTCGGCGCGGGCGCGGACGG     1150
 G  L  A  P  D  G  R  A  K  A  F  G  A  G  A  D  G

TACGAGCTTCGCCGAGGGCGCCGGTGCCCTGGTGGTCGAGCGGCTCTCCG     1200
  T  S  F  A  E  G  A  G  A  L  V  V  E  R  L  S

ACGCGGAGCGCCACGGCCACACCGTCCTCGCCCTCGTACGCGGCTCCGCG     1250
D  A  E  R  H  G  H  T  V  L  A  L  V  R  G  S  A

GCTAACTCCGACGGCGCGTCGAACGGTCTGTCGGCGCCGAACGGCCCCTC     1300
 A  N  S  D  G  A  S  N  G  L  S  A  P  N  G  P  S

CCAGGAACGCGTCATCCACCAGGCCCTCGCGAACGCGAAACTCACCCCCG     1350
  Q  E  R  V  I  H  Q  A  L  A  N  A  K  L  T  P

CCGATGTCGACGCGGTCGAGGCGCACGGCACCGGCACCCGCCTCGGCGAC     1400
A  D  V  D  A  V  E  A  H  G  T  G  T  R  L  G  D

CCCATCGAGGCGCAGGCGCTGCTCGCGACGTACGGACAGGACCGGGCGAC     1450
 P  I  E  A  Q  A  L  L  A  T  Y  G  Q  D  R  A  T

GCCCCTGCTGCTCGGCTCGCTGAAGTCGAACATCGGGCACGCCCAGGCCG     1500
  P  L  L  L  G  S  L  K  S  N  I  G  H  A  Q  A

CGTCAGGGGTCGCCGGGATCATCAAGATGGTGCAGGCCATCCGGCACGGG     1550
A  S  G  V  A  G  I  I  K  M  V  Q  A  I  R  H  G
```

-continued

```
GAACTGCCGCCGACACTGCACGCGGACGAGCCGTCGCCGCACGTCGACTG     1600
 E  L  P  P  T  L  H  A  D  E  P  S  P  H  V  D  W

GACGGCCGGTGCCGTCGAGCTCCTGACGTCGGCCCGGCCGTGGCCGGGGA     1650
  T  A  G  A  V  E  L  L  T  S  A  R  P  W  P  G

CCGGTCGCCCGCGCCGCGCTGCCGTCTCGTCGTTCGGCGTGAGCGGCACG     1700
T  G  R  P  R  R  A  A  V  S  S  F  G  V  S  G  T

AACGCCCACATCATCCTTGAGGCAGGACCGGTGAAAACGGGACCGGTCGA     1750
 N  A  H  I  I  L  E  A  G  P  V  K  T  G  P  V  E

GGCAGGAGCGATCGAGGCAGGACCGGTCGAAGTAGGACCGGTCGAGGCTG     1800
  A  G  A  I  E  A  G  P  V  E  V  G  P  V  E  A

GACCGCTCCCCGCGGCGCCGCCGTCAGCACCGGGCGAAGACCTTCCGCTG     1850
G  P  L  P  A  A  P  P  S  A  P  G  E  D  L  P  L

CTCGTGTCGGCGCGTTCCCCGGAGGCACTCGACGAGCAGATCGGGCGCCT     1900
 L  V  S  A  R  S  P  E  A  L  D  E  Q  I  G  R  L

GCGCGCCTATCTCGACACCGGCCCGGGCGTCGACCGGGCGGCCGTGGCGC     1950
  R  A  Y  L  D  T  G  P  G  V  D  R  A  A  V  A

AGACACTGGCCCGGCGTACGCACTTCACCCACCGGGCCGTACTGCTCGGG     2000
Q  T  L  A  R  R  T  H  F  T  H  R  A  V  L  L  G

GACACCGTCATCGGCGCTCCCCCCGCGGACCAGGCCGACGAACTCGTCTT     2050
 D  T  V  I  G  A  P  P  A  D  Q  A  D  E  L  V  F

CGTCTACTCCGGTCAGGGCACCCAGCATCCCGCGATGGGCGAGCAGCTAG     2100
  V  Y  S  G  Q  G  T  Q  H  P  A  M  G  E  Q  L

CCGATTCGTCGGTGGTGTTCGCCGAGCGGATGGCCGAGTGTGCGGCGGCG     2150
A  D  S  S  V  V  F  A  E  R  M  A  E  C  A  A  A

TTGCGCGAGTTCGTGGACTGGGATCTGTTCACGGTTCTGGATGATCCGGC     2200
 L  R  E  F  V  D  W  D  L  F  T  V  L  D  D  P  A

GGTGGTGGACCGGGTTGATGTGGTCCAGCCCGCTTCCTGGGCGATGATGG     2250
  V  V  D  R  V  D  V  V  Q  P  A  S  W  A  M  M

TTTCCCTGGCCGCGGTGTGGCAGGCGGCCGGTGTGCGGCCGGATGCGGTG     2300
V  S  L  A  A  V  W  Q  A  A  G  V  R  P  D  A  V

ATCGGCCATTCGCAGGGTGAGATCGCCGCAGCTTGTGTGGCGGGTGCGGT     2350
 I  G  H  S  Q  G  E  I  A  A  A  C  V  A  G  A  V

GTCACTACGCGATGCCGCCCGGATCGTGACCTTGCGCAGCCAGGCGATCG     2400
  S  L  R  D  A  A  R  I  V  T  L  R  S  Q  A  I

CCCGGGGCCTGGCGGGCCGGGGCGCGATGGCATCCGTCGCCCTGCCCGCG     2450
A  R  G  L  A  G  R  G  A  M  A  S  V  A  L  P  A

CAGGATGTCGAGCTGGTCGACGGGGCCTGGATCGCCGCCCACAACGGGCC     2500
 Q  D  V  H  L  V  D  G  A  W  I  A  A  H  N  G  P

CGCCTCCACCGTGATCGCGGGCACCCCGGAAGCGGTCGACCATGTCCTCA     2550
  A  S  T  V  I  A  G  T  F  E  A  V  D  H  V  L

CCGCTCATGAGGCACAAGGGGTGCGGGTGCGGCGGATCACCGTCGACTAT     2600
T  A  H  E  A  Q  G  V  R  V  R  R  I  T  V  D  Y

GCCTCGCACACCCCGCACGTCGAGCTGATCCGCGACGAACTACTCGACAT     2650
 A  S  H  T  P  H  V  E  L  I  R  D  E  L  L  D  I

CACTAGCGACAGCAGCTCGCAGACCCCGCTCGTGCCGTGGCTGTCGACCG     2700
  T  S  D  S  S  S  Q  T  P  L  V  P  W  L  S  T

TGGACGGCACCTGGGTCGACAGCCCGCTGGACGGGGAGTACTGGTACCGG     2750
V  D  G  T  W  V  D  S  P  L  D  G  E  Y  W  Y  R

AACCTGCGTGAACCGGTCGGTTTCCACCCCGCCGTCAGCCAGTTGCAGGC     2800
 N  L  R  E  P  V  G  F  H  P  A  V  S  Q  L  Q  A

CCAGGGCGACACCGTGTTCGTCGAGGTCAGCGCCAGCCCGGTGTTGTTGC     2850
  Q  G  D  T  V  F  V  H  V  S  A  S  P  V  L  L
```

-continued

```
AGGCGATGGACGACGATGTCGTCACGGTTGCCACGCTGCGTCGTGACGAC      2900
Q  A  M  D  D  D  V  V  T  V  A  T  L  R  R  D  D

GGCGACGCCACCCGGATGCTCACCGCCCTGGCACAGGCCTATGTCCACGG      2950
 G  D  A  T  R  M  L  T  A  L  A  Q  A  Y  V  H  G

CGTCACCGTCGACTGGCCCGCCATCCTCGGCACCACCACAACCCGGGTAC      3000
  V  T  V  D  W  P  A  I  L  G  T  T  T  I  R  V

TGGACCTTCCGACCTACGCCTTCCAACACCAGCGGTACTGGCTCGAGTCG      3050
L  D  L  P  T  Y  A  F  Q  H  Q  R  Y  W  L  E  S

GCTCCCCCGGCCACGGCCGACTCGGGCCACCCCGTCCTCGGCACCGGAGT      3100
 A  P  P  A  T  A  D  S  G  H  P  V  L  G  T  G  V

CGCCGTCGCCGGGTCGCCGGGCCGGGTGTTCACGGGTCCCGTGCCCGCCG      3150
  A  V  A  G  S  F  G  R  V  F  T  G  P  V  P  A

GTGCGGACCGCGCGGTGTTCATCGCCGAACTGGCGCTCGCCGCCGCCGAC      3200
G  A  D  R  A  V  F  I  A  E  L  A  L  A  A  A  D

GCCACCGACTGCGCCACGGTCGAACAGCTCGACGTCACCTCCGTGCCCGG      3250
 A  T  D  C  A  T  V  E  Q  L  D  V  T  S  V  P  G

CGGATCCGCCCGCGGCAGGGCCACCGCGCAGACCTGGGTCGATGAACCCG      3300
  G  S  A  R  G  R  A  T  A  Q  T  W  V  D  H  F

CCGCCGACGGGCGGCGCCGCTTCACCGTCCACACCCGCGTCGGCGACGCC      3350
A  A  D  G  R  R  R  F  T  V  H  T  R  V  G  D  A

CCGTGGACGCTGCACGCCGAGGGGGTTCTCCGCCCCGGCCGCGTGCCCCA      3400
 P  W  T  L  H  A  E  G  V  L  R  P  G  R  V  P  Q

GCCCGAAGCCGTCGACACCGCCTGGCCCCCGCCGGGCGCGGTGCCCGCGG      3450
  P  E  A  V  D  T  A  W  P  P  P  G  A  V  P  A

ACGGGCTGCCCGGGGCGTGGCGACGCGCGGACCAGGTCTTCGTCGAAGCC      3500
D  G  L  P  G  A  W  R  R  A  D  Q  V  F  V  H  A

GAAGTCGACAGCCCTGACGGCTTCGTGGCACACCCCGACCTGCTCGACGC      3550
 E  V  D  S  P  D  G  F  V  A  H  P  D  L  L  D  A

GGTCTTCTCCGCGGTCGGCGACGGGAGCCGCCAGCCGACCGGATGGCGCG      3600
  V  F  S  A  V  G  D  G  S  R  Q  P  T  G  W  R

ACCTCGCGGTGCACGCGTCGGACGCCACCGTGCTGCGCGCCTGCCTCACC      3650
D  L  A  V  H  A  S  D  A  T  V  L  R  A  C  L  T

CGCCGCGACAGTGGTGTCGTGGAGCTCGCCGCCTTCGACGGTGCCGGAAT      3700
 R  R  D  S  G  V  V  E  L  A  A  F  D  G  A  G  M

GCCDGTGCTCACCGCDGADTCGDTGACDCTGGGCGADGTCGCGTCGDCAG      3750
  P  V  L  T  A  E  S  V  T  L  C  E  V  A  S  A

GCGGATCCGACGAGTCGGACGGTCTGCTTCGGCTTGAGTDGTTGCCGGTD      3800
G  G  S  D  E  S  D  D  L  L  R  L  F  W  L  P  V

GCGGAGGCCCACTACGACGGTDCCGACGAGCTGCCCGAGGGCTACACCCT      3850
 A  E  A  H  Y  D  G  A  D  E  L  P  E  G  Y  T  L

CATCACCDCCACACACCCCGACGACCCCGACGACCCCACCAACCCCCACA      3900
  I  T  A  T  H  P  D  D  P  D  D  P  T  N  P  H

ACACACCCACACGCACCCACACACAAACCACACGCGTCCTCACCGCCCTC      3950
N  T  P  T  R  T  H  T  Q  T  T  R  V  L  T  A  L

CAACACCACCTCATCACCACCAACCACACCCTCATCGTCCACACCACCAC      4000
 Q  H  H  L  I  T  T  N  H  T  L  I  V  H  T  T  T

CGACCCCCCCAGGCGCCGCCGTCACCGGCCTCACCCGCACCGCAAAAACG      4050
  D  P  P  C  A  A  V  T  D  L  T  R  T  A  Q  N

AACACCCCGGCCGCATCCACCTCATCGAAACCCACCACCCCCACACCCCA      4100
E  H  P  G  R  I  H  L  I  E  T  H  H  P  H  T  P

CTCCCCCTCACCCAACTCACCACCCTCCACCAACCCCACCTACGCCTCAC      4150
 L  P  L  T  Q  L  T  T  L  H  Q  P  H  L  R  L  T
```

-continued

```
CAACAACACCCTCCACACCCCCCACCTCACCCCCATCACCACCCACCACA      4200
  N  N  T  L  H  T  P  H  L  T  P  I  T  T  H  H

ACACCACCACAACCACCCCCAACACCCCACCCCTCAACCCCAACCACGCC      4250
N  T  T  T  T  T  P  N  T  P  P  L  N  P  N  H  A

ATCCTCATCACCGGCGGCTCCGGCACCCTCGCCGGCATCCTCDCCCGCCA      4300
 I  L  I  T  G  G  S  D  T  L  A  G  I  L  A  R  H

CCTCAACCACCCCCACACCTACCTCCTCTCCCGCACACCACCACCCCCCA      4350
  L  N  H  P  H  T  Y  L  L  S  R  T  P  P  P  P

CCACACCCGGCACCCACATCCCCTGCGACCTCACCGACCCCACCCAAATC      4400
T  T  P  D  T  H  I  P  C  D  L  T  D  P  T  Q  I

ACCCAAGCCCTCACCCACATACCACAACCCCTCACCGGCATCTTCCACAC      4450
 T  Q  A  L  T  H  I  P  Q  P  L  T  D  I  F  H  T

CGCCGCCACCCTCGACGACGCCACCCTCACCAACCTCACCCCCCAACACC      4500
  A  A  T  L  D  D  A  T  L  T  N  L  T  P  Q  H

TCACCACCACCCTCCAACCCAAADCCGACDCCGCCTDGCACCTCCACCAC      4550
L  T  T  T  L  Q  P  K  A  D  A  A  W  H  L  H  H

CACACCCAAAACCAACCCCTCACCCACTTCGTCCTCTACTCCAGCGCCGC      4600
 H  T  Q  N  Q  P  L  T  H  F  V  L  Y  S  S  A  A

CGCCACCCTCGGCAGCCCCGGCCAAGCCAACTACGCCGCCGCCAACGCCT      4650
  A  T  L  D  S  P  D  Q  A  N  Y  A  A  A  N  A

TCCTCGACGCCCTCGCCACCCACCGCCACACCCAAGGACAACCCGCCACC      4700
F  L  D  A  L  A  T  H  R  H  T  Q  D  Q  P  A  T

ACCATCGCCTGGGGCATGTGGCACACCACCACCACACTCACCAGCCAACT      4750
 T  I  A  W  G  M  W  H  T  T  T  T  L  T  S  Q  L

CACCGACAGCGACCGCGACCGCATCCGCCGCGGCGGCTTCCTGCCGATCT      4800
  T  D  S  D  R  D  R  I  R  R  D  C  F  L  P  I

CDGACGACDAGDGCATGC
S  D  D  E  D  M
```

EXAMPLE 3

Recombinant PKS Genes for 13-desmethoxy FK-506 and FK-520

The present invention provides a variety of recombinant PKS genes in addition to those described in Examples 1 and 2 for producing 13-desmethoxy FK-506 and FK-520 compounds. This Example provides the construction protocols for recombinant FK-520 and FK-506 (from Streptomyces sp. MA6858 (ATCC 55098), described in U.S. Patent Nos. 5,116,756, incorporated herein by reference) PKS genes in which the module 8 AT coding sequences have been replaced by either the rapAT3 (the AT domain from module 3 of the rapamycin PKS), rapAT12, eryAT1 (the AT domain from module 1 of the erythromycin (DEBS) PKS), or eryAT2 coding sequences. Each of these constructs provides a PKS that produces the 13-desmethoxy-13-methyl derivative, except for the rapAT12 replacement, which provides the 13-desmethoxy derivative, i.e., it has a hydrogen where the other derivatives have methyl.

FIG. 7 shows the process used to generate the AT replacement constructs. First, a fragment of ~4.5 kb containing module 8 coding sequences from the FK-520 cluster of ATCC 14891 was cloned using the convenient restriction sites SacI and SphI (Step A in FIG. 7). The choice of restriction sites used to clone a 4.0–4.5 kb fragment comprising module 8 coding sequences from other FK-520 or FK-506 clusters can be different depending on the DNA sequence, but the overall scheme is identical. The unique SacI and SphI restriction sites at the ends of the FK-520 module 8 fragment were then changed to unique Bgl II and NsiI sites by ligation to synthetic linkers (described in the preceding Examples, see Step B of FIG. 7). Fragments containing sequences 5' and 3' of the AT8 sequences were then amplified using primers, described above, that introduced either an AvrII site or an NheI site at two different KS/AT boundaries and an XhoI site at the AT/DH boundary (Step C of FIG. 7). Heterologous AT domains from the rapamycin and erythromycin gene clusters were amplified using primers, as described above, that introduced the same sites as just described (Step D of FIG. 7). The fragments were ligated to give hybrid modules with in-frame fusions at the KS/AT and AT/DH boundaries (Step E of FIG. 7). Finally, these hybrid modules were ligated into the BamHI and PstI sites of the KC515 vector. The resulting recombinant phage were used to transform the FK-506 and FK-520 producer strains to yield the desired recombinant cells, as described in the preceding Examples.

The following table shows the location and sequences surrounding the engineered site of each of the heterologous AT domains employed. The FK-506 hybrid construct was used as a control for the FK-520 recombinant cells produced, and a similar FK-520 hybrid construct was used as a control for the FK-506 recombinant cells.

| Heterologous AT | Enzyme | Location of Engineered Site |
|---|---|---|
| FK-506 AT8 (hydroxymalonlyl) | AvrII | GGCCGTccgcgcCGTGCGGCGGTCTCGTCGTTC<br>G R P R R A A V S S F |
| | NheI | ACCCAGCATCCCGCGATGGGTGAGCGgctcgcC<br>T Q H P A M G E R L A |
| | XhoI | TACGCCTTCCAGCGGCGGCCCTACTGGatcgag<br>Y A F Q R R P Y W I E |
| rapamycin AT3 (methylmalonyl) | AvrII | GACCGGccccgtCGGGCGGGCGTGTCGTCCTTC<br>D R P R R A G V S S F |
| | NheI | TGGCAGTGGCTGGGGATGGGCAGTGCcctgcgG<br>W Q W L G M G S A L R |
| | XhoI | TACGCCTTCCAACACCAGCGGTACTGGgtcgag<br>Y A F Q H Q R Y W V E |
| rapamycin AT12 (malonyl) | AvrII | GGCCGAgcgcgcCGGGCAGGCGTGTCGTCCTTC<br>G R A R R A G V S S F |
| | NheI | TCGCAGCGTGCTGGCATGGGTGAGGAactggcC<br>S Q R A G M G H E L A |
| | XhoI | TACGCCTTCCAGCACCAGCGCTACTGGctcgag<br>Y A F Q H Q R Y W L E |
| DEBS AT1 (methylmalonyl) | AvrII | GCGCGAccgcgcCGGGCGGGGGTCTCGTCGTTC<br>A R P K R A G V S S F |
| | NheI | TGGCAGTGGGCGGGCATGGCCGTCGAcctgctC<br>W Q W A G M A V D L L |
| | XhoI | TACCCGTTCCAGCGCGAGCGCGTCTGGctcgaa<br>Y P F Q R H R V W L E |
| DEBS AT2 (methylmalonyl) | AvrII | GACGGGgtgcgcCGGGCAGGTGTGTCGGCGTTC<br>D G V R R A G V S A F |
| | NheI | GCCCAGTGGGAAGGCATGGCGCGGGAgttgttG<br>A Q W E G M A R E L L |
| | XhoI | TATCCTTTCCAGGGCAAGCGGTTCTGGctgctg<br>Y P F Q G K R F W L L |

The sequences shown below provide the location of the KS/AT boundaries chosen in the FK-520 module 8 coding sequences. Regions where AvrII and NheI sites were engineered are indicated by lower case and underlining.

CCGGCGCCGTCGAACTGCTGACGTCGGCGCGGCCGTGGCCCGAGACCGACCGGgcacggC
A G A V E L L T S A R P W P E T D R P R GTGCCGCCGTCTCCTCGTTCGGGGTGAGCGGCACCAACGCCCACGTCATCCTGGAGGCCG
R A A V S S F G V S G T N A H V I L E A GACCGGTAACGGAGACGCCCGCGGCATCGCCTTCCGGTGACCTTCCCCTGCTGGTGTCGG
G P V T E T P A A S P S G D L P L L V S CACGCTCACCGGAAGCGCTCGACGAGCAGATCCGCCGACTGCGCGCCTACCTGGACACCA
A R S P E A L D E Q I R R L R A Y L D T CCCCGGAGGTCGACCGGGTGGCCGTGGCACAGACGCTGGCCCGGCGCACACACTTCGCCC
T P D V D R V A V A Q T L A R R T H F A ACCGCGCCGTGCTGCTCGGTGACACCGTCATCACCACACCCCCCGCGGACCGGCCCGACG
H R A V L L G D T V I T T P P A D R P D AACTCGTCTTCGTCTACTCCGGCCAGGGCACCCAGCATCCCGCGATGGGCGAGCAgctcg
E L V F V Y S G Q G T Q H P A M G E Q L cCGCCGCCCATCCCGTGTTCGCCGACGCCTGGCATGAAGCGCTCCGCCGCCTTGACAACC
A A A H P V F A D A W H E A L R R L D N The sequences shown below provide the location of the AT/DH boundary chosen in the FK-520 module 8 coding sequences. The region where an XhoI site was engineered is indicated by lower case and underlining.

```
TCCTCGGGGCTGGGTCACGGCACGACGCGGATGTGCCCGCGTACGCGTTCCAACGGCGGC
I  L  G  A  G  S  R  H  D  A  D  V  P  A  Y  A  F  Q  R  R

ACTACTGGatcgagTCGGCACGCCCGGCCGCATCCGACGCGGGCCACCCCGTGCTGGGCT
H  Y  W  I  E  S  A  R  P  A  A  S  D  A  G  H  P  V  L  G

TCGGCCAGGCCGTGGCCGCGGACCGGCCGTccgcgcCGTGCGGCGGTCTCGTCGTTCGGG
 S  A  R  P  W  P  R  T  D  R  P  R  R  A  A  V  S  S  F  G

GTGAGCGGCACCAACGCCCACATCATCCTGGAGGCCGGACCCGACCAGGAGGAGCCGTCG
 V  S  G  T  N  A  H  I  I  L  H  A  G  P  D  Q  H  E  P  S

GCAGAACCGGCCGGTGACCTCCCGCTGCTCGTGTCGGCACGGTCCCCGGAGGCACTGGAC
 A  E  P  A  G  D  L  P  L  L  V  S  A  R  S  P  E  A  L  D

GAGCAGATCGGGCGCCTGCGCGACTATCTCGACGCCGCCCCCGGCGTGGACCTGGCGGCC
 E  Q  I  G  R  L  R  D  Y  L  D  A  A  P  G  V  D  L  A  A

GTGGCGCGGACACTGGCCACGCGTACGCACTTCTCCCACCGCGCCGTACTGCTCGGTGAC
 V  A  R  T  L  A  T  R  T  H  F  S  H  R  A  V  L  L  G  D

ACCGTCATCACCGCTCCCCCCGTGGAACAGCCGGGCGAGCTCGTCTTCGTCTACTCGGGA
 T  V  I  T  A  P  P  V  E  Q  P  G  H  L  V  F  V  Y  S  G

CAGGGCACCCAGCATCCCGCGATGGGTGAGCGgctcgcCGCAGGCTTCCCCGTGTTCGCC
 Q  G  T  Q  H  P  A  M  G  H  R  L  A  A  A  F  P  V  F  A

GACCCGGACGTACCCGCCTACGCCTTCCAGCGGCGGCCCTACTGGATCGAGTCCGCGCCG
 D  P  D  V  P  A  Y  A  F  Q  R  R  P  Y  W  I  B  S  A  P
```

The sequences shown below provide the location of the KS/AT boundaries chosen in the FK-506 module 8 coding sequences. Regions where AvrII and NheI sites were engineered are indicated by lower case and underlining.

The sequences shown below provide the location of the AT/DH boundary chosen in the FK-506 module 8 coding sequences. The region where an XhoI site was engineered is indicated by lower case and underlining.

```
GACCCGGACGTACCCGCCTACGCCTTCCAGCGGCGGCCCTACTGGatcgagTCCGCGCCG
 D  P  D  V  P  A  Y  A  F  Q  R  R  P  Y  W  I  E  S  A  P
```

EXAMPLE 4

Replacement of Methoxyl with Hydrogen or Methyl at C-15 of FK-506 and FK-520

The methods and reagents of the present invention also provide novel FK-506 and FK-520 derivatives in which the methoxy group at C-15 is replaced by a hydrogen or methyl. These derivatives are produced in recombinant host cells of the invention that express recombinant PKS enzymes the produce the derivatives. These recombinant PKS enzymes are prepared in accordance with the methodology of Examples 1 and 2, with the exception that AT domain of module 7, instead of module 8, is replaced. Moreover, the present invention provides recombinant PKS enzymes in which the AT domains of both modules 7 and 8 have been changed. The table below summarizes the various compounds provided by the present invention.

| Compound | C-13 | C-15 | Derivative Provided |
|---|---|---|---|
| FK-506 | hydrogen | hydrogen | 13,15-didesmethoxy-FK-506 |
| FK-506 | hydrogen | methoxy | 13-desmethoxy-FK-506 |
| FK-506 | hydrogen | methyl | 13,15-didesmethoxy-15-methyl-FK-506 |
| FK-506 | methoxy | hydrogen | 15-desmethoxy-FK-506 |

-continued

| Compound | C-13 | C-15 | Derivative Provided |
|---|---|---|---|
| FK-506 | methoxy | methoxy | Original Compound -- FK-506 |
| FK-506 | methoxy | methyl | 15-desmethoxy-15-methyl-FK-506 |
| FK-506 | methyl | hydrogen | 13,15-didesmethoxy-13-methyl-FK-506 |
| FK-506 | methyl | methoxy | 13-desmethoxy-13-methyl-FK-506 |
| FK-506 | methyl | methyl | 13,15-didesmethoxy-13,15-dimethyl-FK-506 |
| FK-520 | hydrogen | hydrogen | 13,15-didesmethoxy-FK-520 |
| FK-520 | hydrogen | methoxy | 13-desmethoxy FK-520 |
| FK-520 | hydrogen | methyl | 13,15-didesmethoxy-15-methyl-FK-520 |
| FK-520 | methoxy | hydrogen | 15-desmethoxy-FK-520 |
| FK-520 | methoxy | methoxy | Original Compound -- FK-520 |
| FK-520 | methoxy | methyl | 15-desmethoxy-15-methyl-FK-520 |

-continued

| Compound | C-13 | C-15 | Derivative Provided |
|---|---|---|---|
| FK-520 | methyl | hydrogen | 13,15-didesmethoxy-13-methyl-FK-520 |
| FK-520 | methyl | methoxy | 13-desmethoxy-13-methyl-FK-520 |
| FK-520 | methyl | methyl | 13,15-didesmethoxy-13,15-dimethyl-FK-520 |

EXAMPLE 5

Replacement of Methoxyl with Ethyl at C-13 and/or C-15 of FK-506 and FK-520

The present invention also provides novel FK-506 and FK-520 derivative compounds in which the methoxy groups at either or both the C-13 and C-15 positions are instead ethyl groups. These compounds are produced by novel PKS enzymes of the invention in which the AT domains of modules 8 and/or 7 are converted to ethylmalonyl specific AT domains by modification of the PKS gene that encodes the module. Ethylmalonyl specific AT domain coding sequences can be obtained from, for example, the FK-520 PKS genes, the niddamycin PKS genes, and the tylosin PKS genes. The novel PKS genes of the invention include not only those in which either or both of the AT domains of modules 7 and 8 have been converted to ethylmalonyl specific AT domains but also those in which one of the modules is converted to an ethylmalonyl specific AT domain and the other is converted to a malonyl specific or a methylmalonyl specific AT domain.

EXAMPLE 6

Neurotrophic Compounds

The compounds described in Examples 1–4, inclusive have immunosuppressant activity and can be employed as immunosuppressants in a manner and in formulations similar to those employed for FK-506. The compounds of the invention are generally effective for the prevention of organ rejection in patients receiving organ transplants and in particular can be used for immunosuppression following orthotopic liver transplantation. These compounds also have pharmacokinetic properties and metabolism that are more advantageous for certain applications relative to those of FK-506 or FK-520. These compounds are also neurotrophic; however, for use as neurotrophins, it is desirable to modify the compounds to diminish or abolish their immunosuppressant activity. This can be readily accomplished by hydroxylating the compounds at the C-18 position using established chemical methodology or novel FK-520 PKS genes provided by the present invention.

Thus, in one aspect, the present invention provides a method for stimulating nerve growth that comprises administering a therapeutically effective dose of 18-hydroxy-FK-520. In another embodiment, the compound administered is a C-18,20-dihydroxy-FK-520 derivative. In another embodiment, the compound administered is a C-13-desmethoxy and/or C-15-desmethoxy 18-hydroxy-FK-520 derivative. In another embodiment, the compound administered is a C-13-desmethoxy and/or C-15-desmethoxy 18,20-dihydroxy-FK-520 derivative. In other embodiments, the compounds are the corresponding analogs of FK-506. The 18-hydroxy compounds of the invention can be prepared chemically, as described in U.S. Pat. No. 5,189,042, incorporated herein by reference, or by fermentation of a recombinant host cell provided by the present invention that expresses a recombinant PKS in which the module 5 DH domain has been deleted or rendered non-functional.

The chemical methodology is as follows. A compound of the invention (~200 mg) is dissolved in 3 mL of dry methylene chloride and added to 45 μL of 2,6-lutidine, and the mixture stirred at room temperature. After 10 minutes, tert-butyldimethylsilyl trifluoromethanesulfonate (64 μL) is added by syringe. After 15 minutes, the reaction mixture is diluted with ethyl acetate, washed with saturated bicarbonate, washed with brine, and the organic phase dried over magnesium sulfate. Removal of solvent in vacuo and flash chromatography on silica gel (ethyl acetate: hexane (1:2) plus 1% methanol) gives the protected compound, which is dissolved in 95% ethanol (2.2 mL) and to which is added 53 μL of pyridine, followed by selenium dioxide (58 mg). The flask is fitted with a water condenser and heated to 70° C. on a mantle. After 20 hours, the mixture is cooled to room temperature, filtered through diatomaceous earth, and the filtrate poured into a saturated sodium bicarbonate solution. This is extracted with ethyl acetate, and the organic phase is washed with brine and dried over magnesium sulfate. The solution is concentrated and purified by flash chromatography on silica gel (ethyl acetate: hexane (1:2) plus 1% methanol) to give the protected 18-hydroxy compound. This compound is dissolved in acetonitrile and treated with aqueous HF to remove the protecting groups. After dilution with ethyl acetate, the mixture is washed with saturated bicarbonate and brine, dried over magnesium sulfate, filtered, and evaporated to yield the 18-hydroxy compound. Thus, the present invention provides the C-18-hydroxyl derivatives of the compounds described in Examples 1–4.

Those of skill in the art will recognize that other suitable chemical procedures can be used to prepare the novel 18-hydroxy compounds of the invention. See, e.g., Kawai et al., January 1993, Structure-activity profiles of macrolactam immunosuppressant FK-506 analogues, FEBS Letters 316 (2): 107–113, incorporated herein by reference. These methods can be used to prepare both the C18-[S]-OH and C18-[R]-OH enantiomers, with the R enantiomer showing a somewhat lower $IC_{50}$, which may be preferred in some applications. See Kawai et al., supra. Another preferred protocol is described in Umbreit and Sharpless, 1977, JACS 99(16): 1526–28, although it may be preferable to use 30 equivalents each of $SeO_2$ and t-BuOOH rather than the 0.02 and 3–4 equivalents, respectively, described in that reference.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. A polyketide having the structure

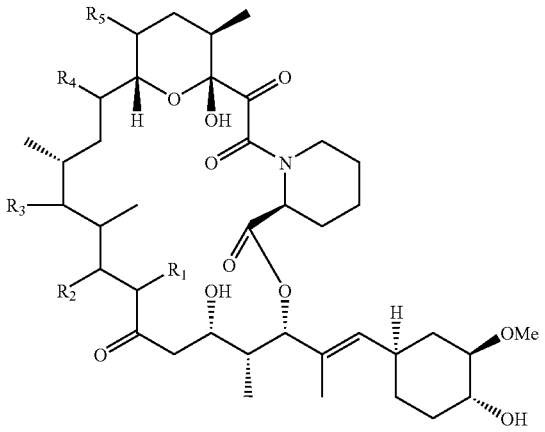

wherein, $R_1$ is hydrogen, methyl, ethyl, or allyl; $R_2$ is hydrogen or hydroxyl, provided that when $R_2$ is hydrogen, there is a double bond between C-20 and C-19; $R_3$ is hydrogen or hydroxyl; $R_4$ is methoxyl, hydrogen, methyl, or ethyl; and $R_5$ is methoxyl, hydrogen, methyl, or ethyl; [but not including FK-506, FK-520, 18-hydroxy-FK-520, and 18-hydroxy-FK-506] *wherein at least one of $R_4$ or $R_5$ is not methoxyl.*

2. The polyketide as in claim 1 wherein $R_2$ is hydrogen and there is a double bond between C-20 and C-19.

3. The polyketide as in claim 1 wherein $R_4$ is hydrogen, methyl or ethyl.

4. The polyketide as in claim 3 wherein $R_3$ is hydroxyl.

5. The polyketide as in claim 1 wherein $R_5$ is hydrogen, methyl or ethyl.

6. The polyketide as in claim 5 wherein $R_3$ is hydroxy.

7. A compound of the formula

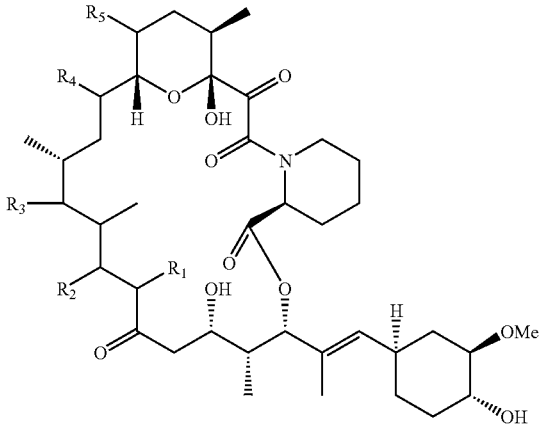

wherein:

$R_1$ is ethyl or allyl;

$R_2$ is hydrogen and there is a double bond between C-20 and C-19;

$R_3$ is hydrogen;

$R_4$ is methoxyl, hydrogen, methyl, or ethyl; and $R_5$ is methoxyl, hydrogen, methyl, or ethyl; provided that at least one [or] *of* $R_4$ or $R_5$ is not methoxyl.

8. The compound as in claim 7 wherein $R_1$ is ethyl.

9. The compound as in claim 8 wherein $R_4$ is methoxyl and $R_5$ is hydrogen or methyl.

10. The compound as in claim 8 wherein $R_4$ is hydrogen or methyl and $R_5$ is methoxyl.

11. The compound as in claim 7 that is 13-desmethoxy-FK-520.

12. The compound as in claim 7 that is 13-desmethoxyl-13-methyl-FK-520.

13. The compound as in claim 7 that is 15-desmethoxy-FK-520.

14. The compound as in claim 7 that is 15-desmethoxy-15-methyl-FK-520.

15. The compound as in claim 7 that is 13,15-didesmethoxy-FK-520.

16. The compound as in claim 7 that is 13,15-didesmethoxy-13-methyl-FK-520.

17. The compound as in claim 7 that is 13,15-didesmethoxy-15-methyl-FK-520.

18. The compound as in claim 7 that is 13,15-didesmethoxy-13,15-dimethyl-FK-520.

19. The compound as in claim 7 that is 13-desmethoxy-FK-506.

20. The compound as in claim 7 that is 13-desmethoxy-13-methyl-FK-506.

21. The compound as in claim 7 that is 15-desmethoxy-FK-506.

22. The compound as in claim 7 that is 15-desmethoxy-15-methyl-FK-506.

23. The compound as in claim 7 that is 13,15-didesmethoxy-FK-506.

24. The compound as in claim 7 that is 13,15-didesmethoxy-13-methyl-FK-506.

25. The compound as in claim 7 that is 13,15-didesmethoxy-15-methyl-FK-506.

26. The compound as in claim 7 that is 13,15-didesmethoxy-13,15-dimethyl-FK-506.

27. A compound of the formula

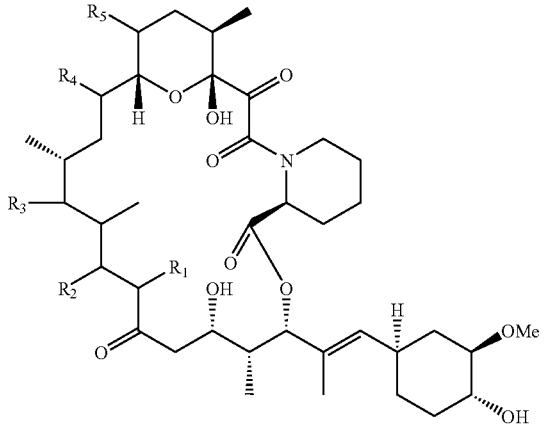

wherein:

$R_1$ is ethyl or allyl;

$R_2$ is hydrogen and there is a double bond between C-20 and C-19;

$R_3$ is hydroxyl;

$R_4$ is methoxyl, hydrogen, methyl, or ethyl; and $R_5$ is methoxyl, hydrogen, methyl, or ethyl; provided that at least one [or] *of* $R_4$ or $R_5$ is not methoxyl.

28. The compound as in claim 27 wherein $R_1$ is ethyl.

29. The compound as in claim 27 wherein $R_4$ is methoxyl and $R_5$ is hydrogen or methyl.

30. The compound as in claim 27 wherein $R_4$ is hydrogen or methyl and $R_5$ is methoxyl.

31. The compound as in claim 27 that is 13-desmethoxy-18-hydroxyl-FK-520.

32. The compound as in claim 27 that is 13-desmethoxy-13-methyl-18-hydroxyl-FK-520.

33. The compound as in claim 27 that is 15-desmethoxy-18-hydroxyl-FK-520.

34. The compound as in claim 27 that is 15-desmethoxy-15-methyl-18-hydroxyl-FK-520.

35. The compound as in claim 27 that is 13,15-didesmethoxy-18-hydroxyl-FK-520.

36. The compound as in claim 27 that is 13,15-didesmethoxy-13-methyl-18-hydroxyl-FK-520.

37. The compound as in claim 27 that is 13,15-didesmethoxy-15-methyl-18-hydroxyl-FK-520.

38. The compound as in claim 27 that is 13,15-didesmethoxy-13,15-dimethyl-18-hydroxyl-FK-520.

39. The compound as in claim 27 that is 13-desmethoxyl-18-hydroxyl-FK-506.

40. The compound as in claim 27 that is 13-desmethoxyl-13-methyl-18-hydroxyl-FK-506.

41. The compound as in claim 27 that is 15-desmethoxy-18-hydroxyl-FK-506.

42. The compound as in claim 27 that is 15-desmethoxy-15-methyl-18-hydroxyl-FK-506.

43. The compound as in claim 27 that is 13,15-didesmethoxy-18-hydroxyl-FK-506.

44. The compound as in claim 27 that is 13,15-didesmethoxy-13-methyl-18-hydroxyl-FK-506.

45. The compound as in claim 27 that is 13,15-didesmethoxy-15-methyl-18-hydroxyl-FK-506.

46. The compound as in claim 27 that is 13,15-didesmethoxy-13,15-dimethyl-18-hydroxyl-FK-506.

* * * * *